US009248141B2

(12) United States Patent
Green et al.

(10) Patent No.: US 9,248,141 B2
(45) Date of Patent: Feb. 2, 2016

(54) METHODS OF TREATMENT BY ADMINISTERING ANTI-CONNEXIN PROTEINS AND MIMETICS

(75) Inventors: Colin R. Green, Auckland (NZ); David L. Becker, Langley (GB)

(73) Assignee: CoDa Therapeutics, Inc., San Diego, CA (US)

( * ) Notice: Subject to any disclaimer, the term of this patent is extended or adjusted under 35 U.S.C. 154(b) by 1133 days.

(21) Appl. No.: 11/883,739

(22) PCT Filed: Feb. 3, 2006

(86) PCT No.: PCT/IB2006/001961
§ 371 (c)(1),
(2), (4) Date: Apr. 17, 2008

(87) PCT Pub. No.: WO2006/134494
PCT Pub. Date: Dec. 21, 2006

(65) Prior Publication Data
US 2009/0142295 A1 Jun. 4, 2009

Related U.S. Application Data

(60) Provisional application No. 60/650,075, filed on Feb. 3, 2005.

(51) Int. Cl.
| C07K 7/06 | (2006.01) |
| C07K 7/08 | (2006.01) |
| C07K 14/705 | (2006.01) |
| A61K 38/08 | (2006.01) |
| A61K 38/10 | (2006.01) |
| A61K 38/16 | (2006.01) |
| A61K 38/17 | (2006.01) |
| A61K 31/70 | (2006.01) |

(52) U.S. Cl.
CPC ............... *A61K 31/70* (2013.01); *A61K 38/177* (2013.01); *A61K 38/08* (2013.01); *A61K 38/10* (2013.01); *C07K 7/06* (2013.01); *C07K 7/08* (2013.01); *C07K 14/705* (2013.01)

(58) Field of Classification Search
None
See application file for complete search history.

(56) References Cited

U.S. PATENT DOCUMENTS

| 3,687,808 | A | 8/1972 | Merigan et al. |
| 4,861,757 | A | 8/1989 | Antoniades et al. |
| 5,034,506 | A | 7/1991 | Summerton et al. |
| 5,044,810 | A | 9/1991 | Matsuoka et al. |
| 5,166,195 | A | 11/1992 | Ecker |
| 5,998,148 | A | 12/1999 | Bennett et al. |
| 6,458,590 | B1 | 10/2002 | Mukherjee et al. |
| 6,506,559 | B1 | 1/2003 | Fire et al. |
| 6,752,987 | B1 | 6/2004 | Hammond et al. |
| 7,098,190 | B1 | 8/2006 | Becker et al. |
| 7,153,822 | B2 | 12/2006 | Jensen et al. |
| 7,521,191 | B2 | 4/2009 | Khvorova et al. |
| 2003/0105165 | A1* | 6/2003 | Griffith .................. 514/651 |
| 2003/0148968 | A1 | 8/2003 | Hammond |
| 2003/0215424 | A1 | 11/2003 | Seul et al. |
| 2004/0092429 | A1 | 5/2004 | Jensen et al. |
| 2004/0259768 | A1 | 12/2004 | Lauermann |
| 2005/0119211 | A1 | 6/2005 | Chowrira et al. |
| 2006/0105013 | A1 | 5/2006 | Ashkar et al. |
| 2007/0232526 | A1 | 10/2007 | Kvistgaard et al. |
| 2008/0261867 | A1 | 10/2008 | Klagsbrun et al. |
| 2010/0150877 | A1 | 6/2010 | O'Brien et al. |

FOREIGN PATENT DOCUMENTS

| EP | 1 514 929 A1 | 3/2005 |
| JP | 2002-535377 A | 10/2002 |
| JP | 2003-238441 A | 8/2003 |
| WO | WO 94/12633 | 6/1994 |
| WO | WO 96/19194 | 6/1996 |
| WO | WO 98/24797 | 6/1998 |
| WO | WO 00/44409 | 8/2000 |
| WO | WO 02/056910 | 7/2002 |
| WO | WO 03/032964 | 4/2003 |
| WO | WO 03/063891 A1 | 8/2003 |
| WO | WO 2005/053600 | 6/2005 |
| WO | WO 2005/053600 A3 | 6/2005 |
| WO | WO 2005/119211 | 12/2005 |
| WO | WO 2006/069181 | 6/2006 |
| WO | WO 2006/134494 | 12/2006 |
| WO | WO 2006/134494 A3 | 5/2008 |
| WO | WO 2008/060622 A2 | 5/2008 |
| WO | WO 2008/073479 | 6/2008 |
| WO | WO 2008/060622 A3 | 7/2008 |
| WO | WO 2008/073479 A3 | 7/2008 |

(Continued)

OTHER PUBLICATIONS

Ilvesaro et al. Connexin-mimetic peptide Gap 27 decreases osteoclastic activity. BMC Musculoskel Dis 2:10, 2001 (6 pages total).*
Oviedo-Orta et al. Gap junctions and connexins: potential contributors to the immunological synpase. J Leuk Biol 72: 636-642, 2002.*
Herve et al. Diversity in protein-protein interactions of connexins: emerging roles. Biochim Biophys Acta 1662: 22-41, 2004.*
Jackowski et al. Brit J Neurosurg 9: 303-317, 1995.*
Skolnick et al. From genes to protein structure and function: novel applications of computational approaches in the genomic era. Trends in Biotech 18(1): 34-39, 2000.*

(Continued)

*Primary Examiner* — Bridget E Bunner
(74) *Attorney, Agent, or Firm* — Duane Morris LLP

(57) ABSTRACT

Methods and compositions for modulating the activities of connexins are provided, including, for example, for use for treatment of cardiovascular, vascular, neurological, for wounds and for other indications. These compounds and methods can be used therapeutically, for example, to reduce the severity of adverse effects associated diseases and disorders where localized disruption in direct cell-cell communication or prevention of hemichannel opening is desirable.

54 Claims, 16 Drawing Sheets

(56) References Cited

FOREIGN PATENT DOCUMENTS

| WO | WO 2008/151022 A2 | 12/2008 |
|---|---|---|
| WO | WO 2009/075881 A2 | 6/2009 |
| WO | WO 2009/075881 A3 | 6/2009 |
| WO | WO 2009/075882 A2 | 6/2009 |
| WO | WO 2009/075882 A3 | 6/2009 |
| WO | WO 2009/085268 A2 | 7/2009 |
| WO | WO 2009/085269 A2 | 7/2009 |
| WO | WO 2009/085270 A2 | 7/2009 |
| WO | WO 2009/085271 A2 | 7/2009 |
| WO | WO 2009/085272 A2 | 7/2009 |
| WO | WO 2009/085273 A2 | 7/2009 |
| WO | WO 2009/085274 A2 | 7/2009 |
| WO | WO 2009/085275 A2 | 7/2009 |
| WO | WO 2009/085277 A2 | 7/2009 |
| WO | WO 2009/085268 A3 | 8/2009 |
| WO | WO 2009/085269 A3 | 8/2009 |
| WO | WO 2009/085270 A3 | 8/2009 |
| WO | WO 2009/085271 A3 | 8/2009 |
| WO | WO 2009/085273 A3 | 8/2009 |
| WO | WO 2009/085274 A3 | 8/2009 |
| WO | WO 2009/085275 A3 | 8/2009 |
| WO | WO 2009/097077 A2 | 8/2009 |
| WO | WO 2009/085277 A3 | 10/2009 |
| WO | WO 2009/148613 A1 | 12/2009 |
| WO | WO 2009/085272 A3 | 6/2010 |

OTHER PUBLICATIONS

Bork, A. Powers and pitfalls in sequence analysis: the 70% hurdle. Genome Res 10: 398-400, 2000.*
Doerks et al. Protein annotation: detective work for function prediction. Trends in Genetics 14(6): 248-250, 1998.*
Smith et al. The challenges of genome sequence annotation or "The devil is in the details". Nature Biotech 15: 1222-1223, 1997.*
Brenner, S.E. Errors in genome function. Trends in Genetics 15(4): 132-133, 1999.*
Bork et al. Go hunting in sequence databases but watch out for the traps. Trends in Genetics. 12(10): 425-427, 1996.*
Wells. J.A. Additivity of mutational effects in proteins. Biochemistry 29 (37): 8509-8517, 1990.*
Ngo et al. Computational complexity, protein structure prediction, and the Levinthal paradox. The Protein Folding Problem and Tertiary Structure Prediction, pp. 492-495, 1994.*
Papangelou et al. Curr Treatment Options in Neurol 11:64-73, 2009.*
Mattu et al. Emerg Med Clin N Am 23: 1105-1125, 2005.*
Lemanske et al. J Allergy Clin Immunol 111:S502-19, 2003.*
Johnsson et al. Transplant Int 12: 235-243, 1999.*
Johnson et al. Am J Opthalmol 147: 11-21, 2009.*
Cotter et al. Curr Opin Cardiol 16: 159-163, 2001.*
Marmarou, A. Neurosurg Focus 22(5): E1-10, 2007.*
Rabinstein, A. Neurologist 12: 59-73, 2006.*
Sica, D. Heart Failure Clin 4: 511-518, 2008.*
Kaal et al. Curr Opin Oncol 16: 593-600, 2004.*
Saez et al. Physiol Rev 83:1359-1400, 2003.*
Schumacher et al. Circulation 97: 645-650, 1998.*
Landau et al. Am Heart J 129(5): 924-931, 1995.*
Examination Report, NZ 548204, Mail Date Aug. 5, 2009.
Examination Report, NZ 561098, Mail Date Mar. 17, 2009.
Written Opinion—PCT/IB2006/001961—May 13, 2008.
Examiner's Fourth Report, CA 2,361,251, Dated Mar. 17, 2008.
Examiner's Second Report, CA 2,361,251, Dated Nov. 20, 2006.
Examiner's Third Report, CA 2,361,251, Dated Jun. 27, 2007.
Final Office Action, U.S. Appl. No. 09/890,363, Mail Date Jul. 22, 2005.
Final Office Action, U.S. Appl. No. 11/447,599, Mail Date Sep. 18, 2009.
Final Office Action, U.S. Appl. No. 11/510,498, Mail Date Feb. 4, 2010.
Final Office Action, U.S. Appl. No. 11/512,725, Mail Date Aug. 27, 2009.
Final Office Action, U.S. Appl. No. 11/512,730, Mail Date Nov. 26, 2008.
Final Office Action, U.S. Appl. No. 11/512,735, Mail Date Nov. 26, 2008.
Non Final Office Action, U.S. Appl. No. 09/890,363, Mail Date Apr. 30, 2003.
Non Final Office Action, U.S. Appl. No. 11/447,599, Mail Date Mar. 13, 2008.
Non Final Office Action, U.S. Appl. No. 11/510,496, Mail Date Mar. 14, 2008.
Non Final Office Action, U.S. Appl. No. 11/510,498, Mail Date Dec. 2, 2008.
Non Final Office Action, U.S. Appl. No. 11/512,725, Mail Date Nov. 26, 2008.
Non Final Office Action, U.S. Appl. No. 11/512,730, Mail Date Feb. 8, 2008.
Non Final Office Action, U.S. Appl. No. 11/512,735, Mail Date Feb. 7, 2008.
Non Final Office Action, U.S. Appl. No. 10/581,813, Mail Date Dec. 22, 2008.
Requirement for Restriction/Election, U.S. Appl. No. 10/581,813, Mail Date Nov. 5, 2009.
Official Action, AU 2004294824, Mail Date May 28, 2009.
First Official Action, CN 200480041251.9, Issue Date Jul. 4, 2008.
Examination Report, EA 200601071, Mail Date Jul. 19, 2007.
International Preliminary Report on Patentability—PCT/GB00/00238—Apr. 10, 2001.
International Search Report—PCT/GB00/00238—Jun. 19, 2000.
A chinese procedure involving stem cell transplants is providing some very interesting results. Oct. 24, 2003. Canadian Paraplegic Association. Sep. 27, 2006 http://www.canparaplegic.org/national/level12.tpl?var1=story&var2=20031024154627.
Agrawal, ed., "Antisense Oligonucleotides, towards clinical trials." Protocols for Oligonucleotides and Analogs, Synthesis and Properties Human Press Inc., "Antisense Oligonucleotides, towards clinical trials." New Jersey, 1993.
Aguayo, A.J., et al. J. Exp. Biol. 95:231-240 (1981).
Ahmadi, et al. Int. Ophthalmol. Clinics, 42(3):13-22 (2002).
Altschul S.F. J Mol Biol 215:403-10 (1990).
Altschul S.F. J Mol Evol 36:290-300 (1993).
Examiner's First Report, CA 2,361,251 Dated Apr. 11, 2006.
Antisense Research and Applictions (1993), CRC Press, Chps. 2, 19, 28, 32.
Arnold, et. al., Seminars in Ophthalmology 17:39-46 (2002).
Ashcroft, et al. Nat Cell Biol. 1:260-6 (1999).
Baker, D.W. et al., "ACC/AHA Guidelines for the Evaluation and Management of Chronic Heart Failure in the Adult." 2001 American College of Cardiology and the American Heart Association.
Baldwin, Heather C., et. al., "Growth factors in corneal wound healing following refractive surgery: A Review" ACTA Ophthalmologica Scandinavica 80(3):Jun. 2002.
Barany and Merrifield, "The Peptides," eds. E. Gross and F. Meienhofer, vol. 2 (Academic Press, 1980) pp. 3-285.
BBC News "Gels 'heal wounds more quickly'"; http://news.bbc.co.uk/1/hi/health/3243633.stm. (May 26, 2006).
Beaucage et al., eds., Current Protocols in Nucleic Acid Chemistry John Wiley & Sons, Inc., New York, 2000.
Becker DL, Green CR (2001) Gap junction-mediated interactions between cells. Chapter 3 in Cell-Cell Interactions—A Practical Approach ed. TP Fleming. Oxford University Press, pp. 47-70.
Becker, D.L. and Davies, C.S. (1995) The role of gap junctions in the development of the preimplantation mouse embryo. In Microscopy of Intercellular Communicating Junctions. Ed. R. Gourdie. Microsc. Res. Tech. 31, 364-374.
Becker, D.L. and Mobbs, P. (1999) Connexin alpha1 and cell proliferation in the developing chick retina. Expl. Neurol. 156(2): 326-332.
Becker, D.L. et al. Roles for a1 connexin in morphogenesis of chick embryos revealed using a novel antisense approach. Devel. Genetics, 24:33-42, 1999.
Becker, D.L., Bittman, K., Cicirata, F. and Parnavelas, J.G. (2002) Connexin expression in homotypic and heterotypic cell coupling in the developing cerebral cortex. J. Compo Neurol 443, 201-212.

(56) References Cited

OTHER PUBLICATIONS

Becker, D.L., Bonness, V., and Mobbs, P. (1998) Cell coupling in the retina: Patterns and purpose. Cell Biol. Int. 22, 781-792.
Becker, D.L., Bonness, V., Catsicas, M. and Mobbs, P. (2002) Changing patterns of ganglion cell coupling and connexin expression during chick retinal development. J. Neurobiol. 52, 280-293.
Becker, D.L., Ciantar, D., Catsicas, M., Pearson, R. and Mobbs, P. (2002) Use of pIRES vectors to express EGFP and connexin constructs in studies of the role of gap junctional communication in the early development of the chick retina and brain. Cell Commun. Adhes. 8, 355-359.
Becker, D.L., Cook, J.E., Davies, C.S., Evans, W.H. and Gourdie, R. (1998) Expression of major gap junction connexin types in the working myocardium of eight chordates. Cell Biol. Int. 22, 527-543.
Becker, D.L., David-Leclerc, C. and Warner A.E. (1992) The relationship of gap junctions and compaction in the preimplantation mouse embryo. Development Suppl., 113-118.
Becker, D.L., Evans, W.H., Green C.R. and Warner, A.E. (1995) Functional analysis of amino acid sequences in connexin 43 involved in intercellular communication through gap junctions. J. Cell Sci. 108, 1455-1467.
Becker, D.L., Evans, W.H., Green C.R. and Warner, A.E. (1995) Functional block of gap junctional communication using antipeptide antibodies: Molecular localization of the putative binding sites. Intercellular communication through gap junctions: Ed. Y. Kanno. Progress in Cell Research, 4; 427-430.
Becker, D.L., Lin, J.S. and Green G.R. (1999) Pluronic gel as a means of antisense delivery. In Antisense techniques in the CNS. A practical approach. Eds. R. Leslie, A.J. Hunter and H.A. Robertson. pp. 149-157.
Becker, D.L., McGonnell, I., Makarenkova, H., Patel, K., Tickle, C., Lorimer, J., and Green, C.R. (1999) Roles for alpha1 connexin in morphogenesis of chick embryos using a novel antisense approach. Dev. Genetics. 24, 33-42.
Examiner's Sixth Report, CA 2,361,251 Dated Oct. 23, 2009.
Beeley N., Trends Biotechnol. Jun;12(6): 213-6 (1994).
Bennett MV, Zukin RS. Electrical coupling and neuronal synchronization in the Mammalian brain. Neuron. Feb. 19, 2004; 41(4):495-511.
Berge, et al., J. of Pharma Sci. 66, 1-19 (1977).
Berkovitz, B.K.B. and Becker, D.L. (2003) The detailed morphology and distribution of gap junction protein associated with cells from the intra-articular disc of the rat temporomandibular joint. Conn. Tiss. Res. 44, 12-18.
Bernstein, et. al. Invest Ophthalmol Vis Sci 44:4153-4162 (2003).
Berthoud, V.M. and Seul, K.H., Am J. Physiol. Jung Cell Mol. Physiol. 279:L619-L622 (2000).
Bioconjugate Techniques (Greg T. Hermanson, ed., Academic Press, 1996), Chapter 2 and 17.
Blackburn JP, Connat JL, Severs NJ, Green CR. Connexin43 gap junction levels during development of the thoracic aorta are temporally correlated with elastic laminae deposition and increased blood pressure. Cell Biol Int. Feb. 1997;21(2):87-97. PMID: 9080656 [PubMed—indexed for MEDLINE.
Blackburn JP, Peters NS, Yeh HI, Rothery S, Green CR, Severs NJ. Upregulation of connexin43 gap junctions during early stages of human coronary atherosclerosis. Arterioscler Thromb Vasc Biol. Aug. 1995;15(8):1219-28. PMID: 7627716 [PubMed—indexed for MEDLINE].
Boitano S. and Evans W., Am J Physiol Lung Cell Mol Physiol 279:L623-L630 (2000).
Braasch, D.A. and Corey, D.R., Biochemistry 41, 4503-4510 (2002).
Braet, K., et al., "Pharmacological senstivity of aTP release triggered by photoliberation of inositol-1,4,5-triphosphate and zero extracellular calcium in brain endothelial cells," Journal of Cellular Physiology, 197(2):205-213 (2003).
Branch, A.D. Hepatology 24, 1517-1529 (1996).
Brandner, et. al., "Connexins 26, 30, and 43: Differences Among Spontaneous, Chronic, and Accelerated Human Wound Healing." J. Invest Dermatol. 122:1310-20 (2004).

Brummelkamp T., et al., Science 296:550-553 (2002).
Brunton. Chapter 38. In: Goodman & Gilman's The Pharmacological Basis of Therapeutics, 9th Ed., 1996.
Brysch, W. Antisense Technology in the Ventral Nervous System, ed. H.A. Robertson; Oxford University Press. pp. 21-41 (1999).
Buono, et. al. Survey of Ophthalmology 50:15-26 (2005).
Buur, et al. J. Control Rel. 14:43-51 (1990).
Cairns, et al. Nat. Biotech 17:480-486 (1999).
Camelliti P, Devlin GP, Matthews KG, Kohl P, Green CR. Spatially and temporally distinct expression of fibroblast connexins after sheep ventricular infarction. Cardiovasc Res. May 1, 2004;62(2):415-25. PMID: 15094361 [PubMed—indexed for MEDLINE].
Camelliti P, Green CR, Kohl P. Structural and functional coupling of cardiac myocytes and fibroblasts. Adv Cardiol. 2006;42:132-49. Review. PMID: 16646588 [PubMed—indexed for MEDLINE].
Caplen N. et al., Proc Natl Acad Sci 98:9742-9747 (2001).
Cech, Biotechnology 13:323 (1995) Group I Introns: New Molecular Mechanisms for MRNA repair.
Chakraborti, S. and Banerjea, A.C., Mol. Ther. 7, 817-826 (2003).
Cheng et al., J. Biol. Chem. 263:15110-15117 No. 29, (Oct. 15, 1998).
Cheng, H., et al. Science 273:510-513, 1996.
Chonn, et al., Current Op. Biotech. 6, 698-708 (1995).
Chou, et al. Ad. Enzyme Reg. 22:27-55 (1984).
Coffey KL, Krushinsky A, Green CR, Donaldson PJ. Molecular profiling and cellular localization of connexin isoforms in the rat ciliary epithelium. Exp Eye Res. Jul. 2002;75(1):9-21. PMID: 12123633 [PubMed—indexed for MEDLINE].
Collaborative Neuroscience the Spinal Cord Injury Project. Care Cure Community Postings for "Gel 'is helping wounds heal in half the time'/nexagon." Sep. 29, 2006 http://sci.rutgers.edu/forum/showthread.php?t=6653.
Collignon et al., Ophthalmology 111:1663-1672 (2004).
Common, J.E.A, Becker, D.L., Di, W.L., Leigh, I.M., O'Toole, E.A. and Kelsell, D.P. (2002) Functional studies of human skin disease- and deafness-associated Connexin 30 mutations. Biochem. Biophys. Res. Commun. 298, 651-656.
Concise Encyclopedia of Polymer Science and Engineering, pp. 858-859 (1990).
Cook, J.E. and Becker, D.L. (1995) Gap Junctions in the vertebrate retina. In Microscopy of Intercellular Communicating Junctions. Ed. R. Gourdie. Microsc. Res. Tech. 31, 408-419.
Cotrina, et al. "Astrocytic gap junctions remain open during eschemic conditions." J. Neurosci., 18:2520-2537, 1998.
Courtman, et al. J Biomed Mater Res 28:655-666 (1994).
Coutinho, P., Frank, S., Qiu, C., Wang, C.M., Brown, T., Green, C.R. and Becker D.L. (2005) Limiting wound extension by transient inhibition of connexin43 expression at the site of injury. Brit. J. Plast. Surg. 58, 658-667.
Cronin M, Anderson PN, Green CR, Becker DL. Antisense delivery and protein knockdown within the intact central nervous system, Front Biosci 11: 2967-2975, 2006.
Crooke et al., J. Pharmacol. Exp. Ther. 277, 923-937, 1996.
Current Protocols in Immunology (J.E. Coligan et al., eds., 1991) vol. I, Ch. 1.
Current Protocols in Molecular Biology (F.M. Ausubel et al., 1987, including supplements through 2001).
Dagle et al., Nucleic Acids Research 19:1805 (1991).
Dahl G., et al., Biophys J 67:1816-1822 (1994).
Examiner's Fifth Report, CA 2,361,251 Dated Dec. 10, 2008.
Davis, et al. "Modulation of Connexin43 Expression: Effects on Cellular Coupling" Journal of Cardiovascular Electrophysiology, Futura Publishing Co., 6(2):103-114 (1995).
De Vriese A.S., et al. Kidney Int. 61:177-185 (2001).
Devereux, et al. Nucleic Acids Research 12:387-395 (1984).
Devlin, G., et al. J. "An ovine model of chronic stable heart failure" J. Card. Fail. 6:140-143 (2000).
DeVries, S.H. and E.A. Schwartz, "Hemi-gap-junction channels in solitary horizontal cells of the catfish retina," Journal of Physiology, 445:201-230 (1992).
Di, W.-L., Lachelin, G.C.L., McGarrigle, H.H.G., Thomas, N.S.B. and Becker, D.L. (2001) Oestriol and oestradiol increase cell to cell

(56) References Cited

OTHER PUBLICATIONS communication and connexin 43 protein expression in cultured human myometrial cells. Mol. Human Reprod. 7, 671-679.
Dias, N. and Stein, C.A. Mol. Cancer Thor. 1347-355 (2002).
Dietz, et al. Ophthalmology 93:1284 (1986).
Dovi, J.V., et al. J Leukoc Biol 73:448-55 (2003).
Sundstrom, Drug Discovery Today 10:993-1000 (2005).
Eckstein, F., ed. Oligonucleotides and Analogues, A Practical Approach, IRL Press at Oxford University Press (1991).
Edgington, Biotechnology 10:256 (1992).
Einarson, M.B. and Orlinich, J.R., "Identification of Protein-Protein Interactions with Glutathione S-Transferase Fusion Proteins," In Protein-Protein Interactions: A Molecular Cloning Manual, Cold Springs Harbor Laboratory Press, pp. 37-57 (2002).
Elbashir S., et al., "Duplexes of 21-nucleotide RNAs mediate RNA interference in cultured mammalian cells." Nature 411:494-498 (2001).
El-Hariri, et al. J. Pharm. Pharmacol. 44:651-654 (1992).
Englisch et al., Angewandte Chemie, International Edition, 30, 613-722 (1991).
Evans, J. Med. Chem. 30:1229 (1987).
Evans, W.H. and Boitano, S., Biochem. Soc. Trans. 29:606-612 (2001).
Fauchere, J. Adv. Drug Res. 15:29 (1986).
Ferrin and Camerini-Otero, Science 354:1494 (1991).
Flower NE, Green CR. A new type of gap junction in the phylum Brachiopoda. Cell Tissue Res. 1982;227(1):231-4.
Fonseca CG, Green CR, Nicholson LF. Upregulation in astrocytic connexin 43 gap junction levels may exacerbate generalized seizures in mesial temporal lobe epilepsy. Brain Res. Mar. 1, 2002; 929(1):105-16. PMID: 11852037 [PubMed—indexed for MEDLINE].
Foote, et al., J Cell Biol 140(5):1187-97 (1998).
Forge, A, Becker, D.L., Casalotti, S., Edwards, J., Evans, W.H., Lench, N. and Souter, M. (1999) Gap junctions and connexin expression in the inner ear. In gap junction-mediated intercellular signalling in health and disease. Novartis foundation symposium 219. 134-156. Wiley.
Forge, A., Becker, D.L., Casalotti, S., Edwards, J., Marziano, N. and Nevill, G. (2003) Distribution and connexin composition of gap junctions in the inner ear: Evidence for heteromeric Cx26/Cx30 connexons. J. Compo Neurol. 467, 207-231.
Forge, A., Becker, D.L., Casalotti, S., Edwards, J., Marziano, N. and Nickel, R. (2002) Connexins and gap junctions in the inner ear. Audiol. Neuro. Otol. 7,141-145.
Forge, A., Marziano, N., Casalotti, S.O., Becker, D.L. and Jagger, D. (2003). The inner ear contains heteromeric channels composed of Cx26 and Cx30 and deafness-related mutations in Cx26 have a dominant negative effect on Cx30. Cell Commun. Adhes. 10, 341-346.
Fortes, P. et al., Proc. Natl. Acad. Sci. USA 100, 8264-8269 (2003).
Foulkes MR, et al., Stroke 19:547-54 (1988).
Frantseva, M., et al. "Ischemia-Induced Brain Damage Depends on Specific Gap-Junctional Coupling." Journal of Cerebral Blood Flow and Metabolism, 22:453-462 (2002).
Fraser SE, Green CR, Bode HR, Gilula NB. Selective disruption of gap junctional communication interferes with a patterning process in hydra. Science. Jul. 3, 1987;237(4810):49-55. PMID: 3037697 [PubMed—indexed for MEDLINE].
Galasso, et. al. Seminars in Ophthalmology 19:75-77 (2004).
Garcia-Dorada et al., Circulation 96:3579-3586 (1997).
Gee et al., in Huber and Carr, 1994, "Molecular and Immunologic Approaches," Futura Publishing co, Mt. Kisco NY.
Gerrits, et al., Pediatr Res 57(3):342-6 (2005).
Giaume, C., et al. "Control of gap-junctional communication in astrocytic networks." TINS, 19:319-325, 1996.
Giepmans B., J. Biol. Chem., 276(11):8544-8549 (Mar. 16, 2001).
Gil, J., Esteban M., "Induction of apoptosis by the dsRNA-dependent protein kinase (PKR): Mechanisms of action." Apoptosis 2000, 5:107-114.
Goodenough D.A. J Cell Biol 107:1817-1824 (1988).

Görbe, A., Becker, D.L, Dux, L. and Krenács, T. (2005) In differentiating prefusion myoblasts connexin43 gap junction coupling is upregulated before myoblast alignment then reduced in postmitotic cells. Histochem Cell Biol 123:573-583 [Epub May 14, 2005].
Görbe, A., Becker, DL., Dux, L., Stelkovics, E., Krenács, L., Bagdi, E., and Krenács, T. (2005) Transient upregulation of connexin 43 gap junction coupling in myoblasts may synchronize cell cycle control preceding syncytial fusion during skeletal muscle differentiation Histochem. Cell Biol. 123; 573-583.
Gourdie RG, Green CR, Severs NJ, Anderson RH, Thompson RP. Evidence for a distinct gap-junctional phenotype in ventricular conduction tissues of the developing and mature avian heart. Circ Res. Feb. 1993;72(2):278-89. PMID: 8380357 [PubMed—indexed for MEDLINE].
Gourdie RG, Green CR, Severs NJ, Thompson RP. Immunolabelling patterns of gap junction connexins in the developing and mature rat heart. Anat Embryol (Berl). 1992;185(4):363-78. PMID: 1319120 [PubMed—indexed for MEDLINE].
Gourdie RG, Green CR, Severs NJ. Gap junction distribution in adult mammalian myocardium revealed by an anti-peptide antibody and laser scanning confocal microscopy. J Cell Sci. May 1991;99 (Pt 1):41-55. PMID: 1661743 [PubMed—indexed for MEDLINE].
Gourdie RG, Harfst E, Severs NJ, Green CR. Cardiac gap junctions in rat ventricle: localization using site-directed antibodies and laser scanning confocal microscopy. Cardioscience. Mar. 1990;1(1):75-82. PMID: 1966373 [PubMed—indexed for MEDLINE].
Gourdie, et al. "Immunolabeling patterns of gap junction connexins in the developing and mature rat heart." Anat Embryol 185:363-378 (1992).
Gourdie, et al. "The spatial distribution and relative abundance of gap-junctional connexin40 and connexin43 correlate to functional properties of components of the cardiac atrioventricular conduction system." Journal of Cell Science 105, 985-991 (1993).
Grazul-Bilska, et al. Abstract, Biology Reproduction, 58(1):78 (1998).
Green C.R, Law, L.Y., Lin, J.S. and Becker, D.L. (2001) "Spatiotemporal depletion of connexins using antisense oligonucleotides. Techniques in the study of gap junctions." Connexin methods and protocols 154 175-185. Eds R. Bruzzone and C. Giuame.
Green CR, Bowles L, Crawley A, Tickle C. Expression of the connexin43 gap junctional protein in tissues at the tip of the chick limb bud is related to the epithelial-mesenchymal interactions that mediate morphogenesis. Dev Biol. Jan. 1994;161(1):12-21. PMID: 8293868 [PubMed—indexed for MEDLINE].
Green CR, Harfst E, Gourdie RG, Severs NJ. Analysis of the rat liver gap junction protein: clarification of anomalies in its molecular size. Proc R Soc Lond B Biol Sci. Mar. 22, 1988;233(1271):165-74. PMID: 2898146 [PubMed—indexed for MEDLINE].
Green CR, Peters NS, Gourdie RG, Rothery S, Severs NJ. Validation of immunohistochemical quantification in confocal scanning laser microscopy: a comparative assessment of gap junction size with confocal and ultrastructural techniques. J Histochem Cytochem. Sep. 1993;41 (9):1339-49. PMID: 8354875 [PubMed—indexed for MEDLINE].
Green CR, Severs NJ. Connexon rearrangement in cardiac gap junctions: evidence for cytoskeletal control? Cell Tissue Res. 1984;237(1):185-6. PMID: 6090023 [PubMed—indexed for MEDLINE].
Green CR, Severs NJ. Gap junction connexon configuration in rapidly frozen myocardium and isolated intercalated disks. J Cell Biol. Aug. 1984;99(2):453-63.
Green CR, Severs NJ. Robert Feulgen Prize Lecture. Distribution and role of gap junctions in normal myocardium and human ischaemic heart disease. Histochemistry. Feb. 1993;99(2):105-20. Review.
Green CR. Evidence mounts for the role of gap junctions during development. Bioessays. Jan. 1988;8(1):7-10. Review. No abstract available. PMID: 2835035 [PubMed—indexed for MEDLINE].
Green, C., et al. "Spatiotemporal depletion of connexins using antisense oligonucleotides." Methods in Molecular Biology, 154:175-185 (2001).
Guan, et al., Neuroscience 95(3):831-839 (1999).
Gunn, et al., J Clin Invest 99(2):248-256 (1997).

(56) References Cited

OTHER PUBLICATIONS

Gunn, et al., Pediatr Res 46(3):274-280 (1999).
Hall, Celia. "Gel is helping wounds heal in half the time." Telegraph UK. Oct. 20, 2003. http://www.telegraph.co.uk/news/main.jhtmil?xml=/news/2003/10/20/nge120.xml&sSheet= . . . .
Hardman, et al. McGraw-Hill, New York, N.Y., 934-935 (1996).
Hardy, K., Spanos, S. and Becker, D.L. (2003) Cell death (Apoptosis) in human blastocysts. Chpt. 9 p. 185-202 An Atlas of Human Blastocysts. Eds. L.L. Veeck and N. Zaninovic. CRC Press.
Hardy, K., Warner, A.E., Winston, R.M.L. and Becker, D.L. (1996) Expression of intercellular junctions during the preimplantation development of the human embryo. Molec. Human Reprod. 2, 621-632.
Harfst E, Severs NJ, Green CR. Cardiac myocyte gap junctions: evidence for a major connexon protein with an apparent relative molecular mass of 70,000. J Cell Sci. Aug. 1990;96 (Pt 4):591-604.
Harlow and Lane (1988) Antibodies, A Laboratory Manual, Cold Spring Harbor Publications, New York.
Haseloff and Gerlach, Nature Aug. 18;334(6183):585-91 (1988).
Heasman, J., Dev. Biol., 243, 209-214 (2002).
Henikoff and Henikoff Proc. Natl. Acad. Sci. USA 89:10915-10919 (1992).
Hennemann, H., et al. Eur. J. Cell Biol. 58(1):81-9, 1992.
Ho, et. al., Journal of Neurosurgical Anesthesiology 17:38-44 (2005).
Hodgins, M. "Connecting Wounds with Connexins" J. Invest. Dermatol. 122:(5):ix-x commentary (2004).
Huang, et al. J Cell Biol 143:1725-34 (1998).
J. Goliger, et al., Molecular Biology of the Cell. 6:1491-1501 (1995).
Janes, Andrew. "Speed healing." Dec. 1, 2004. Issue 67. Unlimited. Sep. 29, 2006 http://unlimited.co.nz/unlimited.nsf/ulfuture/250EA628CE599A70CC256F6B00046325.
Jen, et al., Stem Cells 18:307-319 (2000).
Jester, et al., Cornea 11:191 (1992).
Kabanov et al., FEBS Lett. 259, 327 330 (1990).
Kandel ER, Schwartz JH, Jessell TM. Principles of Neural Science, 4th ed., pp. 178-180. McGraw-Hill, New York (2000).
Karlin and Altschul Proc. Natl. Acad. Sci. USA 90:5873-5787 (1993).
Keirstead, H.S., et al. Exp. Neurol. 159:225-236 (1999).
Khosla, et. al., Journal of Postgraduate Medicine 50:219-221 (2004).
Kieber-Emmons T, et al., Curr Opin Biotechnol. Aug;8(4):435-41 (1997).
Kurpakus-Wheater, et al. Biotech. Histochem. 74:146-59 (1999).
Lampugnani, M.G., "Cell Migration into a wounded area in vitro" Methods Mol Biol 96:177-182, 1999.
Laux-Fenton WT, Donaldson PJ, Kistler J, Green CR. Connexin expression patterns in the rat cornea: molecular evidence for communication compartments. Cornea. Jul. 2003;22(5):457-64. PMID: 12827052 [PubMed—indexed for MEDLINE].
Law, L.-Y., Lin, J.S, Becker, D.L. and Green, C.R. (2002) Knockdown of Connexin 43 mediated regulation of ZPA activity in the developing chick limb bud leads to digit truncation. Dev. Growth Differ. 44, 537-547.
Lee et al. Critical Reviews in Therapeutic Drug Carrier Systems 8:91-192 (1991).
Letsinger et al., Proc. Natl. Acad. Sci. USA 86, 6553-6556 (1989).
Leybeart et. al., Cell Commun Adhes 10:251-257 (2003).
Li, et al. Dev. 129:2031-42 (2002).
Li, H., et al., "properties and regulation of gap junctional hemichannels in the plasma membranes of cultured cells," Journal of Cell Biology 134(4):1019-1030 (1996).
Lin, J.H. et al.,"Gap-Junction-mediated propogation and amplification of cell injury." Nature Neurosci. 1:431-432 (1998).
Makarenkova, H., Becker, D.L., Tickle, C. and Warner, A.E. (1997) Fibroblast growth factor 4 directs gap junction expression in the mesenchyme of the vertebrate limb bud. J. Cell Biol. 138, 1-13.
Malone, et al. J Vasc Surg 1:181-91 (1984).
Manoharan et al. Nucleosides & Nucleotides 14, (3-5) 969-973 (1995).
Manoharan et al., Bioorg (1992). Med. Chem. Let. 3(12), 2765-2770 (1993).
Manoharan et al., Bioorg. Med. Chem. Lett. 4, 1053-1060 (1994).
Manoharan et al., Tetrahedron Lett. 36(21), 3651-3654 (1995).
Martin et al., Helv. Chim. Acta 1995, 78, 486-504.
Martin, P. Science 276:75-81 (1997).
Martin, P., et al. Curr Biol 13:1122-8 (2003).
Marziano, N., Casalotti, S.O., Portelli A.E., Becker, D.L. and Forge, A. (2003) Deafness-related mutations in gap junction protein connexin 26 have a dominant negative effect on connexin 30. Human Molecular Genetics 203, 805-812.
McDonald, et al. Scientific American. 55-63 (Sep. 1999).
McDonnel and Schanzlin, Arch. Ophthalmol. 106:212 (1988).
McGonnell, I., Green, C.R., Tickle, C. and Becker, D.L. (2001) Communication through connexin 43 gap junction channels contributes to the normal development of the embryonic face. Dev. Dynam. 222, 420-438.
Medical Futures—Innovation Awards. May 26, 2006 http://www.medicalfutures.co.uk/runner.php?txtWin=1.
Meienhofer in "Hormonal Proteins and Peptides," ed.; C.H. Li, vol. 2 (Academic Press, 1973) pp. 48-267.
Melton, D.A. Antisense RNA and DNA, Ed., Cold Spring Harbor Laboratory, Cold Spring Harbor, NY (1988).
Merrifield, J. Am. Chem. Soc. 85 2149 (1963).
Methods of Immunological Analysis (R. Masseyeff, W.H. Albert, and N.A. Staines, eds., Weinheim: VCH Verlags gesellschaft mbH, 1993) vol. I, Ch. 1, 2, 3, 4, vol. III, Ch. 4.
Meyer R.A., J Cell Biol. 119:179-189 (1992).
Miller, J.M., & Calos, M.P., eds. 1987) Gene Transfer Vectors for Mammalian Cells, Introduction.
Mishra et al., Biochim. Biophys. Acta 1264, 229-237 (1995).
Molecular cloning: A Laboratory Manual, 3rd Edition Chapter 10 (Sambrook and Russel, 2001).
Moore, et al., Am. J. Physiology. 267(5):C1371-C1388 (Nov. 1, 1994).
Mori, R., et al. "Impairment of skin wound healing in beta-1,4-galactosyltransferase-deficient mice with reduced leukocyte recruitment." Am J. Pathol. 164:1303-14, 2004.
Morrissey, et al. J. Neuroscience 11:2433-2442 (1991).
Muranishi. Critical Reviews in Therapeutic Drug Carrier Systems. 7:1-33 (1990).
Mustoe, T.A., et al. Science 237, 1333-6 (1987).
Nadarajah, B., Makarenkova, H., Becker, D.L., Evans, W.H. and Pamavelas, J.G. (1998) Basic FGF increases communication between cells of the developing neocortex. J. Neurosci. 18, 7881-7890.
Neckers, et al. "Anti-sense technology: biological utility and practical considerations." Am. J. Physiol. 265 (lung cell mol physiol), L1-L12, 1993.
News bio-active gel cuts wound healing time in half. Oct. 20, 2003. UCL Media Relations. University College London. Sep. 29, 2006 http://www.ucl.ac.uk/media/library/nexagon0.
Nice blurb on biologics on cbsnews.com. Laxat. Sep. 9, 2006 http://www.laxat.com/Nice-blurb-on-biologics-on-cbsnews-com-1219610.html.
Nickel, R., Becker, D.L. and Forge, A. Molecular and functional characterization of gap junctions in the avian inner ear. J. Neurosci. Jun. 7, 2006;26(23):6190-9.
Nielsen et al., Science 254:1497 (1991).
Oberhauser et al., Nucl. Acids Res. 20, 533-538 (1992).
Oligonucleotide Synthesis Chapter 1 (M.J. Gait, ed., 1984).
Oviedo-Orta E., et. al. "Gap Junctions and Connexin-Mediated Communication in the Immune System." Biochimica et Biophysica Acta. Biomembranes, Amsterdam, NL vol. 1662, No. 1-2, 23, Mar. 2004, pp. 102-112.
Paddison, P., Caudy A., Bernstein, E., Hannon, G., Conklin, D., "Short hairpin RNAs (shRNAs) induce sequence-specific silencing in mammalian cells." Genes & Dev 16:948-958 (2002).
Paddison, P., Caudy A., Hannon G., "Stable suppression of gene expression by RNAi in mammalian cells." Proc Natl Acad Sci USA 99:1443-1448 (2002).
Parker, J.D., et al. Nucleic Acids Res 19:3055-60 (1991).

(56) References Cited

OTHER PUBLICATIONS

PCR: The Polymerase Chain Reaction Chapter 1-19 (Mullis et al., eds., 1994).
Pearson, R., Lüneborg N., Becker D.L. and Mobbs P. (2005) Gap junctions modulate interkinetic nuclear migration in retinal progenitor cells. J. Neurosci. 25, 10803-10814.
Penn, et. al., Autoimmunity Reviews 2:199-203 (2003).
Pepose, J.S., et al. "The cornea; Adler's Physiology of the eye: Clinical application," 9th Ed. St. Louis: Mosby Year Book, 1992, 29-47.
Peters NS, Green CR, Poole-Wilson PA, Severs NJ. Cardiac arrhythmogenesis and the gap junction. J Mol Cell Cardiol. Jan. 1995;27(1):37-44. Review. No abstract available. PMID: 7760358 [PubMed—indexed for MEDLINE].
Peters NS, Green CR, Poole-Wilson PA, Severs NJ. Reduced content of connexin43 gap junctions in ventricular myocardium from hypertrophied and ischemic human hearts. Circulation. Sep. 1993;88(3):864-75. PMID: 8394786 [PubMed—indexed for MEDLINE].
Peters NS, Rowland E, Bennett JG, Green CR, Anderson RH, Severs NJ. The Wolff-Parkinson-White syndrome: the cellular substrate for conduction in the accessory atrioventricular pathway. Eur Heart J. Jul. 1994;15(7):981-7. PMID: 7925521 [PubMed—indexed for MEDLINE].
Peters NS, Severs NJ, Rothery SM, Lincoln C, Yacoub MH, Green CR. Spatiotemporal relation between gap junctions and fascia adherens junctions during postnatal development of human ventricular myocardium. Circulation. Aug. 1994;90(2):713-25. PMID: 8044940 [PubMed—indexed for MEDLINE].
Peters, T., et al. EMBO J. 24:3400-10 (2005).
Postlethwaite, A.E., et al. J Exp Med 165:251-6, 1987.
Qiu, C., Coutinho, P., Frank, S., Franke, S., L-Y. Law, Martin, P., Green, C.R. and Becker D.L. (2003) Accelerated rate of wound repair by targeting connexin 43 expression. Current Biology 13, 1697-1703.
Qui, et al., "Targeting connexin43 expression accelerates the rate of wound repair." Current Biology 13:1967-1703 (2003).
R. Ruch, et al. Molecular Carcinogenesis, 14:269-274, 1995.
Ramdas et al., J. Biol. Chem. 264:17395 (1989).
Ramer, et al. Spinal Cord. 38:449-472 (2000).
Ramezani A., et al., Frontiers in Bioscience 7:a,29-36 (2002).
Ratkay-Traub, I., Hopp, B., Bor, Zs., Dux, L., Becker, D.L. and Krenács, T. (2001) Regeneration of rabbit cornea following excimer laser photorefractive keratectomy: a study on gap junctions, epithelial junctions and epidermal growth factor receptor expression in correlation with cell proliferation. Exp. Eye Res. 73, 291-302.
Reddy, K., et al., Pediatric Research 43(5):674-682 (1998).
Rennick RE, Connat JL, Burnstock G, Rothery S, Severs NJ, Green CR. Expression of connexin43 gap junctions between cultured vascular smooth muscle cells is dependent upon phenotype. Cell Tissue Res. Feb. 1993;271(2):323-32. PMID: 8384084 [PubMed—indexed for MEDLINE].
Reynolds, et al. Nat. Med. 11:167-74 (2005).
Rigas et al., Proc. Natl. Acad. Sci U.S.A. 83:9591 (1986).
Rininslund et al., Proc. Natl. Acad. Sci. USA 94:5854 (1997).
Robbins, S. and Cotran, R. 1979 Pathologic basis of disease. 2nd edition. Chapters 1-3 WB Saunders Co., Philadelphia.
Roberts, et al. Proc Natl Acad Sci USA 83:4167-71 (1986).
Roberts, R., Iatropoulou, A., Ciantar, D., Stark, J., Becker, D.L., Franks, S. and Hardy, K. (2005) Follicle-stimulating hormone affects metaphase I chromosome alignment and increases aneuploidy in mouse oocytes matured in vitro. Biol. Reprod. 72, 107-118.
Roelfsema, et .al., J Cereb Blood Flow Metab 24(8):877-886 (2004).
Rosendaal M, Green CR, Rahman A, Morgan D. Up-regulation of the connexin43+ gap junction network in haemopoietic tissue before the growth of stem cells. J Cell Sci. Jan. 1994; 107 (Pt 1):29-37.
Rozenthal, et al. "Stable Transfection With Connexin43 Inhibits Neuronal Differentiation of PC12 Cells" Society for Neuroscience Abstracts, Society for Neuroscience 23(1-3), Oct. 25, 1997, p. 22.
Rutherford, R.B., Vascular Surgery, 3rd Ed. (W.B. Saunders Co. 1989).
Sabiston, D., The Textbook of Surgery, 14th Ed. Chapter 56 (W.B. Saunders Co. 1991).
Saison-Behmoaras et al. EMBO J. 10, 1111-11118 (1991).
Saitongdee, P., Becker, D.L., Milner, P., Knight, G.E., and Burnstock, G. (2004) Levels of gap junction proteins in coronary arterioles and aorta of hamsters exposed to cold and during hibernation and arousal. J. Histochem Cytochem 52), 603-615.
Saitongdee, P., Milner, P., Becker, D.L., Knight, G.E., and Burnstock, G. (2000) Increased connexin43 gap unction protein in hamster cardiomyocytes during cold acclimatization and hibernation . . . Cardiovascular Res. 47, 108-115.
Sambrook, et al. Molecular Cloning: Chapter 11-12 A Laboratory Manual (1989).
Sanghvi, Y.S., Chapter 15, Antisense Research and Applications, pp. 276-278 Crooke, S.T. and Lebleu, B., ed., CRC Press (1993).
Santoro, S.W. and Joyce, G.F. "A General Purpose RNA-Cleaving DNA Enzyme." Proc. Natl. Acad. Sci. USA 94, 4262-4266 (1997).
Santoro, S.W. and Joyce, G.F. Biochem. 37:13330-13342 (1998).
Scatchard et al., Ann. N.Y. Acad. Sci. 51(4):660 (1949).
Scherer, L.J. and Rossi, J.J. Nature Biotechnol. 21(12):1457-1465 (2003).
Schmidt, C.E., et al. Ann. Rev. Biomed. Eng. 5:293-347 (2003).
Schubert, S. et al., Nucleic Acids Res. 31, 5982-5992 (2003).
Schuck, P., "Reliable determination of binding affinity and kinetics using surface plasmon resonance biosensor," Current Opinion in Biotechnology, 8(4):498-502 (1997).
Marx, Jean. "Interfering with Gene Expression." Science 288:1370-1372 (2000).
Severs NJ, Gourdie RG, Harfst E, Peters NS, Green CR. Intercellular junctions and the application of microscopical techniques: the cardiac gap junction as a case model. J Microsc. Mar. 1993;169 (Pt 3):299-328. Review. PMID: 8478912 [PubMed—indexed for MEDLINE].
Severs NJ, Shovel KS, Slade AM, Powell T, Twist VW, Green CR. Fate of gap junctions in isolated adult mammalian cardiomyocytes. Circ Res. Jul. 1989;65(1):22-42. PMID: 2736737 [PubMed—indexed for MEDLINE].
Severs NJ, Slade AM, Powell T, Twist VW, Green CR. Integrity of the dissociated adult cardiac myocyte: gap junction tearing and the mechanism of plasma membrane resealing. J Muscle Res Cell Motil. Apr. 1990;11(2):154-66. PMID: 2351753 [PubMed—indexed for MEDLINE].
Shah, et al. Am. J. Pathol. 154:1115-24 (1999).
Shea et al., Nucl. Acids Res. 18, 3777-3783 (1990).
Simons, et al. "Anti-sense c-myb oligonucleotides inhibit intimal arterial smooth muscle cell accumulation in vivo." Nature 359:67-70, 1992.
Smith JH, Green CR, Peters NS, Rothery S, Severs NJ. Altered patterns of gap junction distribution in ischemic heart disease. An immunohistochemical study of human myocardium using laser scanning confocal microscopy. Am J Pathol. Oct. 1991;139(4):801-21. PMID: 1656760 [PubMed—indexed for MEDLINE].
Spanos, S., Rice, S., Karagiannis, P., Taylor, D., Becker, D.L., Winston, R.M.L. and Hardy, K. (2002) Caspase activity and expression of cell death genes during human preimplantation embryo development. J. Reprod. 124, 353-363.
Spencer, W.H., "The cornea: Ophthalmic Patholgy: an atlas and textbook" 4th Ed. Philadelphia: W.B. Saunders Co., 1996, 157-165.
Stein C.A. and Krieg A.M. (eds), Chapters 7, 10, 22. Applied Antisense Oligonucleotide Technology, 1998 (Wiley-Liss).
Stein, C.A.. "Anti-sense oligodeoxynucleotides—promises and pitfalls." Leukemia 6:967-974, 1992.
Stewart, et al., "Solid Phase Peptide Synthesis," Chapter 2 Part B, Chapter 3. W.H. Freeman Co., San Francisco (1969).
Stilinovic A., Green, C.R., Klette R., Franke S., Klette G and Becker D.L. (2004) Texture analysis of collagen fibers in scar tissue. In Proc. Image Vision Computing New Zealand Nov. 21, pp. 185-190.
Strobel et al., Science 254:1639 (1991).
Sui., G., et al., Proc Natl Acad Sci 99(8):5515-5520 (2002).
Svinarchuk et al., Biochimie 75, 49-54 (1993).
Takahashi, et al. J. Pharm. Pharmacol. 40:252-257 (1998).

(56) References Cited

OTHER PUBLICATIONS

Tan, et al., Ann Neurol 32(5):677-682 (1992).
Tanaka, T., et al. Jpn. J. Ophthalmol. 43:348-54 (1999).
Tarnow, et al. Scand J. Plast Reconstr Hand Surg. 28:255-259 (1994).
The Immunoassay Handbook (D. Wild, ed., Stockton Press NY 1994).
Topol, E.J. (ed.) The Textbook of Interventional Cardiology, 2nd Ed. (W.B. Saunders Co. 1994).
Uhlmann, et al., Chem. Reviews 90:543-584 (1990).
Veber and Freidinger, TINS, 392 (1985).
Vikis, H.G. And Guan, K.L. Glutathione-S-Transferase-Fusion Based Assays for Studying Protein-Protein Interactions in Protein-Protein Interactions, Methods and Applications, Methods in Molecular Biology, 261, Fu, H.Ed. Humana Press, Totowa, N.J., pp. 175-186 (2004).
Vis JC, Nicholson LF, Faull RL, Evans WH, Severs NJ, Green CR. Connexin expression in Huntington's diseased human brain. Cell Biol Int. Nov. 1998;22(11-12):837-47. PMID: 10873295 [PubMed—indexed for MEDLINE].
Waggett A.D., et al. Connexin 32 and 43 gap junctions differentially modulate tenocyte esonse to cyclic mechanical load. Eur. J. Cell. Biol. 085:1145-1154 (2006).
Wagner, R.W., et al. "Gene inhibition using anti-sense oligodeoxynucleotides." Nature 372:333-335 (1994).
Walker, et al. Dev biol 284:479-98 (2005).
Waring, et al., Amer. J. Ophthalmol. 111:133 (1991).
Welcome to the lab of David Becker and Jeremy Cook. Becker/Cook Lab. May 26, 2006 http://www.anat.ucl.ac.uk/research/becker/people.htm.
Wier, D.M. & C.C. Blackwell, eds. Handbook of Experimental Immunology, 1986.
Willecke Klaus, et al., "Structural and functional diversity of connexin genes in the mouse and human genome." Biological Chemistry 383(5) May 2002.
Willecke, K., et al. Biol. Chem., 383:725-37 (2002).
Wilson, et al. "Accellular Matrix" Trans Am Soc Artif Intern 36:340-343 (1990).
Wound-healing technology shortlisted for award. UCL News. University College London. Sep. 27, 2006 http://www.ucl.ac.uk/news-archive/archive/2003/october-2003/latest/newsitem.shtml?0309 . . . .
Wright, C.S., Becker, D.L., Lin, S.J., Warner, A.E. and Hardy, K. (2001) Stage-specific and differential expression of gap junctions in the mouse ovary: connexin-specific roles in follicular regulation. J. Reprod. Fert. 121, 77-88.
Wyngaarden J.B., et al. (eds.), The Cecil Textbook of Medicine, 19th Ed. (W.B. Saunders, 1992).
Xu, X.M., et al. J. Comp. Neurol. 351:145-160 (1995).
Xu, X.M., et al. J. Neuroscience. 11:1723-1740 (1999).
Yamashita, et al. J. Pharm. Pharmacol. 39:621-626 (1987).
Yang, Lihu, et al. Proc. Natl. Acad. Sci. 1;95(18):10836-10841 (Sep. 1, 1998).
Yick, L.W., et al. Exp. Neurol. 159:131-138 (1999).
Zhang, X., Oglesbee, M., "Use of surface plasmon resonance for the measurement of low affinity binding interactions between HSP72 and measles virus nucleocapsid protein." Biological Procedures Onlin 5(1):170-181 (2003).
Zimmer DB, Green CR, Evans WH, Gilula NB. Topological analysis of the major protein in isolated intact rat liver gap junctions and gap junction-derived single membrane structures. J Biol Chem. Jun. 5, 1987;262(16):7751-63. PMID: 3034905 [PubMed—indexed for MEDLINE].
Zlotnik, A., et al. Annu rev Immunol 18:217-42 (2000).
Zon, G., Ann. N.Y. Acad. Sci., 616, 161-172 (1990).
Coutinho, et al. "Dynamic Changes in connexin expression correlate with key events in the wound healing process." Cell Biology International 27 (2003) 525-541.
Non Final Office Action, U.S. Appl. No. 09/890,363, Mail Date Jan. 6, 2004, United States Patent Office.
Non Final Office Action, U.S. Appl. No. 09/890,363, Mail Date Dec. 2, 2004, United States Patent Office.
Non Final Office Action, U.S. Appl. No. 11/510,280, Mail Date Feb. 8, 2008, United States Patent Office.
Non Final Office Action, U.S. Appl. No. 11/512,728, Mail Date Mar. 17, 2008, United States Patent Office.
Final Office Action, U.S. Appl. No. 11/510,280, Mail Date Dec. 11, 2008, United States Patent Office.
Non Final Office Action, U.S. Appl. No. 11/447,599, Mail Date Dec. 24, 2008, United States Patent Office.
Non Final Office Action, U.S. Appl. No. 12/001,498, Mail Date Apr. 22, 2009, United States Patent Office.
Final Office Action, U.S. Appl. No. 11/510,496, Mail Date Sep. 18, 2009, United States Patent Office.
Non Final Office Action, U.S. Appl. No. 11/512,735, Mail Date Feb. 4, 2010, United States Patent Office.
Non Final Office Action, U.S. Appl. No. 12/001,498, Mail Date Apr. 1, 2010, United States Patent Office.
Non Final Office Action, U.S. Appl. No. 11/510,496, Mail Date Apr. 12, 2010, United States Patent Office.
Final Office Action, U.S. Appl. No. 10/581,813, Mail Date May 21, 2010, United States Patent Office.
Final Office Action, U.S. Appl. No. 12/001,498, Mail Date Dec. 17, 2010, United States Patent Office.
Non Final Office Action, U.S. Appl. No. 12/809,974, Mail Date Feb. 4, 2011, United States Patent Office.
Non Final Office Action, U.S. Appl. No. 12/592,668, Mail Date Feb. 10, 2011, United States Patent Office.
Non Final Office Action, U.S. Appl. No. 12/809,886, Mail Date Apr. 28, 2011, United States Patent Office.
Non Final Office Action, U.S. Appl. No. 12/592,668, Mail Date May 26, 2011, United States Patent Office.
Non Final Office Action, U.S. Appl. No. 11/447,599, Mail Date May 27, 2011, United States Patent Office.
Non Final Office Action, U.S. Appl. No. 12/812,017, Mail Date May 31, 20.11, United States Patent Office.
Non Final Office Action, U.S. Appl. No. 12/812,017, Mail Date Sep. 23, 2011, United States Patent Office.
Non Final Office Action, U.S. Appl. No. 12/809,933, Mail Date Oct. 13, 2011, United States Patent Office.
Final Office Action, U.S. Appl. No. 12/809,974, Mail Date Dec. 9, 2011, United States Patent Office.
Non Final Office Action, U.S. Appl. No. 12/809,933, Mail Date Dec. 23, 2011, United States Patent Office.
Non Final Office Action, U.S. Appl. No. 12/809,989, Mail Date Jan. 4, 2012, United States Patent Office.
Final Office Action, U.S. Appl. No. 11/447,599, Mail Date Jan. 5, 2012, United States Patent Office.
Final Office Action, U.S. Appl. No. 12/592,668, Mail Date Jan. 5, 2012, United States Patent Office.
Final Office Action, U.S. Appl. No. 12/809,886, Mail Date Feb. 3, 2012, United States Patent Office.
Final Office Action, U.S. Appl. No. 12/812,017, Mail Date Apr. 25, 2012, United States Patent Office.
Non Final Office Action, U.S. Appl. No. 12/747,863, Mail Date Apr. 30, 2012, United States Patent Office.
Examiner's Report, Australian Application No. 21193/00, Mail Date May 2, 2003, Australian Patent Office.
Examiner's Report, Australian Application No. 21193/00, Mail Date May 25, 2004, Australian Patent Office.
Examiner's Report, Australian Application No. 2011200868, Mail Date Sep. 20, 2011, Australian Patent Office.
Examiner's Report, Australian Application No. 2011200924, Mail Date Nov. 11, 2011, Australian Patent Office.
Examiner's Report, Chinese Application No. 200680010590.X, Mail Date Jun. 27, 2011, Chinese Patent Office.
Examiner's Report, Chinese Application No. 200880126536.0, Mail Date Jul. 22, 2011, Chinese Patent Office.
Examiner's Report, Chinese Application No. 200780051207.X, Mail Date Nov. 10, 2011, Chinese Patent Office.
Examiner's Report, Chinese Application No. 200880126536.0, Mail Date Mar. 31, 2012, Chinese Patent Office.
Examiner's Report, Eurasian Application No. 201100953/26, Mail Date Dec. 21, 2011, Eurasian Patent Office.

(56) References Cited

OTHER PUBLICATIONS

Communication pursuant to Article 96(2) EPC, European Application No. 00901236.0, Mail Date Dec. 8, 2003, European Patent Office.
Communication, European Application No. 05016736.0, Mail Date Dec. 19, 2005, European Patent Office.
Communication pursuant to Article 94(3) EPC, European Application No. 05016736.0, Mail Date Jan. 25, 2008, European Patent Office.
Communication pursuant to Article 94(3) EPC, European Application No. 04817632.5, Mail Date Nov. 28, 2008, European Patent Office.
Communication pursuant to Rules 161 and 162 EPC, European Application No. 07853353.2107, Mail Date Jul. 27, 2009, European Patent Office.
Communication pursuant to Article 94(3) EPC, European Application No. 04817632.5-1212, Mail Date May 3, 2010, European Patent Office.
Communication pursuant to Article 94(3) EPC, European Application No. 06795121.0, Mail Date Jun. 6, 2010, European Patent Office.
Communication pursuant to Rules 161(1) and 162 EPC, European Application No. 08860470.7-2406, Mail Date Jul. 28, 2010, European Patent Office.
Communication pursuant to Rules 161(1) and 162 EPC, European Application No. 08859398.3-2405, Mail Date Jul. 28, 2010, European Patent Office.
Communication pursuant to Rules 161(1) and 162 EPC, European Application No. 08867503.8, Mail Date Aug. 9, 2010, European Patent Office.
Communication pursuant to Rules 161(1) and 162 EPC, European Application No. 08866327.3-2107, Mail Date Aug. 12, 2010, European Patent Office.
Communication pursuant to Rules 161(1) and 162 EPC, European Application No. 08867884.2-2107, Mail Date Aug. 12, 2010, European Patent Office.
Communication pursuant to Rules 161(1) and 162 EPC, European Application No. 08868841.1-2107, Mail Date Aug. 12, 2010, European Patent Office.
Communication pursuant to Rules 161(1) and 162 EPC, European Application No. 08866069.1-2107, Mail Date Aug. 23, 2010, European Patent Office.
Communication pursuant to Article 94(3) EPC, European Application No. 07853353.6-2107, Mail Date Aug. 20, 2010, European Patent Office.
Communication pursuant to Rules 161(1) and 162 EPC, European Application No. 08868457.6-2107, Mail Date Aug. 23, 2010, European Patent Office.
Communication pursuant to Rules 161(1) and 162 EPC, European Application No. 08868684.5-2107, Mail Date Aug. 23, 2010, European Patent Office.
Communication pursuant to Rules 161(1) and 162 EPC, European Application No. 09705465.4-2403, Mail Date Nov. 18, 2010, European Patent Office.
Communication pursuant to Article 94(3) EPC, European Application No. 06795121.0-2107, Mail Date Jan. 17, 2012, European Patent Office.
Communication pursuant to Article 94(3) EPC, European Application No. 08860470.7-2406, Mail Date Jan. 19, 2011, European Patent Office.
Communication pursuant to Rules 161(1) and 162 EPC, European Application No. 09758776.0-2107, Mail Date Feb. 2, 2011, European Patent Office.
Communication, European Application No. 10013180.4-2107, Mail Date Mar. 23, 2011, European Patent Office.
Communication pursuant to Article 94(3) EPC, European Application No. 04817632.5-1212, European Patent Office, Dec. 20, 2011.
First Examination Report, Indian Application No. 1827/KOLNP/2006, Mail Date Nov. 5, 2009, Indian Patent Office.
Hearing Notice, Indian Application No. 1827/KOLNP/2006, Mail Date Dec. 12, 2011, Indian Patent Office.
First Examination Report, Indian Application No. 3287/KOLNP/2006, Mail Date Dec. 29, 2011, Indian Patent Office.
Examiner's Report, Israeli Application No. 176067, Mail Date May 17, 2009, Israeli Patent Office.
Examiner's Report, Israeli Application No. 176067, Mail Date Jun. 17, 2010, Israeli Patent Office.
Examiner's Report, Japanese Application No. 2000-595711, Mail Date Aug. 31, 2010, Japanese Patent Office.
Examiner's Report, Japanese Application No. 2006-542058, Mail Date Apr. 20, 2012, Japanese Patent Office.
Examination Report, New Zealand Application No. 513154, Mail Date May 23, 2002, New Zealand Patent Office.
Examination Report, New Zealand Application No. 548204, Mail Date Jan. 30, 2008, New Zealand Patent Office.
Examination Report, New Zealand Application No. 561098, Mail Date Mar. 17, 2009, New Zealand Patent Office.
Examination Report, New Zealand Application No. 578734, Mail Date Aug. 5, 2009, New Zealand Patent Office.
Examination Report, New Zealand Application No. 577673, Mail Date Jul. 20, 2010, New Zealand Patent Office.
Examination Report, New Zealand Application No. 588010, Mail Date Sep. 17, 2010, New Zealand Patent Office.
Examination Report, New Zealand Application No. 590937, Mail Date Feb. 10, 2011, New Zealand Patent Office.
Examination Report, New Zealand Application No. 597736, Mail Date Jan. 24, 2012, New Zealand Patent Office.
Examination Report, New Zealand Application No. 597900, Mail Date Feb. 7, 2012, New Zealand Patent Office.
Examination Report, New Zealand Application No. 598866, Mail Date Mar. 19, 2012, New Zealand Patent Office.
Official Action, Russian Application No. 2009126594, Mail Date Mar. 14, 2012, Russian Patent Office.
Notification, Russian Application No. 2009126594, Mail Date Nov. 11, 2011, Russian Patent Office.
Official Action, Russian Application No. 2009122370, Mail Date Mar. 16, 2012, Russian Patent Office.
Invitation to Respond to Written Opinion, Singaporean Application No. 200705664-1, Mail Date May 27, 2009, Singaporean Patent Office.
International Preliminary Examination Report, PCT Application No. PCT/GB00/00238, Mail Date Apr. 4, 2011, World Intellectual Property Office.
International Search Report, PCT Application No. PCT/GB00/00238, Mail Date Jun. 19, 2000, World Intellectual Property Office.
International Search Report, PCT Application No. PCT/US09/003408, Mail Date, Nov. 23, 2009, World Intellectual Property Office.
International Search Report, PCT Application No. PCT/US09/00129, Mail Date Nov. 13, 2009, World Intellectual Property Office.
Singaporean Search Report, Singaporean Application No. 200603748-5, Mail Date Dec. 8, 2011, Danish Patent & Trademark Office.
Written Opinion of the International Searching Authority, PCT Application No. PCT/US08/013655, Mail Date Jul. 31, 2007, World Intellectual Property Office.
Written Opinion of the International Searching Authority, PCT Application No. PCT/US09/003408, Mail Date Dec. 4, 2010, World Intellectual Property Office.
Written Opinion of the International Searching Authority, PCT Application No. PCT/US08/014023, Mail Date Jun. 21, 2010, World Intellectual Property Office.
Written Opinion of the International Searching Authority, PCT Application No. PCT/US09/000129, Mail Date Jul. 7, 2010, World Intellectual Property Office.
Written Opinion of the International Searching Authority, PCT Application No. PCT/US08/014019, Mail Date Jun. 21, 2010, World Intellectual Property Office.
Written Opinion of the International Searching Authority, PCT Application No. PCT/US08/014024, Mail Date Jun. 21, 2010, World Intellectual Property Office.
Written Opinion of the International Searching Authority, PCT Application No. PCT/US08/014022, Mail Date Jun. 21, 2010, World Intellectual Property Office.

(56) References Cited

OTHER PUBLICATIONS

Written Opinion of the International Searching Authority, PCT Application No. PCT/US08/014020, Mail Date Jun. 21, 2010, World Intellectual Property Office.
Written Opinion of the International Searching Authority, PCT Application No. PCT/US08/014026, Mail Date Jun. 21, 2010, World Intellectual Property Office.
Written Opinion of the International Searching Authority, PCT Application No. PCT/US08/014021, Mail Date Jun. 21, 2010, World Intellectual Property Office.
Written Opinion of the International Searching Authority, PCT Application No. PCT/US08/013656, Mail Date Jun. 11, 2010, World Intellectual Property Office.
Written Opinion of the International Searching Authority, PCT Application No. PCT/US07/025446, Mail Date Jun. 11, 2009, World Intellectual Property Office.
Written Opinion of the International Searching Authority, PCT Application No. PCT/US07/024085, Mail Date May 15, 2009, World Intellectual Property Office.
Written Opinion of the International Searching Authority, PCT Application No. PCT/IB04/004431, Mail Date Jun. 3, 2006, World Intellectual Property Office.
Written Opinion of the International Searching Authority, PCT Application No. PCT/IB06/001961, Mail Date May 23, 2008, World Intellectual Property Office.
Written Opinion of the International Searching Authority, PCT Application No. PCT/US08/014025, Mail Date Jun. 21, 2010, World Intellectual Property Office.
Written Opinion of the International Searching Authority, PCT Application No. PCT/US08/014028, Mail Date Jun. 21, 2010, World Intellectual Property Office.
Adwan, et. al. "Downregulation of osteopontin and bone sialoprotein II is related to reduced colony formation and metastasis formation of MDA-MB-231 human breast cancer cells." Cancer Gene Therapy (2004) 11: p. 109-120: Nature Publishing Group.
Aitken, et. al. "Adenoviral Down-Regulation of Osteopontin Inhibits Human Osteoclast Differentiation in Vitro." Journal of Cellular Biochemistry (2004) 93: p. 896-903. Wiley-Liss, Inc.
Bashyam, Hema. "Scar-free healing." (Jan. 7, 2008) JEM 205(1): p. 2-3.
Behrend, et. al. "Reduced Malignancy of ras-transformed NIH 3T3 Cells Expressing Antisense Osteopontin RNA." Cancer Research (Feb. 1, 1994) 54: p. 832-837.
Branch, et. al. "A good antisense molecule is hard to find." TIBS (Feb. 1998) 23: p. 45-50. Elsevier Science Ltd.
Celetti, et. al. "Overexpression of the Cytokine Osteopontin Identifies Aggressive Laryngeal Squamous Cell Carcinomas and Enhances Carcinoma Cell Proliferation and Invasiveness." (2005) Clinical Cancer Res 11(22): p. 8019-8027. AACR Journals.
Cooper, et.al. "Wound healing and inflammation genes revealed by array analysis of macrophageless PU.I null mice." Genome Biology (2004) 6(I): Article 5.
Cotrina, et. al. "Astrocytic gap junctions remain open during ischemic conditions." (Apr. 1,1998) J. Neurosci., 18: p. 2520-2537.
Database Geneseq, Dec. 28, 2007, "Viral regulatory miRNA SEQ ID No. 263327" Retrieved from EBI accession No. GSN: AJK11008.
Database Geneseq, Dec. 28, 2007, "Viral regulatory miRNA SEQ ID No. 286128" Retrieved from EBI accession No. GSN AJK33809.
Database EMBL, Jul. 9, 2006, "Rattus norvegicus piRNA piR-152346, complete sequence." Retrieved from EBI accession No. EMBL: DQ737024.
STN Biosis Caesar accession No. 1231, Bilska, Grazul. "Transfection of bovine luteal cells with gap junctional protein connexin 43 (Cx43) antisense oligonucleotide affects progesterone secretion." AN (1998):379610.
STN Biosis Caesar accession No. 1233. Moore, Lisa. "Selective block of gap unction channel expression with connexin-specific antisense oligodeoxynucleotides." AN (1995):31398.

Dang, et. al. "The carboxy-tail of connexin-43 localizes to the nucleus and inhibits cell growth." Molecular and Cellular Biochemistry (2003) 242: p. 35-38. Kluwer Academic Publishers. Netherlands.
Diegelmann, et. al. "Wound Healing: An Overview of Acute, Fibrotic and Delayed Healing." (Jan. 1, 2004) Frontiers in Bioscience 9: p. 283-289. Irvine, CA.
Dublin, et. al. "Satellite glial cells in sensory ganglia: Their possible contribution to inflammatory pain." (2007) Brain, Behaviior, and Immunity 21: p. 592-598. Elsevier Inc.
Gourdie, et. al. "The Unstoppable Connexin43 Carboxyl-Terminus" (2006) Ann. N.Y. Acad. Sci. 1080: p. 49-62. New York Academy of Sciences.
Herbertt, et. al. "Protein Kinase C a Expression is required for heparin inhibition of rat smotth muscle cell proliferation in vitro and in vivo." (Oct. 18, 1996) J Biol Chem. 271(42):259 p. 28-35. The American Society for Biochemistry and Molecular Biology, Inc. U.S.A.
Hunter, et al. "Zonula occludens-1 alters connexin43 gap junction size and organization by influencing channel accretion." (Dec. 2005) Molecular Biology of the Cell 16: p. 5686-5698. The American Society for Cell Biology.
Kandyba, et al. "A murine living skin equivalent amenable to live cell imaging: analysis of the roles of connexins in the epidermis." (Apr. 2008) The Society for Investigative Dermatology.
Law, et. al. "In vitro optimization of antisense ologodeoxynucleotide design: an example using the connexin gene family." Journal of Biomolecular techniques. (Sep. 2006) 17(4): p. 270-282.
Liaw, et. al. "Altered wound healing in mice lacking a functional osteopontin gene (sppl)" (Apr. 1998) The Journal of Clinical Investigation 101(7): p. 1468-1478.
Lin, et. al. "v-Src phosphorylation of connexin 43 on Tyr247 and Tyr265 disrupts gap junctional communication." (Aug. 20, 2001) Journal of Cell Biology. 154: p. 815-827. The Rockefeller University Press.
Liu, et al. "The Inhibition of in vivo tumorigenesis of osteosarcoma (OS)-732 Cells by antisense human osteopontin RNA." (2008) 13: p. 11-19. University of Wroclaw, Poland.
Miyazaki, et. al. "Corneal Wound Healing in an Osteopontin-Deficient Mouse." (Apr. 2008) Investigative Ophthalmology & Visual Science 49(4): p. 1367-1375. Association for Research in Vision and Ophthalmology.
Mori, et al., "Acute downregulation of connexin43 at wound sites leads to a reduced inflammatory response, enhanced keratinocyte proliferation and wound fibroblast migration." Journal of Cell Science. 119(24): p. 5193-5203 (Dec. 2006). The Compny of Biologists 2006.
Mori, et al. Supplemental Materials and Methods. Online Supplemental Material. (2008) http://www.jem.org/cgi/content/full/jem.20071412/DC1 JEM the Rockefeller University Press.
Mori, et al. "Molecular mechanisms linking wound inflammation and fibrosis: knock down of osteopontin leads to rapid repair and reduced scarring." Department of Physiology and Biochemistry, School of Medical Sciences, University of Bristol, Bristol BS8 1TD, United Kingdom. (Jan. 7, 2008); p. 43-55.
Muramatsu, et. al. "Inhibition of osteopontin expression and function in oral cancer cell lines by antisense oligonucleotides." (2005) Cancer Letters 217:87-95. Elsevier.
Nakano, et. al. "Changes in the expression of the gap junction protein connexin43 during wound healing of the rat corneal endothelium." (Dec. 2004) Bioimages 12(2-4). Bioimaging Society.
Okada, et. al. "Osteopontin expressed by renal tubular epithelium mediates interstitial monocyte infiltration in rats." Am Physiol Renal Physiol. (2000) 278:F110-F121. The American Physiological Society.
Qiu, et al; "Supplemental Data: Targeting Connexin43 Expression Accelerates the Rate of Wound Repair"; (2003) S1.
Rhett, et. al. "Novel therapies for scar reduction and regenerative healing of skin wounds." (Mar. 4, 2008). Trends in Biotechnology. 26(4): 173-180. Cell Press.
Santoro, S.W. et. al. "A General Purpose RNA-Cleaving DNA Enzyme." Proc. Natl. Acad. Sci. USA 94, p. 4262-4266 (1997). The National Academy of Sciences of the USA.

(56) References Cited

OTHER PUBLICATIONS

Shevde, et. al "Osteopontin knockdown suppresses tumorigenicity of human metastatic breast carcinoma, MDA-MB-435." Clin Exp Metastasis (2006) 23: p. 123-133. Springer Science + Business Media B.V.
Simons, et. al. "Anti-sense c-myb oligonucleotides inhibit intimal arterial smooth muscle cell accumulation in vivo." (Sep. 3, 1992): Nature, 359: p. 67-70. Nature Publishing Group.
Singh, et. al. "Inhibition of connexin 43 synthesis by antisense RNA in rat glioma cells." (1997) Cytobios 91: p. 103-123. The Faculty Press. Great Britain.
Suzuki, et. al. Protective effects of recombinant osteopontin on early brain injury after subarachnoid hemorrhage in rats. (2010) Crit Care Med 38(2): p. 612-618.
Wai, et. al. "Osteopontin silencing by small interfering RNA suppresses in vitro and in vivo CT26 murine colon adenocarcinoma metastasis." (2005) Carcinogenesis 26(4): p. 741-751. Oxford University Press.
Willecke, et. al. "Mouse connexin37: Cloning and functional expression of a gap function gene highly expressed in lung." (Sep. 1991) The Journal of Cell Biology 114(5): p. 1049-1057. The Rockefeller University Press.
Wright, et. al. "Connexin mimetic peptides improve cell migration rates of human epidermal keratinocytes and dermal fibroblasts in vitro." (2009) Wound Rep Reg 17: p. 240-249. The Wound Healing Society.
Zhou, et. al. "Blockade of Osteopontin Inhibits Glomerular Fibrosis in a Model of Anti-Glomerular Basement Membrane Glomerulonephritis." (Aug. 19, 2010) Am J Nephrol 32: p. 324-331. Karger AG, Basel. (Published Online.).
Partial European Search Report dated Sep. 26, 2013, from corresponding European Patent Application No. 12172475.1, 8 pages.
Extended European Search Report dated Jan. 21, 2014, from corresponding European Patent Application No. 12172475.1, 12 pages.
Decision of Rejection dated Feb. 13, 2014, from corresponding Chinese Patent Application No. 200680010590.X, 20 total pages.
Further Examination Report dated May 19, 2014 in corresponding New Zealand Patent Application No. 615534, 3 pages.
Office Action dated Jul. 10, 2014 in corresponding Chinese Patent Application No. 200680010590.X, 9 total pages.
Office Action (Inquiry) dated Jul. 10, 2014 in corresponding Japanese Patent Application No. 2007-553747, 13 total pages.
Office Action (Notice of Rejection) dated Jul. 28, 2014 in corresponding Korean Patent Application No. 10-2007-7020138, 7 total pages.
Examination Report dated Aug. 27, 2014, from corresponding Canadian Patent Application No. 2,596,412, 4 pages.
Examination Report dated Sep. 19, 2013 in corresponding New Zealand Patent Application No. 615534, 3 pages.
Notice of Preliminary Rejection (Non-Final) dated Sep. 5, 2013 in corresponding Korean Patent Application No. 10-2007-7020138, 10 pages.
Office Action dated Aug. 27, 2013 in corresponding Chinese Patent Application No. 200680010590.X, 15 pages.
Office Action dated Jul. 29, 2013 in corresponding Japanese Patent Application No. 2012-047133, 6 pages.
Communication dated Jan. 27, 2015, from related European Patent Application No. 12172478.5, 7 pages.
Communication dated Jan. 27, 2015, from related European Patent Application No. 12172477.7, 6 pages.
Communication dated Jan. 27, 2015, from related European Patent Application No. 12172475.1, 6 pages.
Patent Examination Report No. 1 dated May 17, 2015, from related Australian Patent Application No. 2013216578, 5 pages.
Official Action dated Apr. 2, 2015, from related Japanese Patent Application No. 2007-553747, 12 pages.
Notification of Sixth Office Action dated Mar. 31, 2015, from related Chinese Patent Application No. 200680010590X, 15 pages.
Official Action dated May 12, 2015, from related Japanese Patent Application No. 2014-121150, 1 page.
Kanter, H. Lee, et al., *Molecular Cloning of Two Human Cardiac Gap Junction Proteins, Connexin40 and Connexin45*, Nov. 18, 1993, 861-864, vol. 26, J Mol Cell Cardiol, Academic Press Limited.

\* cited by examiner

FIG. 1A
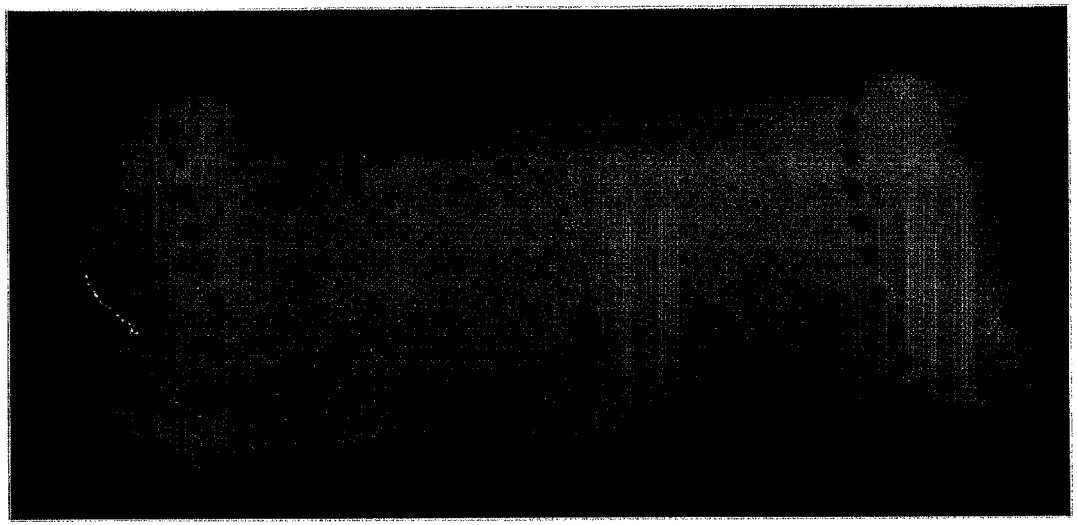
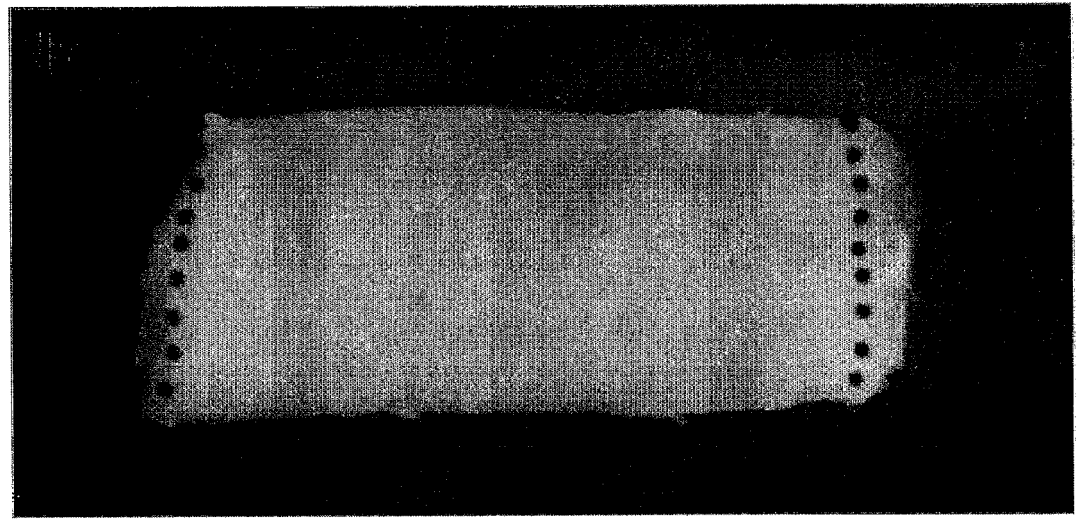
FIG. 1B

FIG. 5A
FIG. 5B
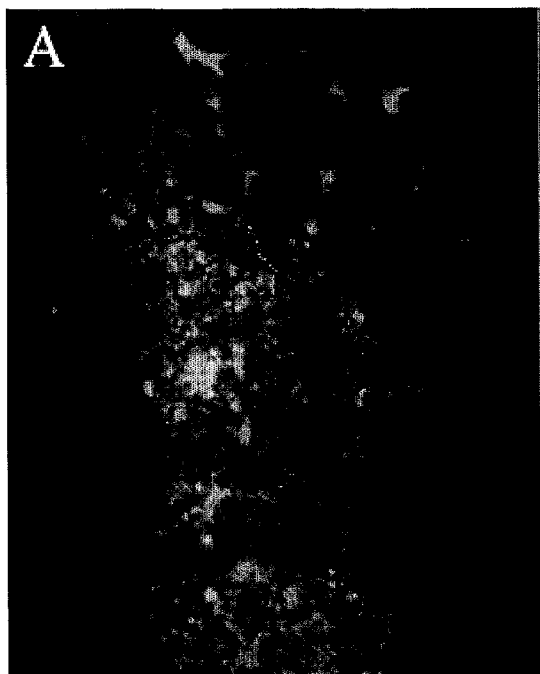 

METHODS OF TREATMENT BY ADMINISTERING ANTI-CONNEXIN PROTEINS AND MIMETICS

CROSS REFERENCE TO RELATED APPLICATIONS

This application is a National Phase Stage Application under 35 U.S.C. §371 of International Application No. PCT/IB2006/001961, filed on Feb. 3, 2006, which claims the benefit of priority to U.S. Provisional Application No. 60/650,075, filed on Feb. 3, 2005 [2004]. The disclosures of both are incorporated herein by reference.

FIELD

The present disclosure relates to pharmaceuticals, including agents, compounds, compositions, formulations, and methods for modulation of gap-junctions and hemichannels that are useful, for example, in the prevention and treatment of various diseases, disorders and conditions, including but not limited to cardiovascular, neurological, and vascular diseases, disorders and conditions.

BACKGROUND

The following includes information that may be useful in understanding the present inventions. It is not an admission that any of the information provided herein is prior art, or relevant, to the presently described or claimed inventions, or that any publication or document that is specifically or implicitly referenced is prior art.

Coronary heart disease is the leading cause of death in most western countries. Mortality rates for cardiovascular disease have been reported to vary from 29 (in males, 24 for females) per 100,000 in Canada up to 213 (males, females 154) in the Russian Federation. For other Western countries the rate is 31-55 (43-26). Approximately half the deaths attributable to stroke are the result of medical complications, such as pneumonia and sepsis, and half are attributable to neurological complications, such as new cerebral infarction and cerebral edema. Brott, T. and Bogousslavsky, J., *New Engl. J. Med.* 343: 710-722 (2000).

Strokes are the third leading cause of death in developed countries and have a devastating impact on public health. About 700,000 new stroke cases occur in America every year (American Stroke Association). About 25% of stroke sufferers die as a result of the stroke or its resulting complications. Additionally, almost 50% of stroke victims have moderate to severe health impairments and long-term disabilities. Although the incidence of ischemic stroke has declined over the past 20 years, the mean age of the population has risen, resulting in a continual increase in the absolute number of strokes. Recent projections indicate that by the year 2050, more than 1 million strokes will occur each year in the United States. Strokes are generally the result of several underlying conditions that decrease the flow of blood to the brain and cause disability or death. Approximately 85 percent of strokes are ischemic in nature (blood clot or blockage of a blood vessel). Foulkes M R, et al., *Stroke;* 19:547-54 (1988). An ischemic stroke can be caused by a blood clot that forms inside the artery of the brain (thrombotic stroke), or by a clot that forms somewhere else in the body and travels to the brain (embolic stroke), with thrombotic strokes representing about 52% of all ischemic strokes. Thrombotic strokes are generally a result of atherosclerosis (where blood vessels become clogged with a buildup of fatty deposits, calcium, and blood clotting factors such as fibrinogen and cholesterol).

Inflammation is a multifactorial process, and is manifest in many diseases, disorders, and conditions which have enormous cumulative health consequences. Inflammatory diseases, including rheumatoid arthritis, lupus, psoriasis, multiple sclerosis and asthma remain a major cause of mortality and morbidity worldwide. Autoimmune diseases are also associated with inflammation and on the rise, reportedly affecting more than 50 million people in the U.S. In many autoimmune diseases, cell, tissue, joint and organ damage results from the uncontrolled activation of a immense array of inflammatory pathways. Rheumatoid arthritis (RA) is one such chronic inflammatory disease characterized by inflammation of the joints, leading to swelling, pain, and loss of function. RA affects at least an estimated 2.5 million people in the United States, and is caused by a combination of events including an initial infection or injury, an abnormal immune response, and genetic factors. Any one of at least 80 different autoimmune diseases can result when the immune system becomes unregulated and attacks healthy tissue.

Connexins, also known as gap junction proteins, are four-pass transmembrane proteins with cytoplasmic C and N termini. Six connexins combine together to form a ohemichannel called a "connexon."

Gap junctions are structures that provide direct cell-to-cell communication. The gap junction is composed of two connecting connexons, one contributed by each of the abutting cells that upon docking form a functional gap junction.

As they are being translated by ribosomes, connexins are inserted into the membrane of the endoplasmic reticulum. Bennett M V, Zukin R S. Electrical coupling and neuronal synchronization in the Mammalian brain. *Neuron.* 2004 Feb. 19; 41(4):495-511. There they gather to form hemichannels (connexons), which are carried to the cell membrane in vesicles and diffuse through the membrane until they meet a hemichannel from the other cell, with which they can dock to form a channel. Id. Molecules on a connexin allow it to "recognize" the other connexins in their hemichannel and those of the other cell's hemichannel, and cause correct alignment and formation of the channel. Kandel E R, Schwartz J H, Jessell T M. *Principles of Neural Science,* 4th ed., pp. 178-180. McGraw-Hill, New York (2000).

Connexin proteins have a common transmembrane topology, with four alpha-helical transmembrane domains, two extracellular loops, a cytoplasmic loop, and cytoplasmic N- and C-terminal domains. The sequences are most conserved in the transmembrane and extracellular domains, yet many of the key functional differences between connexins are determined by amino-acid differences in these largely conserved domains. Each extracellular loop contains three cysteines with invariant spacing (save one isoform) that are required for channel function. The junctional channel is composed of two end-to-end hemichannels, each of which is a hexamer of connexin subunits. In junctional channels, the cysteines in the extracellular loops form intra-monomer disulfide bonds between the two loops, not intermonomer or inter-hemichannel bonds. The end-to-end homophilic binding between hemichannels is via non-covalent interactions. Mutagenesis studies suggest that the docking region contains beta structures, and may resemble to some degree the beta-barrel structure of porin channels. The two hemichannels that compose a junctional channel are rotationally staggered by approximately 30 degrees relative to each other so that the alpha-helices of each connexin monomer are axially aligned with the alpha-helices of two adjacent monomers in the apposed hemichannel.

Each connexon or hemichannel in the membrane should, under normal conditions, remain closed until it docks with a connexon of a neighboring cell. However, the inventors believe that when a cell expressing a hemichannel is subjected to a stress (e.g. physiological, mechanical, etc.) hemichannels can open even when they are not docked. The inhibition of extracellular hemmichannel communication includes the inhibition of the flow of small molecules through an open hemichannel to and from an extracellular or periplamic space. While not intending to be bound by or limited to any mechanism, modes of action include blocking (partial or complete) of the hemichannel, triggering internalization of the connexon which is then removed from the membrane, inducing a conformational change in the connexin proteins to bring about closure of the connexon, and masking or binding to sites involved in triggering channel opening (such calcium binding sites).

Antisense (AS) nucleotides to connexins and uses thereof have been described. See WO00/44409 to Becker et al., filed Jan. 27, 2000, "Formulations Comprising Antisense Nucleotides to Connexins."

BRIEF SUMMARY

The inventions described and claimed herein have many attributes and embodiments including, but not limited to, those set forth or described or referenced in this Brief Summary. The inventions described and claimed herein are not limited to, or by, the features or embodiments identified in this Summary, which is included for purposes of illustration only and not restriction.

The inventions described and claimed herein relate to anti-connexin compounds, including polypeptides (e.g. mimetic peptides and peptiditomimetics, antibodies, and antibody fragments and synthetic constructs) and polynucleotides (e.g., antisense polynucleotides), for modulation of connexins, hemichannels, and gap junctions in selected tissues, cells, and patients, for example, patients suffering from or at risk for cardiovascular conditions, inflammatory conditions, neurological conditions, vascular conditions, wounds and other conditions and disorders, and complications thereof.

Anti-connexin compounds and compositions useful for the treatment of various diseases, conditions and disorders in which modulation of connexins, hemichannels, and gap junctions would be of benefit, for example, cardiovascular, neurological, vascular, and other conditions or disorders, including wound treatment, are provided. Also provided are methods of using these compounds and compositions as well as pharmaceutical formulations, kits, and medical devices, for example.

In one aspect, compounds, compositions, and methods for treating a subject with a vascular disorder are provided. Such methods include administering to the subject an anti-connexin compound, for example, an antisense compound, mimetic peptide, or other anti-connexin compound, including those provided herein, capable of inhibiting the expression, formation, or activity of a connexin, hemichannel or gap junction.

In another aspect, anti-connexin compounds, compositions, and methods for treating a subject with an inflammatory disorder are provided. Such methods include administering to the subject an antisense compound, mimetic peptide, or other anti-connexin compound, including those provided herein, capable of inhibiting the expression, formation, or activity of a connexin, hemichannel, or gap junction.

In another aspect, anti-connexin compounds, compositions, and methods for treating a subject having a wound are provided. Such methods include administering to the subject an antisense compound, mimetic peptide, or other anti-connexin compound, including those provided herein, capable of inhibiting the expression, formation, action, or activity of a connexin, hemichannel, or gap junction.

In another aspect, anti-connexin compounds, compositions, and methods for treating a subject in connection with a transplant or grafting procedure are provided. Such methods include administering to the subject an antisense compound, mimetic peptide, or other anti-connexin compound, including those provided herein, capable of inhibiting the expression, formation, action, or activity of a connexin hemichannel. Such methods are also capable of inhibiting and/or preventing tissue edema associated with transplant and grafting procedures.

In another aspect, anti-connexin binding proteins, including mimetics peptides, antibodies, antibody fragments, and the like, are provided that are capable of binding or modulating the expression, formation, action, or activity of a connexin hemichannel. Binding proteins are useful as modulators of gap junctions and hemichannels.

In certain non-limiting embodiments, the anti-connexin compound comprises a peptide comprising an amino acid sequence corresponding to a transmembrane region of a connexin. Such connexins include, for example, connexins 45, 43, 26, 30, 31.1, and 37. Human connexins are a preferred species.

In a non-limiting but preferred embodiment, an anti-connexin compound comprises a peptide comprising an amino acid sequence corresponding to a portion of a transmembrane region of a connexin 45. In particular non-limiting embodiments, for example, the anti-connexin compound is a peptide having an amino acid sequence that comprises about 3 to about 30 contiguous amino acids of SEQ ID NO:62, a peptide having an amino acid sequence that comprises about 5 to about 20 contiguous amino acids of SEQ ID NO:62, a peptide having an amino acid sequence that comprises about 8 to about 15 contiguous amino acids of SEQ ID NO:62, or a peptide having an amino acid sequence that comprises about 11, 12, or 13 contiguous amino acids of SEQ ID NO:62. Other non-limiting embodiments include an anti-connexin compound that is a peptide having an amino acid sequence that comprises at least about 3, 4, 5, 6, 7, 8, 9, 10, 11, 12, 13, 14, 15, 20, 25, or 30 contiguous amino acids of SEQ ID NO:62. In certain anti-connexin compounds provided herein, mimetic peptides are based on the extracellular domains of connexin 45 corresponding to the amino acids at positions 46-75 and 199-228 of SEQ ID NO: 62. Thus, certain peptide described herein have an amino acid sequence corresponding to the regions at positions 46-75 and 199-228 of SEQ ID NO: 62. The peptides need not have an amino acid sequence identical to those portions of SEQ ID NO: 62, and conservative amino acid changes may be made such that the peptides retain binding activity or functional activity in the assays described herein and otherwise known in the art. In other embodiments, mimetic peptides are based on peptide target regions within the connexin protein other than the extracellular domains (e.g. portions of SEQ ID NO:62 not corresponding to positions 46-75 and 199-228).

In another non-limiting but preferred embodiment, an anti-connexin compound comprises a peptide comprising an amino acid sequence corresponding to a portion of a transmembrane region of a connexin 43. In particular non-limiting embodiments, the anti-connexin compound is a peptide having an amino acid sequence that comprises a peptide having an amino acid sequence that comprises about 3 to about 30 contiguous amino acids of SEQ ID NO:63, about 5 to about 20 contiguous amino acids of SEQ ID NO:63, a peptide having an amino acid sequence that comprises about 8 to about 15 contiguous amino acids of SEQ ID NO:63, or a peptide having an amino acid sequence that comprises about 11, 12, or 13 contiguous amino acids of SEQ ID NO:63. Other non-limiting embodiments include an anti-connexin compound that is a peptide having an amino acid sequence that comprises at least about 5, 6, 7, 8, 9, 10, 11, 12, 13, 14, 15, 20, 25, or 30 contiguous amino acids of SEQ ID NO:63. In other anti-connexin compounds, mimetic peptides are based on the extracellular domains of connexin 43 corresponding to the amino acids at positions 37-76 and 178-208 of SEQ ID NO: 63. Thus, certain peptides described herein have an amino acid sequence corresponding to the regions at positions 37-76 and 178-208 of SEQ ID NO: 63. The peptides need not have an amino acid sequence identical to those portions of SEQ ID NO: 63, and conservative amino acid changes may be made such that the peptides retain binding activity or functional activity in the assays described herein and otherwise known in the art. In other embodiments, mimetic peptides are based on peptide target regions within the connexin protein other than the extracellular domains (e.g. the portions of SEQ ID NO:63 not corresponding to positions 37-76 and 178-208).

Other particular compounds, methods of making these compounds, and methods of measuring their activity are described in greater detail herein.

Alternatively, anti-connexin compounds, including those provided and used in certain embodiments, comprise one or more antisense compounds. Suitable antisense compounds may be selected, for example, from the group consisting of antisense oligonucleotides, antisense polynucleotides, deoxyribozymes, morpholino oligonucleotides, RNAi molecules, siRNA molecules, PNA molecules, DNAzymes, and 5'-end-mutated U1 small nuclear RNAs, and analogs of the preceding. These and other compounds may be used alone or in combination with one more mimetic or other binding peptides.

An anti-connexin compound such as an antisense compound or mimetic peptide may be targeted, for example, towards one or more of connexins 45, 43, 26, 37, 30 and/or 31.1. In certain non-limiting but preferred embodiments, an antisense compound or mimetic peptide is targeted towards connexin 45 or connexin 43. In certain non-limiting but preferred embodiments, an anti-connexin compound such as an antisense compound targeted to at least about 8 nucleobases of a nucleic acid molecule encoding a connexin having a nucleobase sequence selected from SEQ ID NO:12-31. An antisense compound may comprise, for example, an antisense compound targeted to at least about 12 nucleobases of a nucleic acid molecule encoding a connexin having a nucleobase sequence selected from SEQ ID NO: 12-31. In certain other embodiments, an antisense compound comprises a nucleobase sequence selected from SEQ ID NO:1-11. An antisense compound may comprise, for example, an antisense oligonucleotide of between about 15 and about 35 nucleobases in length, for example about 25-30 or about 30.

An antisense compound may comprise, for example, an antisense oligonucleotide comprising naturally occurring nucleobases and an unmodified internucleoside linkage (e.g. at least one modified internucleoside linkage). The modified internucleoside linkage may comprise a phosphorothioate linkage. Other antisense compounds may, for example, comprise an oligonucleotides having at least one modified sugar moiety. Still other antisense compounds may, for example, comprise oligonucleotides having at least one modified nucleobase.

In certain embodiments, an anti-connexin compound such as an antisense compound or mimetic peptide may be used in combination with a second compound useful for reducing tissue damage or promoting healing. The second compound, for example, may be a growth factor or a cytokine or the like. Suitable coadministration compounds include, for example, FGF, NGF, NT3, PDGF, TGF, VEGF, BDGF, EGF, KGF, integrins, interleukins, plasmin, and semaphorins. For human therapy, such coadministration compounds as those listed above are human or of human origin.

Methods of administering anti-connexin compounds to a subject, target organ, target tissue, or target cell are provided in which hemichannel modulation would be of benefit.

Methods of administering anti-connexin compounds to a subject, target organ, target tissue, or target cell are provided. Thus, in certain non-limiting embodiments a subject is treated by administration of an anti-connexin compound that is capable of binding to or modulating a hemichannel for one or more of the following: cardiovascular disease, coronary heart disease, heart failure, myocardial infarction, atherosclerosis, ischemic heart disease, cardioplegic or other organ transport or storage medium, reperfusion injury, respiratory or metabolic acidosis, pulmonary edema (including exposure to toxic gases such as nitrogen dioxide), vascular pathophysiology whereby endothelial cells are disrupted (such as diet induced hypercholestrolemic lesions), vascular disorders (microvascular and macrovascular), stroke, cerebrovascular disease (cerebral ischemia), thromboses, vascular injuries resulting from trauma (e.g. subcutaneous wounds, stent insertion, restenosis, or angioplasty), vascular damage resulting from elevated levels of glucose (diabetes), vascular diseases of the extremities, organ ischemia, optic neuropathies, inflammation, and rheumatoid arthritis (RA), sub-chronic or chronic inflammation, epilepsy (epileptic events and lesions spread following epileptic events), diabetic retinopathy, macular degeneration, and certain other indications described in greater detail in Harrison's, Principles of Internal Medicine 15$^{th}$ Edition (McGraw Hill, Inc., New York), incorporated by reference herein.

In certain other non-limiting embodiments a subject is treated by administration of an anti-connexin compound that is capable of binding to or otherwise modulating a hemichannel for one or more of the following, for example: (1) prevention or treatment of oedema in the spinal cord following or as a result of, for example, ischaemia or trauma; (2) prevention or treatment of blood vessel wall degradation in tissues following or as a result of, for example, ischaemia or trauma (e.g. in brain, optic nerve, spinal cord and heart); (3) prevention or treatment of inflammatory arthritis and other inflammatory disorders in which, for example, oedema and/or inflammation are symptomatic, or in which, by way of example, blood vessel die back occurs as a result of, for example, persistent inflammation; (4) prevention or treatment of sub-acute or chronic wounds, for example, wounds to the cornea of the eye in which, by way of example, prevention of blood vessel die back allows recovery from limbal ischaemia; (5) prevention or treatment of sub-acute or chronic wounds, for example, wounds to the cornea of the eye as a means, by way of example, to trigger re-epithelialisation; (6) treatment of burns, for example, chemical burns in the eye in order, by way of example, to trigger epithelial recovery and to bring about recovery from sub-acute limbal ischaemia; (7) prevention or treatment of sub-acute or chronic skin wounds, including, for example, diabetic ulcers, in which, by way of example, prevention of continued blood vessel die back will allow recovery from tissue ischaemia; (8) treatment of chronic wounds, including, for example, diabetic ulcers in which, by way of example, continued expression of connexin 43, for example at the leading edge, prevents re-epithelialisation; (9) prevention or treatment of perinatal ischaemia using connexin mimetic peptides, which may, for example, be delivered directly to ventricles of the brain or via spinal column and/or spinal cord; (10) inhibition or prevention of oedema following perinatal ischaemia using connexin mimetic peptides delivered, for example, directly to ventricles of the brain or via spinal column and/or spinal cord; (11) treatment for perinatal ischaemia using connexin mimetic peptides delivered systemically, for example; (12) treatment for stroke or CNS ischaemia using connexin mimetic peptides delivered, for example, systemically and/or directly to ventricles of the brain or via spinal column and/or spinal cord; (13) prevention of epileptiform activity (e.g. epilepsy) in the brain, including epileptiform activity following ischaemia; and/or, (14) prevention of lesion spread, oedema (and rejection) with reperfusion following organ transplantation. Anti-connexin compounds capable of binding or modulating connexins and gap junctions for the prevention and/or treatment of such methods and indications are provided.

An anti-connexin compound may be administered at various predetermined times.

In certain non-limiting embodiments, a connexin hemichannel activity, action, expression or formation is inhibited in endothelial cells.

In certain non-limiting embodiments, a connexin hemichannel activity, action, expression or formation is inhibited in epithelial cells.

In certain non-limiting embodiments, a subject may be treated for a vascular disorder comprising a stroke.

In certain non-limiting embodiments, a subject may be treated for a vascular disorder comprising an ischemia. Such an ischemia may be, for example, a tissue ischemia, a myocardial ischemia, or a cerebral ischemia.

In certain non-limiting embodiments, a subject treated herein is at risk of loss of neurological function by ischemia.

In certain non-limiting embodiments, a subject may be treated for a vascular disorder comprising treating or ameliorating cell death or degeneration in the central or peripheral nervous system that may be caused by an ischemia.

In certain non-limiting embodiments, a subject may treated for a vascular disorder wherein an anti-connexin compound, for example, an antisense compound, mimetic peptide, or other binding peptide is administered in connection with a vascular or coronary procedure performed on a subject. In other non-limiting embodiments, an anti-connexin compound, for example, an antisense compound, mimetic peptide, or other binding peptide is administered during said vascular or coronary procedure. The anti-connexin compound may also be administered before or after a vascular or coronary procedure, or both.

In certain non-limiting embodiments, an anti-connexin compound, including an antisense compound, mimetic peptide, or other binding peptide is administered within about 1 hour after a vascular or coronary procedure is performed, or, for example, within about 2 hours after a vascular or coronary procedure is performed. In other embodiments, the anti-connexin compound is administered within about 24 hours. Anti-connexin compounds may also be administered outside these timeframes, as desired or necessary.

In certain embodiments, an anti-connexin compound, including an antisense compound, mimetic peptide, or other binding peptide is administered in connection with a heart procedure, such as heart surgery, performed on a patient.

In certain other embodiments, an anti-connexin compound, including an antisense compound, mimetic peptide, or other binding peptide is administered in connection with a medical device for performing a vascular or other procedure.

In another aspect, a pharmaceutical formulation for administration to a subject is provided, the formulation comprising a pharmaceutically acceptable carrier and an agent capable of modulating a connexin hemichannel and subsequent connexon formation, such as, for example, by blocking or ameliorating hemichannel expression, formation, action, and/or activity.

BRIEF DESCRIPTION OF THE DRAWINGS

FIG. 1 shows rat spinal cord segments 24 hours after placing into organotypic culture. In the control cord (FIG. 1A) significant swelling is observed at the cut ends (dotted lines mark the original cuts). The connexin 43 specific antisense ODN treated segment (FIG. 1B) shows little swelling or oedema.

FIG. 3 shows immunohistochemical labeling of connexin 43 using antibodies which bind to the extracellular loop (location of binding of Gap7M antibodies shown in FIG. 3A) and to the cytoplasmic carboxyl tail of the protein (location of binding of Gap1A shown in FIG. 3A). The cytoplasmic antibody labels all connexin 43 proteins, and the Gap7M can only label exposed extracellular loops of hemichannels, as it is sterically hindered from binding to docked connexons which are forming intact channels between cells.

FIG. 5 shows sections of spinal cord tissue 5 mm rostral to a crush wound. Four hours after crushing the cord, FITC tagged BSA was injected into the animal tail vein, and the tissue then removed and sectioned. In the control cord (FIG. 5A) the dye has leaked out extensively from the blood vessels, up to 5 mm from the injury site, indicating rupture of blood capillary vessel walls and disruption of the blood brain barrier. In the connexin 43 specific antisense ODN treated cord (FIG. 5B) there is very little dye that is not contained within capillaries indicating vessel integrity has been retained.

Figure 2:
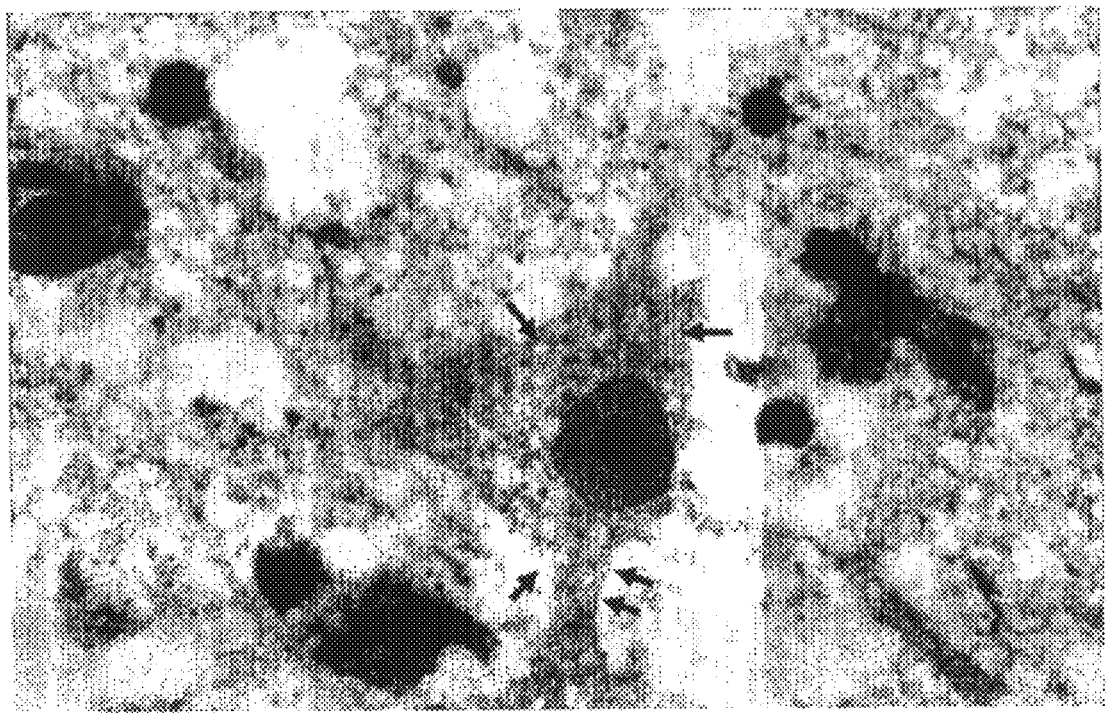
FIG. 2 shows coomassie Blue staining of resin sections of control spinal cord after 24 hours in organotypic culture. The neurons are vacuolated and oedematous with "blebbing" evident along the membrane where hemichannels are opening and allowing extracellular fluids to enter the cell (arrows).

All colors referenced herein are represented on a grey-scale in the corresponding black-and-white figures.

DETAILED DESCRIPTION

Practice of the present inventions may include or employ various conventional techniques of molecular biology (including recombinant techniques), microbiology, cell biology, biochemistry, nucleic acid chemistry, and immunology, which are within the skill of the art. Such techniques are explained fully in the literature, and include but are not limited to, by way of example only, Molecular Cloning: A Laboratory Manual, second edition (Sambrook et al., 1989) and Molecular Cloning: A Laboratory Manual, third edition (Sambrook and Russel, 2001), jointly and individually referred to herein as "Sambrook"; Oligonucleotide Synthesis (M. J. Gait, ed., 1984); Animal Cell Culture (R. I. Freshney, ed., 1987); Handbook of Experimental Immunology (D. M. Weir & C. C. Blackwell, eds.); Gene Transfer Vectors for Mammalian Cells (J. M. Miller & M. P. Calos, eds., 1987); Current Protocols in Molecular Biology (F. M. Ausubel et al., eds., 1987, including supplements through 2001); PCR: The Polymerase Chain Reaction, (Mullis et al., eds., 1994); Current Protocols in Immunology (J. E. Coligan et al., eds., 1991); The Immunoassay Handbook (D. Wild, ed., Stockton Press N.Y., 1994); Bioconjugate Techniques (Greg T. Hermanson, ed., Academic Press, 1996); Methods of Immunological Analysis (R. Masseyeff, W. H. Albert, and N. A.

Staines, eds., Weinheim: V C H Verlags gesellschaft mbH, 1993), Harlow and Lane (1988) Antibodies, A Laboratory Manual, Cold Spring Harbor Publications, New York, and Harlow and Lane (1999) Using Antibodies: A Laboratory Manual Cold Spring Harbor Laboratory Press, Cold Spring Harbor, N.Y. (jointly and individually referred to herein as Harlow and Lane), Beaucage et al. eds., Current Protocols in Nucleic Acid Chemistry John Wiley & Sons, Inc., New York, 2000); and Agrawal, ed., Protocols for Oligonucleotides and Analogs, Synthesis and Properties Humana Press Inc., New Jersey, 1993).

DEFINITIONS

Before further describing the inventions in general and in terms of various nonlimiting specific embodiments, certain terms used in the context of the describing the invention are set forth. Unless indicated otherwise, the following terms have the following meanings when used herein and in the appended claims. Those terms that are not defined below or elsewhere in the specification shall have their art-recognized meaning.

Amino acids used in compounds provided herein (e.g. peptides and proteins) can be genetically encoded amino acids, naturally occurring non-genetically encoded amino acids, or synthetic amino acids. Both L- and D-enantiomers of any of the above can be utilized in the compounds. The following abbreviations may be used herein for the following genetically encoded amino acids (and residues thereof): alanine (Ala, A); arginine (Arg, R); asparagine (Asn, N); aspartic acid (Asp, D); cyteine (Cys, C); glycine (Gly, G); glutamic acid (Glu, E); glutamine (Gln, Q); histidine (His, H); isoleucine (Ile, I); leucine (Leu, L); lysine (Lys, K); methionine (Met, M); phenylalanine (Phe, F); proline (Pro, P); serine (Ser, S); threonine (Thr, T); tryptophan (Trp, W); tyrosine (Tyr, Y); and valine (Val, V).

Certain commonly encountered amino acids that are not genetically encoded and that can be present in the compounds of the invention include, but are not limited to, β-alanine (b-Ala) and other omega-amino acids such as 3-aminopropionic acid (Dap), 2,3-diaminopropionic acid (Dpr, Z), 4-aminobutyric acid and so forth; α-aminoisobutyric acid (Aib); ε-aminohexanoic acid (Aha); δ-aminovaleric acid (Ava); methylglycine (MeGly); ornithine (Orn); citrulline (Cit); t-butylalanine (t-BuA); t-butylglycine (t-BuG); N-methylisoleucine (MeIle); phenylglycine (Phg); cyclohexylalanine (Cha); norleucine (Nle, J); 2-naphthylalanine (2-Nal); 4-chlorophenylalanine (Phe(4-Cl)); 2-fluorophenylalanine (Phe(2-F)); 3-fluorophenylalanine (Phe(3-F)); 4-fluorophenylalanine (Phe(4-F)); penicillamine (Pen); 1,2,3,4-tetrahydroisoquinoline-3-carboxylic acid (Tic); beta-2-thienylalanine (Thi); methionine sulfoxide (MSO); homoarginine (hArg); N-acetyl lysine (AcLys); 2,3-diaminobutyric acid (Dab); 2,3-diaminobutyric acid (Dbu); p-aminophenylalanine (Phe(pNH$_2$)); N-methyl valine (MeVal); homocysteine (hCys); 3-benzothiazol-2-yl-alanine (BztAla, B); and homoserine (hSer). Additional amino acid analogs contemplated include phosphoserine, phosphothreonine, phosphotyrosine, hydroxyproline, gamma-carboxyglutamate, hippuric acid, octahydroindole-2-carboxylic acid, statine, α-methylalanine, para-benzoyl-phenylalanine, propargylglycine, and sarcosine. Peptides that are encompassed within the scope of the invention can have any of the foregoing amino acids in the L- or D-configuration, or any other amino acid described herein or known in the art, whether currently or in the future.

Amino acids that are substitutable for each other generally reside within similar classes or subclasses. As known to one of skill in the art, amino acids can be placed into different classes depending primarily upon the chemical and physical properties of the amino acid side chain. For example, some amino acids are generally considered to be hydrophilic or polar amino acids and others are considered to be hydrophobic or nonpolar amino acids. Polar amino acids include amino acids having acidic, basic or hydrophilic side chains and nonpolar amino acids include amino acids having aromatic or hydrophobic side chains. Nonpolar amino acids may be further subdivided to include, among others, aliphatic amino acids. The definitions of the classes of amino acids as used herein are as follows:

"Nonpolar Amino Acid" refers to an amino acid having a side chain that is uncharged at physiological pH, that is not polar and that is generally repelled by aqueous solution. Examples of genetically encoded hydrophobic amino acids include Ala, Ile, Leu, Met, Trp, Tyr and Val. Examples of non-genetically encoded nonpolar amino acids include t-BuA, Cha and Nle.

"Aromatic Amino Acid" refers to a nonpolar amino acid having a side chain containing at least one ring having a conjugated π-electron system (aromatic group). The aromatic group may be further substituted with substituent groups such as alkyl, alkenyl, alkynyl, hydroxyl, sulfonyl, nitro and amino groups, as well as others. Examples of genetically encoded aromatic amino acids include phenylalanine, tyrosine and tryptophan. Commonly encountered non-genetically encoded aromatic amino acids include phenylglycine, 2-naphthylalanine, β-2-thienylalanine, 3-benzothiazol-2-yl-alanine, 1,2,3,4-tetrahydroisoquinoline-3-carboxylic acid, 4-chlorophenylalanine, 2-fluorophenylalanine, 3-fluorophenylalanine and 4-fluorophenylalanine.

"Aliphatic Amino Acid" refers to a nonpolar amino acid having a saturated or unsaturated straight chain, branched or cyclic hydrocarbon side chain. Examples of genetically encoded aliphatic amino acids include Ala, Leu, Val and Ile. Examples of non-encoded aliphatic amino acids include Nle.

"Polar Amino Acid" refers to a hydrophilic amino acid having a side chain that is charged or uncharged at physiological pH and that has a bond in which the pair of electrons shared in common by two atoms is held more closely by one of the atoms. Polar amino acids are generally hydrophilic, meaning that they have an amino acid having a side chain that is attracted by aqueous solution. Examples of genetically encoded polar amino acids include asparagine, cysteine, glutamine, lysine and serine. Examples of non-genetically encoded polar amino acids include citrulline, homocysteine, N-acetyl lysine and methionine sulfoxide.

"Acidic Amino Acid" refers to a hydrophilic amino acid having a side chain pK value of less than 7. Acidic amino acids typically have negatively charged side chains at physiological pH due to loss of a hydrogen ion. Examples of genetically encoded acidic amino acids include aspartic acid (aspartate) and glutamic acid (glutamate).

"Basic Amino Acid" refers to a hydrophilic amino acid having a side chain pK value of greater than 7. Basic amino acids typically have positively charged side chains at physiological pH due to association with hydronium ion. Examples of genetically encoded basic amino acids include arginine, lysine and histidine. Examples of non-genetically encoded basic amino acids include ornithine, 2,3-diaminopropionic acid, 2,4-diaminobutyric acid and homoarginine.

"Ionizable Amino Acid" refers to an amino acid that can be charged at a physiological pH. Such ionizable amino acids include acidic and basic amino acids, for example, D-aspartic acid, D-glutamic acid, D-histidine, D-arginine, D-lysine, D-hydroxylysine, D-ornithine, L-aspartic acid, L-glutamic acid, L-histidine, L-arginine, L-lysine, L-hydroxylysine or L-ornithine.

As will be appreciated by those having skill in the art, the above classifications are not absolute. Several amino acids exhibit more than one characteristic property, and can therefore be included in more than one category. For example, tyrosine has both a nonpolar aromatic ring and a polar hydroxyl group. Thus, tyrosine has several characteristics that could be described as nonpolar, aromatic and polar. However, the nonpolar ring is dominant and so tyrosine is generally considered to be nonpolar. Similarly, in addition to being able to form disulfide linkages, cysteine also has nonpolar character. Thus, while not strictly classified as a hydrophobic or nonpolar amino acid, in many instances cysteine can be used to confer hydrophobicity or nonpolarity to a peptide.

In some embodiments, polar amino acids contemplated by the present invention include, for example, arginine, asparagine, aspartic acid, cysteine, glutamic acid, glutamine, histidine, homocysteine, lysine, hydroxylysine, ornithine, serine, threonine, and structurally related amino acids. In one embodiment the polar amino is an ionizable amino acid such as arginine, aspartic acid, glutamic acid, histidine, hydroxylysine, lysine, or ornithine.

Examples of polar or nonpolar amino acid residues that can be utilized include, for example, alanine, valine, leucine, methionine, isoleucine, phenylalanine, tryptophan, tyrosine and the like.

"Anti-connexin compounds" include those compounds that affect or modulate the activity, expression or formation of a connexin, a connexin hemichannel (connexon), or a gap junction. Anti-connexin compounds include without limitation antisense compounds (e.g. antisense polynucleotides), antibodies and binding fragments thereof, and peptides and polypeptides which include "peptidomimetic" and "mimetic" peptides.

"Antisense compounds" include different types of molecules that act to inhibit gene expression, translation, or function, including those that act by sequence-specific targeting of mRNAs for therapeutic applications. Antisense compounds include antisense DNA compounds and antisense RNA compounds. While antisense oligonucleotides are a preferred form of antisense compound, the present invention comprehends other oligomeric antisense compounds, including but not limited to oligonucleotide mimetics. The antisense compounds in accordance with this invention preferably comprise from about 8 to about 50 nucleobases (i.e. from about 8 to about 50 linked nucleosides). Particularly preferred antisense compounds are antisense oligonucleotides, even more preferably those comprising from about 12 to about 30 nucleobases. Antisense compounds include ribozymes, external guide sequence (EGS) oligonucleotides (oligozymes), and other short catalytic RNAs or catalytic oligonucleotides which hybridize to the target nucleic acid and modulate its expression. They also include phosphorothioate oligodeoxynucleotides (S-ODNs).

Antisense compounds thus include, for example, the major nucleic-acid based gene-silencing molecules such as, for example, chemically modified antisense oligodeoxyribonucleic acids (ODNs), ribozymes and siRNAs (Scherer, L. J. and Rossi, J. J. *Nature Biotechnol.* 21: 1457-1465 (2003). Antisense compounds may also include antisense molecules such as, for example, peptide nucleic acids (PNAs) (Braasch, D. A. and Corey, D. R., *Biochemistry* 41, 4503-4510 (2002)), morpholino phosphorodiamidates (Heasman, J., *Dev. Biol.,* 243, 209-214 (2002), DNAzymes (Schubert, S. et al., *Nucleic Acids Res.* 31, 5982-5992 (2003). Chakraborti, S. and Banerjea, A. C., *Mol. Ther.* 7, 817-826 (2003), Santoro, S. W. and Joyce, G. F. *Proc. Natl. Acad. Sci. USA* 94, 4262-4266 (1997), and the recently developed 5'-end-mutated U1 small nuclear RNAs (Fortes, P. et al., *Proc. Natl. Acad. Sci. USA* 100, 8264-8269 (2003).

The term "antisense sequences" refers to polynucleotides having antisense compound activity and include, but are not limited to, sequences complementary or partially complementary or corresponding to, for example, to an RNA sequence. Antisense sequences thus include, for example, include nucleic acid sequences that bind to mRNA or portions thereof to block transcription of mRNA by ribosomes. Antisense methods are generally well known in the art. See, for example, PCT publication WO94/12633, and Nielsen et al., Science 254:1497 (1991); Oligonucleotides and Analogues, A Practical Approach, edited by F. Eckstein, IRL Press at Oxford University Press (1991); Antisense Research and Applications (1993, CRC Press. Antisense sequences to chosen targets may or may not also result in non-specific binding to non-target sequences. Antisense sequences with minimal, no, or nondetectable non-specific binding to non-target sequences are preferred.

As used herein, "messenger RNA" includes not only the sequence information to encode a protein using the three letter genetic code, but also associated ribonucleotide sequences which form the 5'-untranslated region, the 3'-untranslated region, and the 5' cap region, as well as ribonucleotide sequences that form various secondary structures. Oligonucleotides may be formulated in accordance with this invention which are targeted wholly or in part to any of these sequences.

In general, nucleic acids (including oligonucleotides) may be described as "DNA-like" (i.e., having 2'-deoxy sugars and, generally, T rather than U bases) or "RNA-like" (i.e., having 2'-hydroxyl or 2'-modified sugars and, generally U rather than T bases). Nucleic acid helices can adopt more than one type of structure, most commonly the A- and B-forms. It is believed that, in general, oligonucleotides which have B-form-like structure are "DNA-like" and those which have A-form-like structure are "RNA-like".

The term "complementary" generally refers to the natural binding of polynucleotides by base pairing, for example under permissive salt and temperature conditions. For example, the sequence "A-G-T" binds to the complementary sequence "T-C-A". Complementarity between two single-stranded molecules may be "partial", such that only some of the nucleic acids bind, or it may be "complete", such that total complementarity exists between the single stranded molecules. The degree of complementarity between nucleic acid molecules has significant effects on the efficiency and strength of the hybridization between them. "Hybridizable" and "complementary" are terms that are used to indicate a sufficient degree of complementarity such that binding, preferably stable binding sufficient to carry out an intended action, for example, occurs between the DNA or RNA target and the oligonucleotide. It is understood that an oligonucleotide need not be 100% complementary to its target nucleic acid sequence to be hybridizable, and it is also understood that the binding may be target-specific, or may bind to other non-target molecules so long as the non-specific binding does not significantly or undesirably thwart the therapeutic or other objective. An oligonucleotide is used to interfere with the normal function of the target molecule to cause a loss or diminution of activity, and it is preferred that there is a sufficient degree of complementarity to avoid non-specific or unwanted binding of the oligonucleotide to non-target sequences under conditions in which specific binding is desired, i.e., under physiological conditions in the case of in vivo assays or therapeutic treatment or, in the case of in vitro assays, under conditions in which the assays are conducted. Absolute complementarity is not required. Polynucleotides that have sufficient complementarity to form a duplex having a melting temperature of greater than 20° C., 30° C., or 40° C. under physiological conditions, are generally preferred.

A "disorder" is any condition that would benefit from treatment with a molecule or composition of the invention, including those described or claimed herein. This includes chronic and acute disorders or diseases including those pathological conditions that predispose the mammal to the disorder in question.

As used herein, "subject" refers to any animal classified as a mammal, including humans, domestic and farm animals, and zoo, sports, or pet animals, such as dogs, horses, cats, sheep, pigs, cows, etc. The preferred subject is a human.

"Targeting" an oligonucleotide to a chosen nucleic acid target can be a multistep process. The process may begin with identifying a nucleic acid sequence whose function is to be modulated. This may be, for example, a cellular gene (or mRNA made from the gene) whose expression is associated with a particular disease state. The targeting process may also include determination of a site or sites within the nucleic acid sequence for the oligonucleotide interaction to occur such that the desired effect, i.e., inhibition of protein expression, modulation of activity, etc., will result. Once a target site or sites have been identified, antisense compounds (e.g., oligonucleotides) are chosen which are sufficiently or desirably complementary to the target, i.e., hybridize sufficiently and with an adequate or otherwise desired specificity, to give a desired activity. In the present invention, targets include nucleic acid molecules encoding one or more connexins. The targeting process may also include determination of a site or sites for the antisense interaction to occur such that the desired effect will result. A preferred intragenic site, for example, is the region encompassing the translation initiation or termination codon of the open reading frame (ORF) of the gene. The translation initiation codon is typically 5'-AUG (in transcribed mRNA molecules; 5'-ATG in the corresponding DNA molecule), and may also referred to as the "AUG codon," the "start codon" or the "AUG start codon." A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (in prokaryotes). It is also known in the art that eukaryotic and prokaryotic genes may have two or more alternative start codons, any one of which may be preferentially utilized for translation initiation in a particular cell type or tissue, or under a particular set of conditions.

The term "oligonucleotide" includes an oligomer or polymer of nucleotide or nucleoside monomers consisting of naturally occurring bases, sugars and intersugar (backbone) linkages. The term "oligonucleotide" also includes oligomers or polymers comprising non-naturally occurring monomers, or portions thereof, which function similarly. Such modified or substituted oligonucleotides are often preferred over native forms because of properties such as, for example, enhanced cellular uptake, increased stability in the presence of nucleases, or enhanced target affinity. A number of nucleotide and nucleoside modifications have been shown to make the oligonucleotide into which they are incorporated more resistant to nuclease digestion than the native oligodeoxynucleotide (ODN). Nuclease resistance is routinely measured by incubating oligonucleotides with cellular extracts or isolated nuclease solutions and measuring the extent of intact oligonucleotide remaining over time, usually by gel electrophoresis. Oligonucleotides, which have been modified to enhance their nuclease resistance, can survive intact for a longer time than unmodified oligonucleotides. A number of modifications have also been shown to increase binding (affinity) of the oligonucleotide to its target. Affinity of an oligonucleotide for its target is routinely determined, for example, by measuring the Tm (melting temperature) of an oligonucleotide/ target pair, which is the temperature at which the oligonucleotide and target dissociate. Dissociation may be detected spectrophotometrically. The greater the Tm, the greater the affinity of the oligonucleotide has for the target. In some cases, oligonucleotide modifications which enhance target-binding affinity are also able to enhance nuclease resistance.

A "polynucleotide" means a plurality of nucleotides. Thus, the terms "nucleotide sequence" or "nucleic acid" or "polynucleotide" or "oligonculeotide" or "oligodeoxynucleotide" all refer to a heteropolymer of nucleotides or the sequence of these nucleotides. These phrases also refer to DNA or RNA of genomic or synthetic origin which may be single-stranded or double-stranded and may represent the sense or the antisense strand, to peptide nucleic acid (PNA) or to any DNA-like or RNA-like material.

A polynucleotide that encodes a connexin, a connexin fragment, or a connexin variant includes a polynucleotide encoding: the mature form of the connexin found in nature (and naturally occurring and species variants thereof); the mature form of the connexin found in nature and additional coding sequence, for example, a leader or signal sequence or a proprotein sequence (and naturally occurring and species variants thereof); either of the foregoing and non-coding sequences (for example, introns or non-coding sequence 5' and/or 3' of the coding sequence for the mature form(s) of the polypeptide found in nature); fragments of the mature form(s) of the connexin found in nature; and, as noted, variants of the mature form(s) of the connexin found in nature. Thus, "connexin-encoding polynucleotide" and the like encompass polynucleotides that have only a coding sequence for a desired connexin, fragment, or variant, as well as polynucleotides that includes other nucleotides such as additional coding and/or non-coding sequences.

In the context of the invention, messenger RNA includes not only the information to encode a protein using the three letter genetic code, but also associated ribonucleotides which form a region known to such persons as the 5'-untranslated region, the 3'-untranslated region, the 5' cap region and intron/ exon junction ribonucleotides. Thus, oligonucleotides may be formulated in accordance with the present invention that are targeted wholly or in part to these associated ribonucleotides as well as to the informational ribonucleotides. The oligonucleotide may therefore be specifically hybridizable with a transcription initiation site region, a translation initiation codon region, a 5' cap region, an intron/exon junction, coding sequences, a translation termination codon region or sequences in the 5'- or 3'-untranslated region. A minority of genes have a translation initiation codon having the RNA sequence 5'-GUG, 5'-UUG or 5'-CUG, and 5'-AUA, 5'-ACG and 5'-CUG have been shown to function in vivo. Thus, the terms "translation initiation codon" and "start codon" can encompass many codon sequences, even though the initiator amino acid in each instance is typically methionine (in eukaryotes) or formylmethionine (prokaryotes). It is also known in the art that eukaryotic and prokaryotic genes may have two or more alternative start codons, any one of which may be preferentially utilized for translation initiation in a particular cell type or tissue, or under a particular set of conditions. In the context of the invention, "start codon" and "translation initiation codon" refer to the codon or codons that are used in vivo to initiate translation of an mRNA molecule transcribed from a gene encoding connexin, regardless of the sequence(s) of such codons. It is also known in the art that a translation termination codon (or "stop codon") of a gene may have one of three sequences, i.e., 5'-UAA, 5'-UAG and 5'-UGA (the corresponding DNA sequences are 5'-TAA, 5'-TAG and 5'-TGA, respectively). The terms "start codon region," "AUG region" and "translation initiation codon region" refer to a portion of such an mRNA or gene that encompasses from about 25 to about 50 contiguous nucleotides in either direction (i.e., 5' or 3) from a translation initiation codon. This region is a preferred target region. Similarly, the terms "stop codon region" and "translation termination codon region" refer to a portion of such an mRNA or gene that encompasses from about 25 to about 50 contiguous nucleotides in either direction (i.e., 5' or 3') from a translation termination codon. This region is a preferred target region. The open reading frame (ORF) or "coding region," which is known in the art to refer to the region between the translation initiation codon and the translation termination codon, is also a region which may be targeted effectively. Other preferred target regions include the 5' untranslated region (5'UTR), known in the art to refer to the portion of an mRNA in the 5' direction from the translation initiation codon, and thus including nucleotides between the 5' cap site and the translation initiation codon of an mRNA or corresponding nucleotides on the gene and the 3' untranslated region (3'UTR), known in the art to refer to the portion of an mRNA in the 3' direction from the translation termination codon, and thus including nucleotides between the translation termination codon and 3' end of an mRNA or corresponding nucleotides on the gene. The 5' cap of an mRNA comprises an N7-methylated guanosine residue joined to the 5'-most residue of the mRNA via a 5'-5' triphosphate linkage. The 5' cap region of an mRNA is considered to include the 5' cap structure itself as well as the first 50 nucleotides adjacent to the cap. The 5' cap region may also be a preferred target region.

Although some eukaryotic mRNA transcripts are directly translated, many contain one or more regions, known as "intron." which are excised from a pre-mRNA transcript to yield one or more mature mRNA. The remaining (and therefore translated) regions are known as "exons" and are spliced together to form a continuous mRNA sequence. mRNA splice sites, i.e., exon-exon or intron-exon junctions, may also be preferred target regions, and are particularly useful in situations where aberrant splicing is implicated in disease, or where an overproduction of a particular mRNA splice product is implicated in disease. Aberrant fusion junctions due to rearrangements or deletions are also preferred targets. Targeting particular exons in alternatively spliced mRNAs may also be preferred. It has also been found that introns can also be effective, and therefore preferred, target regions for antisense compounds targeted, for example, to DNA or pre-mRNA.

The terms "peptidomimetic" and "mimetic" include naturally occurring and synthetic chemical compounds that may have substantially the same structural and functional characteristics of protein regions which they mimic. For connexins these may mimic, for example, the extracellular loops of opposing connexins involved in connexon-connexon docking and cell-cell channel formation.

Peptide analogs with properties analogous to those of the template peptide may be non-peptide drugs. "Peptide mimetics" or "peptidomimetics," which include peptide-based compounds, also include such non-peptide based compounds (Fauchere, *J. Adv. Drug Res.* 15: 29 (1986); Veber and Freidinger; *TINSS;* 392 (1985); and Evans et al., *J. Med. Chem.* 30: 1229 (1987); Beeley N., *Trends Biotechnol.* June; 12(6): 213-6 (1994); Kieber-Emmons T, et al.; *Curr Opin Biotechnol.* August; 8(4): 435-41 (1997). Peptide mimetics that are structurally similar to therapeutically useful peptides may be used to produce an equivalent or enhanced therapeutic or prophylactic effect. Generally, peptidomimetics are structurally identical or similar to a paradigm polypeptide (i.e., a polypeptide that has a biological or pharmacological function or activity), but can also have one or more peptide linkages optionally replaced by a linkage selected from the group consisting of, for example, —CH2NH—, —CH2S-, —CH2-CH2-, —CH═CH— (cis and trans), —COCH2-, —CH(OH) CH2-, and —CH2SO—. The mimetic can be either entirely composed of natural amino acids, or non-natural analogues of amino acids, or, is a chimeric molecule of partly natural peptide amino acids and partly non-natural analogs of amino acids. The mimetic can also comprise any amount of natural amino acid conservative substitutions as long as such substitutions also do not substantially alter mimetic activity. For example, a mimetic composition is within the scope of the invention if it is capable of down-regulating biological actions or activities of connexin proteins or connexons, such as, for example, preventing the docking of connexons to form gap-junction-mediated cell-cell communication, or preventing the opening connexons to expose the cell cytoplasm to the extracellular millieu. Peptidomimetics, mimetic peptides, and connexin modulating peptides encompass those described such peptidomimetics, mimetic peptides, and connexin modulating peptides set forth herein, as well as those as may be known in the art, whether now known or later developed.

The term "composition" is intended to encompass a product comprising one or more ingredients.

The terms "modulator" and "modulation" of connexin activity, as used herein in its various forms, is intended to encompass inhibition in whole or in part of the expression or action or activity of a connexin. Such modulators include small molecules antagonists of connexin function or expression, antisense molecules, ribozymes, triplex molecules, and RNAi polynucleotides, gene therapy methods, etc., and others.

The phrase "percent (%) identity" refers to the percentage of sequence similarity found in a comparison of two or more sequences. Percent identity can be determined electronically using any suitable software, for example. Likewise, "similarity" between two sequences (or one or more portions of either or both of them) is determined by comparing the sequence of one sequence to a second sequence.

"Pharmaceutically acceptable" compounds and other ingredients of a composition or formulation, for example, a carrier, diluent or excipient, are those that are suitable for administration to a recipient thereof.

In general, the term "protein" refers to any polymer of two or more individual amino acids (whether or not naturally occurring) linked via peptide bonds, as occur when the carboxyl carbon atom of the carboxylic acid group bonded to the alpha-carbon of one amino acid (or amino acid residue) becomes covalently bound to the amino nitrogen atom of the amino group bonded to the alpha-carbon of an adjacent amino acid. These peptide bond linkages, and the atoms comprising them (i.e., alpha-carbon atoms, carboxyl carbon atoms (and their substituent oxygen atoms), and amino nitrogen atoms (and their substituent hydrogen atoms)) form the "polypeptide backbone" of the protein. In addition, as used herein, the term "protein" is understood to include the terms "polypeptide" and "peptide" (which, at times, may be used interchangeably herein). Similarly, protein fragments, analogs, derivatives, and variants are may be referred to herein as "proteins," and shall be deemed to be a "protein" unless otherwise indicated. The term "fragment" of a protein refers to a polypeptide comprising fewer than all of the amino acid residues of the protein. A "domain" of a protein is also a fragment, and comprises the amino acid residues of the protein often required to confer activity or function.

The term "stringent conditions" refers to conditions that permit hybridization between polynucleotides. Stringent conditions can be defined by salt concentration, the concentration of organic solvent (for example, formamide), temperature, and other conditions well known in the art. Stringency can be increased by reducing the concentration of salt, increasing the concentration of organic solvents, (for example, formamide), or raising the hybridization temperature. For example, stringent salt concentration will ordinarily be less than about 750 mM NaCl and 75 mM trisodium citrate, preferably less than about 500 mM NaCl and 50 mM trisodium citrate, and most preferably less than about 250 mM NaCl and 25 mM trisodium citrate. Low stringency hybridization can be obtained in the absence of organic solvent, for example, formamide, while high stringency hybridization can be obtained in the presence of an organic solvent (for example, at least about 35% formamide, most preferably at least about 50% formamide). Stringent temperature conditions will ordinarily include temperatures of at least about 30° C., more preferably of at least about 37° C., and most preferably of at least about 42° C. Varying additional parameters, for example, hybridization time, the concentration of detergent, for example, sodium dodecyl sulfate (SDS), and the inclusion or exclusion of carrier DNA, are well known to those skilled in the art. Various levels of stringency are accomplished by combining these various conditions as needed, and are within the skill in the art. Stringent hybridization conditions may also be defined by conditions in a range from about 5° C. to about 20° C. or 25° C. below the melting temperature (Tm) of the target sequence and a probe with exact or nearly exact complementarity to the target. As used herein, the melting temperature is the temperature at which a population of double-stranded nucleic acid molecules becomes half-dissociated into single strands. Methods for calculating the Tm of nucleic acids are well known in the art (see, for example, Berger and Kimmel, Methods In Enzymology, Vol. 152: *Guide To Molecular Cloning Techniques*, San Diego (1987): Academic Press, Inc. and Sambrook et al., Molecular Cloning (1989): A Laboratory Manual, 2nd Ed., Vols. 1-3, Cold Spring Harbor Laboratory). As indicated by standard references, a simple estimate of the Tm value may be calculated by the equation: Tm=81.5+0.41 (% G+C), when a nucleic acid is in aqueous solution at 1 M NaCl (see for example, Anderson and Young, "Quantitative Filter Hybridization" in Nucleic Acid Hybridization (1985)). The melting temperature of a hybrid (and thus the conditions for stringent hybridization) is affected by various factors such as the length and nature (DNA, RNA, base composition) of the probe and nature of the target (DNA, RNA, base composition, present in solution or immobilized, and the like), and the concentration of salts and other components (for example for example, the presence or absence of formamide, dextran sulfate, polyethylene glycol). The effects of these factors are well known and are discussed in standard references in the art, see for example, Sambrook, supra, and Ausubel, supra. Typically, stringent hybridization conditions are salt concentrations less than about 1.0 M sodium ion, typically about 0.01 to 1.0 M sodium ion at pH 7.0 to 8.3, and temperatures at least about 30° C. for short probes (for example, 10 to 50 nucleotides) and at least about 60° C. for long probes (for example, greater than 50 nucleotides). As noted, stringent conditions may also be achieved with the addition of destabilizing agents such as formamide, in which case lower temperatures may be employed. In the present invention, the polynucleotide may be a polynucleotide which hybridizes to the connexin mRNA under conditions of medium to high stringency such as 0.03M sodium chloride and 0.03M sodium citrate at from about 50 to about 60 degrees centigrade.

The term "therapeutically effective amount" means the amount of the subject compound that will elicit a desired response, for example, a biological or medical response of a tissue, system, animal or human that is sought, for example, by a researcher, veterinarian, medical doctor, or other clinician.

"Treatment" refers to both therapeutic treatment and prophylactic or preventive measures. Those in need of treatment include those already with the disorder as well as those in which the disorder is to be prevented.

The term "vector" refers to a nucleic acid molecule amplification, replication, and/or expression vehicle in the form of a plasmid, phage, viral, or other system (be it naturally occurring or synthetic) for the delivery of nucleic acids to cells where the plasmid, phage, or virus may be functional with bacterial, yeast, invertebrate, and/or mammalian host cells. The vector may remain independent of host cell genomic DNA or may integrate in whole or in part with the genomic DNA. The vector will generally but need not contain all necessary elements so as to be functional in any host cell it is compatible with. An "expression vector" is a vector capable of directing the expression of an exogenous polynucleotide, for example, a polynucleotide encoding a binding domain fusion protein, under appropriate conditions.

As described herein, the terms "homology and homologues" include polynucleotides that may be a homologue of sequence in connexin polynucleotide (e.g. mRNA). Such polynucleotides typically have at least about 70% homology, preferably at least about 80%, 90%, 95%, 97% or 99% homology with the relevant sequence, for example over a region of at least about 15, 20, 30, 40, 50, 100 more contiguous nucleotides (of the homologous sequence).

Homology may be calculated based on any method in the art. For example the UWGCG Package provides the BESTFIT program which can be used to calculate homology (for example used on its default settings) (Devereux et al., Nucleic Acids Research 12, p387-395 (1984)). The PILEUP and BLAST algorithms can be used to calculate homology or line up sequences (typically on their default settings), for example as described in Altschul S. F.; *J Mol Evol* 36: 290-300 (1993); Altschul, S. F. et al.; *J Mol Biol* 215: 403-10 (1990). Software for performing BLAST analyses is publicly available through the National Center for Biotechnology Information (http://www.ncbi.nlm.nih.gov/L). This algorithm involves first identifying high scoring sequence pair by identifying short words of length W in the query sequence that either match or satisfy some positive-valued threshold score T when aligned with a word of the same length in a database sequence. T is referred to as the neighborhood word score threshold (Altschul et al., supra). These initial neighborhood word hits act as seeds for initiating searches to find HSPs containing them. The word hits are extended in both directions along each sequence for as far as the cumulative alignment score can be increased. Extensions for the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T and X determine the sensitivity and speed of the alignment. The BLAST program uses as defaults a word length (W) of 11, the BLOSUM62 scoring matrix (see Henikoff and Henikoff Proc. Natl. Acad. Sci. USA 89: 10915-10919 (1992)) alignments (B) of 50, expectation (I) of 10, M=5, N=4, and a comparison of both strands.

The BLAST algorithm performs a statistical analysis of the similarity between two sequences; see e.g., Karlin and Altschul Proc. Natl. Acad. Sci. USA 90: 5873-5787 (1993). One measure of similarity provided by the BLAST algorithm is the smallest sum probability (P(N)), which provides an indication of the probability by which a match between two nucleotide or amino acid sequences would occur by chance. For example, a sequence is considered similar to another sequence if the smallest sum probability in comparison of the first sequence is less than about 1, preferably less than about 0.1, more preferably less than about 0.01, and most preferably less than about 0.001.

The homologous sequence typically differs from the relevant sequence by at least (or by no more than) about 1, 2, 5, 10, 15, 20 or more mutations (which may be substitutions, deletions or insertions). These mutations may be measured across any of the regions mentioned above in relation to calculating homology. The homologous sequence typically hybridizes selectively to the original sequence at a level significantly above background. Selective hybridization is typically achieved using conditions of medium to high stringency (for example 0.03M sodium chloride and 0.03M sodium citrate at from about 50 degrees C. to about 60 degrees C.). However, such hybridization may be carried out under any suitable conditions known in the art (see Sambrook et al., Molecular Cloning: A Laboratory Manual (1989)). For example, if high stringency is required, suitable conditions include 0.2×SSC at 60 degrees C. If lower stringency is required, suitable conditions include 2×SSC at 60 degrees C.

A "cell" means any living cell suitable for the desired application. Cells include eukaryotic and prokaryotic cells.

The term "gene product" refers to an RNA molecule transcribed from a gene, or a polypeptide encoded by the gene or translated from the RNA.

The term "recombinant" refers to a polynucleotide synthesized or otherwise manipulated in vitro (for example, "recombinant polynucleotide"), to methods of using recombinant polynucleotides to produce gene products in cells or other biological systems, or to a polypeptide ("recombinant protein") encoded by a recombinant polynucleotide. Thus, a "recombinant" polynucleotide is defined either by its method of production or its structure. In reference to its method of production, the process refers to use of recombinant nucleic acid techniques, for example, involving human intervention in the nucleotide sequence, typically selection or production. Alternatively, it can be a polynucleotide made by generating a sequence comprising a fusion of two or more fragments that are not naturally contiguous to each other. Thus, for example, products made by transforming cells with any non-naturally occurring vector is encompassed, as are polynucleotides comprising sequence derived using any synthetic oligonucleotide process. Similarly, a "recombinant" polypeptide is one expressed from a recombinant polynucleotide.

A "recombinant host cell" is a cell that contains a vector, for example, a cloning vector or an expression vector, or a cell that has otherwise been manipulated by recombinant techniques to express a protein of interest.

The connexin gene family is diverse, with 20 identified members in the sequenced human genome. Different connexin gene products combine to form gap junctions with different properties, including pore conductance, size selectivity, charge selectivity, voltage gating properties, and chemical gating properties, and are expressed in different tissues, and at different times of development or during disease processes. In recent literature, connexins are most commonly named according to their molecular weights, e.g. Cx26 is the connexin protein of 26 Kd. This can lead to confusion when connexin genes from different species are compared, e.g. human Cx36 is homologous to zebrafish Cx35. As used herein, therefore, it is to be understood that reference to a particular connexin is a reference to all species variants thereof, even if their molecular weights are different. Thus, for example, a reference to "connexin 43" means not only human connexin 43 but to the analogous connexin in each other species, no matter whether they are also 43 Kd. Similarly, reference to a non-human "connexin 43" is a reference to the connexin 43 analog or variant in that species. Thus, for example, reference to "horse connexin 43" is a reference to the relevant analog or variant of human connexin 43 in horse even if it does not have a 43 Kd molecular weight.

Compounds

Compounds described herein are useful for ameliorating, treating, or preventing a variety of disorders and conditions, including but not limited to cardiovascular, inflammatory, neurological, and vascular conditions, as well as wound treatment. The compounds are also useful in pharmaceutical compositions and in connection with medical devices and procedures, including, for example, surgeries, grafting procedures, and organ or tissue transplants. Certain preferred compounds described herein are capable of modulating or affecting the transport of molecules into and out of cells (e.g. blocking or inhibiting). Thus certain anti-connexin compounds described herein modulate cellular communication (e.g. cell to cell). Certain anti-connexin compounds modulate or effect transmission of molecules between the cell cytoplasm and the periplasmic or extracellular space. Such compounds are generally targeted to hemmichannels (connexons), because hemichannels are independently involved in the exchange of small molecules between the cell cytoplasm and an extracellular space or tissue. Thus, a compound provided herein may directly or indirectly reduce coupling between cells or between a cell and an extracellular space or tissue, and the modulation of transport of molecules from a cell into an extracellular space is within the scope of certain compounds and embodiments of the invention.

Any molecule that is capable of eliciting a desired inhibition of the passage (e.g. transport) of molecules through a gap junction or connexin hemichannel may be used in embodiments of the invention. Compounds that modulate the passage of molecules through a gap junction or connexin hemichannel are also provided in particular embodiments (e.g., those that modulate the passage of molecules from the cytoplasm of a cell into an extracellular space). Such compounds may modulate the passage of molecules through a gap junction or connexin hemichannel with or without gap junction uncoupling (blocking the transport of molecules through gap junctions). Such compounds include, for example, proteins and polypeptides, polynucleotides, and any other organic compound, and they may, for example block the function or expression of a gap junction or a hemichannel in whole or in part. For a listing of some gap junction inhibitors, see for example Evans, W. H. and Boitano, S. *Biochem. Soc. Trans.* 29: 606-612 (2001).

Peptide and Polypeptide Connexin Inhibitors

Binding proteins, including peptides, peptide mimetics, antibodies, antibody fragments, and the like, etc., are suitable modulators of gap junctions and hemichannels and gap junction in certain embodiments. Binding proteins include, for example, monoclonal antibodies, polyclonal antibodies, antibody fragments (including, for example, Fab, F(ab')$_2$ and Fv fragments; single chain antibodies; single chain Fvs; and single chain binding molecules such as those comprising, for example, a binding domain, hinge, CH2 and CH3 domains, all as described in WO02/056910 by Ledbetter et al. published Jul. 25, 2002); recombinant antibodies and antibody fragments which are capable of binding an antigenic determinant (i.e., that portion of a molecule, generally referred to as an epitope) that makes contact with a particular antibody or other binding molecule. These binding proteins, including antibodies, antibody fragments, and so on, may be chimeric or humanized or otherwise made to be less immunogenic in the subject to whom they are to be administered, and may be synthesized, produced recombinantly, or produced in expression libraries. Any binding molecule known in the art or later discovered is envisioned, such as those referenced herein and/or described in greater detail in the art. See Harlow, E., and Lane, D., "Antibodies: A Laboratory Manual," Cold Spring Harbor Laboratory, Cold Spring Harbor, N.Y., 349 (1988), incorporated by reference herein. For example, binding proteins include not only antibodies, and the like, but also ligands, receptors, mimetic peptides, or other binding fragments or molecules (for example, produced by phage display) that bind to a target (e.g. connexin, hemichannel, or associated molecules).

Binding molecules will generally have a desired specificity, including but not limited to binding specificity, and desired affinity. Affinity, for example, may be a $K_a$ of greater than or equal to about $10^4 \, M^{-1}$, greater than or equal to about $10^6 \, M^{-1}$, greater than or equal to about $10^7 \, M^{-1}$, greater than or equal to about $10^8 \, M^{-1}$. Affinities of even greater than about $10^8 \, M^{-1}$ are suitable, such as affinities equal to or greater than about $10^9 \, M^{-1}$, about $10^{10} \, M^{-1}$, about $10^{11} \, M^{-1}$, and about $10^{12} \, M^{-1}$. Affinities of binding proteins according to the present invention can be readily determined using conventional techniques, for example those described by Scatchard et al., 1949 *Ann. N.Y. Acad. Sci.* 51: 660.

Peptide inhibitors (e.g., mimetic peptides) of gap junctions and hemichannels are preferred in certain embodiments provided herein. See for example Berthoud, V. M. et al., *Am J. Physiol. Lung Cell Mol. Physiol.* 279: L619-L622 (2000); Evans, W. H. and Boitano, S. *Biochem. Soc. Trans.* 29: 606-612, and De Vriese A. S., et al. *Kidney Int.* 61: 177-185 (2001).

By using data obtained from hydropathy plots, it has been proposed that a connexin contains four-transmembrane-spanning regions and two short extra-cellular loops. Paul D L. *J Cell Biol* 103: 123-134 (1996). The positioning of the first and second extracellular regions of connexin was further characterized by the reported production of anti-peptide antibodies used for immunolocalization of the corresponding epitopes on split gap junctions. Goodenough D. A. *J Cell Biol* 107: 1817-1824 (1988); Meyer R. A., *J Cell Biol* 119: 179-189 (1992).

The extracellular domains of a hemichannel contributed by two adjacent cells "dock" with each other to form complete gap junction channels. Reagents that interfere with the interactions of these extracellular domains will impair cell-to-cell communication. Short peptides corresponding to sequences within the extracellular loops of connexins were reported as inhibiters of intercellular communication. Boitano S. and Evans W. *Am J Physiol Lung Cell Mol Physiol* 279: L623-L630 (2000). The use of peptides as inhibitors of cell-cell channel formation produced by connexin (Cx) 32 expressed in paired *Xenopus* oocytes has been reported. Dahl G, et al., *Biophys J* 67: 1816-1822 (1994). Berthoud, V. M. and Seul, K. H., summarized some of these results. *Am J. Physiol. Lung Cell Mol. Physiol.* 279: L619-L622 (2000). The modulation of hemichannel function by phosphorylation of a tyrosine residue has been reported by Jensen et al. (US2004/0092429), the teachings of which do not encompass the anti-connexin compounds and methods provided herein.

In another aspect, a anti-connexin compound comprises a peptide comprising an amino acid sequence corresponding to a transmembrane region (e.g. $1^{st}$ to $4^{th}$) of a connexin (e.g. connexin 45, 43, 26, 30, 31.1, and 37). In certain embodiments, the anti-connexin compound comprises a peptide comprising an amino acid sequence corresponding to a portion of a transmembrane region of a connexin 45. In certain embodiments, the anti-connexin compound is a peptide having an amino acid sequence that comprises 5 to 20 contiguous amino acids of SEQ ID NO:62, a peptide having an amino acid sequence that comprises 8 to 15 contiguous amino acids of SEQ ID NO:62, or a peptide having an amino acid sequence that comprises 11 to 13 contiguous amino acids of SEQ ID NO:62. Other embodiments are directed to an anti-connexin compound that is a peptide having an amino acid sequence that comprises at least 5, 6, 7, 8, 9, 10, 11, 12, 13, 14, 15, 20, 25, or 30 contiguous amino acids of SEQ ID NO:62. In certain anti-connexin compounds provided herein, the extracellular domains of connexin 45 corresponding to the amino acids at positions 46-75 and 199-228 of SEQ ID NO: 62 are used to develop the particular peptide sequences. Thus, certain peptide described herein have an amino acid sequence corresponding to the regions at positions 46-75 and 199-228 of SEQ ID NO: 62. The peptides need not have an amino acid sequence identical to those portions of SEQ ID NO: 62, and conservative amino acid changes may be made such that the peptides retain binding activity or functional activity in the assays described herein and otherwise known in the art. In other embodiments, peptide target region of the connexin protein other than the extracellular domains (e.g. the portions of SEQ ID NO:62 not corresponding to positions 46-75 and 199-228).

In other embodiments, the anti-connexin compound comprises a peptide comprising an amino acid sequence corresponding to a portion of a transmembrane region of a connexin 43. In certain embodiments, the anti-connexin compound is a peptide having an amino acid sequence that comprises 5 to 20 contiguous amino acids of SEQ ID NO:63, a peptide having an amino acid sequence that comprises 8 to 15 contiguous amino acids of SEQ ID NO:63, or a peptide having an amino acid sequence that comprises 11 to 13 contiguous amino acids of SEQ ID NO:63. Other embodiments are directed to an anti-connexin compound that is a peptide having an amino acid sequence that comprises at least 5, 6, 7, 8, 9, 10, 11, 12, 13, 14, 15, 20, 25, or 30 contiguous amino acids of SEQ ID NO:63. In other anti-connexin compounds, the extracellular domains of connexin 43 corresponding to the amino acids at positions 37-76 and 178-208 of SEQ ID NO: 63 are used to develop the particular peptide sequences. Thus, certain peptide described herein have an amino acid sequence corresponding to the regions at positions 37-76 and 178-208 of SEQ ID NO: 63. The peptides need not have an amino acid sequence identical to those portions of SEQ ID NO: 63, and conservative amino acid changes may be made such that the peptides retain binding activity or functional activity in the assays described herein and otherwise known in the art. In other embodiments, peptide target region of the connexin protein other than the extracellular domains (e.g. the portions of SEQ ID NO:63 not corresponding to positions 37-76 and 178-208).

In certain non-limiting embodiments, the anti-connexin peptides comprise sequences corresponding to a portion of the connexin extracellular domains with conservative amino acid substitutions such that peptides are functionally active anti-connexin compounds. Exemplary conservative amino acid substitutions include for example the substitution of a nonpolar amino acid with another nonpolar amino acid, the substitution of an aromatic amino acid with another aromatic amino acid, the substitution of an aliphatic amino acid with another aliphatic amino acid, the substitution of a polar amino acid with another polar amino acid, the substitution of an acidic amino acid with another acidic amino acid, the substitution of a basic amino acid with another basic amino acid, and the substitution of an ionizable amino acid with another ionizable amino acid.

Exemplary peptides targeted to connexin 43 are shown below in Table 1. M1, 2, 3 and 4 refer to the 1$^{st}$ to 4$^{th}$ transmembrane regions of the connexin 43 protein respectively. E2 refer to the first and second extracellular loops respectively.

TABLE 1

Peptidic Inhibitors of Intercellular Communication (cx43)

| | | |
|---|---|---|
| FEVAFLLIQWI | M3 & E2 | (SEQ ID NO:32) |
| LLIQWYIGFSL | E2 | (SEQ ID NO:33) |
| SLSAVYTCKRDPCPHQ | E2 | (SEQ ID NO:34) |
| VDCFLSRPTEKT | E2 | (SEQ ID NO:35) |
| SRPTEKTIFII | E2 & M4 | (SEQ ID NO:36) |
| LGTAVESAWGDEQ | M1 & E1 | (SEQ ID NO:37) |
| QSAFRCNTQQPG | E1 | (SEQ ID NO:38) |
| QQPGCENVCYDK | E1 | (SEQ ID NO:39) |
| VCYDKSFPISHVR | E1 | (SEQ ID NO:40) |

Table 2 provides additional exemplary connexin peptides used in inhibiting hemichannel or gap junction function. In other embodiments, conservative amino acid changes are made to the peptides or fragments thereof.

TABLE 2

Additional Peptidic Inhibitors of Intercellular Communication (cx32, cx43)

| Connexin | Location | | AA's and Sequence | |
|---|---|---|---|---|
| Cx32 | E1 | 39-7 | AAESVWGDEIKSSFICNTLQPGCNSVCYDHFFPISHVR | (SEQ ID NO: 41) |
| Cx32 | E1 | 41-52 | ESVWGDEKSSFI | (SEQ ID NO: 42) |
| Cx32 | E1 | 52-63 | ICNTLQPGCNSV | (SEQ ID NO: 43) |
| Cx32 | E1 | 62-73 | SVCYDHFFPISH | (SEQ ID NO: 44) |
| Cx32 | E2 | 164-188 | RLVKCEAFPCPNTVDCFVSRPTEKT | (SEQ ID NO: 45) |
| Cx32 | E2 | 166-177 | VKCEAFPCPNTV | (SEQ ID NO: 46) |
| Cx32 | E2 | 177-188 | VDCFVSRPTEKT | (SEQ ID NO: 47) |
| Cx32 | E1 | 63-75 | VCYDHFFPISHVR | (SEQ ID NO: 48) |
| Cx32 | E1 | 43-59 | VWGDEKSSFICNTLQPGY | (SEQ ID NO: 49) |
| Cx32 | E1 | 46-59 | DEKSSFICNTLQPGY | (SEQ ID NO: 50) |
| Cx32 | E2 | 182-192 | SRPTEKTVFTV | (SEQ ID NO: 51) |
| Cx32/ Cx43 | E2 | 182-188 201-207 | SRPTEKT | (SEQ ID NO: 52) |
| Cx43 | E1 | 64-76 | VCYDKSFPISHVR | (SEQ ID NO: 53) |
| Cx43 | E2 | 201-211 | SRPTEKTIFII | (SEQ ID NO: 54) |
| Cx32 | E1 | 52-63 | ICNTLQPGCNSV | (SEQ ID NO: 55) |
| Cx40 | E2 | 177-192 | FLDTLHVCRRSPCPHP | (SEQ ID NO: 56) |
| Cx43 | E2 | 180-195 | SLSAVYTCKRDPCPHQ | (SEQ ID NO: 57) |
| Cx43 | E1 | 64-76 | VCYDKSFPISHVR | (SEQ ID NO: 58) |
| Cx43 | E2 | 201-211 | SRPTEKTIFII | (SEQ ID NO: 59) |
| Cx43 | E2 | 188-205 | KRDPCHQVDCFLSRPTEK | (SEQ ID NO: 60) |

Table 3 provides the extracellular loops for connexin family members which are used to develop peptide inhibitors described herein. The peptides and provided in Table 3, and fragments thereof are used as peptide inhibitors in certain non-limiting embodiments. In other non-limiting embodiments, peptides comprising from about 8 to about 15, of from about 11 to about 13 amino contiguous amino acids acids of the petides in this Table are peptide inhibitors of the invention. In other embodiments, conservative amino acid changes are made to the peptides or fragments thereof. See Boitano S. and Evans W. *Am J Physiol Lung Cell Mol Physiol* 279: L623-L630 (2000).

NO:35 and peptide SEQ ID NO:36 shown in bold. Note that last 4 amino acids of peptide SEQ ID NO:36 are part of the fourth membrane domain. Table 4 provides the extracellular domain for connexin family members which are used to develop peptide inhibitors described herein. The peptides and provided in Table 4, and fragments thereof, are used as peptide inhibitors in certain non-limiting embodiments. In other non-limiting embodiments, peptides comprising from about 8 to about 15, of from about 11 to about 13 amino contiguous amino acids acids of the petides in this Table are peptide inhibitors of the invention. In other embodiments, conserva-

TABLE 3

Extracellular loops for various connexin family members

E1

| | | |
|---|---|---|
| huCx26 | KEVWGDEQADFVCNTLQPGCKNVCYDHYFPISHIR | (SEQ ID NO: 66) |
| huCx30 | QEVWGDEQEDFVCNTLQPGCKNVCYDHFFPVSHIR | (SEQ ID NO: 69) |
| huCx30.3 | EEVWDDEQKDFVCNTKQPGCPNVCYDEFFPVSHVR | (SEQ ID NO: 70) |
| huCx31 | ERVWSDEQKDFDCNTKQPGCTNVCYDNYFPISNIR | (SEQ ID NO: 71) |
| huCx31.1 | ERVWSDDHKDFDCNTRQPGCSNVCFDEFFPVSHVR | (SEQ ID NO: 72) |
| huCx32 | ESVWGDEKSSFICNTLQPGCNSVCYDQFFPISHVR | (SEQ ID NO: 73) |
| huCx36 | ESVWGDEQSDFECNTAQPGCTNVCYDQAFPISHIR | (SEQ ID NO: 74) |
| huCx37 | ESVWGDEQSDFECNTAQPGCTNVCYDQAFPISHIR | (SEQ ID NO: 75) |
| huCx40.1 | RPVYQDEQERFVCNTLQPGCANVCYDVFSPVSHLR | (SEQ ID NO: 76) |
| hUCX43 | ESAWGDEQSAFRCNTQQPGCENVCYDKSFPISHVR | (SEQ ID NO: 77) |
| huCx46 | EDVWGDEQSDFTCNTQQPGCENVCYDRAFPISHVR | (SEQ ID NO: 78) |
| huCx46.6 | EAIYSDEQAKFTCNTRQPGCDNVCYDAFAPLSHVR | (SEQ ID NO: 79) |
| huCx40 | ESSWGDEQADFRCDTIQPGCQNVCTDQAFPISHIR | (SEQ ID NO: 80) |
| hUCX45 | GESIYYDEQSKFVCNTEQPGCENVCYDAFAPLSHVR | (SEQ ID NO: 81) |

E2

| | | |
|---|---|---|
| huCx26 | MYVFYVMYDGFSMQRLVKCNAWPCPNTVDCFVSRPTEKT | (SEQ ID NO: 82) |
| huCx30 | MYVFYFLYNGYHLPWVLKCGIDPCPNLVDCFISRPTEKT | (SEQ ID NO: 83) |
| buCx30.3 | LYIFHRLYKDYDMPRVVACSVEPCPHTVDCYISRPTEKK | (SEQ ID NO: 84) |
| huCx31 | LYLLHTLWHGFNMPRLVQCANVAPCPNIVDCYIARPTEKK | (SEQ ID NO: 85) |
| hUCX31.1 | LYVFHSFYPKYILPPVVKCHADPCPNIVDCFISKPSEKN | (SEQ ID NO: 86) |
| huCx32 | MYVFYLLYPGYAMVRLVKCDVYPCPNTVDCFVSRPTEKT | (SEQ ID NO: 87) |
| huCx36 | LYGWTMEPVFVCQRAPCPYLVDCFVSRPTEKT | (SEQ ID NO: 88) |
| huCx37 | LYGWTMEPVFVCQRAPCPYLVDCFVSRPTEKT | (SEQ ID NO: 89) |
| huCx40.1 | GALHYFLFGFLAPKKFPCTRPPCTGVVDCYVSRPTEKS | (SEQ ID NO: 90) |
| huCx43 | LLIQWYIYGFSLSAVYTCKRDPCPHQVDCFLSRPTEKT | (SEQ ID NO: 91) |
| huCx46 | IAGQYFLYGFELKPLYRCDRWPCPNTVDCFISRPTEKT | (SEQ ID NO: 92) |
| huCx46.6 | LVGQYLLYGFEVRPFFPCSRQPCPHVVDCFVSRPTEKT | (SEQ ID NO: 93) |
| huCx40 | IVGQYFIYGIFLTTLHVCRRSPCPHPVNCYVSRPTEKN | (SEQ ID NO: 94) |
| huCx45 | LIGQYFLYGFQVHPFYVCSRLPCHPKIDCFISRPTEKT | (SEQ ID NO: 95) |

Sequences of the E2 domain of different connexin isotypes are shown with amino acids homologous to peptide SEQ ID NO:35 and peptide SEQ ID NO:36 shown in bold.

tive amino acid changes are made to the peptides or fragments thereof.

TABLE 4

Extracellular domains

| | | |
|---|---|---|
| Peptide | VDCFLSRPTEKT | (SEQ ID NO: 35) |
| Peptide | SRPTEKTIFII | (SEQ ID NO: 36) |
| huCx43 | LLIQWYIYGFSLSAVYTCKRDPCPHQVDCFLSRPTEKTIFII | (SEQ ID NO: 96) |
| huCx26 | MYVFYVMYDGFSMQRLVKCNAWPCPNTVDCFVSRPTEKTVFTV | (SEQ ID NO: 97) |
| huCx30 | YVFYFLYNGYHLPWVLKCGIDPCPNLVDCFISRPTEKTVFTI | (SEQ ID NO: 98) |
| huCX30.3 | LYIFHRLYKDYDMPRVVACSVEPCPHTVDCYISRPTEKKVFTY | (SEQ ID NO: 99) |
| huCx31 | LYLLHTLWHGFNMPRLVQCANVAPCPNIVDCYIARPTEKKTY | (SEQ ID NO: 100) |
| huCx31.1 | LYVFHSFYPKYILPPVVKCHADPCPNIVDCFISKPSEKNIFTL | (SEQ ID NO: 101) |
| hucx32 | MYVFYLLYPGYAMVRLVKCDVYPCPNTVDCFVSRPTEKTVFTV | (SEQ ID NO: 102) |
| huCx36 | LYGWTMEPVFVCQRAPCPYLVDCFVSRPTEKTIFII | (SEQ ID NO: 103) |

TABLE 4-continued

Extracellular domains

| | | |
|---|---|---|
| huCx37 | LYGWTMEPVFVCQRAPCPYLVDCFVSRPTEKTIFII | (SEQ ID NO: 104) |
| huCx40.1 | GALHYFLFGFLAPKKFPCTRPPCTGVVDCYVSRPTEKSLLML | (SEQ ID NO: 105) |
| huCx46 | IAGQYFLYGFELKPLYRCDRWPCPNTVDCFISRPTEKTIFII | (SEQ ID NO: 106) |
| huCx46.6 | LVGQYLLYGFEVRPFFPCSRQPCPHVVDCFVSRPTEKTVFLL | (SEQ ID NO: 107) |
| huCX40 | IVGQYFIYGIFLTTLHVCRRSPCPHPVNCYVSRPTEKNVFIV | (SEQ ID NO: 108) |
| huCx45 | LIGQYFLYGFQVHPFYVCSRLPCHPKIDCFISRPTEKTIFLL | (SEQ ID NO: 109) |

Table 5 provides peptides inhibitors of connexin 40 shown with reference to the extracellular loops (E1 and E2) of connexin 40. The bold amino acids are directed to the transmembrane regions of connexin 40.

TABLE 5

Cx40 peptide inhibitors

E1

| | |
|---|---|
| LGTAAESSWGDEQADFRCDTIQPGCQNVCTDQAFPISHIRFWVLQ | (SEQ ID NO: 110) |
| LGTAAESSWGDEQA | (SEQ ID NO: 111) |
| DEQADFRCDTIQP | (SEQ ID NO: 112) |
| TIQPGCQNVCTDQ | (SEQ ID NO: 113) |
| VCTDQAFPISHIR | (SEQ ID NO: 114) |
| AFPISHIRFWVLQ | (SEQ ID NO: 115) |

E2

| | |
|---|---|
| MEVGFIVGQYFIYGIFLTTLHVCRRSPCPHPVNCYVSRPTEKNVFIV | (SEQ ID NO: 116) |
| MEVGFIVGQYF | (SEQ ID NO: 117) |
| IVGQYFIYGIFL | (SEQ ID NO: 118) |
| GIFLTTLHVCRRSP | (SEQ ID NO: 119) |
| RRSPCPHPVNCY | (SEQ ID NO: 120) |
| VNCYVSRPTEKN | (SEQ ID NO: 35) |
| SRPTEKNVFIV | (SEQ ID NO: 36) |

Table 6 provides peptides inhibitors of connexin 45 shown with reference to the extracellular loops (E1 and E2) of connexin 45. The bold amino acids are directed to the transmembrane regions of connexin 45

TABLE 6

Cx45 peptide inhibitors

E1

| | |
|---|---|
| LTAVGGESIYYDEQSKFVCNTEQPGCENVCYDAPAPLSHVRFWVFQ | (SEQ ID NO: 121) |
| LTAVGGESIYYDEQS | (SEQ ID NO: 122) |
| DEQSKFVCNTEQP | (SEQ ID NO: 123) |
| TEQPGCENVCYDA | (SEQ ID NO: 124) |
| VCYDAFAPLSHVR | (SEQ ID NO: 125) |
| APLSHVRFWVFQ | (SEQ ID NO: 126) |

E2

| | |
|---|---|
| FEVGFLIGQYFLYGFQVHPFYVCSRLPCHPKIDCFISRPTEKTIFLL | (SEQ ID NO: 127) |
| FEVGFLIGQYF | (SEQ ID NO: 128) |
| LIGQYFLYGFQV | (SEQ ID NO: 129) |
| GFQVHPFYVCSRLP | (SEQ ID NO: 130) |
| SRLPCHPKIDCF | (SEQ ID NO: 131) |
| IDCFISRPTEKT | (SEQ ID NO: 36) |
| SRPTEKTIFLL | (SEQ ID NO: 37) | gap junctions. While not wishing to be bound to any particular theory or mechanism, it is also believed that certain mimetic peptides (e.g. VCYDKSFPISHVR, SEQ ID NO: 53) block hemichannels without causing uncoupling of gap junctions (See Leybeart et al., *Cell Commun Adhes* 10: 251-257 (2003)). The peptide SRPTEKTIFII (SEQ ID NO: 54) may also be used, for example to block hemichannels without uncoupling of gap junctions. The peptide SRGGEKNVFIV (SEQ ID NO: 61) may be used that as a control sequence (De Vriese et al., *Kidney Internat.* 61: 177-185 (2002)). Examples In certain embodiments it is preferred that certain peptide inhibitors block hemichannels without a desired blocking of of peptide inhibitors for connexin 45 YVCSRLPCHP (SEQ ID NO:132), QVHPFYVCSRL (SEQ ID NO:133), FEVGFLIGQYFLY (SEQ ID NO:134), GQYFLYGFQVHP (SEQ ID NO:135), GFQVHPFYVCSR (SEQ ID NO:136), AVGGESIYYDEQ (SEQ ID NO:137), YDEQSKFVCNTE (SEQ ID NO:138), NTEQPGCENVCY (SEQ ID NO:139), CYDAFAPLSHVR (SEQ ID NO:140), FAPLSHVRFWVF (SEQ ID NO:141) and LIGQY SEQ ID NO:142), QVHPF (SEQ ID NO:143), YVCSR (SEQ ID NO:144), SRLPC (SEQ ID NO:145), LPCHP (SEQ ID NO:146) and GESIY (SEQ ID NO:147), YDEQSK (SEQ ID NO: 148), SKFVCN (SEQ ID NO:149), TEQPGCEN (SEQ ID NO:150), VCYDAFAP (SEQ ID NO:151), LSHVRFWVFQ (SEQ ID NO:152) The peptides may only be 3 amino acids in length, including SRL, PCH, LCP, CHP, IYY, SKF, QPC, VCY, APL, HVR, or longer, for example: LIQYFLYGFQVHPF (SEQ ID NO:153), VHPFYCSRLPCHP (SEQ ID NO:154), VGGESIYYDEQSKFVCNTEQPG (SEQ ID NO:155), TEQPGCENVCYDAFAPLSHVRF (SEQ ID NO:156), AFAPLSHVRFWVFQ (SEQ ID NO: 157).

In certain non-limiting embodiments, peptides comprising from about 3 to about 30, about 8 to about 15, of from about 11 to about 13 contiguous amino acids of the peptides in Formula 1A are peptide inhibitors of the invention.

Formula 1A $X_1$-$X_2$-$X_3$-$X_4$-$X_5$-Gly-$X_7$-$X_8$-$X_9$-$X_{10}$-$X_{11}$-$X_{12}$-$X_{13}$-$X_{14}$-$X_{15}$-$X_{16}$-$X_{17}$-$X_{18}$-Cys-$X_{20}$-$X_{21}$-$X_{22}$-$X_{23}$-Pro-Gly-$X_{26}$-$X_{27}$-$X_{28}$-$X_{29}$-Cys-$X_{31}$-$X_{32}$-$X_{33}$-$X_{34}$-$X_{35}$-Pro-$X_{37}$-$X_{38}$-$X_{39}$-$X_{40}$-$X_{41}$-$X_{42}$-$X_{43}$-$X_{44}$-$X_{45}$-$X_{46}$ (Formula 1A)

wherein $X_1$ and $X_{37}$ are independently selected from a group consisting of Leu, Ile, Met and Val; $X_2$ is selected from a group consisting of Thr, Asn, Ser and Ala; $X_3$ is selected from a group consisting of Ala, Ser, Gly and Thr; $X_4$, $X_{18}$, $X_{29}$, $X_{40}$ and $X_{44}$ are independently selected from a group consisting of Val, Ile, Met and Leu; Xs is selected from a group consisting of Gly, Glu, Asp, Ser and Ala; $X_7$, $X_{13}$, $X_{22}$ and $X_{27}$ are independently selected from a group consisting of Glu, Asp, Gln and Lys; $X_8$, $X_{15}$ and $X_{38}$ are independently selected from a group consisting of Ser, Ala, Asn and Thr; $X_9$ is selected from a group consisting of Ile, Val, Leu and Met; $X_{10}$, $X_{11}$ and $X_{31}$ are independently selected from a group consisting of Tyr, Phe, Trp and His; $X_{12}$ and $X_{32}$ are independently selected from a group consisting of Asp, Glu and Asn; $X_{14}$ and $X_{23}$ are independently selected from a group consisting of Gln, Glu, Arg and Lys; $X_{16}$ is selected from a group consisting of Lys, Arg, Glu and Gln; $X_{17}$ and $X_{34}$ are independently selected from a group consisting of Phe, Tyr and Trp; $X_{20}$ and $X_{28}$ are independently selected from a group consisting of Asn, Ser, His and Asp; $X_{21}$ is selected from a group consisting of Thr and Ser; $X_{33}$ and $X_{35}$ are independently selected from a group consisting of Ala and Ser; $X_{39}$ is selected from a group consisting of His, Tyr and Asn;

$X_{41}$ is selected from a group consisting of Arg, Lys and Gln; $X_{42}$ and $X_{45}$ are independently selected from a group consisting of Phe, Tyr, Cys, Leu and Tyr; $X_{43}$ is selected from a group consisting of Trp, Tyr, Arg, Lys, Cys and Phe; and $X_{46}$ is selected from a group consisting of Gln, His, Glu, Lys, Arg, Asn and Asp.

In certain non-limiting embodiments, peptides comprising from about 3 to about 30, about 8 to about 15, of from about 11 to about 13 contiguous amino acids of the peptides in Formula 1B are peptide inhibitors of the invention.

Formula 1B:

$X_1$-$X_2$-$X_3$-$X_4$-$X_5$-$X_6$-$X_7$-Gly-$X_9$-$X_{10}$-$X_{11}$-$X_{12}$-$X_{13}$-Gly-$X_{15}$-$X_{16}$-$X_{17}$-$X_{18}$-Pro-$X_{20}$-$X_{21}$-$X_{22}$-Cys- $X_{24}$-$X_{25}$-$X_{26}$-Pro-Cys-$X_{29}$-P-$X_{31}$-$X_{32}$-$X_{33}$-Cys-$X_{35}$-$X_{36}$-$X_{37}$-$X_{38}$-Pro-$X_{40}$-$X_{41}$-$X_{42}$-$X_{43}$-$X_{44}$-$X_{45}$-$X_{46}$-$X_{47}$-$X_{48}$ (Formula 1B)

and $X_{22}$ are independently selected from a group consisting of Val, Ile, Met and Leu; $X_4$ is selected from a group consisting of Gly, Glu, Asp, Ser and Ala; $X_6$, $X_{12}$ and $X_{26}$ are independently selected from a group consisting of Leu, Ile, Met and Val; $X_7$, $X_{32}$, $X_{36}$, $X_{44}$ and $X_{48}$ are independently selected from a group consisting of Ile, Val, Leu and Met; $X_9$, and $X_{16}$ are independently selected from a group consisting of Gln, Glu, Arg and Lys; $X_{10}$, $X_{13}$ and $X_{21}$ are independently selected from a group consisting of Tyr, Phe, Trp and His; $X_{11}$, $X_{15}$, $X_{20}$ and $X_{35}$ are independently selected from a group consisting of Phe, Tyr and Trp; $X_{18}$ and $X_{29}$ are independently selected from a group consisting of His, Tyr and Asn; $X_{24}$ and $X_{37}$ are independently selected from a group consisting of Ser, Ala, Asn and Thr; $X_{25}$ and $X_{38}$ are independently selected from a group consisting of Arg, Lys and Gln; $X_{31}$ and $X_{42}$ are independently selected from a group consisting of Lys, Arg, Glu and Gln; $X_{33}$ is selected from a group consisting of Asp, Glu and Asn; $X_{40}$ and $X_{43}$ are independently selected from a group consisting of Thr and Ser; $X_{41}$ is selected from a group consisting of Glu, Asp, Gln and Lys; and $X_{46}$ and $X_{47}$ are independently selected from a group consisting of Val, Ile, Met, Leu and Phe.

In certain non-limiting embodiments, peptides comprising from about 3 to about 30, from about 8 to about 15, of from about 11 to about 13 contiguous amino acids of the peptides in Formula 2A are peptide inhibitors of the invention.

Formula 2A $X_1$-$X_2$-$X_3$-$X_4$-$X_5$-$X_6$-$X_7$-$X_8$-$X_9$-Gly-$X_{11}$-$X_{12}$-$X_{13}$-$X_{14}$-$X_{15}$-$X_{16}$-$X_{17}$-Cys-$X_{19}$-$X_{20}$-$X_{21}$-$X_{22}$-Pro-Gly-Cys-$X_{26}$-$X_{27}$-$X_{28}$-Cys-$X_{30}$-$X_{31}$-$X_{32}$-$X_{33}$-$X_{34}$-Pro-$X_{36}$-$X_{37}$-$X_{38}$-$X_{39}$-$X_{40}$-$X_{41}$-$X_{42}$-$X_{43}$-$X_{44}$-$X_{45}$ (Formula 2A)

wherein $X_1$ and $X_{44}$ are independently selected from a group consisting of Leu, Ile, Met, Val and Pro; $X_2$ is selected from a group consisting of Gly, Glu, Asp, Ser and Ala; $X_3$ is selected from a group consisting of Thr, Ser, Asn and Ala; $X_4$ is selected from a group consisting of Ala, Ser, Gly and Thr; $X_5$, $X_{28}$, $X_{39}$ and $X_{43}$ are independently selected from a group consisting of Val, Ile, Met and Leu; $X_6$, $X_{12}$, and $X_{26}$ are independently selected from a group consisting of Glu, Asp, Gln and Lys; $X_7$, $X_{14}$, $X_{33}$ and $X_{37}$ are independently selected from a group consisting of Ser, Ala, Asn and Thr; $X_8$ and $X_{15}$ are independently selected from a group consisting of Ala and Ser; $X_9$ is selected from a group consisting of Trp, Tyr and Phe; $X_{11}$ and $X_{31}$ are independently selected from a group consisting of Asp, Glu and Asn; $X_{13}$, $X_{21}$, and $X_{22}$ are independently selected from a group consisting of Gln, Glu, Arg and Lys; $X_{16}$ and $X_{34}$ are independently selected from a group consisting of Phe, Tyr and Trp; $X_{17}$ and $X_{40}$ are independently selected from a group consisting of Arg, Lys and Gln; $X_{19}$ and $X_{27}$ are independently selected from a group consisting of Asn, Ser, His and Asp; $X_{20}$ is selected from a group consisting of Thr and Ser; $X_{30}$ is selected from a group consisting of Tyr, Phe, Trp and His; $X_{32}$ is selected from a group consisting of Lys, Arg, Glu and Gln; $X_{36}$ is selected from a group consisting of Ile, Val, Leu and Met; $X_{38}$ is selected from a group consisting of His, Tyr and Asn; $X_{41}$ is selected from a group consisting of Phe, Tyr, Cys, Leu and Trp; $X_{42}$ is selected from a group consisting of Trp, Tyr, Phe, Arg, Lys and Cys; and $X_{45}$ is selected from a group consisting of Gln, His, Glu, Lys, Arg, Asn and Asp.

In certain non-limiting embodiments, peptides comprising from about 3 to about 30, from about 8 to about 15, of from about 11 to about 13 contiguous amino acids of the peptides in Formula 2B are peptide inhibitors of the invention.

Formula 2B $X_1$-$X_2$-$X_3$-$X_4$-$X_5$-$X_6$-$X_7$-$X_8$-$X_9$-$X_{10}$-$X_{11}$-$X_{12}$-$X_{13}$-Gly-$X_{15}$-$X_{16}$-$X_{17}$-$X_{18}$-$X_{19}$-$X_{20}$-$X_{21}$-$X_{22}$-Cys-$X_{24}$-$X_{25}$-$X_{26}$-Pro-Cys-Pro-$X_{30}$-$X_{31}$-$X_{32}$-$X_{33}$-Cys-$X_{35}$-$X_{36}$-$X_{37}$-$X_{38}$-Pro-$X_{40}$-$X_{41}$-$X_{42}$-$X_{43}$-$X_{44}$-$X_{45}$-$X_{46}$-$X_{47}$-$X_{48}$ (Formula 2B)

wherein $X_1$, $X_5$ and $X_{45}$ are independently selected from a group consisting of Phe, Tyr, Cys, Trp and Leu; $X_2$ is selected from a group consisting of Glu, Asp, Gln, Gly, His, Arg, Asn and Lys; $X_3$, $X_{17}$ and $X_{22}$ are independently selected from a group consisting of Val, Ile, Met and Leu; $X_4$ is selected from a group consisting of Gly, Glu, Asp, Ser and Ala; $X_6$, $X_{12}$ and $X_{26}$ are independently selected from a group consisting of Leu, Ile, Met and Val; $X_7$, $X_{32}$, $X_{36}$, $X_{44}$ and $X_{48}$ are independently selected from a group consisting of Ile, Val, Leu and Met; $X_9$, and $X_{16}$ are independently selected from a group consisting of Gln, Glu, Arg and Lys; $X_{10}$, $X_{13}$ and $X_{21}$ are independently selected from a group consisting of Tyr, Phe, Trp and His; $X_{11}$, $X_{15}$, $X_{20}$ and $X_{35}$ are independently selected from a group consisting of Phe, Tyr and Trp; $X_{18}$ and $X_{29}$ are independently selected from a group consisting of His, Tyr and Asn; $X_{24}$ and $X_{37}$ are independently selected from a group consisting of Ser, Ala, Asn and Thr; $X_{25}$ and $X_{38}$ are independently selected from a group consisting of Arg, Lys and Gln; $X_{31}$ and/or $X_{42}$ is selected from a group consisting of Lys, Arg, Glu and Gln; $X_{33}$ is selected from a group consisting of Asp, Glu and Asn; $X_{40}$ and $X_{43}$ are independently selected from a group consisting of Thr and Ser; $X_{41}$ is selected from a group consisting of Glu, Asp, Gln and Lys; and $X_{46}$ and $X_{47}$ are independently selected from a group consisting of Val, Ile, Met, Leu and Phe.

Affinity Binding Assays for Peptides

Pull-down assays may be used as to verify protein-peptide interaction. In this assay the peptide can be tagged, with a protein-reactive or fusion tag i.e. GST (Glutathione-S-Transferase), which will be used to capture and 'pull-down' a protein-binding partner via attachment to a cellulose, agarose or nickel bead. Following elution of the complex utilizing either SDS-PAGE loading buffer or alternatively competitive analyte elution, the complex is visualised by running on an SDS-PAGE gel and using Western Analysis detection methods. Art known methods of performing binding assays are described in Einarson, M. B. and Orlinick, J. R., "Identification of Protein-Protein Interactions with Glutathione S-Transferase Fusion Proteins" In Protein-Protein Interactions: A Molecular Cloning Manual, Cold Spring Harbor Laboratory Press, pp. 37-57 (2002), Einarson, M. B. Detection of Protein-Protein Interactions Using the GST Fusion Protein Pulldown Technique. In Molecular Cloning: A Laboratory Manual, 3rd Edition, Cold Spring Harbor Laboratory Press, pp. 18.55-18.59 (2001), and Vikis, H. G. and Guan, K. L. Glutathione-S-Transferase-Fusion Based Assays for Studying Protein-Protein Interactions. In Protein-Protein Interactions, Methods and Applications, Methods in Molecular Biology, 261, Fu, H. Ed. Humana Press, Totowa, N.J., pp. 175-186 (2004), each of which is incorporated by reference in its entirety.

Interactions and affinity of proteins and peptides can be assessed using surface plasmon resonance technology which enables these interactions to be measured in real time (available through BIAcore). This approach has the advantage of detecting low affinity protein interactions. Surface plasmon resonance relies on an optical phenomenon that is used to measure changes in the solution concentration of molecules at a biospecific surface. This signal arises in thin metal films under conditions of total internal reflection. This signal depends on the refractive index of solutions in contact with the surface. Molecules in solution exhibit changes in refractive index and thus give rise to a measurable signal if a biospecific interaction occurs. Typically, the protein is immobilized by one of several possible methods onto a carboxymethylated dextran-gold surface. The interacting peptide of interest is injected over the surface and the kinetics of binding are measured in real time. Art known methods of performing binding assays are described in Schuck, P., "Reliable determination of binding affinity and kinetics using surface plasmon resonance biosensors", *Current Opinion in Biotechnology*, 8(4):498-502 (1997), and Zhang, X., Oglesbee, M. "Use of surface plasmon resonance for the measurement of low affinity binding interactions between HSP72 and measles virus nucleocapsid protein." *Biological Procedures Online*. 5(1): 170-181 (2003).

Functional Assays

Functional assays can be used to determine whether mimetic peptides are able to block the opening of hemichannels. HeLa human cervical cancer cell line is stably transfected with Cx43, Cx45, or another particular connexin of interest. The cells are incubated in a zero calcium solution (HBSS-HEPES containing 1 mM EGTA), which has been shown to activate connexin hemichannels (See Braet, K., et al., "Pharmacological sensitivity of ATP release triggered by photoliberation of inositol-1,4,5-trisphosphate and zero extracellular calcium in brain endothelial cells. Journal of Cellular Physiology", 197(2): p. 205-213 (2003), DeVries, S. H. and E. A. Schwartz, "Hemi-gap-junction channels in solitary horizontal cells of the catfish retina." Journal of Physiology, 445: p. 201-230 (1992), and Li, H., et al., Properties and regulation of gap junctional hemichannels in the plasma membranes of cultured cells. Journal of Cell Biology, 134(4): p. 1019-1030 (1996)). Cells will then be incubated for 30 minutes in a solution of HBSS-HBEPES containing 1 mM EGTA and 2 mM propidium iodide. Propidium iodide is a fluorescent dye which is membrane impermeable but because of its small molecular weight is able to enter through hemichannels. Propidium iodide uptake will be determined using fluorescence microscopy. Cells will be incubated with propidium iodide in the presence of the mimetic peptides to determine if these can prevent dye uptake.

Polynucleotide and Nucleic Acid Connexin Inhibitors

Antisense compounds may also be used in certain embodiments. Antisense compounds include polynucleotides such as antisense deoxynucleotides, morpholino nucleotides, RNAi and deoxyribozymes targeted to specific connexin isoforms which result in reduced translation of the protein isoform and interfere with the function of cell gap junctions. Administration of these antisense compounds results in the reduction of gap-junction-mediated cell-cell communication at the site at which connexin expression is down-regulated.

Antisense compounds, for example, have been used for the modulation of the expression for genes implicated in viral, fungal and metabolic diseases. U.S. Pat. No. 5,166,195, proposes oligonucleotide inhibitors of HIV. U.S. Pat. No. 5,004,810 proposes oligomers for hybridizing to herpes simplex virus Vmw65 mRNA and inhibiting replication.

Antisense compounds are provided, including oligonucleotides, for use in modulating the function of nucleic acid molecules encoding connexins, ultimately modulating the amount of connexins produced. This is accomplished by providing, for example, oligonucleotides which specifically hybridize with nucleic acids, preferably mRNA, encoding connexins.

An antisense oligonucleotide or polynucleotide may, for example, hybridize to all or part of a connexin mRNA. Typically the antisense polynucleotide hybridizes to the ribosome binding region or the coding region of the connexin mRNA. The polynucleotide may be complementary to all of or a region of a connexin mRNA. For example, the polynucleotide may be the exact complement of all or a part of connexin mRNA. The antisense polynucleotide may inhibit transcription and/or translation of the connexin. Preferably the polynucleotide is a specific inhibitor of transcription and/or translation of the connexin gene, and does not inhibit transcription and/or translation of other genes. The product may bind to the connexin gene or mRNA either (i) 5' to the coding sequence, and/or (ii) to the coding sequence, and/or (iii) 3' to the coding sequence. Generally the antisense polynucleotide will cause the expression of connexin mRNA and/or protein in a cell to be reduced. The antisense polynucleotide is generally antisense to the connexin mRNA. Such a polynucleotide may be capable of hybridizing to the connexin mRNA and may inhibit the expression of connexin by interfering with one or more aspects of connexin mRNA metabolism including transcription, mRNA processing, mRNA transport from the nucleus, translation or mRNA degradation. The antisense polynucleotide typically hybridizes to the connexin mRNA to form a duplex which can cause direct inhibition of translation and/or destabilization of the mRNA. Such a duplex may be susceptible to degradation by nucleases.

Hybridization of antisense oligonucleotides with mRNA interferes with one or more of the normal functions of mRNA. The functions of mRNA to be interfered with include all vital functions such as, for example, translocation of the RNA to the site of protein translation, translation of protein from the RNA, splicing of the RNA to yield one or more mRNA species, and catalytic activity which may be engaged in by the RNA. Binding of specific protein(s) to the RNA may also be interfered with by antisense oligonucleotide hybridization to the RNA.

The overall effect of interference with mRNA function is modulation of expression of connexin. In the context of this invention "modulation" includes either inhibition or stimulation; i.e., either a decrease or increase in expression. This modulation can be measured in ways which are routine in the art, for example by Northern blot assay of mRNA expression, or reverse transcriptase PCR, as taught in the examples of the instant application or by Western blot or ELISA assay of protein expression, or by an immunoprecipitation assay of protein expression. Effects on cell proliferation or tumor cell growth can also be measured, as taught in the examples of the instant application. Inhibition is presently preferred.

Once the target site or sites have been identified, oligonucleotides are chosen which are sufficiently complementary to the target, i.e., hybridize sufficiently well and with sufficient specificity, to give the desired modulation. The antisense nucleic acids (DNA, RNA, modified, analogues, and the like) can be made using any suitable method for producing a nucleic acid. Oligodeoxynucleotides directed to other connexin proteins can be selected in terms of their nucleotide sequence by any art recognized approach, such as, for example, the computer programs MacVector and OligoTech (from Oligos etc. Eugene, Oreg., USA). Equipment for such synthesis is available through several vendors including MacVector and OligoTech (from Oligos etc. Eugene, Oreg., USA). For general methods relating to antisense polynucleotides, see Antisense RNA and DNA, D. A. Melton, Ed., Cold Spring Harbor Laboratory, Cold Spring Harbor, N.Y. (1988)). See also, Dagle et al., *Nucleic Acids Research*, 19: 1805 (1991). For antisense therapy, see, for example, Uhlmann et al., *Chem. Reviews*, 90: 543-584 (1990). Typically, at least a portion of the nucleotide sequence is known for connexins in which the inhibition of expression is desired. Polynucleotide targets may be further identified by gene walking techniques and walking PCR. Such approaches for identifying unknown polynucleotide sequences adjacent to known nucleotide sequences are well known in the art. See for example Parker J. D., et al. *Nucleic Acids Res* 19:3055-60 (1991) for a description of walking PCR). All of the preceding references, as well as others referenced herein, are incorporated by reference herein in their entirety. Preferably, an antisense compound is targeted to one or more specific connexin isotypes. Particular connexin isotypes may be targeted, for example, based upon their temporal or spatial expression. Gap junctions are expressed in vascular tissues and, in certain embodiments, connexin isotypes expressed in vascular tissues (e.g. endothelial cells) are targeted. See Camelliti P. et al., *Cardiovasc. Res.* 62: 414-425 (2004). Endothelial cells, endothelial progenitor cells, and smooth muscle cells have been reported to express connexins 37, 40, 43 and 45. See De Wit, (2004); Haefliger et al., (2004), Sohl and Willecke, (2004), and Szmitko et al., (2003). It has also been reported that connexin 43 is upregulated in the blood vessels adjacent to wound sites. Qiu C et al., Current Biology, 13: 1967-1703 (2003).

In other embodiments, other isotypes are be targeted. Specific isotypes of connexins that may be targeted by the antisense compounds include, without limitation 45, 43, 37, 31.1, 26, and others described herein. In certain embodiments the anti-connexin compound targets connexin 43, 45 and/or 40, and in others the anti-connexin compound targets connexin 7, 32 and/or 26. One or more than one connexin may be targeted In certain embodiments one anti-connexin compound targets more than one connexin (e.g. connexin 43 and connexin 45). In other embodiments, more than one anti-connexin compound is included in a formulation or composition (e.g. a pharmaceutical composition). The invention contemplated that any connexin may be targeted by one or more than one anti-connexin compound described herein, known in the art, or later discovered.

It is preferred, but not required, that the targeted connexins are human. A connexin may, for example, have a nucleobase sequence selected from SEQ ID NO:12-31. In certain embodiments, antisense compounds are targeted to at least 8 nucleobases of a nucleic acid molecule encoding a connexin having a nucleobase sequence selected from SEQ ID NO:12-31.

Connexin targets will vary depending upon the type of tissue to be engineered or remodeled and the precise sequence of the antisense polynucleotide used in the invention will depend upon the target connexin protein. The connexin protein or proteins targeted by the oligonucleotides will be dependent upon the site at which downregulation is to be directed. This reflects the nonuniform make-up of gap junction (s) at different sites throughout the body in terms of connexin sub-unit composition. Some connexin proteins are however more ubiquitous than others in terms of distribution in tissue. As described herein, Oligonucleotides either alone or in combination may be targeted towards connexin 45, 43, 26, 37, 30 and/or 31.1 (e.g. see SEQ. ID. NOS:12-31) which are suitable for corneal engineering or remodeling application. In one aspect of the invention, the oligodeoxynucleotides may be unmodified phosphodiester oligomers. In another aspect of the invention, the polynucleotides may be single or double stranded.

In certain non-limiting examples, antisense compounds are targeted to specific regions of a connexin mRNA or pre-mRNA molecule, including exons, introns, mRNA splice sites (exon-exon or intron-exon junctions), the 5'-untranslated region, and the 3'-untranslated region.

It is also contemplated that oligonucleotides targeted at separate connexin proteins may be used in combination (for example one, two, three, four or more different connexins may be targeted). For example, ODNs targeted to connexin 45, and one or more other members of the connexin family (such as connexin 43, 26, 30, 31.1, 37 and 43) can be used in combination. It is also contemplated that individual antisense polynucleotides may be specific to a particular connexin, or may target 1, 2, 3 or more different connexins. Specific polynucleotides will generally target sequences in the connexin gene or mRNA which are not conserved between connexins, whereas non-specific polynucleotides will target conserved sequences. Thus, in certain embodiments, antisense compounds are targeted to at least 8 nucleobases of a nucleic acid molecule encoding human connexin 26, connexin 30, connexin 31.1, human connexin 37, connexin 43, connexin 45, wherein said antisense compound inhibits the expression of a human connexin protein in cells associated with the eye of said patient.

In certain embodiments, the nucleic acid molecules corresponding to a connexin have a nucleobase sequence selected from SEQ. ID NO: 12-31 included in the sequence listing of this application (corresponding to includes for example complements, cDNA's, portions encoding a connexin protein, etc.). In certain embodiments, the compositions target two or more human connexin proteins and inhibit the expression of two or more human connexin proteins. In further certain embodiments, the antisense compounds are antisense oligonucleotides. Exemplary antisense oligonucleotides to connexin 43 include GTA ATT GCG GCA AGA AGA ATT GTT TCT GTC (SEQ ID NO: 1); GTA ATT GCG GCA GGA GGA ATT GTT TCT GTC (SEQ ID NO: 2); and GGC AAG AGA CAC CAA AGA CAC TAC CAG CAT (SEQ ID NO: 3). An example of an antisense oligonucleotide to connexin 26 has the sequence TCC TGA GCA ATA CCT AAC GAA CAA ATA (SEQ ID NO: 4). Exemplary antisense oligonucleotide to connexin 37 selected include 5' CAT CTC CTT GGT GCT CAA CC 3' (SEQ ID NO: 5) and 5' CTG AAG TCG ACT TGG CTT GG 3' (SEQ ID NO: 6). Exemplary antisense oligonucleotide to connexin 30 selected include 5' CTC AGA TAG TGG CCA GAA TGC 3' (SEQ ID NO: 7) and 5' TTG TCC AGG TGA CTC CAA GG 3' (SEQ ID NO: 8). Exemplary antisense oligonucleotide to connexin 31.1 selected include 5' CGT CCG AGC CCA GAA AGA TGA GGT C3' (SEQ ID NO: 9); 5' AGA GGC GCA CGT GAG ACA C3' (SEQ ID NO: 10); and 5' TGA AGA CAA TGA AGA TGT T 3' (SEQ ID NO: 11).

In a further embodiment, oligodeoxynucleotides selected from the following sequences are particularly suitable for down-regulating connexin 43 expression:

```
                                            (SEQ ID NO: 1)
5' GTA ATT GCG GCA AGA AGA ATT GTT TCT GTC 3'

(SEQ ID NO: 2)
5' GTA ATT GCG GCA GGA GGA ATT GTT TCT GTC 3';
and (SEQ ID NO: 3)
5' GGC AAG AGA CAC CAA AGA CAC TAC CAG CAT 3'
```

In yet another embodiment, oligodeoxynucleotides selected from the group following sequences are particularly suitable for connexins 26, 37, 30, and 31.1:

```
                                            (SEQ ID NO: 4)
5' TCC TGA GCA ATA CCT AAC GAA CAA ATA 3'
(connexin26)

(SEQ ID NO: 5)
5' CAT CTC CTT GGT GCT CAA CC 3' (connexin37)

(SEQ ID NO: 6)
5' CTG AAG TCG ACT TGG CTT GG 3' (connexin37)

(SEQ ID NO: 7)
5' CTC AGA TAG TGG CCA GAA TGC 3' (connexin30)

(SEQ ID NO: 8)
5' TTG TCC AGG TGA CTC CAA GG 3' (connexin30)

(SEQ ID NO: 9)
5' CGT CCG AGC CCA GAA AGA TGA GGT C 3'
(connexin31.1)

(SEQ ID NO: 10)
5' AGA GGC GCA CGT GAG ACA C 3' (connexin31.1)

(SEQ ID NO: 11)
5' TGA AGA CAA TGA AGA TGT T 3' (connexin31.1)
```

Antisense compounds provided herein generally comprise from about 8 to about 40 nucleobases (i.e. from about 8 to about 40 linked nucleosides), and more typically those comprising from about 12 to about 40 nucleobases, and even more typically about 30 nucleobases. Antisense compounds comprising polynucleotides may be at least about 40, for example at least about 60 or at least about 80, nucleotides in length and up to 100, 200, 300, 400, 500, 1000, 2000 or 3000 or more nucleotides in length. Suitable antisense compounds include, for example, a 30 mer ODN.

In certain embodiments, antisense compounds are targeted to at least about 8 nucleobases of a nucleic acid molecule encoding a connexin having a nucleobase sequence selected from SEQ ID NO: 12-31. In other embodiments, the antisense compound is targeted to at least about 10, at least about 12, at least about 14, at least about 16, at least about 18, at least about 20, at least about 25, at least about 30, and at least about 35 nucleobases of a nucleic acid molecule encoding a connexin having a nucleobase sequence selected from SEQ ID NO:12-31. The size of the antisense compounds, including oligonucleotides targeted to between at least about 8 and 35 nucleobases of a nucleic acid molecule encoding a human connexin, may be 8 nucleobases in length or longer, between 8 and 100 nucleobases, between eight and 50 nucleobases, between eight and 40 nucleobases, between 10 and 50 nucleobases, between 12 and 50 nucleobases, between 14 and 50 nucleobases, between 16 and 50 nucleobases, between 18 and 50 nucleobases, between 20 and 50 nucleobases, between 25 and 50 nucleobases, between 15 and 35 nucleobases in length, and the like. Other antisense compounds of the invention may be or smaller or larger is size, for example having more than 100 nucleobases in length.

Antisense compounds include without limitation antisense oligonucleotides (ODN), antisense polynucleotides, deoxyribozymes, morpholino oligonucleotides, RNAi molecules or analogs thereof, siRNA molecules or analogs thereof, PNA molecules or analogs thereof, DNAzymes or analogs thereof, 5'-end-mutated U1 small nuclear RNAs and analogs thereof.

As provided herein, the antisense compound may include the use of oligodeoxynucleotides (ODNs). ODNs are generally about 20 nucleotides in length and act by hybridizing to pre-mRNA and mRNA to produce a substrate for ribonuclease H(RNase H), which specifically degrades the RNA strand of the formed RNA-DNA duplexes. If modified in a way to prevent the action of RNase H, ODNs can inhibit translation of mRNA via steric hindrance, or inhibit splicing of pre-mRNAs. ODNs and modifications thereof have been used to target dsDNA for the inhibition of transcription by the formation of triple helices. ODN may be obtained by art-recognized methods of automated synthesis and it is relatively straightforward to obtain ODNs of any sequence and to block gene expression via antisense base pairing.

In certain aspects, the phosphodiester backbone of ODNs can be modified to increase their efficacy as target-specific agents for blocking gene expression. These backbone modifications were developed to improve the stability of the ODNs and to enhance their cellular uptake. The most widely used modification is one in which the nonbridging oxygen is replaced by a sulfur atom, creating phosphorothioate ODNs. At least one phosphorothioate ODN has been approved by the FDA, and several other phosphorothioate antisense ODNs are in earlier stages of clinical trials for a variety of cancers and inflammatory diseases.

The mechanisms of action of ODNs with respect to blocking gene function vary depending upon the backbone of the ODN (Branch, A. D. Hepatology 24, 1517-1529 (1996); Dias, N. and Stein, C. A. Mol. Cancer. Thor. 1, 347-355 (2002); Stein, C. A. and Cohen, J. S., Cancer Res. 48, 2659-2668 (1988); Zon, G. Ann. N.Y. Acad. Sci., 616, 161-172 (1990). Net negatively charged ODNs, such as phosphodiesters and phorphorothioates, elicit RNAse H-mediated cleavage of the target mRNA. Other backbone modifications that do not recruit RNAse H, because of their lack of charge or the type of helix formed with the target RNA, can be classified as steric hindrance ODNs. Popularly used members of this latter group include morpholinos, U-O-methyls, 2"-O-allyls, locked nucleic acids and peptide nucleic acids (PNAs). These ODNs can block splicing, translation, nuclear-cytoplasmic transport and translation, among other inhibition targets.

In another aspect, modulation of the connexin expression involves the use of ribozymes. Ribozymes are RNA molecules that act as enzymes, even in the complete absence of proteins. They have the catalytic activity of breaking and/or forming covalent bonds with extraordinary specificity, thereby accelerating the spontaneous rates of targeted reactions by many orders of magnitude.

Ribozymes bind to RNA through Watson-Crick base pairing and act to degrade target RNA by catalysing the hydrolysis of the phosphodiester backbone. There are several different classes of ribozymes, with the 'hammerhead' ribozyme being the most widely studied. As its name implies, the hammerhead ribozyme forms a unique secondary structure when hybridized to its target mRNA. The catalytically important residues within the ribozyme are flanked by target-complementary sequences that flank the target RNA cleavage site. Cleavage by a ribozyme requires divalent ions, such as magnesium, and is also dependent on target RNA structure and accessibility. Co-localizing a ribozyme with a target RNA within the cell through the use of localization signals greatly increases their silencing efficiency. The hammerhead ribozymes are short enough to be chemically synthesized or can be transcribed from vectors, allowing for the continuous production of ribozymes within cells.

The ability of RNA to serve as a catalyst was first demonstrated for the self-splicing group I intron of Tetrahymena thermophila and the RNA moiety of RNAse. After the discovery of these two RNA enzymes, RNA-mediated catalysis has been found associated with the self-splicing group II introns of yeast, fungal and plant mitochondria (as well as chloroplasts) single-stranded plant viroid and virusoid RNAs, hepatitis delta virus and a satellite RNA from *Neurospora crassa* mitochondria. Ribozymes occur naturally, but can also be artificially engineered for expression and targeting of specific sequences in cis (on the same nucleic acid strand) or trans (a noncovalently linked nucleic acid). New biochemical activities are being developed using in vitro selection protocols as well as generating new ribozyme motifs that act on substrates other than RNA.

The group I intron of *T. thermophila* was the first cis-cleaving ribozyme to be converted into a trans-reacting form, which we refer to as an intron/ribozyme, making it useful both in genomic research and as a possible therapeutic. In the trans-splicing reaction, a defective exon of a targeted mRNA can be exchanged for a correct exon that is covalently attached to the intron/ribozyme. This occurs via a splicing reaction in which the exon attached to the intron is positioned by base pairing to the target mRNA so that it can be covalently joined to the 5" end of the target transcript in a transesterification reaction. This reaction has been used to trans-splice wild-type sequences into sickle cell globin transcripts and mutant p53 transcripts and replace the expanded triplets in the 3"-UTR of protein kinase transcripts in a myotonic dystrophy allele.

The endoribonuclease RNAse P is found in organisms throughout nature. This enzyme has RNA and one or more protein components depending upon the organism from which it is isolated. The RNA component from the *Escherichia coli* and *Bacillus subtilis* enzymes can act as a site-specific cleavage agent in the absence of the protein trader certain salt and ionic conditions. Studies of the substrate requirements for human and bacterial enzymes have shown that the minimal substrates for either enzyme resemble a segment of a transfer RNA molecule. This structure can be mimicked by uniquely designed antisense RNAs, which pair to the target RNA, and serve as substrates for RNAse P-mediated, site-specific cleavage both in the test tube and in cells. It has also been shown that the antisense component can be covalently joined to the RNAse P RNA, thereby directing the enzyme only to the target RNA of interest. Investigators have taken advantage of this property in the design of antisense RNAs, which pair with target mRNAs of interest to stimulate site-specific cleavage of the target and for targeted inhibition of both herpes simplex virus and cytomegalovirus in cell culture.

A number of small plant pathogenic RNAs (viroids, satellite RNAs and virusoids), a transcript from a *N. crassa* mitochondrial DNA plasmid and the animal hepatitis delta virus undergo a self-cleavage reaction in vitro in the absence of protein. The reactions require neutral pH and $Mg^{2+}$. The self-cleavage reaction is an integral part of the in vivo rolling circle mechanism of replication. These self-cleaving RNAs can be subdivided into groups depending on the sequence and secondary structure formed about the cleavage site. Small ribozymes have been derived from a motif found in single-stranded plant viroid and virusoid RNAs. On the basis of a shared secondary structure and a conserved set of nucleotides, the term "hammerhead" has been given to one group of this self-cleavage domain. The hammerhead ribozyme is composed of 30 nucleotides. The simplicity of the hammerhead catalytic domain has made it a popular choice in the design of trans-acting ribozymes. Using Watson-Crick base pairing, the hammerhead ribozyme can be designed to cleave any target RNA. The requirements at the cleavage site are relatively simple, and virtually any UH sequence motif (where H is U, C or A) can be targeted.

A second plant-derived, self-cleavage motif, initially identified in the negative strand of the tobacco ringspot satellite RNA, has been termed the 'hairpin' or "paperclip." The hairpin ribozymes cleave RNA substrates in a reversible reaction that generates 2", Y-cyclic phosphate and 5"-hydroxT1 termini-engineered versions of this catalytic motif also cleave and turn over multiple copies of a variety of targets in trans.

Substrate requirements for the hairpin include a GUC, with cleavage occurring immediately upstream of the G. The hairpin ribozyme also catalyzes a ligation reaction, although it is more frequently used for cleavage reactions.

There have been numerous applications of both hammerhead and hairpin ribozymes in cells for downregulating specific cellular and viral targets. Haseloff and Gerlach designed a hammerhead motif (Haseloff and Gerlach; Nature. August 18; 334(6183): 585-91 (1988)) that can be engineered to cleave any target by modifying the arms that base pair with right target. Ramemzani et al. demonstrated that this hammerhead ribozyme motif had potential therapeutic applications in a study in which there was a virtual complete inhibition of viral gene expression and replication using cells engineered to express an anti-human immunodeficiency virus (HIV) gag ribozyme (Ramezani A. et al., *Frontiers in Bioscience* 7: a, 29-36; (2002)).

In another aspect, modulation of the connexin expression involves the use of catalytic DNAs (or DNAzymes). Small DNAs capable of site specifically cleaving RNA targets have been developed via in vitro evolution (as no known DNA enzymes occur in nature). Two different catalytic motifs, with different cleavage site specificities have been identified. The most commonly used 10-20 enzymes bind to their RNA substrates via Watson-Crick base pairing and site specifically cleave the target RNA, as do the hammerhead and hairpin ribozymes, resulting in 2; 3"-cyclic phosphate and 5"-OH termini. Cleavage of the target mRNAs results in their destruction and the DNAzymes recycle and cleave multiple substrates. Catalytic DNAs are relatively inexpensive to synthesize and have good catalytic properties, making them useful substitutes for either antisense DNA or ribozymes.

Several applications of DNAzymes in cell culture have been published including the inhibition of veg FmRNA and consequent prevention of angiogenesis, and inhibition of expression of the bcr/abl fusion transcript characteristic of chronic myelogenous leukemia. Catalytic DNAs can be delivered exogenously, and they can be backbone-modified to in order to optimize systemic delivery in the absence of a carrier.

In another aspect of the present invention, the modulation of the constitutive connexin gene involves the use of oligonucleotides having morpholino backbone structures. Summerton, J. E. and Weller, D. D. U.S. Pat. No. 5,034,506.

In another aspect of the invention, the antisense polynucleotides may be chemically modified in order to enhance their resistance to nucleases and increase the efficacy of cell entry. For example, mixed backbone oligonucleotides (MBOs) containing segments of phosphothioate oligodeoxynucleotides and appropriately placed segments of modified oligodeoxyor oligoribonucleotides may be used. MBOs have segments of phosphorothioate linkages and other segments of other modified oligonucleotides, such as methylphosphonates, phosphoramidates, phosphorodithioates, N3'P5'-phosphoramidates and oligoribonucleotide phosphorothioates and their 2'-O-alkyl analogs and 2'-O-methylribonucleotide methylphosphonates, which are non-ionic, and very resistant to nucleases or 2'-O-alkyloligoribonucleotides.

As is known in the art, a nucleoside is a base-sugar combination. The base portion of the nucleoside is normally a heterocyclic base. The two most common classes of such heterocyclic bases are the purines and the pyrimidines. Nucleotides are nucleosides that further include a phosphate group covalently linked to the sugar portion of the nucleoside. For those nucleosides that include a pentofuranosyl sugar, the phosphate group can be linked to either the 2', 3' or 5' hydroxyl moiety of the sugar. In forming oligonucleotides, the phosphate groups covalently link adjacent nucleosides to one another to form a linear polymeric compound. In turn the respective ends of this linear polymeric structure can be further joined to form a circular structure, however, open linear structures are generally preferred. Within the oligonucleotide structure, the phosphate groups are commonly referred to as forming the internucleoside backbone of the oligonucleotide. The normal linkage or backbone of RNA and DNA is a 3' to 5' phosphodiester linkage.

The antisense compounds useful in this invention may include oligonucleotides containing modified backbones or non-natural internucleoside linkages. Oligonucleotides having modified backbones include those that retain a phosphorus atom in the backbone and those that do not have a phosphorus atom in the backbone. In the context of this invention, modified oligonucleotides that do not have a phosphorus atom in their internucleoside backbone can also be considered to be oligonucleosides.

The antisense compounds with modified oligonucleotide backbones useful in this invention may include, for example, phosphorothioates, chiral phosphorothioates, phosphorodithioates, phosphotriesters, aminoalkylphosphotriesters, methyl and other alkyl phosphonates including 3'-alkylene phosphonates and chiral phosphonates, phosphinates, phosphoramidates including 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 51-3' or 2'-5' to 5'-2'. Various salts, mixed salts and free acid forms are also included.

In one aspect, it is contemplated that modified oligonucleotide backbones that do not include a phosphorus atom therein have backbones that are formed by short chain alkyl or cycloalkyl internucleoside linkages, mixed heteroatom and alkyl or cycloalkyl internucleoside linkages, or one or more short chain heteroatomic or heterocyclic internucleoside linkages. These include those having morpholino linkages (formed in part from the sugar portion of a nucleoside); siloxane backbones; sulfide, sulfoxide and sulfone backbones; formacetyl and thioformacetyl backbones; methylene formacetyl and thioformacetyl backbones; alkene containing backbones; sulfamate backbones; methyleneimino and methylenehydrazino backbones; sulfonate and sulfonamide backbones; amide backbones; and others having mixed N, O, S and CH2 component parts.

In one aspect, it is contemplated that oligonucleotide mimetics, both the sugar and the internucleoside linkage, i.e. the backbone of the nucleotide units are replaced with novel groups. The base units are maintained for hybridization with an appropriate nucleic acid target compound. One such oligomeric compound, an oligonucleotide mimetic that has been shown to have excellent hybridization properties, is referred to as a peptide nucleic acid (PNA). In PNA compounds, the sugar-backbone of an oligonucleotide is replaced with an amide containing backbone, in particular an aminoethylglycine backbone. The nucleobases are retained and are bound directly or indirectly to aza nitrogen atoms of the amide portion of the backbone. Further teaching of PNA compounds can be found in Nielsen et al. (Science, 254, 1497-1500 (1991)).

In one aspect, oligonucleotides with phosphorothioate backbones and oligonucleosides with heteroatom backbones, and in particular —CH2-NH—O—CH2-, —CH-2 N(CH)3-O—CH-2 [known as a methylene (methylimino) or MMI backbone], —CH2-O—N(CH3)-CH2-, —CH2-N(CH3)-N (CH3)-CH2- and —O—N(CH3)-CH2-CH2-[wherein the native phosphodiester backbone is represented as —O—P—O—CH2-] are contemplated. In yet another aspect, oligonucleotides having morpholino and amide backbone structures are also contemplated.

In another aspect, it is contemplated that the modified oligonucleotides may also contain one or more substituted sugar moieties. For example, oligonucleotides comprising one of the following at the 2' position: OH; F; O-, S-, or N-alkyl, O-alkyl-O-alkyl, O-, S-, or N-alkenyl, or O-, S- or N-alkynyl, wherein the alkyl, alkenyl and alkynyl may be substituted or unsubstituted C1 to C10 alkyl or C2 to C10 alkenyl and alkynyl. Particularly preferred are O[(CH2)n O]m CH3, O(CH2)n OCH3, O(CH2)2 ON(CH3)2, O(CH2)n NH2, O(CH2)n CH3, O(CH2)n ONH2, and O(CH2)n ON[(CH2)n CH3)]2, where n and m are from 1 to about 10. Other preferred oligonucleotides may comprise one of the following at the 2' position: C1 to C10 lower alkyl, substituted lower alkyl, alkaryl, aralkyl, O-alkaryl or O-aralkyl, SH, SCH3, OCN, Cl, Br, CN, CF3, OCF3, SOCH3, SO2 CH3, ONO2, NO2, N3, NH2, heterocycloalkyl, heterocycloalkaryl, aminoalkylamino, polyalkylamino, substituted silyl, an RNA cleaving group, a reporter group, an intercalator, a group for improving the pharmacokinetic properties of an oligonucleotide, or a group for improving the pharmacodynamic properties of an oligonucleotide, and other substituents having similar properties. A preferred modification includes 2'-methoxyethoxy (2'-O—CH2 CH2 OCH, 3 also known as 2'-O-(2-methoxyethyl) or 2'-MOE) (Martin et al. Helv. Chim. Acta 1995, 78, 486-504) i.e. an alkoxyalkoxy group. Other modification includes 2'-dimethylaminooxyethoxy, i.e., a O(CH2)2 ON(CH3). 2 group, also known as 2'-DMAOE, and 2'-dimethylamino-ethoxyethoxy (2'-DMAEOE), i.e., 2'-O—CH2-O—CH2-N(CH2)2.

It is further contemplated that the modifications may include 2'-methoxy (2'-O—CH3), 2'-aminopropoxy (2'-OCH2 CH2 CH2 NH2) and 2'-fluoro (2'-F). Similar modifications may also be made at other positions on the oligonucleotide, particularly the 3' position of the sugar on the 3' terminal nucleotide or in 2'-5' linked oligonucleotides and the 5' position of 5' terminal nucleotide. Oligonucleotides may also have sugar mimetics such as cyclobutyl moieties in place of the pentofuranosyl sugar.

In another aspect, it is contemplated that the oligonucleotides may also include nucleobase (often referred to in the art simply as "base") modifications or substitutions. As used herein, "unmodified" or "natural" nucleobases include the purine bases adenine (A) and guanine (G), and the pyrimidine bases thymine (I), cytosine (C) and uracil (U). Modified nucleobases include other synthetic and natural nucleobases such as 5-methylcytosine (5-me-C or m5c), 5-hydroxymethyl cytosine, xanthine, hypoxanthine, 2-amincadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl uracil and cytosine, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine and 3-deazaadenine. Further nucleobases include those disclosed in U.S. Pat. No. 3,687,808, those disclosed in the Concise Encyclopedia Of Polymer Science And Engineering, pages 858-859 (1990), Kroschwitz, J. John Wiley & Sons, those disclosed by Englisch et al. (Angewandte Chemie, International Edition, 30, 613-722 (1991)), and those disclosed by Sanghvi, Y. S., Chapter 15, Antisense Research and Applications, pages 289-302, Crooke, S. T. and Lebleu, B., ed., CRC Press (1993). Certain of these nucleobases are particularly useful for increasing the binding affinity of the oligomeric compounds. These include 5-substituted pyrimidines, 6-azapyrimidines and N-2, N-6 and O-6 substituted purines, including 2-aminopropyladenine, 5-propynyluracil and 5-propynylcytosine. 5-methylcytosine substitutions have been shown to increase nucleic acid duplex stability by 0.6-1.2° C. (Sanghvi, Y. S., Crooke, S. T. and Lebleu, B., eds., Antisense Research and Applications, CRC Press, Boca Raton, pages 276-278 (1993)) and are presently preferred base substitutions, even more particularly when combined with 2'-O-methoxyethyl sugar modifications.

In another aspect, it is contemplated that the modification of the oligonucleotides involves chemically linking to the oligonucleotide one or more moieties or conjugates which enhance the activity, cellular distribution or cellular uptake of the oligonucleotide. Such moieties include but are not limited to lipid moieties such as a cholesterol moiety (Letsinger et al., Proc. Natl. Acad. Sci. USA 86, 6553-6556 (1989)), cholic acid (Manoharan et al., Bioorg. Med. Chem. Lett. 4, 1053-1059 (1994)), a thioether, e.g., hexyl-5-tritylthiol (Manoharan et al., Ann. N.Y. Acad. Sci. 660, 306-309; Manoharan et al., Bioorg (1992). Med. Chem. Let. 3, 2765-2770 (1993)), a thiocholesterol (Oberhauser et al., Nucl. Acids Res., 20, 533-538 (1992)), an aliphatic chain, e.g., dodecandiol or undecyl residues (Saison-Behmoaras et al., EMBO J. 10, 1111-1118 (1991); Kabanov et al., FEBS Lett. 259, 327-330 (1990); Svinarchuk et al., Biochimie 75, 49-54 (1993)), a phospholipid, e.g., di-hexadecyl-rac-glycerol or triethylammonium 1,2-di-O-hexadecyl-rac-glycero-3-H-phosphonate (Manoharan et al., Tetrahedron Lett. 36, 3651-3654 (1995); Shea et al., Nucl. Acids Res. 18, 3777-3783 (1990)), a polyamine or a polyethylene glycol chain (Manoharan et al., Nucleosides & Nucleotides 14, 969-973 (1995)), or adamantane acetic acid (Manoharan et al., Tetrahedron Lett. 36, 3651-3654 (1995)), a palmityl moiety (Mishra et al., Biochim. Biophys. Acta 1264, 229-237 (1995)), or an octadecylamine or hexylaminocarbonyl-oxycholesterol moiety (Crooke et al., J. Pharmacol. Exp. Ther. 277, 923-937 (1996)).

Also contemplated are the use of oligonucleotides which are chimeric oligonucleotides. "Chimeric" oligonucleotides or "chimeras," in the context of this invention, are oligonucleotides which contain two or more chemically distinct regions, each made up of at least one nucleotide. These oligonucleotides typically contain at least one region wherein the oligonucleotide is modified so as to confer upon the oligonucleotide increased resistance to nuclease degradation, increased cellular uptake, and/or increased binding affinity for the target nucleic acid. An additional region of the oligonucleotide may serve as a substrate for enzymes capable of cleaving RNA:DNA or RNA:RNA hybrids. By way of example, RNase His a cellular endonuclease which cleaves the RNA strand of an RNA:DNA duplex. Activation of RNase H, therefore, results in cleavage of the RNA target, thereby greatly enhancing the efficiency of antisense inhibition of gene expression. Cleavage of the RNA target can be routinely detected by gel electrophoresis and, if necessary, associated nucleic acid hybridization techniques known in the art. This RNAse H-mediated cleavage of the RNA target is distinct from the use of ribozymes to cleave nucleic acids.

Examples of chimeric oligonucleotides include but are not limited to "gapmers," in which three distinct regions are present, normally with a central region flanked by two regions which are chemically equivalent to each other but distinct from the gap. A preferred example of a gapmer is an oligonucleotide in which a central portion (the "gap") of the oligonucleotide serves as a substrate for RNase H and is preferably composed of 2'-deoxynucleotides, while the flanking portions (the 5' and 3' "wings") are modified to have greater affinity for the target RNA molecule but are unable to support nuclease activity (e.g. fluoro- or 2'-O-methoxyethyl-substituted). Chimeric oligonucleotides are not limited to those with modifications on the sugar, but may also include oligonucleosides or oligonucleotides with modified backbones, e.g., with regions of phosphorothioate (P=S) and phosphodiester (P=O) backbone linkages or with regions of MMI and P=S backbone linkages. Other chimeras include "wingmers," also known in the art as "hemimers," that is, oligonucleotides with two distinct regions. In a preferred example of a wingmer, the 5' portion of the oligonucleotide serves as a substrate for RNase H and is preferably composed of 2'-deoxynucleotides, whereas the 3' portion is modified in such a fashion so as to have greater affinity for the target RNA molecule but is unable to support nuclease activity (e.g., 2'-fluoro- or 2'-O-methoxyethyl-substituted), or vice-versa. In one embodiment, the oligonucleotides of the present invention contain a 2'-O-methoxyethyl (2'-O—CH2 CH2 OCH3) modification on the sugar moiety of at least one nucleotide. This modification has been shown to increase both affinity of the oligonucleotide for its target and nuclease resistance of the oligonucleotide. According to the invention, one, a plurality, or all of the nucleotide subunits of the oligonucleotides may bear a 2'-O-methoxyethyl (—O—CH2 CH2 OCH3) modification. Oligonucleotides comprising a plurality of nucleotide subunits having a 2'-O-methoxyethyl modification can have such a modification on any of the nucleotide subunits within the oligonucleotide, and may be chimeric oligonucleotides. Aside from or in addition to 2 1-O-methoxyethyl modifications, oligonucleotides containing other modifications which enhance antisense efficacy, potency or target affinity are also contemplated.

The present invention also provides polynucleotides (for example, DNA, RNA, PNA or the like) that bind to double-stranded or duplex connexin nucleic acids (for example, in a folded region of the connexin RNA or in the connexin gene), forming a triple helix containing, or "triplex" nucleic acid. Triple helix formation results in inhibition of connexin expression by, for example, preventing transcription of the connexin gene, thus reducing or eliminating connexin activity in a cell. Without intending to be bound by any particular mechanism, it is believed that triple helix pairing compromises the ability of the double helix to open sufficiently for the binding of polymerases, transcription factors, or regulatory molecules to occur.

Triplex oligo- and polynucleotides are constructed using the base-pairing rules of triple helix formation (see, for example, Cheng et al., J. Biol. Chem. 263: 15110 (1988); Ferrin and Camerini-Otero, Science 354:1494 (1991); Ramdas et al., J. Biol. Chem. 264:17395 (1989); Strobel et al., Science 254:1639 (1991); and Rigas et al., Proc. Natl. Acad. Sci. U.S.A. 83: 9591 (1986)) and the connexin mRNA and/or gene sequence. Typically, the triplex-forming oligonucleotides comprise a specific sequence of from about 10 to about 25 nucleotides or longer "complementary" to a specific sequence in the connexin RNA or gene (i.e., large enough to form a stable triple helix, but small enough, depending on the mode of delivery, to administer in vivo, if desired). In this context, "complementary" means able to form a stable triple helix. In one embodiment, oligonucleotides are designed to bind specifically to the regulatory regions of the connexin gene (for example, the connexin 5'-flanking sequence, promoters, and enhancers) or to the transcription initiation site, (for example, between −10 and +10 from the transcription initiation site): For a review of recent therapeutic advances using triplex DNA, see Gee et al., in Huber and Carr, 1994, Molecular and Immunologic Approaches, Futura Publishing Co, Mt Kisco N.Y. and Rininsland et al., *Proc. Natl. Acad. Sci. USA* 94:5854 (1997).

The present invention also provides ribozymes useful for inhibition of connexin activity. The ribozymes bind and specifically cleave and inactivate connexin mRNA. Useful ribozymes can comprise 5'- and 3'-terminal sequences complementary to the connexin mRNA and can be engineered by one of skill on the basis of the connexin mRNA sequence. It is contemplated that ribozymes provided herein include those having characteristics of group I intron ribozymes (Cech, *Biotechnology* 13:323 (1995)) and others of hammerhead ribozymes (Edgington, *Biotechnology* 10:256 (1992)).

Ribozymes include those having cleavage sites such as GUA, GUU and GUC. Short RNA oligonucleotides between 15 and 20 ribonucleotides in length corresponding to the region of the target connexin gene containing the cleavage site can be evaluated for secondary structural features that may render the oligonucleotide more desirable. The suitability of cleavage sites may also be evaluated by testing accessibility to hybridization with complementary oligonucleotides using ribonuclease protection assays, or by testing for in vitro ribozyme activity in accordance with standard procedures known in the art.

Further contemplated are antisense compounds in which antisense and ribozyme functions can be combined in a single oligonucleotide. Moreover, ribozymes can comprise one or more modified nucleotides or modified linkages between nucleotides, as described above in conjunction with the description of illustrative antisense oligonucleotides provided herein.

The present invention also provides polynucleotides useful for inhibition of connexin activity by methods such as RNA interference (RNAi). This and other techniques of gene suppression are well known in the art. A review of this technique is found in *Science* 288:1370-1372 (2000). RNAi operates on a post-transcriptional level and is sequence specific. The process comprises introduction of RNA with partial or fully double-stranded character, or precursors of or able to encode such RNA into the cell or into the extracellular environment.

As described by Fire et al., U.S. Pat. No. 6,506,559, the RNA may comprise one or more strands of polymerized ribonucleotide. The double-stranded structure may be formed by a single self-complementary RNA strand or two complementary RNA strands. The RNA may include modifications to either the phosphate-sugar backbone or the nucleosides. RNA duplex formation may be initiated either inside or outside the cell.

Studies have demonstrated that one or more ribonucleases specifically bind to and cleave double-stranded RNA into short fragments. The ribonuclease(s) remains associated with these fragments, which in turn specifically bind to complementary mRNA, i.e., specifically bind to the transcribed mRNA strand for the connexin gene. The mRNA for the connexin gene is also degraded by the ribonuclease(s) into short fragments, thereby obviating translation and expression of the connexin gene, and so inhibiting connexin activity. Additionally, an RNA polymerase may act to facilitate the synthesis of numerous copies of the short fragments, which exponentially increases the efficiency of the system. A unique feature of this gene suppression pathway is that silencing is not limited to the cells where it is initiated. The gene-silencing effects may be disseminated to other parts of an organism and even transmitted through the germ line to several generations.

In one aspect, the double-stranded (ds)RNA-dependent gene specific post transcriptional silencing strategy of RNAi involves the use of short interfering RNAs (siRNA). The use of the general RNAi approach is subject to certain limitations, including the nonspecific antiviral defense mechanism in mammalian cells activated in response to long dsRNA molecules (Gil J, Esteban M, "Induction of apoptosis by the dsRNA-dependent protein kinase (PKR): Mechanisms of action". Apoptosis 2000, 5:107-114). Advances in the field have been made with the demonstration that synthetic duplexes of 21 nucleotide RNAs could mediate gene specific RNAi in mammalian cells without invoking generic antiviral defense mechanisms (Elbashir S, et al., "Duplexes of 21-nucleotide RNAs mediate RNA interference in cultured mammalian cells". Nature, 411:494-498 (2001); Caplen N. et al., Proc Natl Acad Sci, 98:9742-9747 (2001)). Thus, siRNAs are increasingly being recognized as powerful tools for gene-specific modulation.

As described herein, RNAi includes to a group of related gene-silencing mechanisms sharing many common biochemical components in which the terminal effector molecule is for example, but not limited to, a small 21-23-nucleotide antisense RNA. One mechanism uses a relatively long, dsRNA 'trigger'; which is processed by the cellular enzyme Dicer into short, for example, but not limited to, 21-23-nucleotide dsRNAs, referred to as siRNAs. The strand of the siRNA complementary to the target RNA becomes incorporated into a multi-protein complex termed the RNA-induced silencing complex (RISC), where it serves as a guide for endonucleolytic cleavage of the mRNA strand within the target site. This leads to degradation of the entire mRNA; the antisense siRNA can then be recycled. In lower organisms, RNA-dependent RNA polymerase also uses the annealed guide siRNA as a primer, generating more dsRNA front the target, which serves in turn as a Dicer substrate, generating more siRNAs and amplifying the siRNA signal. This pathway is commonly used as a viral defense mechanism in plants.

As described herein, the siRNA may consist of two separate, annealed single strands of for example, but not limited to, 21-23 nucleotides, where the terminal two 3"-nucleotides are unpaired (3" overhang). Alternatively, the siRNA may be in the form of a single stem-loop, often referred to as a short hairpin RNA (shRNA). Typically, but not always, the antisense strand of shRNAs is also completely complementary to the sense partner strand of the si/shRNA.

In mammalian cells, long dsRNAs (usually greater than 30 nucleotides in length) trigger the interferon pathway, activating protein kinase R and 2; 5"-oligoadenylate synthetase. Activation of the interferon pathway can lead to global down-regulation of translation as well as global RNA degradation. However, shorter siRNAs exogenously introduced into mammalian cells have been reported to bypass the interferon pathway.

The siRNA antisense product can also be derived from endogenous microRNAs. In human cells, regardless of the initial form (siRNAs and microRNAs) or processing pathway, a final mature for example, but not limited to, 21-23-nucleotide antisense RNA that is completely homologous to the mRNA will direct mRNA cleavage. In general, the effect of mismatches between siRNAs and target sites can vary from almost none to complete abrogation of activity, for reasons that are only partially understood; however, in at least one case, partial homology resulted in mRNA translation inhibition. In general, siRNA with target mismatches designed to mimic a prototypical microRNA-target interaction can mediate varying degrees of translational repression, depending on both the specific interaction and the number of target sites in the mRNA. RNAi can be activated by either exogenous delivery of preformed siRNAs or via promoter-based expression of siRNAs or shRNAs.

Short interfering RNAs (siRNA) can be chemically synthesized or generated by DNA-based vectors systems. In general, this involves transcription of short hairpin (sh)RNAs that are efficiently processed to form siRNAs within cells (Paddison P, Caudy A, Hannon G: Stable suppression of gene expression by RNAi in mammalian cells. Proc Natl Acad Sci USA 99:1443-1448 (2002); Paddison P, Caudy A, Bernstein E, Hannon G, Conklin D: Short hairpin RNAs (shRNAs) induce sequence-specific silencing in mammalian cells. Genes & Dev 16:948-958 (2002); Sui G, et al., Proc Natl Acad Sci 8:5515-5520 (2002); Brummelkamp T, et al., Science 296:550-553 (2002)). Therefore, in the context, siRNAs can be employed as an effective strategy for the tissue-specific targeting and modulation of gene expression.

Oligonucleotides used in accordance with this invention may be conveniently and routinely made through the well-known technique of solid phase synthesis. Equipment for such synthesis is sold by several vendors known in the art. Any other means for such synthesis may also be employed; the actual synthesis of the oligonucleotides is well recognized in the art. It is well known to use similar techniques to prepare oligonucleotides such as the phosphorothioates and 2'-alkoxy or 21-alkoxyalkoxy derivatives, including 2'-O-methoxyethyl oligonucleotides (Martin, P. Helv. Chim. Acta 78, 486-504 (1995)). It is also well known to use similar techniques and commercially available modified amidites and controlled-pore glass (CPG) products such as biotin, fluorescein, acridine or psoralen-modified amidites and/or CPG (available from Glen Research, Sterling, Va.) to synthesize fluorescently labeled, biotinylated or other conjugated oligonucleotides.

Methods

In another aspect, the invention includes methods of treating a subject (e.g. patient), target organ, target tissue, or target cell by administering compounds provided herein.

Certain embodiments are directed to methods for treating a subject, target organ, target tissue, or target cell with a vascular disorder comprising administering to a subject an antisense compound, mimetic peptide, or other compound provided herein capable of inhibiting the expression, formation, or activity of a connexin hemichannel. Vascular disorders include, for example, any disorder or condition associated with arteries, blood vessels, and the vascular and/or cardiovascular system, including disorder or conditions in associated organs or tissues. Representative examples include, without limitation, atherosclerosis, microvascular disorders, macrovascular disorders, stroke, cerebrovascular disease (cerebral ischemia), thromboses, vascular injuries resulting from trauma (e.g. subcutaneous wounds, stent insertion, restenosis, or angioplasty), vascular damage resulting from elevated levels of glucose (diabetes), diabetic retinopathy, vascular diseases of the extremities, organ ischemia, and endothelial cell disruption.

Other embodiments are directed to methods of treating an inflammatory disorder comprising administering to a subject, target organ, target tissue, or target cell an antisense compound, mimetic peptide, or other compound provided herein capable of inhibiting the expression, formation, or activity of a connexin hemichannel.

Other embodiments are directed to methods for treating a subject, target organ, target tissue, or target cell in connection with a transplant or grafting procedure comprising administration to said patient an antisense compound, mimetic peptide, or other compound provided herein capable of inhibiting the expression, formation or activity of a connexin hemichannel and inhibiting or preventing tissue edema associated with said transplant or grafting procedure.

Other embodiments are directed to methods of treating myocardial infarction and its associated heart diseases comprising administering to a subject an antisense compound, mimetic peptide, or other compound provided herein capable of inhibiting the expression, formation, or activity of a connexin hemichannel.

Still other embodiments are directed to methods of treating coronary artery disease comprising administering to a subject, target organ, target tissue, or target cell an antisense compound, mimetic peptide, or other compound provided herein capable of inhibiting the expression, formation, or activity of a connexin hemichannel.

Other embodiments are directed to methods of treating damage associated with ischemia, including initial ischemic damage and a subsequent reperfusion injury.

Other embodiments are directed to methods of treating myocardial infarction and its associated heart diseases comprising by co-administering to a subject an antisense compound, mimetic peptide, or other compound provided herein capable of inhibiting the expression, formation, or activity of a connexin hemichannel in combination with other known therapeutic approaches or procedures for the treatment of ischemic conditions associated with the heart, including those described in Baker D. W. et al. (ACC/AHA Guidelines for the Evaluation and Management of Chronic Heart Failure in the Adult, 2001; American College of Cardiology and the American Heart Association, the contents of which is hereby incorporated by reference). Such procedures include, for example, cardiac transplantation, surgical and mechanical approaches, mitral valve repair or replacement for hemodynamic and clinical improvements, extra-corporeal devices for circulatory support, left ventricular assist devices, mechanical decompression, left ventriculectomy (Batista procedure), cardiomyoplasty and a variant of the aneurysmectomy procedure for the management of patients with ischemic cardiomyopathy.

Implants and other surgical or medical devices may be coated with (or otherwise adapted to release) agents of the invention (e.g. anti-connexin compounds and compositions) in a variety of manners, including for example: (a) by directly affixing to the implant or device an anti-connexin agent or composition (e.g. by either spraying the implant or device with a polymer/drug film, or by dipping the implant or device into a polymer/drug solution, or by other covalent or noncovalent means); (b) by coating the implant or device with a substance such as a hydrogel which will in turn absorb the anti-connexin composition (or anti-connexin factor above); (c) by interweaving anti-connexin composition coated thread (or the polymer itself formed into a thread) into the implant or device; (d) by inserting the implant or device into a sleeve or mesh which is comprised of or coated with an anti-connexin composition; (e) constructing the implant or device itself with an anti-connexin agent or composition; or (f) by otherwise adapting the implant or device to release the anti-connexin agent. Within preferred embodiments of the invention, the composition should firmly adhere to the implant or device during storage and at the time of insertion. The anti-connexin agent or composition should also preferably not degrade during storage, prior to insertion, or when warmed to body temperature after insertion inside the body (if this is required). In addition, it should preferably coat the implant or device smoothly and evenly, with a uniform distribution of anti-connexin agent, while not changing the stent contour. Within preferred embodiments of the invention, the anti-connexin agent or composition should provide a uniform, predictable, prolonged release of the anti-connexin factor into the tissue surrounding the implant or device once it has been deployed. For vascular stents, in addition to the above properties, the composition should not render the stent thrombogenic (causing blood clots to form), or en cause significant turbulence in blood flow (more than the stent itself would be expected to cause if it was uncoated).

The anti-connexin compounds, compositions, and methods provided herein can be used in a variety of procedures that utilize of implants, medical and surgical devices, and the like. In one aspect, implants, surgical devices or stents, are coated with or otherwise constructed to contain and/or release any of the anti-connexin agents provided herein. Representative examples include cardiovascular devices (e.g., implantable venous catheters, venous ports, tunneled venous catheters, chronic infusion lines or ports, including hepatic artery infusion catheters, pacemaker wires, implantable defibrillators); neurologic/neurosurgical devices (e.g., ventricular peritoneal shunts, ventricular atrial shunts, nerve stimulator devices, dural patches and implants to prevent epidural fibrosis post-laminectomy, devices for continuous subarachnoid infusions); gastrointestinal devices (e.g., chronic indwelling catheters, feeding tubes, and shunts) opthalmologic implants (e.g., multino implants and other implants for neovascular glaucoma, drug eluting contact lenses for pterygiums, splints for failed dacrocystalrhinostomy, drug eluting contact lenses for corneal neovascularity, implants for diabetic retinopathy, drug eluting contact lenses for high risk corneal transplants); otolaryngology devices (e.g., ossicular implants, Eustachian tube splints or stents for glue ear or chronic otitis as an alternative to transtempanic drains); plastic surgery implants (e.g., prevention of fibrous contracture in response to gel- or saline-containing breast implants in the subpectoral or subglandular approaches or post-mastectomy, or chin implants), and orthopedic implants (e.g., cemented orthopedic prostheses).

An antisense compound, mimetic peptide, or other compound provided herein can be administered at a predetermined time in certain embodiments. In certain embodiments, an antisense connexin hemichannel expression, formation, or activity is inhibited in endothelial cells. In certain embodiments, a subject may be treated for a vascular disorder comprising a stroke. In certain embodiments, a subject may be treated for a vascular disorder comprising an ischemia. Such an ischemia may be, for example, a tissue ischemia, a myocardial ischemia, or a cerebral ischemia. In certain embodiments, a subject treated herein is at risk of loss of neurological function by ischemia. In other embodiments, a subject may be treated for a vascular disorder comprising treating or ameliorating cell death or degeneration in the central or peripheral nervous system that is caused by an ischemia. In certain embodiments, a subject may treated for a vascular disorder where an antisense compound, mimetic peptide, or other compound provided herein is administered in connection with a vascular or coronary procedure performed on a subject. In other embodiments, an antisense compound, mimetic peptide, or other compound provided herein is administered during said vascular or coronary procedure.

Administration of compounds provided herein may be before or subsequent to a selected time point. The "selected time point" may, for example, correspond to the onset of a disorder or condition such as a cardiovascular disorder, inflammation, a vascular disorder, or an ischemic event, or with performing a medical procedure such as a vascular or coronary procedure. Compounds provided herein may (e.g. antisense compounds, mimetic peptide, etc.) for example, may be administered before, coincident with, or after a selected time point. In certain embodiments, compounds are administered immediately and up to about 24 hours subsequent to a selected time point. In other embodiments, compounds are administered within about 1 hour after a selected time point, within about 2 hours after selected time point, within about 3 hours after a selected time point, within about 4 hours after a selected time point, within about 5 hours after a selected time point, within about 6 hours after a selected time point, within about 8 hours after a selected time point, within about 10 hours after a selected time point, within about 12 hours after a selected time point, within about 14 hours after a selected time point, within about 16 hours after a selected time point, within about 20 hours after a selected time point, or within about 24 hours after a selected time point. In certain embodiments, a compound provided herein is administered in connection with a heart or other surgery performed on a patient. "Selected time points," as referred to herein, include a time of injury, a time of performing a procedure, e.g., a heart or vascular procedured, etc. In certain other embodiments, a compound provided herein is administered in connection with a medical device for performing a vascular procedure.

In certain embodiments, the vascular disorder treated is selected from one or more of ischemic stroke, transient ischemic attack, intracerebral hemorage, subarachnoid hemorage, thromboembolic stroke, venous thrombosis, pulmonary embolism, embolic stroke, cerebrovascular disorder, peripheral occlusive arterial disease, arteriovenous malformation, and an aneurysm.

In certain embodiments, the vascular disorder treated is associated with one or more of coronary heart disease, coronary vascular disorder, atherosclerotic vascular disease, athersclerotic plaque rupture, and/or thromboembolic, a vascular disorder associated with hypertension, myocardial infarction, angina, ischemic heart disease, aortic disorder, peripheral arterial diseases, fibromuscular dysplasia, moyamo disease, and thromboangiitis.

In certain embodiments, a inflammatory disorder treated is selected from one or more of arthritis, rheumatoid arthritis (RA), inflammation, destruction or damage of joints, inflammatory disorder, grave's disease, hashimoto's disease, rheumatoid arthritis, systemic lupus erythematosus, sjogrens syndrome, immune thrombocytopenic purpura, multiple sclerosis, myasthenia gravis, scleroderma, psoriasis, inflammatory bowel disease, crohn's disease, ulcerative colitis, sepsis and septic shock, and autoimmune diseases of the digestive system.

In certain other embodiments, a subject, a target organ, a target tissue, or a target cell is treated for a condition that is associated with one or more of hemostatis, thrombosis, fibrinolysis, cardiovascular disease, diabetes mellitus, endocrine disorders affecting the heart, cardiovascular disease associated with pregnancy, rheumatic fever, cardiovascular disorders associated with HIV-infection, hematological and oncological disorders associated with heart disease, neurological disorders associated with heart disease, and renal disorders associated with heart disease.

In certain other embodiments, a subject, a target organ, a target tissue, or a target cell is treated in association with a transplant or grafting procedure associated with heart failure, congenital heart disease, acquired heart disease in children, valvular heart disease, infective endocarditis, cardiomypopathy, tumors of the heart, pericardial heart disease, traumatic heart disease, pulmonary embolism, pulmonary hypertension, cor pulmonale, and athletic heart syndrome, peripheral arterial circulation disorder, vascular disorder affecting an organ system, vascular disorder affecting the central nervous system, vascular disorder affecting the brain, vascular disorder affecting the retina, vascular disorder affecting the kidney, vascular disorder affecting and nerves, microvascular disorder, and macrovascular disorder. The subject can be treated with a transplant or grafting procedure associated selected from one or more of a heart transplant, kidney transplant, liver transplant, lung transplant, pancreatic transplant, intestinal transplant, or a combined organ transplant. The subject can be treated with a transplant or grafting procedure involves one or more of eye tissue, skin, heart valves, bones, tendons, veins, ligaments, bone marrow transplants, dental or gum tissue, grafting or implantation associated with cosmetic surgery, grafting or implantation associated with a hip or joint replacement procedure, and tissue grafting or implants involving stem cells.

While not intending being bound by or limited to a particular mechanism, in certain embodiments a subject, target organ, target tissue, or target cell is treated by administration of an anti-connexin compound that is capable of to binding or modulating a connexon (hemichannel) for the purpose of achieving a desired effect, including for example one or more of the following: for the prevention of oedema in the spinal cord following ischaemia or trauma, for the prevention of blood vessel wall degradation in tissues following ischaemia or trauma (e.g. in brain, optic nerve, spinal cord and heart), for the treatment of inflammatory arthritis and other inflammatory disorders in which oedema and inflammation are symptomatic or in which blood vessel die back occurs as a result of persistent inflammation, for the treatment of sub-acute or chronic wounds to the cornea of the eye in which prevention of blood vessel die back allows recovery from limbal ischaemia, for the treatment of sub-acute or chronic wounds to the cornea of the eye as a means to trigger re-epithelialisation, for the treatment of chemical burns in the eye in order to trigger epithelial recovery and to bring about recovery from sub-acute limbal ischaemia, for the treatment of sub-acute or chronic skin wounds or diabetic ulcers in which prevention of continued blood vessel die back will allow recovery from tissue ischaemia, for the treatment of chronic skin wounds or diabetic ulcers in which continued expression of connexin 43 at the leading edge prevents re-epithelialisation, for the treatment of perinatal ischaemia using connexin mimetic peptides delivered directly to ventricles of the brain or via spinal column/cord, for the inhibition or prevention of oedema following perinatal ischaemia using connexin mimetic peptides delivered directly to ventricles of the brain or via spinal column/cord, as a treatment for perinatal ischaemia using connexin mimetic peptides delivered systemically, as a treatment for stroke or CNS ischaemia using connexin mimetic peptides delivered directly to ventricles of the brain or via spinal column/cord, as a treatment for stroke or CNS ischaemia using connexin mimetic peptides delivered systemically, for the prevention of epileptiform activity in the brain following ischaemia, for the prevention of epileptiform activity in the brain (e.g. epilepsy), for the prevention of tissue oedema using connexon mimetic peptides or connexin specific antisense polynucleotides, and/or for the prevention of lesion spread, oedema (and rejection) with reperfusion following organ transplantation.

In another aspect, compounds of the invention are administered in an amount desired to modulate the expression, formation or activity of a connexin, hemichannel, or a gap junction.

While not intending to be bound by or limited to any mechanism and without intending any limitation, it is believed that in certain embodiments a target connexin hemichannel is located on a cell cytoplasmic membrane and it may be desirable to effect an inhibition of undesired transmission of molecules from the cytoplasm of said cell into an extracellular space. Again, without intending on being limited to any particular mechanism, in certain embodiments it may be desirable to administer a compound provided herein capable of inhibiting or preventing progressive infarction and reperfusion injury in the heart by maintaining blood vessel endothelial cell integrity, for promoting reperfusion of blood to damaged tissue in an amount effective to enhance cell survival and/or tissue repair, for maintaining the blood brain barrier by inhibiting endothelial cell disruption subsequent to a stroke or injury to the central nervous system, for maintenance of vascular integrity subsequent to tissue damage, or for inhibiting or preventing tissue edema associated with a transplant or grafting procedure.

Pharmaceutical Compositions

In another aspect, the invention includes pharmaceutical compositions comprising compounds of the invention, including antisense compounds and mimetic peptides.

The antisense compounds provided herein may also include bioequivalent compounds, including pharmaceutically acceptable salts and prodrugs. This is intended to encompass any pharmaceutically acceptable salts, esters, or salts of such esters, or any other compound which, upon administration to an animal including a human, is capable of providing (directly or indirectly) the biologically active metabolite or residue thereof. Peptides, for example, can be altered to enhance their stability in the body. For example synthetic side chains can be added which link to each other resulting in the peptide becoming circular. This circularisation can also be accomplished by linking the N- and C-termini together forming a pro-drug which, after insertion into the body, is made linear by protease activity. Accordingly, for example, the disclosure is also drawn to pharmaceutically acceptable salts of the nucleic acids and prodrugs of such nucleic acids. "Pharmaceutically acceptable salts" are physiologically and pharmaceutically acceptable salts of the nucleic acids provided herein: i.e., salts that retain the desired biological activity of the parent compound and do not impart undesired toxicological effects thereto (see, for example, Berge et al., *J. of Pharma Sci.* 66, 1-19 (1977)).

Peptides or variants thereof, can be synthesized in vitro, e.g., by the solid phase peptide synthetic method or by enzyme catalyzed peptide synthesis or with the aid of recombinant DNA technology. Solid phase peptide synthetic method is an established and widely used method, which is described in references such as the following: Stewart et al., *Solid Phase Peptide Synthesis*, W.H. Freeman Co., San Francisco (1969); Merrifield, *J. Am. Chem. Soc.* 85 2149 (1963); Meienhofer in "Hormonal Proteins and Peptides," ed.; C. H. Li, Vol. 2 (Academic Press, 1973), pp. 48-267; and Bavaay and Merrifield, "The Peptides," eds. E. Gross and F. Meienhofer, Vol. 2 (Academic Press, 1980) pp. 3-285. These peptides can be further purified by fractionation on immunoaffinity or ion-exchange columns; ethanol precipitation; reverse phase HPLC; chromatography on silica or on an anion-exchange resin such as DEAE; chromatofocusing; SDS-PAGE; ammonium sulfate precipitation; gel filtration using, for example, Sephadex G-75; ligand affinity chromatography; or crystallization or precipitation from non-polar solvent or nonpolar/polar solvent mixtures. Purification by crystallization or precipitation is preferred.

The pharmaceutical formulations of the present invention may include, as optional ingredients, pharmaceutically acceptable carriers, diluents, solubilizing or emulsifying agents, and salts of the type that are available in the art. Examples of such substances include normal saline solutions such as physiologically buffered saline solutions and water. Specific non-limiting examples of the carriers and/or diluents that are useful in the pharmaceutical formulations of the present invention include water and physiologically acceptable buffered saline solutions such as phosphate buffered saline solutions pH 7.0-8.0. Suitable pharmaceutical carriers include, but are not limited to sterile water, salt solutions (such as Ringer's solution), alcohols, polyethylene glycols, gelatin, carbohydrates such as lactose, amylose or starch, magnesium stearate, talc, silicic acid, viscous paraffin, fatty acid esters, hydroxymethylcellulose, polyvinyl pyrolidone, etc. The pharmaceutical preparations can be sterilized and desired, mixed with auxiliary agents, e.g., lubricants, preservatives, stabilizers, wetting agents, emulsiers, salts for influencing osmotic pressure, buffers, coloring, and/or aromatic substances and the like which do not deleteriously react with the active compounds. They can also be combined where desired with other active substances, e.g., enzyme inhibitors, to reduce metabolic degradation.

Salts of carboxyl groups of a peptide or peptide variant of the invention may be prepared in the usual manner by contacting the peptide with one or more equivalents of a desired base such as, for example, a metallic hydroxide base, e.g., sodium hydroxide; a metal carbonate or bicarbonate base such as, for example, sodium carbonate or sodium bicarbonate; or an amine base such as, for example, triethylamine, triethanolamine, and the like.

N-acyl derivatives of an amino group of the peptide or peptide variants may be prepared by utilizing an N-acyl protected amino acid for the final condensation, or by acylating a protected or unprotected peptide. O-acyl derivatives may be prepared, for example, by acylation of a free hydroxy peptide or peptide resin. Either acylation may be carried out using standard acylating reagents such as acyl halides, anhydrides, acyl imidazoles, and the like. Both N-acylation and O-acylation may be carried out together, if desired.

Acid addition salts of the peptide or variant peptide, or of amino residues of the peptide or variant peptide, may be prepared by contacting the peptide or amine with one or more equivalents of the desired inorganic or organic acid, such as, for example, hydrochloric acid. Esters of carboxyl groups of the peptides may also be prepared by any of the usual methods known in the art.

For oligonucleotides, examples of pharmaceutically acceptable salts include but are not limited to (a) salts formed with cations such as sodium, potassium, ammonium, magnesium, calcium, polyamines such as spermine and spermidine, etc.; (b) acid addition salts formed with inorganic acids, for example hydrochloric acid, hydrobromic acid, sulfuric acid, phosphoric acid, nitric acid and the like; (c) salts formed with organic acids such as, for example, acetic acid, oxalic acid, tartaric acid, succinic acid, maleic acid, fumaric acid, gluconic acid, citric acid, malic acid, ascorbic acid, benzoic acid, tannic acid, palmitic acid, alginic acid, polyglutamic acid, naphthalenesulfonic acid, methanesulfonic acid, p-toluenesulfonic acid, naphthalenedisulfonic acid, polygalacturonic acid, and the like; and (d) salts formed from elemental anions such as chlorine, bromine, and iodine.

Oligonucleotides provided herein may additionally or alternatively be prepared to be delivered in a "prodrug" form. The term "prodrug" indicates a therapeutic agent that is prepared in an inactive form that is converted to an active form (i.e., drug) within the body or cells thereof by the action of endogenous enzymes or other chemicals and/or conditions. In particular, prodrug versions of the oligonucleotides may be prepared as SATE [(S-acetyl-2-thioethyl)phosphate] derivatives according to the methods disclosed in WO 93/24510 to Gosselin et al., published Dec. 9, 1993.

Compounds provided herein may be formulated in a pharmaceutical composition, which may include pharmaceutically acceptable carriers, thickeners, diluents, buffers, preservatives, surface active agents, neutral or cationic lipids, lipid complexes, liposomes, penetration enhancers, carrier compounds and other pharmaceutically acceptable carriers or excipients and the like in addition to the oligonucleotide.

Pharmaceutical compositions may also include one or more active ingredients such as interferons, antimicrobial agents, anti-inflammatory agents, anesthetics, and the like. Formulations for parenteral administration may include sterile aqueous solutions which may also contain buffers, liposomes, diluents and other suitable additives. Pharmaceutical compositions comprising the oligonucleotides provided herein may include penetration enhancers in order to enhance the alimentary delivery of the oligonucleotides. Penetration enhancers may be classified as belonging to one of five broad categories, i.e., fatty acids, bile salts, chelating agents, surfactants and non-surfactants (Lee et al., Critical Reviews in Therapeutic Drug Carrier Systems 8, 91-192 (1991); Muranishi, Critical Reviews in Therapeutic Drug Carrier Systems 7, 1-33 (1990)). One or more penetration enhancers from one or more of these broad categories may be included.

Various fatty acids and their derivatives which act as penetration enhancers include, for example, oleic acid, lauric acid, capric acid, myristic acid, palmitic acid, stearic acid, linoleic acid, linolenic acid, dicaprate, tricaprate, recinleate, monoolein (a k.a. 1-monooleoyl-rac-glycerol), dilaurin, caprylic acid, arachidonic acid, glyceryl 1-monocaprate, 1-dodecylazacycloheptan-2-one, acylcarnitines, acylcholines, mono- and di-glycerides and physiologically acceptable salts thereof (i.e., oleate, laurate, caprate, myristate, palmitate, stearate, linoleate, etc.). Lee et al., Critical Reviews in Therapeutic Drug Carrier Systems page 92 (1991); Muranishi, Critical Reviews in Therapeutic Drug Carrier Systems 7, 1 (1990); El-Hariri et al., *J. Pharm. Pharmacol.* 44, 651-654 (1992)).

The physiological roles of bile include the facilitation of dispersion and absorption of lipids and fat-soluble vitamins (Brunton, Chapter 38 In: Goodman & Gilman's The Pharmacological Basis of Therapeutics, 9th Ed., Hardman et al McGraw-Hill, New York, N.Y., pages 934-935 (1996)). Various natural bile salts, and their synthetic derivatives, act as penetration enhancers. Thus, the term "bile salt" includes any of the naturally occurring components of bile as well as any of their synthetic derivatives.

Complex formulations comprising one or more penetration enhancers may be used. For example, bile salts may be used in combination with fatty acids to make complex formulations. Chelating agents include, but are not limited to, disodium ethylenediaminetetraacetate (EDTA), citric acid, salicylates (e.g., sodium salicylate, 5-methoxysalicylate and homovanilate), N-acyl derivatives of collagen, laureth-9 and N-amino acyl derivatives of beta-diketones (enamines) [Lee et al., Critical Reviews in Therapeutic Drug Carrier Systems page 92 (1991); Muranishi, Critical Reviews in Therapeutic Drug Carrier Systems 7, 1-33 (1990); Buur et al., J. Control Rel. 14, 43-51 (1990)). Chelating agents have the added advantage of also serving as DNase inhibitors.

Surfactants include, for example, sodium lauryl sulfate, polyoxyethylene-9-lauryl ether and polyoxyethylene-20-cetyl ether (Lee et al, Critical Reviews in Therapeutic Drug Carrier Systems page 92 (1991)); and perfluorochemical emulsions, such as FC-43 (Takahashi et al, J. Pharm. Pharmacol. 40, 252-257 (1988)). Non-surfactants include, for example, unsaturated cyclic ureas, 1-alkyl- and 1-alkenylazacyclo-alkanone derivatives (Lee et al, Critical Reviews in Therapeutic Drug Carrier Systems page 92 (1991)); and non-steroidal anti-inflammatory agents such as diclofenac sodium, indomethacin and phenylbutazone (Yamashita et al., J. Pharm. Pharmacol. 39, 621-626 (1987)).

As used herein, "carrier compound" includes a nucleic acid, or analog thereof, which is inert (i.e., does not possess biological activity per se) but is recognized as a nucleic acid by in vivo processes that reduce the bioavailability of a nucleic acid having biological activity by, for example, degrading the biologically active nucleic acid or promoting its removal from circulation. The coadministration of a nucleic acid and a carrier compound, typically with an excess of the latter substance, can result in a substantial reduction of the amount of nucleic acid recovered in the liver, kidney or other extracirculatory reservoirs, presumably due to competition between the carrier compound and the nucleic acid for a common receptor. In contrast to a carrier compound, a "pharmaceutically acceptable carrier" (excipient) is a pharmaceutically acceptable solvent, suspending agent or any other pharmacologically inert vehicle for delivering one or more nucleic acids to an animal. The pharmaceutically acceptable carrier may be liquid or solid and is selected with the planned manner of administration in mind so as to provide for the desired bulk, consistency, etc., when combined with a nucleic acid and the other components of a given pharmaceutical composition. Typical pharmaceutically acceptable carriers include, but are not limited to, binding agents (e.g., pregelatinized maize starch, polyvinylpyrrolidone or hydroxypropyl methylcellulose, etc.); fillers (e.g., lactose and other sugars, microcrystalline cellulose, pectin, gelatin, calcium sulfate, ethyl cellulose, polyacrylates or calcium hydrogen phosphate, etc); lubricants (e.g., magnesium stearate, talc, silica, colloidal silicon dioxide, stearic acid, metallic stearates, hydrogenated vegetable oils, corn starch, polyethylene glycols, sodium benzoate, sodium acetate, etc.); disintegrates (e.g., starch, sodium starch glycolate, etc.); or wetting agents (e.g., sodium lauryl sulphate, etc.).

The compositions provided herein may additionally contain other adjunct components conventionally found in pharmaceutical compositions, at their art-established usage levels. Thus, for example, the compositions may contain additional compatible pharmaceutically-active materials such as, e.g., antipruritics, astringents, local anesthetics or anti-inflammatory agents, or may contain additional materials useful in physically formulating various dosage forms of the composition of present invention, such as dyes, flavoring agents, preservatives, antioxidants, opacifiers, thickening agents and stabilizers. However, such materials, when added, should not unduly interfere with the biological activities of the components of the compositions provided herein.

Regardless of the method by which compounds (e.g. oligonucleotides, mimetic peptides, etc.) are introduced into a patient, colloidal dispersion systems may be used as delivery vehicles to enhance the in vivo stability of the oligonucleotides and/or to target the oligonucleotides to a particular organ, tissue or cell type. Colloidal dispersion systems include, but are not limited to, macromolecule complexes, nanocapsules, microspheres, beads and lipid-based systems including oil-in-water emulsions, micelles, mixed micelles, liposomes and lipid:oligonucleotide complexes of uncharacterized structure. A preferred colloidal dispersion system is a plurality of liposomes. Liposomes are microscopic spheres having an aqueous core surrounded by one or more outer layers made up of lipids arranged in a bilayer configuration (see, generally, Chonn et al., Current Op. Biotech. 6, 698-708 (1995)).

In certain embodiments, antisense compounds and mimetic peptides can be incorporated into or used in conjunction with a biodistribution directing moiety, including one or more polymer, to direct the biodistribution of the antisense compound, mimetic peptide, or other compound provided herein to the proximity of the a desired target or to allow for continuous release of thereof. Active agents include, for example, compounds useful for increasing therapeutic efficacy, for optimizing biodistribution and bioavailability, for reducing tissue damage, for promoting healing, or for increasing patient comfort; exemplary active agents include vasoactive agents, anesthetics, therapeutic agents for ischemia, growth factors and cytokines. Alternatively, microparticulate or nanoparticulate polymeric bead dosage forms may be used in composition provided herein. Compounds provided herein may be used in combination with an active agent and encapsulated in a particulate dosage form with a number of ligand or anti-ligand molecules attached thereto.

In this manner, mimetic peptides, antisense compounds, and other compounds provided here, alone or in combination with other active agents, are released at that site over time to provide a sustained therapeutic benefit. Sustained release dosage forms are also useful with regard to other active agents useful in the practice of the present invention, such as growth factors, cytokines, and the like. Release of the active agent from the particulate dosage forms of the present invention can occur as a result of both diffusion and particulate matrix erosion. Biodegradation rate directly impacts active agent release kinetics.

In certain embodiments, controlled release parenteral formulations of the mimetic peptide compositions, antisense compounds, and compounds of the present invention can be made as implants, oily injections, or as particulate systems. Particulate systems include microspheres, microparticles, microcapsules, nanocapsules, nanospheres, and nanoparticles. Microcapsules contain the therapeutic protein as a central core. In microspheres the therapeutic is dispersed throughout the particle. Liposomes can be used for controlled release as well as drug targeting of entrapped drug.

Antisense polynucleotides may be present in a substantially isolated form. It will be understood that the product may be mixed with carriers or diluents which will not interfere with the intended purpose of the product and still be regarded as substantially isolated. A product may also be in a substantially purified form, in which case it will generally comprise 90%, e.g. at least about 95%, 98% or 99% of the polynucleotide or dry mass of the preparation.

In certain embodiments, the pharmaceutical composition of the invention, including antisense compounds or mimetic peptides, can be administered locally, nasally, orally, gastrointestinally, intrabronchially, intravesically, intravaginally, into the uterus, sub-cutaneously, intramuscularly, periarticularly, intraarticularly, into the cerebrospinal fluid (ICSF), into the brain tissue (e.g. intracranial administration), into the spinal medulla, into wounds, intraperitoneally or intrapleurally, or systemically, e.g. intravenously, intraarterially, intraportally or into the organ directly, such as the heart. An intravenously administered agent becomes bioavailable faster than an agent administered via other routes, therefore generally rendering intravenous administered agents more toxic. Alternatively, intraarterial administration of the antisense compounds, mimetic peptides, and other compounds of the invention can be applied to disease targets present in organs or tissues for which supply arteries are accessible. Applications for intraarterial delivery include, for example, treatment of liver-related conditions through hepatic artery administration, brain-related conditions through carotid artery administration, lung-related conditions through bronchial artery administration and kidney-related conditions through renal artery administration. Thus, for example, in certain embodiments the compound is a peptide/polypeptide (e.g. mimetic peptide) for systemic delivery, and in other embodiments the compound is a peptide/polypeptide (e.g. mimetic peptide) for direct delivery (e.g. to the ventricles of the brain or into the spinal cord).

For example, U.S. Pat. No. 6,752,987 and US published app. No. 20030148968 to Hammond, incorporated by reference herein, which describe in vivo delivery for heart disease, which can be accomplished by injection of the pharmaceutical composition into a blood vessel or other conduit directly supplying the myocardium or tissue. Preferably, the injection can be performed by administration into one or both coronary arteries or other tissue-specific arteries (or by a bolus injection into peripheral tissue). By way of illustration, for delivery to the myocardium, such injection is preferably achieved by catheter introduced substantially (typically at least about 1 cm) within the lumen of one or both coronary arteries or one or more saphenous veins or internal mammary artery grafts or other conduits delivering blood to the myocardium. Preferably the injection is made in both left and right coronary arteries to provide general distribution to all areas of the heart. To further augment the localized delivery of the peptide mimetics or peptide mimetics in combination with active agent, and to enhance delivery efficiency, in accordance with the present invention, one can infuse a vasoactive agent, preferably histamine or a histamine agonist or a vascular endothelial growth factor (VEGF) protein or a nitric oxide donor (e.g. sodium nitroprusside), into the tissue to be treated, either coincidentally with or, preferably, within several minutes before, introduction of the peptide mimetics or peptide mimetics in combination with active agents.

In one aspect, methods of spinal administration include but not limited to, techniques of spinal injections known in the art. General methods of intra-spinal injection or administration include, for example, epidural injections (including caudal block, translumbar, and transforaminal injections); facet joint injections (including interarticular and nerve block injections); hardware injections; sacroiliac joint injections, and differential lower extremity injections. With most spinal injections, a local anesthetic (numbing medication) such as, for example, lidocaine (or Xylocalne) or Bupivacaine (Marcaine), is co-injected into a specific area of the spine.

In certain aspects, the antisense compounds or mimetic peptides can be administered alone or co-administered in combination with agents used for general treatment of stroke and ischemia. These include, for example, ischema stroke, which is treated by removing obstruction and restoring blood flow to the brain, and 2) hemorrhagic stroke, which involves the introduction of an obstruction to prevent rupture and bleeding of aneurysms and arteriovenous malformations. In one aspect, treatments for ischemic stroke can include the use of clot-busters, such as tPA. Generally, tPA is administered within a three-hour window from the onset of symptoms. In another aspect, treatment may include preventative measure with administration of anticoagulants/antiplatelets. Antiplatelet agents such as aspirin, and anticoagulants such as warfarin interfere with the blood's ability to clot and can be used to prevent stroke onset. In one aspect, treatments for ischemic stroke can include Carotid Endarterectomy, which is a procedure where a blood vessel blockage is surgically removed from the carotid artery. In another aspect, treatments for ischemic stroke can include Angioplasty/Stents, which involves the use of balloon angioplasty and implantable steel screens called stents to treat cardiovascular disease in which mechanical devices are used to remedy fatty buildup clogging the vessel. For hemorrhagic stroke, surgical treatment is often recommended to either place a metal clip at the base, called the neck, of the aneurysm or to remove the abnormal vessels comprising an Arteriovenous Malformation (AVM). One such example is the Endovascular Procedures, e.g., "coils," which is less invasive and involve the use of a catheter introduced through a major artery in the leg or arm, guided to the aneurysm or AVM where it deposits a mechanical agent, such as a coil, to prevent rupture.

In certain aspects, the antisense compounds or mimetic peptides can be co-administered as a combined modality for surgical treatment of stroke and ischemia. Surgical interventions for treatment of stroke includes, but is not limited to, conventional surgical modalities for treatment of stroke, which can be used to prevent stroke, to treat acute stroke, or to repair vascular damage or malformations (for example, AVM) in and around the brain. These include, for example, carotid endarterectomy which is a procedure used to remove atherosclerotic plaque from the carotid artery when this vessel is blocked; and Extracranial/intracranial (EC/IC) bypass; which is a procedure that restores blood flow to a blood-deprived area of brain tissue by rerouting a healthy artery in the scalp to the area of brain tissue affected by a blocked artery.

In other aspects, surgical modalities for stroke or ischemia include, for example, clipping technique, which is useful for treatment of brain aneurysms that cause subarachnoid hemorrhage. Clipping involves clamping off the aneurysm from the blood vessel, which reduces the chance that it will burst and bleed. In another aspect, surgical modality can include "detachable coil technique" for the treatment of high-risk intracranial aneurysms. The technique generally involves the insertion of a small platinum coil through an artery in the thigh and threaded through the arteries to the site of the aneurysm. The coil is then released into the aneurysm, where it evokes an immune response from the body. The body produces a blood clot inside the aneurysm, strengthening the artery walls and reducing the risk of rupture. Once the aneurysm is stabilized, a neurosurgeon can clip the aneurysm with less risk of hemorrhage and death to the patient. It is also contemplated that the surgical treatment of stroke include recently developed techniques such as Stereotactic Microsurgery for AVMs and Aneurysms. It employs sophisticated computer technology and geometric principles to pinpoint the precise location of the AVM. During the procedure, a custom-fitted frame is attached to the patient's head and three-dimensional reference points are established using CT or MRI. This technique allows neurosurgeons to locate the AVM within one or two millimeters so they can operate, using microscope-enhanced methods and delicate instruments, without affecting normal brain tissue. Other modalities include, for example, Stereotactic Radiosurgery for AVMs, which is a minimally invasive, relatively low-risk procedure that uses the same basic techniques as stereotactic microsurgery to pinpoint the precise location of the AVM. Once located, the AVM can be obliterated by focusing a beam of radiation that causes it to clot and then disappear. Due to the precision of this technique, normal brain tissue usually is not affected. Other modalities include, for example, Hypothermia, which utilizes hypothermia (cooling of the body) to prevent stroke during surgical treatment of giant and complex aneurysms or difficult AVMs. Dropping the brain temperature gives the surgeon the necessary time to operate with minimal risk of surgery-induced stroke. Special equipment known as a cardiopulmonary bypass machine is sometimes used to completely shunt blood flow away from the brain while the body is placed under deep hypothermia. Other modalities include, for example, revascularization, which is a surgical technique for treating aneurysms or blocked cerebral arteries. The technique essentially provides a new route of blood to the brain by grafting another vessel to a cerebral artery or providing a new source of blood flow to the brain.

In certain embodiments, targeted administration can be conducted using antisense compounds or mimetic peptides alone or in combination with other active agents such as, for example, compounds useful for increasing efficacy, reducing tissue damage, promoting healing, or increasing patient comfort. US published patent application 20040259768 describes methods and agents for targeted release and the contents of which is hereby incorporated by reference.

A variety of catheters and delivery routes can be used to achieve intracoronary delivery, as is known in the art. For example, a variety of general-purpose catheters, as well as modified catheters, suitable for use in the present invention are available from commercial suppliers such as Advanced Cardiovascular Systems (ACS), Target Therapeutics and Cordis. Also, where delivery to the myocardium is achieved by injection directly into a coronary artery (which is presently most preferred), a number of approaches can be used to introduce a catheter into the coronary artery, as is known in the art. By way of illustration, a catheter can be conveniently introduced into a femoral artery and threaded retrograde through the iliac artery and abdominal aorta and into a coronary artery. Alternatively, a catheter can be first introduced into a brachial or carotid artery and threaded retrograde to a coronary artery. Detailed descriptions of these and other techniques can be found in the art (see, e.g., Topol, E J (ed.), The Textbook of Interventional Cardiology, 2nd Ed. (W.B. Saunders Co. 1994); Rutherford, R B, Vascular Surgery, 3rd Ed. (W.B. Saunders Co. 1989); Wyngaarden J B et al. (eds.), The Cecil Textbook of Medicine, 19th Ed. (W.B. Saunders, 1992); and Sabiston, D, The Textbook of Surgery, 14th Ed. (W.B. Saunders Co. 1991)).

The compounds provided herein may be administered parentally. It is sometimes preferred that certain compounds are combined with a pharmaceutically acceptable carrier or diluent to produce a pharmaceutical composition. Suitable carriers and diluents include isotonic saline solutions, for example phosphate-buffered saline. The composition may be formulated for parenteral, intramuscular, intracerebral, intravenous, subcutaneous, or transdermal administration. Uptake of nucleic acids by mammalian cells is enhanced by several known transfection techniques, for example, those that use transfection agents. The formulation which is administered may contain such agents. Example of these agents include cationic agents (for example calcium phosphate and DEAE-dextran) and lipofectants (for example Lipofectam™ and Transfectam™).

Formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated gloves, condoms, and the like may also be useful. Compositions for oral administration include powders or granules, suspensions or solutions in water or non-aqueous media, capsules, sachets or tablets. Thickeners, flavoring agents, diluents, emulsifiers, dispersing aids or binders may be desirable.

Compositions for parenteral administration may include sterile aqueous solutions which may also contain buffers, diluents and other suitable additives. In some cases it may be more effective to treat a patient with an oligonucleotide in conjunction with other traditional therapeutic modalities in order to increase the efficacy of a treatment regimen. As used herein, the term "treatment regimen" is meant to encompass therapeutic, palliative and prophylactic modalities.

Dosing can be dependent on a number of factors, including severity and responsiveness of the disease state to be treated, and with the course of treatment lasting from several days to several months, or until a cure is effected or a diminution of the disease state is achieved. Toxicity and therapeutic efficacy of compounds provided herein can be determined by standard pharmaceutical procedures in cell cultures or experimental animals. For example, for determining The $LD_{50}$ (the dose lethal to 50% of the population) and the $ED_{50}$ (the dose therapeutically effective in 50% of the population). The dose ratio between toxic and therapeutic effects is the therapeutic index and it can be expressed as the ratio $LD_{50}/ED_{50}$. Compounds which exhibit large therapeutic indices are preferred. While compounds that exhibit toxic side effects may be used, care should be taken to design a delivery system that targets such compounds to the site of affected tissues in order to minimize potential damage to uninfected cells and, thereby, reduce side effects.

The data obtained from the cell culture assays and animal studies can be used in formulating a range of dosage for use in humans. The dosage of such compounds lies preferably within a range of circulating concentrations that include the $ED_{50}$ with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the $IC_{50}$ (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography. Dosing schedules can be calculated from measurements of drug accumulation in the body of the patient. Dosages may vary depending on the relative potency of individual compounds, including peptide mimetics or oligonucleotides, and can generally be estimated based on EC50 s found to be effective In vitro and in in vivo animal models.

Suitable dosage amounts may, for example, vary from about 0.1 ug up to a total dose of about 1 gram, depending upon the route of administration. Guidance as to particular dosages and methods of delivery is provided in the literature and generally available to practitioners in the art. Those skilled in the art will employ different formulations for nucleotides than for proteins or their inhibitors. Similarly, delivery of polynucleotides, polypeptides, and compounds provided herein will be specific to particular cells, conditions, and locations. In general, dosage is from 0.01 mg/kg to 100 mg per kg of body weight, and may be given once or more daily, weekly, monthly or yearly, or even once every 2 to 20 years. In certain embodiments, the dosage may be given from immediately post surgery to 24 hours, in another embodiment; the dosage is given from 2 hours and up to 24 hours. Long-acting compositions may be administered every 3 to 4 days, every week, or biweekly depending on the half-life and clearance rate of the particular formulation. Persons of ordinary skill in the art can easily estimate repetition rates for dosing based on measured residence times and concentrations of the drug in bodily fluids or tissues. Following successful treatment, it may be desirable to have the patient undergo maintenance therapy to prevent the recurrence of the disease state, wherein the mimetic peptide is administered in maintenance doses, ranging from 0.01 mg/kg to 100 mg per kg of body weight, once or more daily, to once every 20 years. In the treatment or prevention of conditions which require connexin modulation an appropriate dosage level will generally be about 0.001 to 100 mg per kg patient body weight per day which can be administered in single or multiple doses. A suitable dosage level can be about 1 to about 40 mg/kg per day. In certain embodiments, compounds provided herein, including specifically antisense compounds or mimetic peptides, are administered in an amount to achieve in vivo concentrations from about 1 micromolar to about 1 millimolar, from about 10 micromolar to about 500 micromolar, or from about 30 micromolar to about 300 micromolar, and from about 25 micromolar to about 300 micromolar final concentration over the damaged site, and including, about 25 micromolar, or about 160 micromolar, or about 300 micromolar final concentration over the damaged site, and still more typically between about 1 micromolar to about 10 micromolar.

In another aspect, peptide inhibitors and mimetic peptides may be administered to achieve from about 0.1 micrograms per ml to about 1 mg per ml, from about 10 micrograms per ml to about 500 micrograms per ml, or from about 100 micrograms per ml to about 500 micrograms per ml, about 250 micrograms per ml, or about 300 micrograms per ml final concentration over the damaged site.

The anti-connexin compound (e.g. peptide mimetic molecules) are introduced at a number of different concentrations preferably between $1\times10^{-10}$ M to $1\times10^{-4}$ M. Once the minimum concentration that can adequately modulate a connexin (including control gene expression is identified, the optimized dose is translated into a dosage suitable for use in vivo. Thus, an anti-connexin compound can be administered to achieve at desired concentration in vivo in a particular cell, tissue, or organ of a subject (e.g. a mammal). For example, in certain embodiments a mimetic peptide or other peptide-based anti-connexin compound is administered (e.g. systemically, orally, or parenterally, e.g., IV, etc.) to achieve a final in vivo peptide concentration of about 0.1 micromolar $1\times10^{-7}$ M), about 1 micromolar ($1\times10^{-6}$ M), about 2 micromolar ($2\times10^{-6}$ M), about 3 micromolar ($3\times10^{-6}$ M), about 5 micromolar ($5\times10^{-6}$ M), about 10 micromolar ($1\times10^{-5}$ M), about 50 micromolar ($5\times10^{-5}$ M), about 250 micromolar ($2.5\times10^{-4}$ M, about 500 micromolar ($5\times10^{-4}$ M), and 1 milimolar ($1\times10^{-3}$ M), and 5 milimolar ($1\times10^{-3}$ M) or greater. With some mimetic peptides an in vivo concentration of between about 1 to 10 micromolar ($1\times10^{-6}$ M to $1\times10^{-5}$ M), including about 5 micromolar ($5\times10^{-6}$ M), is desirable. In another aspect, a peptide-based anti-connexin compound is administered directly to a tissue (e.g. ventricles of the brain of a mammal) in an amount of about 0.1 micromol/kg, 1 micromol/kg, 10 micromol/kg, 50 micromol/kg, 250 micromol/kg, 500 micromol/kg, 1000 micromol/kg, 5000 micromol/kg. For example, an inhibiting concentration in culture of $1\times10^{-7}$ M translates into a dose of approximately 0.6 mg/kg bodyweight for certain compounds. Levels of an anti-connexin compound (e.g. antisense compound or mimetic peptide molecules) approaching 100 mg/kg bodyweight or higher may be possible after testing the toxicity of the compound in laboratory animals. It is also contemplated that cells from the vertebrate are removed, treated with the mimetic peptide, and reintroduced into the vertebrate.

Compounds described herein can be used in diagnostics, therapeutics, prophylaxis, and as research reagents and in kits. Since the oligonucleotides of this invention hybridize to nucleic acids encoding connexin, sandwich, calorimetric and other assays can easily be constructed to exploit this fact. Provision of means for detecting hybridization of oligonucleotide with the connexin genes or mRNA can routinely be accomplished. Such provision may include enzyme conjugation, radiolabel ling or any other suitable detection systems. Kits for detecting the presence or absence of connexin may also be prepared.

The compounds of the invention may also be used for research purposes. Thus, the specific hybridization exhibited by the oligonucleotides may be used for assays, purifications, cellular product preparations and in other methodologies which may be appreciated by persons of ordinary skill in the art.

Various aspects of the invention will now be described with reference to the following experimental section which will be understood to be provided by way of illustration only and not to constitute a limitation on the scope of the invention.

The following Examples are included for illustration and not limitation.

Example 1

Central Nervous System

Damage to the central nervous system can be devastating with enormous long-term cost to society in patient care. The pathological changes that occur in severely injured neuronal tissue share common characteristics. Within 24-48 hours after injury the damage spreads significantly increasing the size of the area affected. This spread is propagated by the gap junction-mediated bystander effect by which gap junction channels spread neurotoxins and calcium waves from the damage site to otherwise healthy tissue. Lin, J. H. et al. *Nature Neurosci.* 1: 431-432 (1998). This is, however, also accompanied by inflammatory swelling which results in closure of the extracellular space and cell death over the following 24-48 hours. In fetal brain damage the swelling, for example, can be tracked as a change in cortical electrical impedance which measures cytotoxic edema Reddy, K., et al., *Pediatric Research* 43: 674-682 (1998). This new damage, which is not an immediate result of the initial insult but subsequent events, occurs between 6 and 48 hours after injury, but may be as early as two hours, provides a window of opportunity for treatment preventing damage spread.

FIG. 1 shows that oedema and swelling occurs even when the cord is excised from the animal (FIG. 1A). In both cases, the oedema can be blocked using antisense oligodexoynucleotides (ODNs) which prevent translation of the gap junction protein Connexin 43 (FIG. 1B). In the excised cord segments, the volume of swelling assessed is significantly different between treated and controls (assessed by measuring area of swelling viewed from the top –p=0.001).

Figures 3A, 3B, 3C:
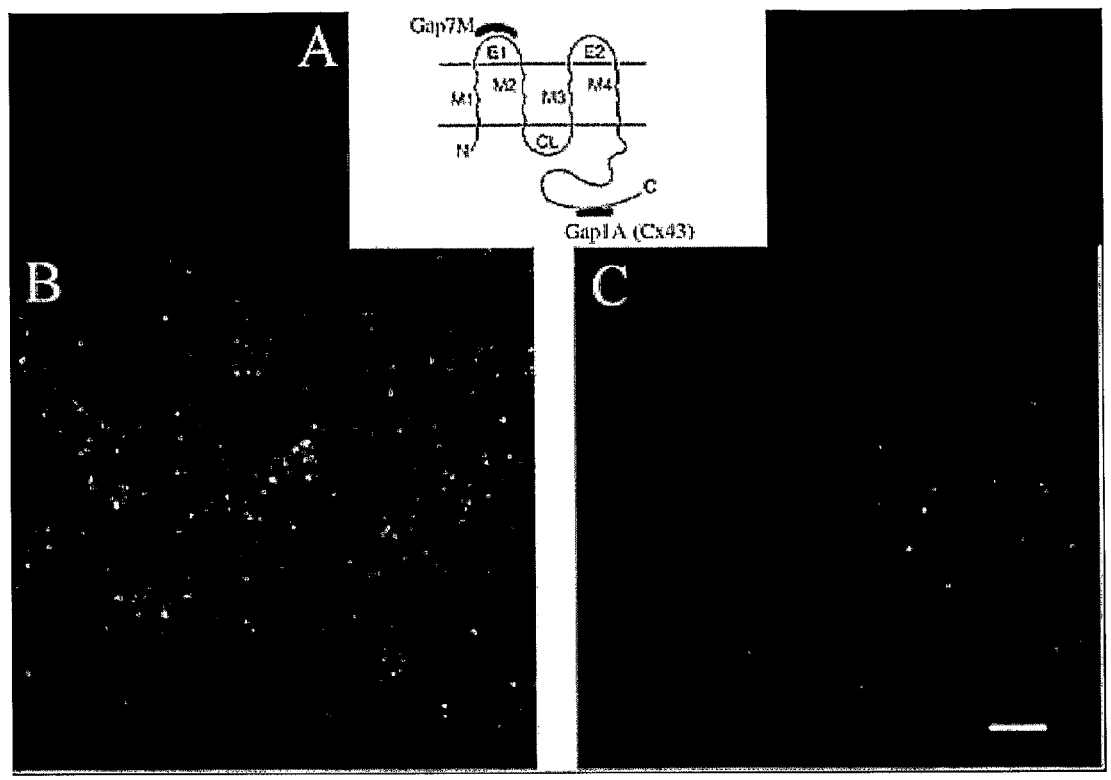
FIG. 3B shows dual labeling with the two antibodies in spinal cord 24 hours after a crush wound. Based on observation of the overlap in binding of the two labeled antibodies, most of the two antibodies colocalised, indicating that a significant portion of the protein present has not docked with neighboring cells connexons and remains as hemichannels. Connexin 43 specific antisense ODNs prevent protein translation and few hemichannels are seen in treated cords (FIG. 3C).
Figure 4:
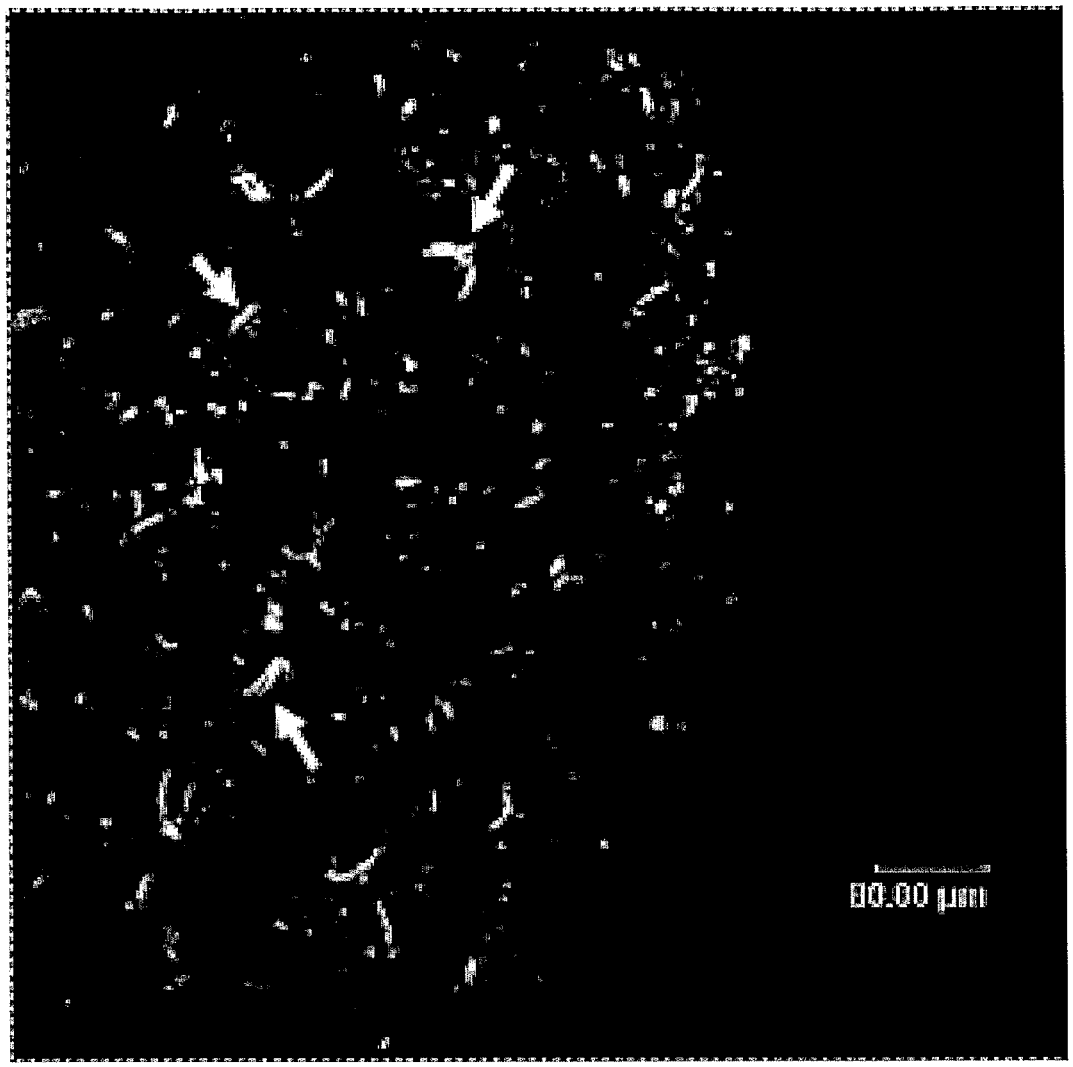
FIG. 4 shows Isolectin B4 labeling of a tissue slice from a spinal cord which had been in organotypic culture for five days. The lectin binds to both microglial and blood vessel endothelial cells. The capillary vessels in this connexin 43 specific antisense ODN treated segment remain intact after five days (arrows). In control cords few vessels remain fully intact after two days; by five days the pedominant labeling in controls is of activated macrophage phenotype glial cells.

This swelling observed after CNS damage and blocked using connexin specific antisense ODNs indicates that gap junction hemichannels are being expressed and are opening under pathological conditions leading to a direct pathway between the cell cytoplasm and the extracellular space. Neurons subsequently die. Examination of cells 24 hours after injury shows vacuolation and membrane inward blebbing (FIG. 2) caused by the uptake of extracellular fluid. As described in the FIG. 3A legends, immunohistochemical labeling of connexin43 using antibodies which bind to the extracellular loop (broad band top left of the connexin topography diagram and labelled Gap7M) and antibodies to the cytoplasmic carboxyl tail of the protein (broad band at bottom right of connexin topography diagram and labelled GAP1A). The cytoplasmic antibody labels all connexin43 proteins and is used with a red fluorescently tagged secondary antibody. The Gap7M antibody can only label exposed extracellular loops of hemichannels and is used with a green fluorescently tagged secondary antibody. Gap7M is sterically hindered from binding to docked connexons which are forming intact channels between cells and the only connexons which label with both antibodies (and will therefore appear yellow when both the red and green secondary antibody are colocalised) are existing as hemichannels. FIG. 3B: As described in the Figure legends, this image shows dual labeling with the two antibodies described in FIG. 3A applied to spinal cord sections 24 hours after a crush wound. The image has small bright spots which are labelled connexins and large, lighter shaded spots marking cell nuclei labelled with DAPI. A significant portion of the connexin labelling in combined images indicates that the two antibodies (Gap7M and GAP1A) are colocalised. This means that the connexin extracellular loops are exposed and most of the connexons present have not docked with the neighboring cell's connexons and remains as hemichannels. FIG. 3C: As described in the Figure legends, this image shows dual labeling with the two connexin antibodies described in FIG. 3A applied to spinal cord 24 hours after a crush wound. In this case the application of Connexin43 specific antisense ODNs has been applied to prevent protein translation. Hemichannels will appear as bright spots (due to colocalisation of green fluorescently tagged Gap7M and red fluoresecently tagged GAP1A). In the Figure, the larger, lighter spots are cell nuclei labelled with DAPI. Little gap junction protein is labelled, and few hemichannels are seen in these treated cords.

Furthermore, gap junction antibodies which bind and label the extracellular loops of the connexin protein (Gap7M antibodies —FIG. 3A) were shown to label extensive protein levels 24 hours following rat spinal cord injury (FIG. 3B). These antibodies only bind to the portions of hemichannels that interact to form a multimer upon docking in the membrane. These data indicates that much of the connexin 43 upregulation seen in early stages after CNS damage remains in hemichannel form.

The expression of the connexin protein and hemichannel formation is blocked using connexin 43 specific antisense ODNs applied in a Pluronic F-127 (Poloxamer) gel at the time of wounding (FIG. 3C).

This treatment indicates that ODN treatment in an explant model has maximum effect on protein levels (maximum knockdown) at 6-8 hours after application with knockdown apparent within 2 hours and protein levels recovering after about 24 hours (see Qiu et al, 2003; Becker et al, 1999). In the brain similarly, slices of tissue placed into culture swell, but the swelling can be blocked using the connexin 43 specific antisense ODNs preventing hemichannel formation (C Green—data not shown).

Following injury, upregulation of connexin levels leads to hemichannel formation causing cellular oedema and death. This is not, however, restricted to the neural population. In the excised spinal cord segments, Isolectin B4 label (which binds to carbohydrates on the surface of microglial cells and endothelial cells of blood vessels) outlines blood capillaries even after 5 days in culture in the antisense treated tissue (FIG. 5). In control segments few capillaries remain after two days (and after 5 days the predominant Isolectin B4 labeling is of activated macrophage phenotype (foam) glial cells). In connexin 43 antisense treated brain slices, capillaries remain intact even after two weeks in culture; while none remain in control slices (data not shown).

Following injury to rat spinal cord in vivo, rats were treated with connexin specific antisense ODNs and 24 hours later injected fluoresceinated—Bovine Serum Albumin (FITC tagged BSA) into the rat-tail vein. Control animals show extensive leakage of the dye from the vascular system into surrounding tissues even 5 mm rostral to the wound site (FIG. 5A). In sharp contract, antisense treated animals show little sign of leakage with the dye restricted to the capillary bed (FIG. 5B). The capillary endothelial cells, which express connexin 43, are also forming hemichannels and becoming disrupted. Importantly, the connexin 43 specific antisense ODN treatment provided herein prevents the breakdown of the blood-brain barrier, breakdown of the vascular system (necessary for reperfusion and recovery), and the spread of damage. The results show that this breakdown in the capillary/blood vessel system is not restricted to the central nervous system, and that a broader range of applications, such as for treatment vascular conditions, would benefit from modulation of connexins. As described in the FIG. 5A legends, this image shows triple labeling of sheep heart ventricle wall 24 hours after an ischemic infarct. The four panels comprising this image are from tissue distant to the infarcted region. The tissue is labeled with Isolection B4 (top left panel) which is binding to blood vessel endothelial cells, and with antibodies to Gap7M (top right panel) and antibodies to connexin43 (bottom left panel). The Gap7M antibodies recognize conserved extracellular loop regions of the connexin proteins so are not connexin isoform specific, but do mark hemichannels (they are sterically hindered from accessing their epitope in intact channels). The top left image shows normal capillary structure is present in this region. No hemichannels are present (top right) but connexin43 is present in intercalated disks of the working myocardium (bottom left). The bottom right panel shows an overlay of the other three images. Little connexin43 label overlies the capillary vessel walls as it is predominantly associated with the muscle cells. As described in the FIG. 5B legends, this image shows triple labeling of sheep heart ventricle wall 24 hours after an ischemic infarct. The region seen is away from the infarct but closer to it than is shown in FIG. 5B shows the tissue is labeled with Isolection B4 (top left panel) which is binding to blood vessel endothelial cells. Most of the vessels are still intact but the vessel walls are disrupted in areas (areas of broader dispersed labelling). Antibodies to Gap7M (top right panel) label hemichannels. Elongated patches of dense hemichannel label are evident. The bottom left panel shows antibody labelling of connexin 43. Careful comparison between these first three panels, or analysis of the patterns present on the bottom right panel which shows the other three merged, shows that the connexin43 is uniquely associated with muscle cells. However, the hemichannel antibody has colabelled regions of the blood vessel wall that appear disrupted, indicating the presence of connexon hemichannels in those areas. As described in the FIG. 5C legends, this image shows triple labeling of sheep heart ventricle wall 24 hours after an ischemic infarct. The region shown is within the infarcted area itself. The tissue is labeled with Isolection B4 (top left panel) which is binding to blood vessel endothelial cells. Most of the vessels appear disrupted (areas of broader dispersed labelling in discontinuous lines). Antibodies to Gap7M (top right panel) label hemichannels. Multiple patches of dense hemichannel label are evident across the whole panel. The bottom left panel shows antibody labelling of connexin43. Careful comparison between these first three panels, or analysis of the patterns present on the bottom right panel which shows the other three panels merged, shows that the connexin43 is associated with muscle cells, but the label is in short patches, quite unlike the usual labelling of connexin43 in the intercalated disks of cardiac muscle. This indicates that the myocytes have also become severely damaged in this central infarct region. The hemichannel antibody has colabelled extensive regions of the blood vessel wall that appear disrupted, indicating the presence of connexon hemichannels in the blood vessel wall. Few capillaries remain intact apparently following this hemichannel expression. Here, as in FIG. 6B, the Gap7M antibody label does not colocalise with the connexin43 label (as it does in the spinal cord—FIG. 2B), indicating they must be of a different gap junction protein isoform, most likely connexin45 (See Camelliti, P., et aI., Cardiovasc. Res. 62: 414-425 (2004).

Example 2

Cardiovascular System

Figure 6A:
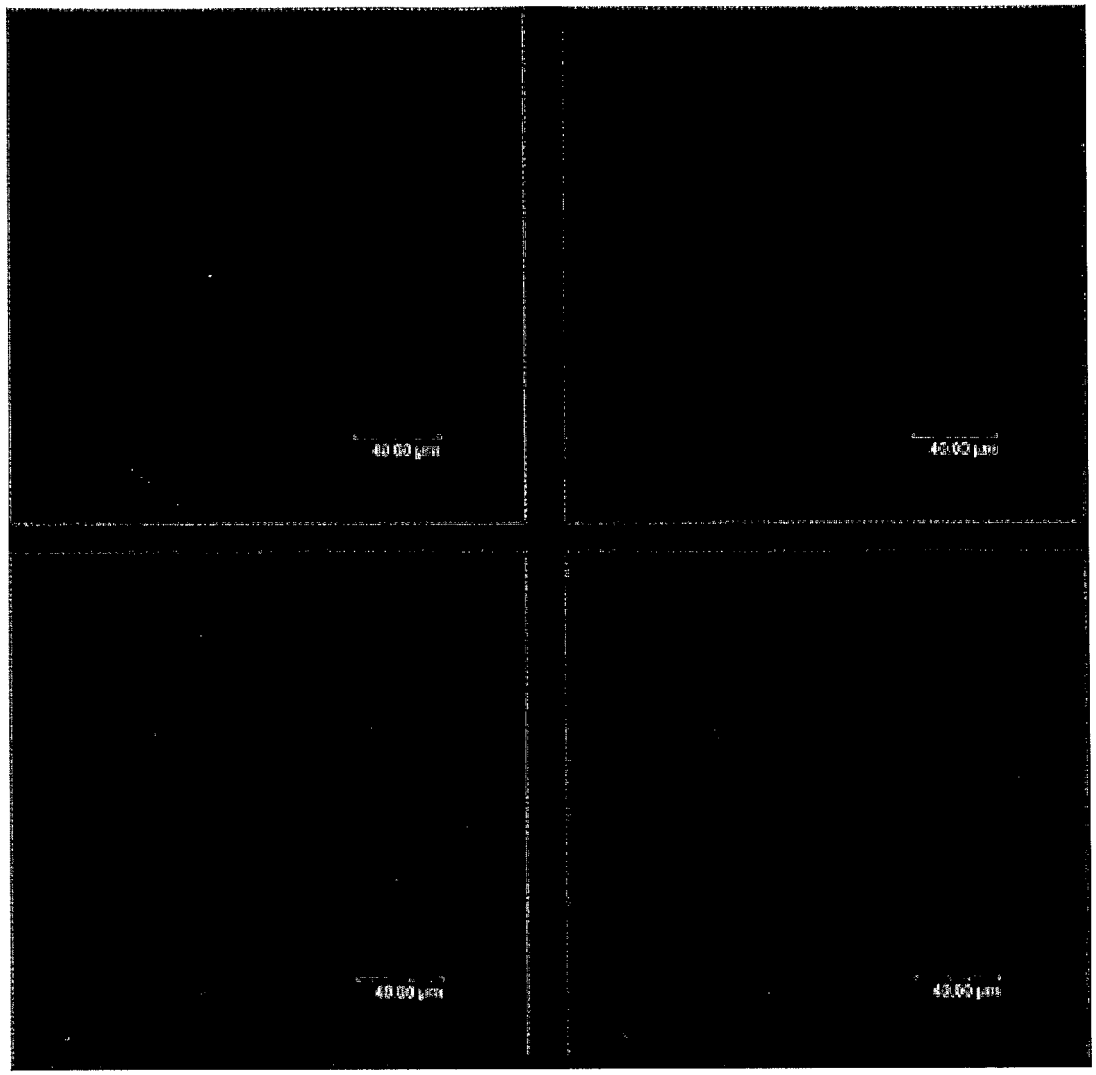
FIG. 6A shows a set of four images from tissue distant from the infarcted region showing Isolection B4 label of capillaries (top left) and connexin 43 gap junctions in the intercalated discs of myocytes (lower left). There is virtually no GAP7M label of hemichannels (top right). The bottom right image is a merge of the other three. The blood vessels remain intact and there is no sign of damage to the myocytes themselves.
Figure 6B:
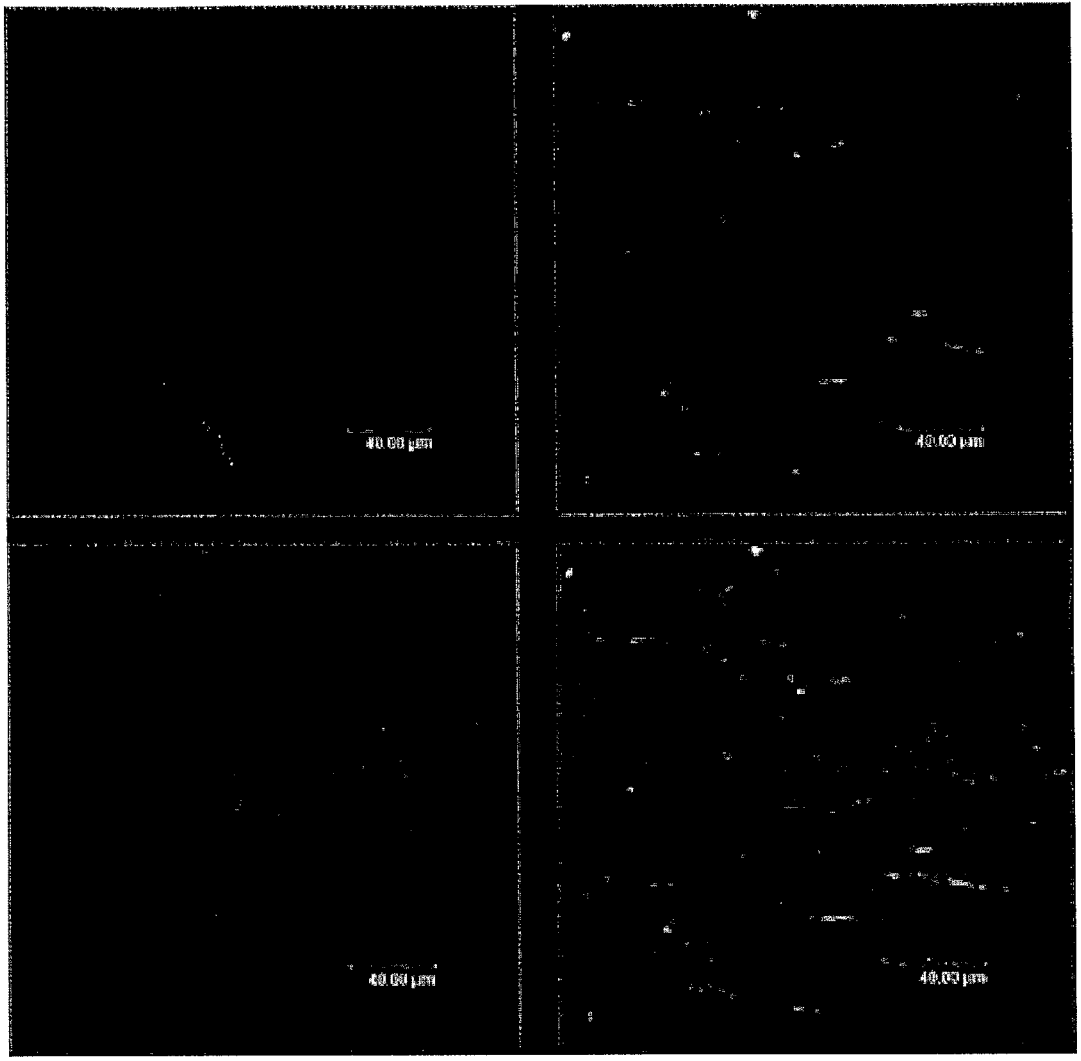
In FIG. 6B a region still away from but closer to the infarct is shown. The same three labels and merged image are shown in this 4-part panel. Most of the vessels are still intact but the vessel walls are disrupted in areas. In these areas hemichannel label colocalises with the ruptured vessel walls. The last panel of four images (FIG. 6C) is within the infarcted area itself. Few capillaries remain intact apparently following extensive hemichannel expression. The connexin 43 label is becoming dispersed and no longer contained in intercalated discs indicating that the myocytes have now become severely damaged. In all cases, the Gap7M antibody label does not colocalise with the connexin 43 label (as it does in the spinal cord), indicating they are a different gap junction protein isoform, most likely connexin 45.
Figure 6C:
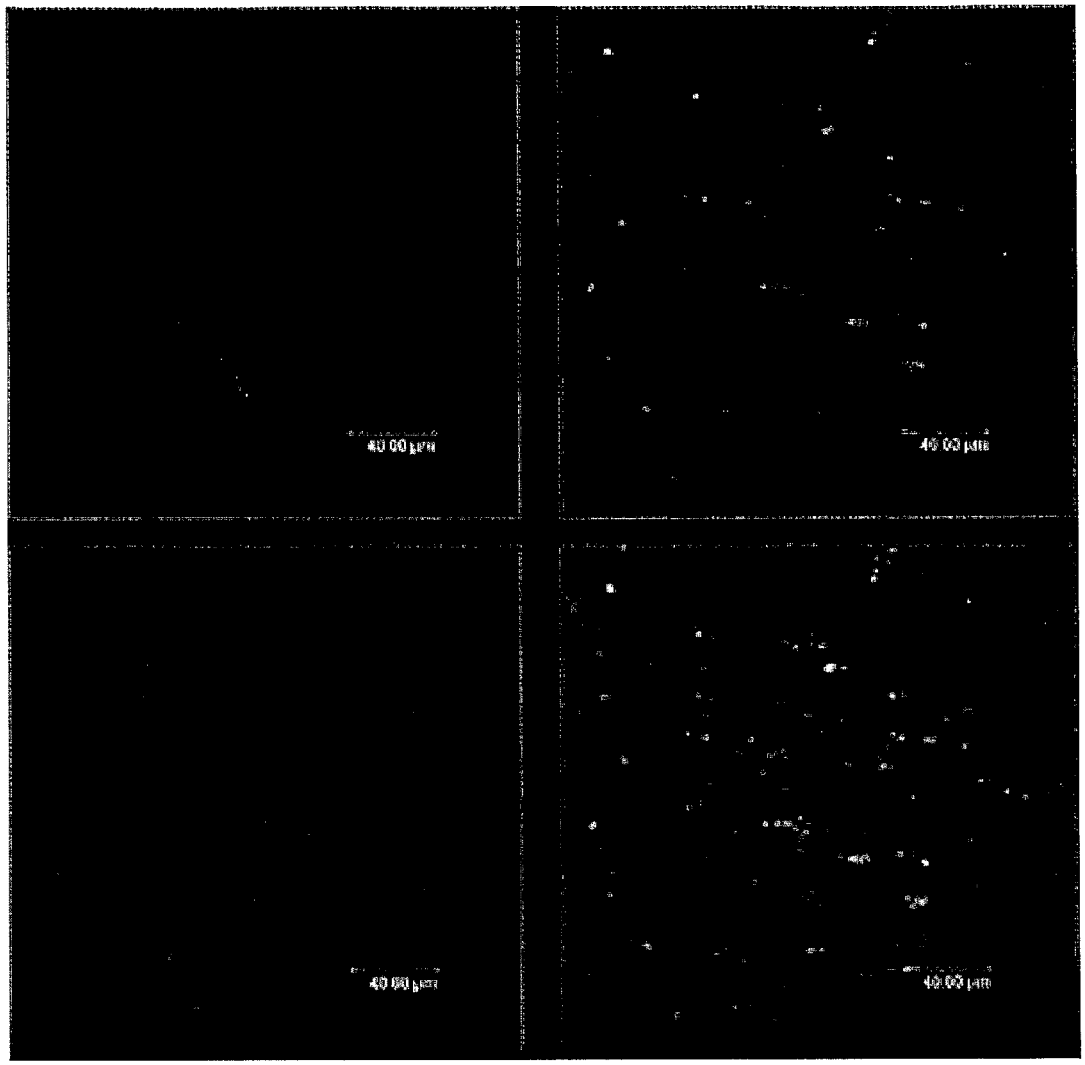
FIG. 6 shows triple labeling of sheep heart tissue in the sheep heart ventricle wall adjacent to ischemic infarct tissue 24 hours after infarction, and within the infarct. The tissue is labeled with Isolection B4 showing the blood vessel endothelial cells (upper left panel), with antibodies to connexin 43 (lower left panel) and with antibodies to Gap7M (upper right panel). The Gap7M antibodies recognize conserved extracellular loop regions of the connexin proteins (not connexin isoform specific), but do mark hemichannels (they are sterically hindered from accessing their epitope in intact channels).

This Example examines the regulation and role of gap junction hemichannels to maintain vascular integrity in the capillary bed adjacent to ischemic tissue damage. A sterile gel foam was delivered through the left anterior descending or circumflex artery to induce transmural myocardial infarcts. The gel was delivered essentially according to the methods of Devlin, G., et al., J. An ovine model of chronic stable heart failure. J. Card Fail. 6: 140-143 (2000). Isolection-B4 labeling of capillary endothelial cells shows that the capillary bed adjacent to ischemic tissue is breaking down. We have recently analyzed progressive infarction in the sheep infarct model (Camelliti et al., Spatially and temporally distinct expression of fibroblast connexins after sheep infarction, Cardiovascular Research, 62:415-425 (2004), and we proposed that this is caused by a gap junction mediated bystander effect. The data presented herein indicate a key role of gap junction mediated bystander effect associated with endothelial cell disruption and following expression of gap junction hemichannels. In triple labeling of 24-hour ischemic sheep heart using Isolectin-B4, connexin 43 and hemichannel antibodies the data show that the hemichannels are not connexin 43 in this case, but instead appear to be connexin 45 (FIGS. 6A, 6B, 6C). Note that Gap7M antibody recognizes conserved regions of the first extracellular loop of the connexin protein and is not connexin specific; it cross reacts with a number of the connexin family members. Connexin 45 is the first connexin to be upregulated following ischemic heart injury (Camelliti et al., 2004). This series of panels (FIGS. 6A, 6B, 6C) show that while damage to the vessel walls is not apparent distant from the infarcted region (FIG. 6A) it becomes progressively worse closer to the infarct region (FIG. 6B) and in conjunction with hemichannel expression. Within the infarct region itself (FIG. 6C) hemichannel protein expression is high, the capillary walls are extensively disrupted, and myocyte intercalated discs (where the connexin 43 gap junctions are located) are becoming dispersed. As described in the FIG. 6 legends, this image shows shows Isolectin B4 (top panel) marking capillary endothelial cells and myomesin antibody labeling (middle panel) marking M lines in the sacromeres of myocytes in a sheep heart ventricular infarct, 24 hours after ischemia. This region is the same as that shown in FIG. 6C. The blood capillaries are completely disrupted and normal myocyte sarcomeric banding pattern has been destroyed indicating muscle cell death is occurring in parallel with vessel wall disintegration. The lower image is a merger of the top two showing the relationship between the disrupted capillaries and abnormal muscle band labelling.

Figure 7:
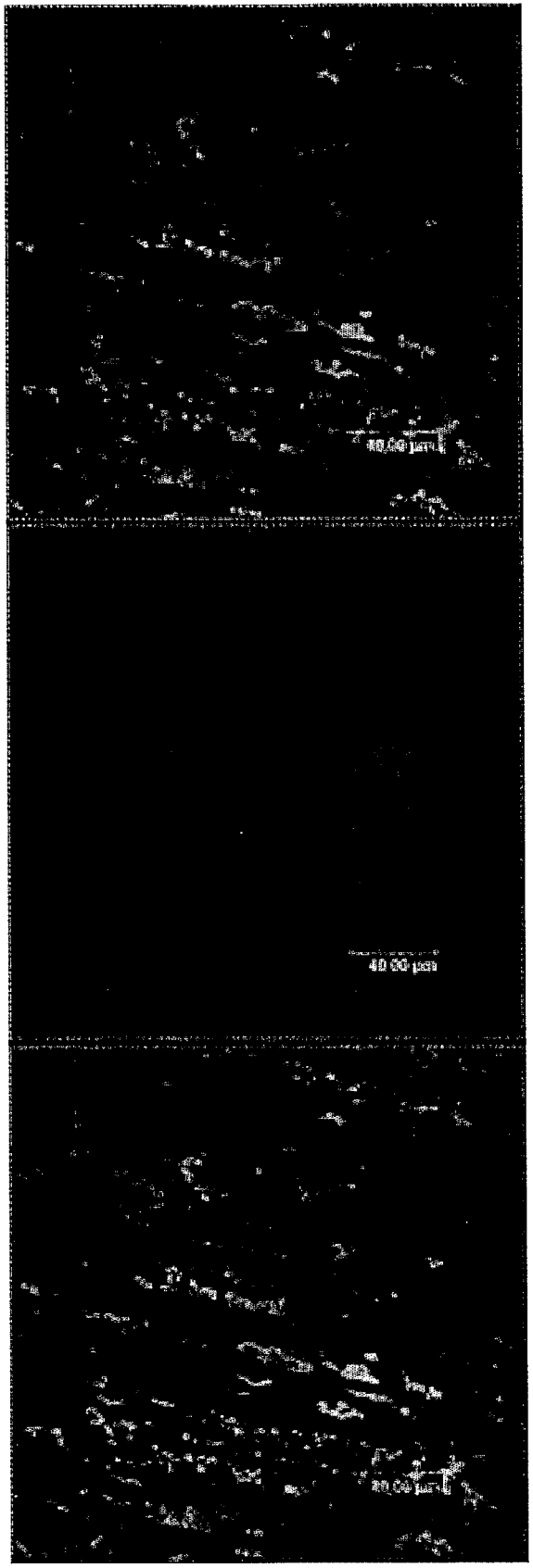
FIG. 7 shows Isolectin B4 (upper panel) marking capillary endothelial cells and myomesin antibody labeling (middle panel) marking M lines in the sacromeres of the myocytes in an infarct 24 hours after ischemia The lower panel shows the merged image, and colocalisation of the two antibodies is observed. This region is the same as that shown in FIG. 6C. The blood capillaries are completely disrupted and normal myocyte sarcomeric banding pattern has been destroyed indicating muscle cell death is occurring in parallel with vessel wall disintegration. The top image in the panel shows the Isolectin B4, the middle image the myomesin labeling, and the lower image is a merger of those two.

FIG. 7 shows Isolectin B4 label of disrupted blood vessels within the infarct zone correlating with sarcomere disruption illustrated using antibodies for myomesin which label the M-bands of the sarcomeres. As in neural tissues, subsequent damage to the blood vessel walls appears to follow hemichannel expression, and cell death in general becomes significant and as a result of hemichannel opening.

It has been reported that in hearts made hypoxic for 30 minutes and reperfused with heptanol (a non-specific gap junction channel blocker) in the medium prevented the oxygen paradox leading to hypercontraction and myocyte death. Garcia-Dorada et al., Circulation 96:3579-3586 (1997). These authors reported that hypercontracture may be transmitted to adjacent myocytes through gap junctions. Our data is consistent with the idea that within 30 minutes hemichannel expression may be playing a significant role in hypercontracture.

Increased gap junction protein expression and hemichannel opening under pathological conditions is leading to endothelial cell disruption and breakdown of the cardiac vascular system in the regions surrounding ischemia damaged tissue. This finding, first described herein, it is believed to have enormous significance for the treatment of reperfusion injury and is a probable mechanism for progressive infarction. Robbins, S. and Cotran, R. 1979. Pathologic basis of disease. $2^{nd}$ Edition, WB Saunders Company, Philadelphia.

Example 3

Mimetic Peptide Design

In this example, nine overlapping peptidomimetics were designed to have the same amino acid sequence as connexin 43 extracellular loop regions believed to be involved in the connexon docking process (Foote et al., *J Cell Biol* 140(5): 1187-97, (1998)). These particular peptides were all designed to be 11-13 residues long. Some peptides included amino acids matching the outer portions of the alpha helical transmembrane subunits, which may show enhanced functional inhibition. Not all of these peptides are necessarily connexin 43 specific due to the conservation of connexin sequences in the extracellular loop regions.

Peptides targeted to connexon 43 (hemichannel) are shown below. M1, 2, 3 and 4 refer to the $1^{st}$ to $4^{th}$ transmembrane regions of the connexon 43 protein respectively. E1 and E2 refer to the first and second extracellular loops respectively:

```
FEVAFLLIQWI      (SEQ ID NO:32)    M3 & E2

LLIQWYIGFSL      (SEQ ID NO:33)    E2

SLSAVYTCKRDPCPHQ (SEQ ID NO:34)    E2

VDCFLSRPTEKT     (SEQ ID NO:35)    E2

SRPTEKTIFII      (SEQ ID NO:36)    E2 & M4

LGTAVESAWGDEQ    (SEQ ID NO:37)    M1 & E1

QSAFRCNTQQPG     (SEQ ID NO:38)    E1

QQPGCENVCYDK     (SEQ ID NO:39)    E1

VCYDKSFPISHVR    (SEQ ID NO:40)    E1
```

Example 5

Functional Testing of Mimetic Peptides

Two functional tests were carried out using peptides. These functional test were (i) blockage of dye (Lucifer Yellow) uptake by cells in spinal cord slices, and (ii) prevention of oedema in spinal cord segments (using connexin 43 specific antisense as a positive control). All peptides used were synthesised by Sigma-Genosys (Australia).

Blockage of Dye (Lucifer Yellow) Uptake by Cells in Spinal Cord Slices.

Lucifer Yellow is a small water soluble, fixable, dye able to pass from cell to cell via gap junction channels, but not across the cell membrane. The addition of Lucifer Yellow to the extracellular medium makes it is possible to check for the presence of open gap junction hemichannels. The dye will appear in the cytoplasm of cells which are expressing open channels.

Wistar p7 rats were anesthetized with carbon dioxide and immediately decapitated. The spinal cord was excised and transferred to cold Hank's balanced salt solution (HBSS) at pH 7.4. Excess branch nerves and ligaments were removed and the cord transferred to a manual tissue chopper and a series of 500 micron thick slices cut. The damage caused by the slicing induces connexin 43 upregulation through the entire slice (exacerbated by the gap junction mediated bystander effect), and leads to the expression of connexin hemichannels. Slices were placed onto 3 cm diameter Millipore inserts in 24 well plates and cultured in the presence of mimetic peptides in the media. The final concentration for all 9 peptides tested was 500 micromolar. Controls were; no peptide added, or with 1% ethanol or 1% DMSO added as some peptides were re-dissolved in these compounds (peptides were received lyophilised). Some slices were also treated at this time with connexin 43 specific antisense oligodeoxynucleotides in 30% Pluronic F-127 gel or with gel only, as control experiments. The slices treated with antisense oligodeoxynucleotides indicated that the antisense prevented connexin expression and subsequently dye uptake, and thus these acted as a positive control.

Slices were incubated for four hours at 37 degrees C., and then 2.5 mg per ml Lucifer Yellow was added to each well for 30 minutes (in the dark). The tissues were then rinsed twice in PBS, with three further 10 minute washes, and the slices fixed with 4% paraformaldehyde. They were then viewed using a Leica TCS4D laser scanning confocal microscope to assess dye uptake into cells, or not.

Results showed that media alone cultured slices, and DMSO, ethanol and gel only treated slices had significant dye uptake. Connexin 43 treated slices had no dye uptake. The peptide treated slices showed considerable dye uptake, with the exception of those treated with the following peptides (which have overlapping sequences):

```
VDCFLSRPTEKT,    (SEQ ID NO:35)
and

SRPTEKTIFII     (SEQ ID NO:36)
```

The level of dye uptake for slices treated with the peptides having SEQ ID NOS:32-34 ((FEVAFLLIQWI (SEQ ID NO:32), LLIQWYIGFSL (SEQ ID NO:33), SLSAVYTCKRDPCPHQ (SEQ ID NO:34)) and SEQ ID NOS:37-40 (LGTAVESAWGDEQ (SEQ ID NO:37), QSAFRCNTQQPG (SEQ ID NO:38), QQPGCENVCYDK (SEQ ID NO:39), and VCYDKSFPISHVR (SEQ ID NO:40)) was comparable with control slices.

In summary, these data show that the spinal cord slices express hemichannels that are open within 4 hours of injury. Importantly, the data also show that peptides corresponding to SEQ ID NO: 35 and 36 are capable of preventing and/or blocking and/or closing the opening of the hemichannels and preventing swelling.

Prevention of Oedema in Spinal Cord

The system described in Example 1 was used to examine the effects of the peptides VDCFLSRPTEKT (SEQ ID NO:35) and SRPTEKTIFII (SEQ ID NO:36) on cultured spinal cord segments to test their ability to block swelling.

The peptide QQPGCENVCYDK (SEQ ID NO:39) was used a negative control because it allowed dye uptake in the slice cultures described above, and was thus believed to not be able to block oedema in the segments. DMSO was again used as an additional control.

5 mm long spinal cord segments were placed in separate wells of a 24 well plate in HBSS. The segments were held to the bottom of the well using a small drop of Superglue. The HBSS was removed and 500 micromolar peptide (final concentration) added to media (no peptide for media alone or DMSO controls). The plates were incubated for 24 hours, the media removed and the tissue fixed with Bouin's fixative for 24 hours. Analysis involved photographing cord segments from above, with ImageJ used to calculate the total area of the cord segment compared with the area of swelling at the cut ends of the segments. Swelling (oedema) was calculated as (cultured area—original area divided by original area) to give % swelling. Single factor Analysis of Variance was used to determine statistical significance, with cut-off level for significance at $p=0.05$.

Figure 8:
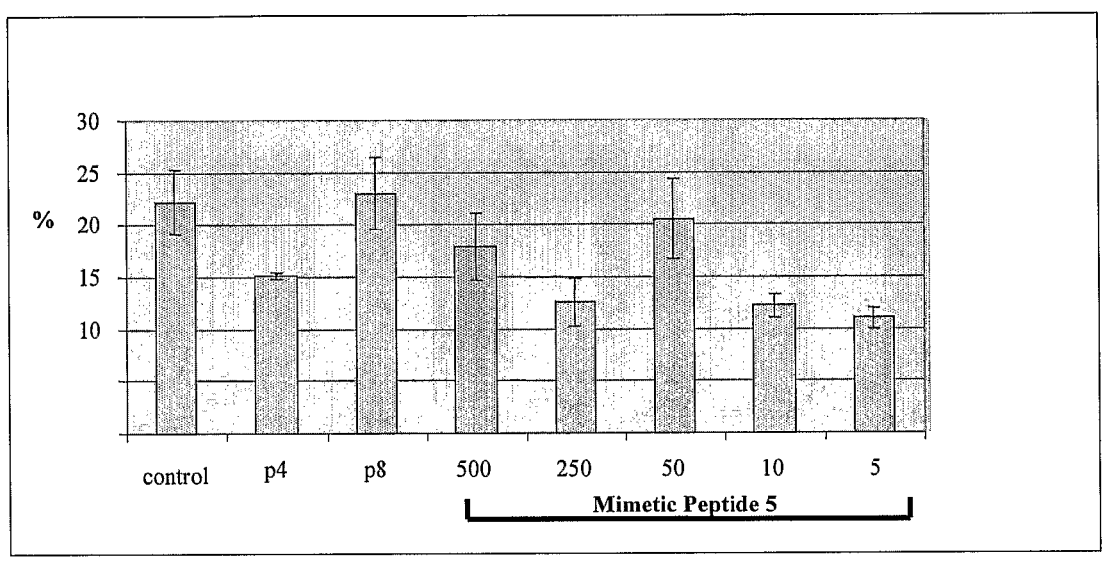
FIG. 8 shows a bar graph representing the percentage swelling compared to total spinal cord segment areas. A control (media only) segment, segments treated with peptides VDCFLSRPTEKT (SEQ ID NO:35) and SRPTEKTIFII (SEQ ID NO:36) which were shown in the dye uptake experiments to block hemichannels (shown as peptides 4 and 5 respectively in FIG. 8), and a segment treated with peptide QQPGCENVCYDK (SEQ ID NO:39) which did not block hemichannels (shown as peptide 8 in FIG. 8), are shown. The peptide SRPTEKTIFII (SEQ ID NO:36, peptide 5 in FIG. 8), a superior blocker based upon histological studies, has been used at 5 different concentrations, the lowest of which was most effective in reducing oedema.

Results were that DMSO treated cord segments swelled the most (33%) with all control cord segments swelling 21-23%. Segments treated with the peptide QQPGCENVCYDK (SEQ ID NO:39) also showed 23% swelling but peptides VDCFLSRPTEKT (SEQ ID NO:35) and SRPTEKTIFII (SEQ ID NO:36) showed a reduced 15 and 17% swelling respectively (FIG. 8). The difference between the peptides VDCFLSRPTEKT (SEQ ID NO:35) and SRPTEKTIFII (SEQ ID NO:36) treated cord segments and controls was significant ($p=0.43$). Subsequent histological examination of the tissues revealed that the peptide SRPTEKTIFII (SEQ ID NO:36) treated segments retained better morphology and so dose response experiments were then carried out with this peptide.

Determining the most effective concentration of the peptide SRPTEKTIFII (SEQ ID NO:36) for blocking of oedema in spinal cord segments was carried out using the same protocol. In this case a dose response was determined with final concentration of peptides used at 5, 10, 50 250 and 500 micromolar. Results are shown in FIG. 8. Interestingly the lowest concentration of the peptide (5 micromolar) gave the best result (least oedema) when compared to media alone ($p=0.001$). The middle range 50 micromolar was somewhat less effective in repeat experiments.

Immunohistochemical analysis showed reduced astrocytosis (GFAP expression) in the peptide SRPTEKTIFII (SEQ ID NO:36) treated segments after 24 hours in culture. Again 5 micromolar was most effective at preventing the inflammatory response although difference between the concentrations used were less marked than in the oedema experiments. All treatments showed significantly reduced glial fibrillary acidic protein (GFAP) expression (area of label per area of section analysed using Image J) (Table 7).

Our experiments have indicated that a dose of 5 µmol/kg brain weight for the perinatal sheep experiment (average 25 g at this fetal age) of the selected peptidomimetic (SEQ ID NO:36) given in 1 ml of artificial CSF i.c.v. (vs. vehicle of CSF alone) over one hour, followed by a further 1 ml per day perfused into the brain for 72 hours had a significant effect. Dosages of about 5 µmol/kg brain, 50 µmol/kg and 250 µmol/kg brain weight are also possible. For intravenous (systemic delivery) the effect of log-order increases in plasma concentrations can be used to determine an appropriate dose, starting with loading doses to achieve 0.5 µmol/L (mean fetal blood volume is approximately 350 ml in our perinetal sheep at this age), then 5, 10, 50, 250, 500 and 5000 µM.

ImageJ is Java script open source, public domain image analysis software originally developed by the NIH (and called NIH Image).

TABLE 7

| Treatment | Area of GFAP label (square units) |
| --- | --- |
| Control | 2450 |
| 5 micromolar peptide 5 | 300 |
| 50 micromolar peptide 5 | 950 |
| 250 micromolar peptide 5 | 1000 |
| 500 micromolar peptide 5 | 750 |

Table 7: Areas of GFAP label in images taken in spinal cord 24 hours after slicing. Control cords have high levels of GFAP indicating an inflammatory response and greater bystander effect than the treated segments. The lower peptide concentration is the most effective at limiting astrocytosis.

Activated microglial cell counts revealed no differences at 24 hours as expected. This secondary inflammatory process (differentiation and proliferation from resting microglial cells to macrophage phenotype) usually takes three-seven days.

Example 6

In Vivo Application of Connexin Specific Mimetic Peptides to Block Ischaemia and Epileptiform Brain Activity in a Perinatal Sheep Model Brain damage resulting from cerebral ischaemia remains a significant problem at all stages of life. In the term newborn, moderate to severe damage at birth occurs in 2 to 3 per 1000 live births. One of the most striking features is that the injury spreads over time from the most severely damaged areas outwards, into previously undamaged regions. Immediately after cerebral ischaemia there is transient recovery of brain metabolism that lasts for some hours. After this, however, there is a progressive mitochondrial failure, coupled with secondary cell swelling, reaching a maximum 36 to 48 h after initial injury.

Active coupling of gap junctions, between glia and neurons, mediates a bystander effect in which cell death signals are transferred from dying cells to less severely injured or healthy cells. Earlier studies showed that in vivo topical application of gap junction protein connexin 43 specific antisense oligodeoxynucleotides can restrict the spread of injury and secondary inflammation following trauma. See WO2000/44409 to Becker, D. and Green. C., entitled "Formulations Comprising Antisense Mucleotides to Connexins."

Figure 9:
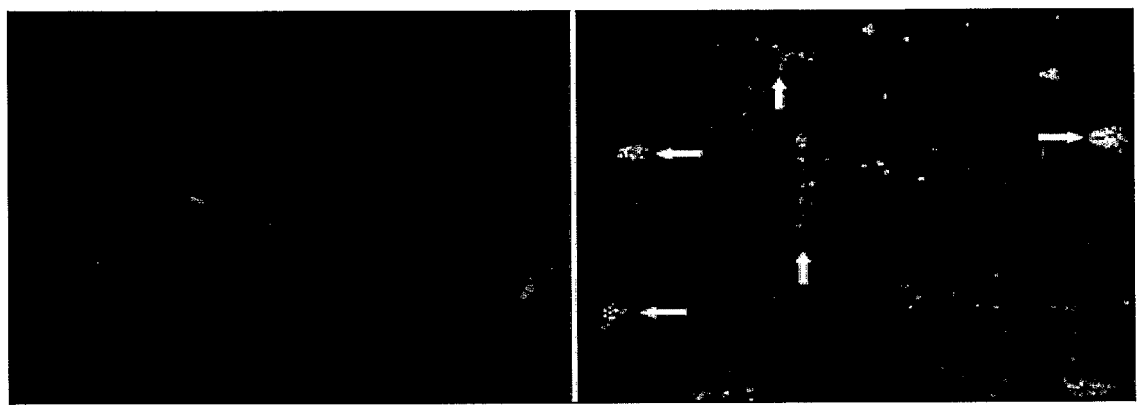
FIG. 9 shows connexin hemichannel labelling in near-term fetal sheep brains from a sham control (left) and 24 h after 30 min. of cerebral ischaemia (right) using an antibody recognising the extracellular loop regions of connexin proteins. In the control brain, no connexin hemichannel labelling is observed, whereas after ischaemia there is extensive upregulation of hemichannels. Hemichannel expression is especially high on cell bodies (horizontal arrows) and in blood vessel endothelial cells (vertical arrows). The major connexin upregulated after ischaemia is connexin 43.

The peptide SRPTEKTIFII (SEQ ID NO:36) was used in an in vivo model of sheep perinatal ischaemia. The data indicate that connexin specific mimetic peptides provide a treatment with potential to significantly reduce secondary damage in the ischaemic perinatal brain or following a stroke. Preliminary analysis showed that 24 h after cerebral ischaemia in the near-term fetal sheep there is increased expression of gap junction hemi-channels (i.e. uncoupled connexons) (FIG. 9).

A Romney-Suffolk cross fetal sheep was instrumented between 117 to 124 days of gestation (0.85 term) under general anaesthesia as described elsewhere in detail (Gerrits et al, Pediatr Res 57(3):342-6, (2005); Guan et al., *Neuroscience* 95(3):831-839, (1999); Guan et al., *J Cereb Blood Flow Metab* 21(5):493-502, (2001); Gunn et al., *J Clin Invest* 99(2): 248-256, (1997), Gunn et al., *Pediatrics* 102(5):1098-1106, (1998), Gunn et al., *Pediatr Res* 46(3):274-280, (1999); Roelfsema et al., *J Cereb Blood Flow Metab* 24(8):877-886, (2004)). Instrumentation included brachial artery and vein catheters, EKG electrodes, an inflatable occluder around a fetal carotid artery (Gunn et al., 1997; Roelfsema et al., 2004), parietal EEG electrodes 5 and 15 mm anterior, and 10 mm lateral to bregma, a pair of electrodes placed lateral to these to measure cortical impedance (a measure of cytotoxic oedema (Gunn et al., 1997) and a 17-mm-long left i.c.v. cannula 4 mm anterior and 6 mm lateral to bregma. The instrumentation was exteriorised to the maternal flank, uterine and abdominal walls closed, and fetal vascular catheters heparinised (20 IU/ml). The maternal wound was infiltrated with a long acting local anaesthetic bupivacaine (100 mg/20 ml).

After 5 days recovery, fetal cerebral hypoperfusion was induced by a 30 minute period of bilateral carotid artery occlusion (Gunn et al., 1997; Roelfsema et al., 2004; Tan et al., *Ann Neurol* 32(5):677-682, (1992); Tan et al., *Pediatr Res* 39(5):791-797, (1996)). An intracerebroventricular infusion of connexin mimetic peptide 5 was started 90 minutes after the ischaemia and continued for 72 hours. A dose of 5 µmol/kg brain weight (average 25 g at this fetal age) of the peptidomimetic 5 was given in 1 ml of artificial CSF i.c.v. (vs. vehicle of CSF alone) over one hour, followed by a further 1 ml per day perfused into the brain for 72 hours. The experiment was ended by a maternal intravenous overdose of sodium pentobarbital (30 ml, 300 mg/ml). The fetal brain was removed for histology and immunohistochemical analysis.

Figure 10:
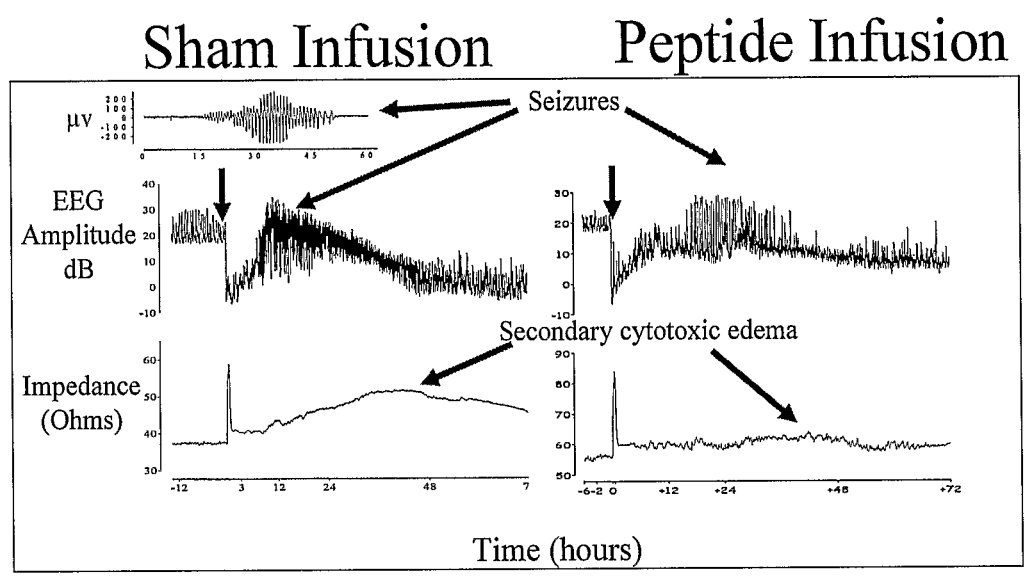
FIG. 10 shows examples of artificial CSF i.c.v. infusion or peptide infusion starting 90 min after a 30 min episode of cerebral ischaemia in near-term fetal sheep. The infusion in these animals was continued until 72 h after ischaemia. The vehicle (artificial CSF) infusion animal (left) shows delayed onset of severe, continuous seizures (status epilepticus; an example is shown in the insert box, top), followed by a progressive rise in cortical impedance (bottom, a measure of cell swelling) maximal at 48 h. Seizures resolved by approximately 48 h. The peptidomimetic infusion (right) changed seizures from continuous to a later onset of discrete, separate seizure events. There was a markedly delayed and attenuated rise in cerebral impedance.

The results (FIG. 10) show that early infusion of the peptide attenuates secondary, delayed seizure activity and cytotoxic oedema.

In summary, these data demonstrate that a peptidomimetic protein that targets the extracellular domain of connexin 43 hemichannels can suppress secondary oedema and inflammation following brain ischaemia. In a near-term fetal sheep, we found that cerebral ischaemia was associated with a dramatic induction of connexin 43 and of hemichannels within 24 h after ischaemia, while an i.c.v infusion of the peptidomimetic protein to the term fetus from 90 min after reperfusion showed significant attenuation of secondary seizures and cytotoxic oedema.

Example 7

Treatment of a Human Patient with Connexin 43 Specific Antisense In a Sub-Acute Wound—Prevention of Blood Vessel Die Back Allows Recovery from Limbal Ischaemia In this study, a patient presented with a sub-acute non-healing wound (chemical burn) to the eye. The eye remained inflamed and limbal ischaemia was still present after 8 days (indicating poor limbal vascularisation). The limbus contains the stem cells necessary for epithelial recovery of the cornea. Following treatment with connexin 43 specific antisense the limbal ischaemia had gone within 20 hours and re-epithelialisation had commenced. The conclusion is that continuing inflammation leads to a persistent die back of the blood vessels exacerbating the injury through limbal ischaemia. Treatment of the eye with the connexin 43 antisense reduced the inflammatory response and triggered epithelial recovery (Qiu et al., *Curr Biol* 13:1697-1703, (2003)). Note however that this was a sub-acute wound implying treatment for chronic wounds is possible—such wounds in humans retain high connexin 43 levels at the epithelial leading edge (Brandner et al., *J Invest Dermatol* 122:1310-1320, (2004)). In addition, the treatment allowed blood vessel recovery. We propose that the mechanism involved is prevention of further hemichannel expression in the vessel wall, allowing vessel regrowth.

Patient: Patient was a 25 year old male. He first presented with alkaline burns to left eye following a building site accident with a high pressure concrete hose (concrete/alkali in the eye, coupled with delay getting to first treatment). The damaged eye had no remaining epithelium covering the front of the eye (including the entire cornea).

Initial Treatment: Patient was put onto 10% ascorbate drops, 10% citrate drops, 1% prednisone acetate (steroid) drops, 1% cyclopentalate and chloramphenicol, plus oral vitamin C and deoxycycline. The prednisone was delivered hourly for first five days, after which the dose was reduced to four times per day.

On day four an amniotic membrane was stitched over the cornea.

Connexin 43 Antisense Treatment (DAY ZERO): At day eight post-injury the patient still had high degree of inflammation, limbal ischaemia, and no sign of epithelial recovery. Ethical permissions were obtained based on lack of any viable treatment alternatives that could save the patient's eye. The other eye has signs of keratoconus and was thus not suitable for limbal transplant at a later date. The injured eye would either have been surgically removed or allowed to become a "conjunctive eye" (wherein the conjunctiva, in the form of a white sheath, grows over the eye to render the patient blind).

Connexin 43 antisense in 30% F-127 Pluronic gel was injected with a catheter needle under the amniotic membrane in two places either side of the cornea Approximately 100 microliters of two micromolar anti-connexin 43 was injected and gently spread around the cornea using a cotton wand over the amniotic membrane. The gel was injected cold and set immediately to a soft jelly-like substance.

The patient was removed from all other treatments for eight hours to avoid any potential adverse effects on the treatment. The patient was then placed back on steroid drops (three times per day), cyclopentalate (once per day), and ascorbate, citrate, chloramphenicol drops (four times each per day).

Connexin 43 Antisense Treatment (DAY ONE): Within 20 hours following connexin 43 antisense treatment the eye had become substantially quieter (reduced inflammation) and the epithelium was growing back in three places. The limbus was well vascularized with good blood flow, and no sign of limbal ischaemia, i.e., there was full blood flow back to the limbus within 20 hours post-treatment.

Connexin 43 Antisense (DAY THREE): Within 72 hours after connexin 43 antisense treatment the patient had continued to improve. The eye was quiet, the limbal blood supply was excellent, and the epithelium was growing back around 360 degrees. On one side there appeared to be a small area of lamellapodial crawling, but on the remainder of the circumference of the cornea there was nice even inward growth.

Connexin 43 Antisense Treatment (DAY SIX): Within six days following treatment (14 days post-injury) the epithelium was fully recovered (completely grown over) although it appeared slightly granular in places and perhaps patchy or thin in places (assessed looking through the amniotic membrane). The limbal region remained well vascularized with full blood flow.

Forty days after treatment the patient had excellent recovery for a chemical burn, showing 6/48 vision unaided and 6/15 pinhole. Two thirds of the epithelium was absolutely healthy, one third at periphery showing some conjunctival growth but not covering the pupil and not vascularised. Very good limbal vascularisation.

Optic Nerve Neuropathy Ischaemic optic neuropathy (ION), also known as stroke of the optic nerve, is a collection of diseases that affects the blood supply to the optic nerve. ION can be categorised based on the locality or aetiology. Anterior ION (AAOIN) referss to diseases affecting nerve segments prior to lamina cribrosa while the opposite is true for Posterior ION (PION) (Buono et al., *Survey of Opthalmology* 50:15-26, (2005); Collignon et al., *Opthalmology* 111:1663-1672, (2004)). PION is less commonly observed, and is believed to be caused by infarction of the intraorbital portion of the optic nerve, most likely due to giant cell arteritis (GCA) or as a secondary complication of surgical procedures (Buono and Foroozan, 2005; Ho et al., *Journal of Neurosurgical Anesthesiology* 17:38-44, (2005)). ION can be also be divided into arteritic (Arteritic ION) and non-arteritic (NAION) based on aetiology. Arteritic ION is always caused by GCA and usually results in thrombotic occlusion of the posterior ciliary artery, which can lead to concomitant obstruction of other arteries in the optic nerve (Galasso et al., *Seminars in Opthalmology* 19:75-77, (2004)). NAION is the most common form of non-glaucomic optic neuropathy with an annual incidence of 2.3/10,000 (Collignon-Robe et al., *Opthalmology* 111:1663-1672, (2004)). GCA is a chronic vasculitis of large and medium vessels in the brain characterised by an increased inflammatory giant cell count (Buono et al., *Survey of Opthalmology* 50:15-26, (2005); Khosla et al., *Journal of Postgraduate Medicine* 50:219-221, (2004); Penn et al., *Autoimmunity Reviews* 2:199-203, (2003)). Visual loss is not common but does occur as a secondary complication owing to occlusion of the anterior vessels supplying the optic nerve, and is often irreversible (Khosla et al., 2004). The incidence of GCA in Western countries range from 1~30/10,000 with much higher prevalence in the population over 50 years of age (Penn and Dasgupta, 2003).

The typical outcome of ION is the degeneration of axon tracts, accompanied by deterioration or even loss of vision (Buono et al., 2005; Khosla et al., 2004; Penn and Dasgupta, 2003).

Conventional treatments of ION include administration of corticosteroids and antiplatelet agents (Arnold et al., *Seminars in Opthalmology* 17: 39-46, (2002)). but patients treated with these drugs have not demonstrated significant improvement from the disease.

In the optic nerve both astrocytes and oligodendrocytes express connexin molecules. Connexin 43 is abundantly found in the astrocytes and is potentially involved in various disease processes. Blood vessel endothelial cells in the optic nerve also express connexin 43.

In this study optic nerve ischaemia was induced in an ex vivo model and nerve segments placed into organotypic culture treated with connexin 43 specific antisense oligodeoxynucleotides delivered in 30% F-127 Pluronic gel, or control gel.

Tissue Preparation:

Wistar rats aged 21 to 25 days postnatal (p21 to p25) were used. The wiener rats were sacrificed by overdosing with carbon dioxide, the skulls opened in a midsagittal orientation, and the brain region caudal to the cerebellum exercised and discarded. Incisions were then made below the olfactory lobes to reveal the intracranial regions of the optic nerve. Approximately 0.3 to 0.5 mm of optic nerve which spans the optic chiasm and terminal point of the optic canal could be obtained through this method. The nerves were then subjected to ischaemia as below.

A viable organotypic culture model of ION protocol was suggested by Sundstrom et al., *Drug Discovery Today* 10:993-1000, (2005), working on CNS ischaemia. Prior to the experiment, 10 mL of medium prepared in a falcon tube without glucose and glutamine was bubbled with 95% $N_2$ and 5% $CO_2$ gas mixture for 30 minutes to remove all the oxygen. The dissected optic nerves were transferred to the oxygen glucose deprived (OGD) solution and sealed with parafilm and cellophane. The optic nerves were incubated in ischaemic solution for two hours at 37° C. and subsequently returned to organotypic culturing conditions for lengths of time as required.

An interphase culturing methodology used. After incubation in OGD solutions, the optic nerves were placed onto a semi-porous membrane and into a six well plate containing 1 ml of Neurobasal medium with B27 supplement, D-glucose and L-glutamine and antibiotics (Gibco, USA). For antisense treatment, 7 μL of Pluronic F-127 gel (#P2443, Sigma, USA) containing 10 μM AS-ODN specific for connexin 43 translational block was administered to cover each optic nerve. This amount was sufficient to cover the whole segment without over-flooding the tissue. For gel only and control groups, the same amount (7 μL) of Pluronic F-127 gel and medium was applied to the nerves, respectively. The culture plates were then placed into an incubator with temperature set at 37° C. with 5% $CO_2$. The main advantage of this culturing technique is that it ensures a constant supply of oxygen from the top while nutrients can diffuse from the bottom.

After culture, the nerves were rinsed for 15 minutes in 1×PBS (# BR14, oxoid, England) and fixed in 4% paraformaldehyde (PFA) for approximately two hours prior to being cryoprotected by going through 20% then 30% sucrose in PBS. The nerves were then stored in 15% sucrose in PBS until ready for further processing. To section the tissues, the optic nerves were embedded in OCT (#4583, Tissue Tek®, USA), frozen at −20° C. and subsequently cut into longitudinal 14 and 18 μm thick sections. The slices were collected onto Histobond slides (#0810001, Marienfeld, Germany) and stored for further processing in a −80° C. freezer.

Swelling (oedema) was assessed by photographing optic nerves from above and measuring (cultured area—original area divided by original area) to give % swelling. Cell death was assessed using propidium iodide to label the nuclei of compromised cells. Cell death was assessed near the cut ends of the nerves and in the middle region of the nerves.

Figures 11A, 11B:
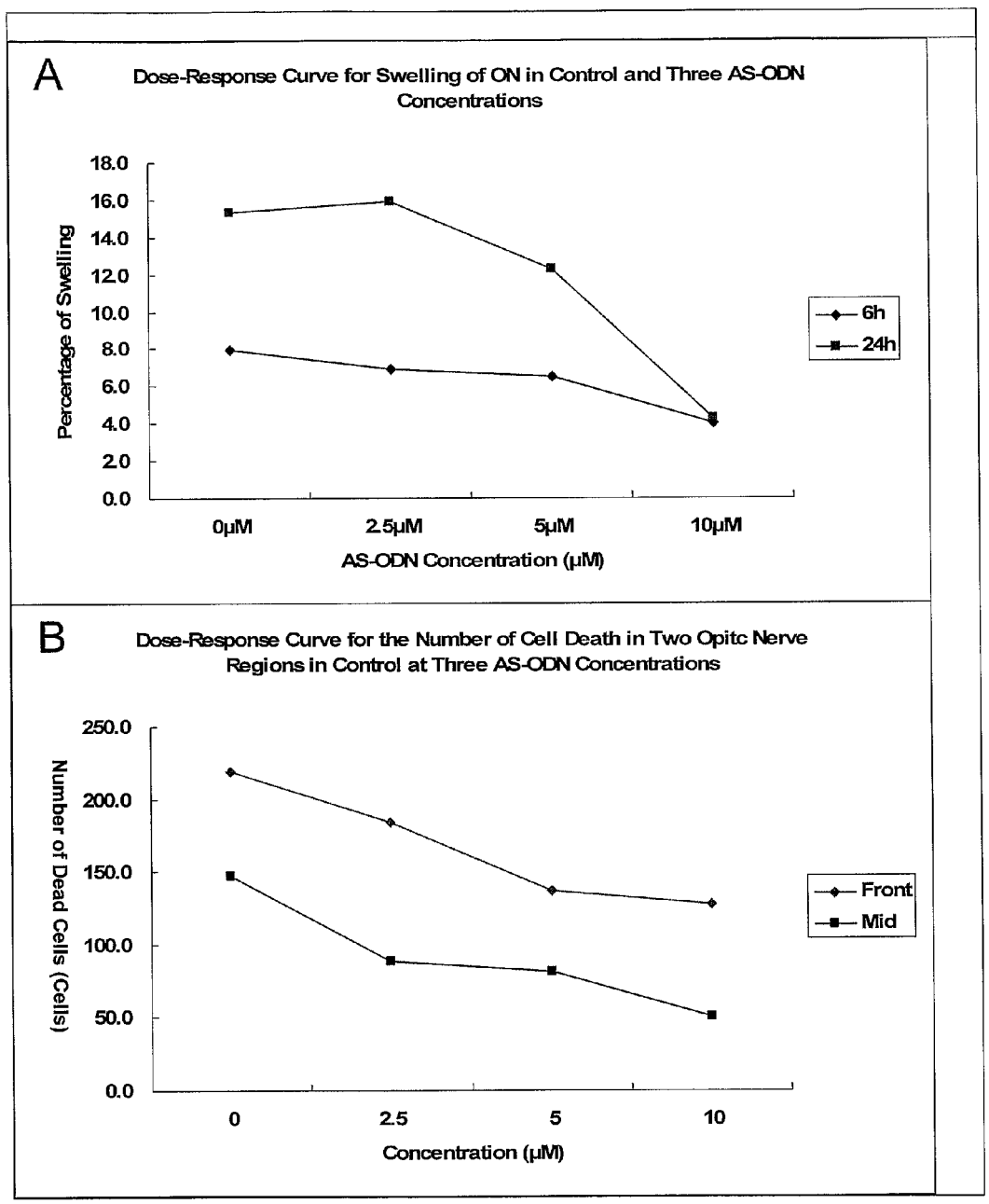
FIG. 11 shows dose-response curves for optic nerve (FIG. 11A) tissue swelling and (FIG. 11B) cell death in control, and with 2.5, 5 and 10 μM concentrations of connexin 43 specific AS-ODN. Both parameters exhibit a decreasing trend with increasing concentration. At 10 μM, swelling of the tissue is reduced as early as 6 h post treatment, and by 69% at 24 h when compared to control. Cell death at both front and middle segment of the optic nerve is diminished with antisense treatments.

FIG. 11 shows a dose response curve for antisense and control treated optic nerves cultured for 6 hours and 24 hours after ischemic injury. FIG. 11A shows percentage swelling, and FIG. 11B cell death assessed using propidium iodide counts at the cut end (front) and in the middle of the nerve. Oedema is reduced in nerves with connexin 43 antisense, especially at the 10 micromolar concentration which we have previously shown to be optimal for crush wounds in spinal cord studies (unpublished). Cell death at both the cut end and toward the middle of the nerve is reduced using the antisense resulting is lower dead cell counts in both regions in a dose dependent manner.

Figure 12:
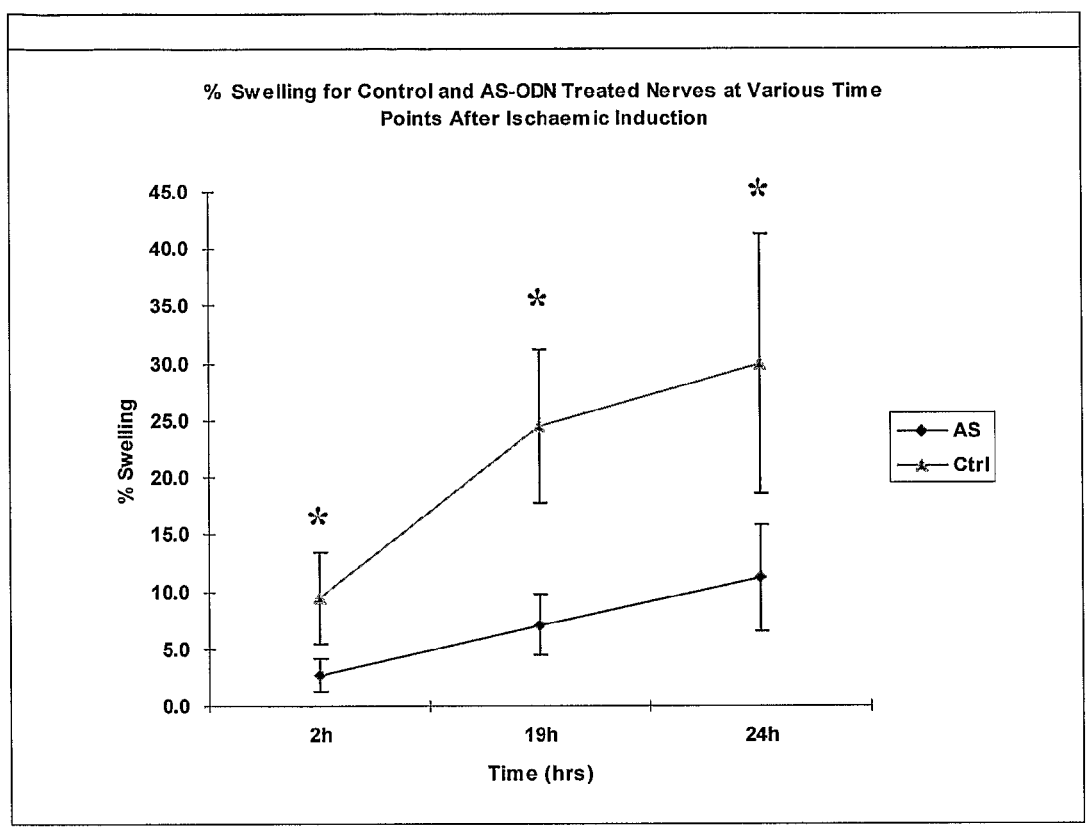
FIG. 12 shows the percentage of swelling in control and AS-ODN treated optic nerves (n=6 for all time points). Oedema is more prominent in the control tissue and the difference is statistically significant at all time points investigated. Asterisks indicate statistical significance between the two groups.
Figure 13:
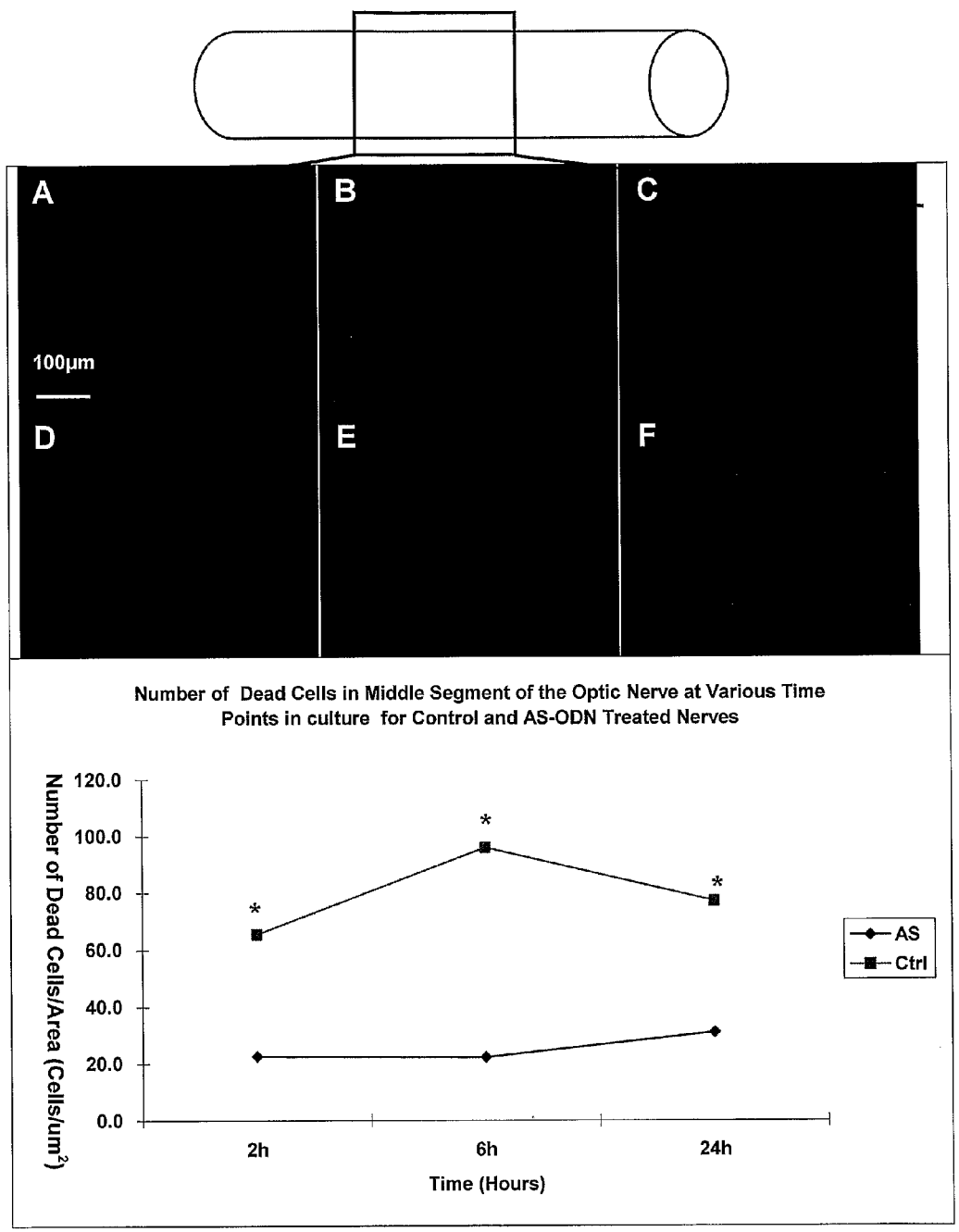
FIG. 13: (Top panel) Propidium iodide staining of dead cells in the middle of control (A, B, C) and AS-ODN treated (D, E, F) optic nerve segments at 2, 6 and 24 hours after ischaemic induction. Little staining is exhibited by the connexin 43 specific AS-ODN treated group when compared to the controls at all three time points (Lower panel). Line graph showing the number of dead cells per unit area in the medial region of the nerve for the control and AS-ODN treated optic nerves. Cell death in the control group initially increases, peaks at six hours and then declines (believed to reflect tissue oedema leaving fewer cells per unit area). Only a very slight increase in cell death even after 24 hours in culture was noted for AS-ODN treated tissue. Asterisks indicate statistical significance between treatments.

FIG. 12 below shows that reduction in swelling (oedema) is maintained over time. FIG. 13 shows propidium iodide staining of dead cells in the middle of control and connexin 43 specific AS-ODN treated optic nerve segments at 2, 6 and 24 hours after ischaemic induction. Little staining is exhibited by the connexin 43 specific AS-ODN treated group when compared to the controls at all three time points. The line graph in FIG. 13 shows the number of dead cells per unit area in the medial region of the nerve for the control and AS-ODN treated optic nerves. Cell death in the control group initially increases, peaks at six hours and then declines slightly (probably owing to tissue oedema leaving fewer cells per unit area). Only a very slight increase in cell death after even 24 hours in culture was noted for AS-ODN treated tissue.

Blood Vessel Segment Lengths—von Willebrand Factor Staining:

In order to demonstrate that blood vessel integrity was being compromised by connexin expression vessels in control and connexin 43 specific antisense treated optic nerves in the ischemic model were labelled with von Willebrand factor, an endothelial cell marker. As vessels broke down increasing numbers of smaller segments could be counted and segment length measured. The mean length and number of blood vessels per section was investigated in more than sixty vessels in six separate sections obtained from two animals for each point.

Figure 14:
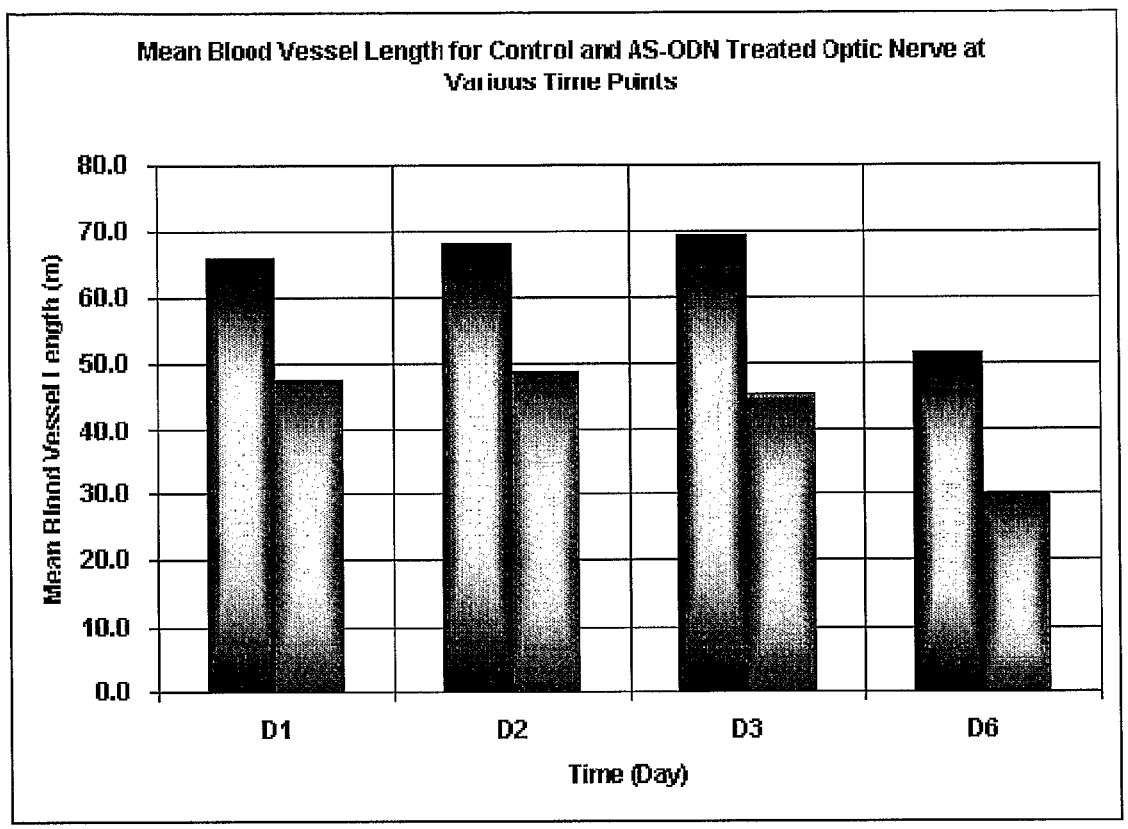
FIG. 14 shows mean blood vessel segment length in control (green) and conenxin43 specific antisense treated optic nerves (blue). At all time points the antisense treated nerves have longer segments indicated less vessel breakdown as a result of connexin expression, presumably in the form of hemichannels, or via a gap junction mediated bystander effect.

On average, the number of blood vessel segments in the controls was fewer than that in connexin 43 specific AS-ODN treated nerves at all but the longest time point investigated (Table 8). The bar graph (FIG. 14) shows that the mean vessel length in connexin 43 specific AS-ODN treated optic nerves remained relatively constant throughout the first three days, but starting to fall by approximately 30% by Day 6. A similar temporal pattern is observed for the control group but for all time points average vessel segment length is significantly shorter than for the antisense treated group.

TABLE 8

Number of Segments per Section

|  | AS | Ctrl |
|---|---|---|
| Day 1 | 10.8 | 23.5 |
| Day 2 | 13.3 | 19.2 |
| Day 3 | 29.7 | 41 |
| Day 6 | 18.2 | 13.8 |

Table B shows the average number of blood vessel segments counted in control and treated groups. In the first three days, AS treated groups, on average, have 28~50% fewer blood vessel segments in comparison to control. Only after 6 days in organotypic culture does the AS treated nerve a greater segment count than in controls, having 24% more vessels counted. Extended culture times may by then be having an effect.

This Example shows that prevention of connexin 43 expression following optic nerve ischaemia reduces oedema (reduced swelling), lesion spread (number of dead cells per unit area away from the original damage zone) and blood vessel degradation. It therefore behaves in a similar manner to that reported in Example 1—spinal cord. It has therapeutic applications as the same oedema and vessel loss is reported in in vivo studies (Bernstein et al., *Invest Opthalmol Vis Sci* 44:4153-4162, (2003)).

All patents, publications, scientific articles, web sites, and other documents and materials referenced or mentioned herein are indicative of the levels of skill of those skilled in the art to which the invention pertains, and each such referenced document and material is hereby incorporated by reference to the same extent as if it had been incorporated by reference in its entirety individually or set forth herein in its entirety. Applicants reserve the right to physically incorporate into this specification any and all materials and information from any such patents, publications, scientific articles, web sites, electronically available information, and other referenced materials or documents.

The specific methods and compositions described herein are representative of preferred embodiments and are exemplary and not intended as limitations on the scope of the invention. Other objects, aspects, and embodiments will occur to those skilled in the art, upon consideration of this specification, and are encompassed within the spirit of the invention as defined by the scope of the claims. It will be readily apparent to one skilled in the art that varying substitutions and modifications may be made to the invention disclosed herein without departing from the scope and spirit of the invention. The invention illustratively described herein suitably may be practiced in the absence of any element or elements, or limitation or limitations, which is not specifically disclosed herein as essential. Thus, for example, in each instance herein, in embodiments or examples of the present invention, any of the terms "comprising", "consisting essentially of", and "consisting of" may be replaced with either of the other two terms in the specification. Also, the terms "comprising", "including", containing", etc. are to be read expansively and without limitation. The methods and processes illustratively described herein suitably may be practiced in differing orders of steps, and that they are not necessarily restricted to the orders of steps indicated herein or in the claims. It is also that as used herein and in the appended claims, the singular forms "a," "an," and "the" include plural reference unless the context clearly dictates otherwise. Under no circumstances may the patent be interpreted to be limited to the specific examples or embodiments or methods specifically disclosed herein. Under no circumstances may the patent be interpreted to be limited by any statement made by any Examiner or any other official or employee of the Patent and Trademark Office unless such statement is specifically and without qualification or reservation expressly adopted in a responsive writing by Applicants.

The terms and expressions that have been employed are used as terms of description and not of limitation, and there is no intent in the use of such terms and expressions to exclude any equivalent of the features shown and described or portions thereof, but it is recognized that various modifications are possible within the scope of the invention as claimed. Thus, it will be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

Other embodiments are within the following claims. In addition, where features or aspects of the invention are described in terms of Markush groups, those skilled in the art will recognize that the invention is also thereby described in terms of any individual member or subgroup of members of the Markush group.

What is claimed is:

1. A method for treating tissue edema associated with a vascular disorder, comprising administering a connexin mimetic peptide comprising the amino acid sequence of SEQ ID NO:35, or SEQ ID NO:36 to a subject in an amount capable of modulating a connexin hemichannel in a tissue associated with said vascular disorder, wherein tissue edema associated with said vascular disorder is ameliorated.

2. The method of claim 1 wherein said connexin mimetic peptide is administered once.

3. The method of claim 1 wherein the modulation of the hemichannel comprises inhibiting extracellular hemichannel communication.

4. The method of claim 1 wherein said vascular disorder is a stroke.

5. The method of claim 1 wherein blood vessel die back is ameliorated.

6. The method of claim 1 wherein blood vessel break down is ameliorated.

7. The method of claim 1 wherein the vascular disorder is a central nervous system injury.

8. The method of claim 1 wherein the vascular disorder comprises an ischemia.

9. The method of claim 8 wherein the ischemia is a tissue ischemia.

10. The method of claim 8 wherein the ischemia is a myocardial ischemia.

11. The method of claim 8 wherein the ischemia is a cerebral ischemia.

12. The method of claim 1 wherein the subject is at risk of loss of neurological function by ischemia.

13. The method of claim 1 wherein the connexin target is connexin 43.

14. The method of claim 1 wherein the vascular disorder is subsequent to a stroke resulting in tissue damage.

15. The method of any one of claims 4-6, 8-12, 1, 13 or 14, further wherein cell death or degeneration in the central or peripheral nervous system resulting from an ischemia is ameliorated.

16. The method of claim 1 wherein the vascular disorder is selected from the group consisting of ischemic stroke, transient ischemic attack, intracerebral hemorrhage, subarachnoid hemorrhage, thromboembolic stroke, venous thrombosis, pulmonary embolism, embolic stroke, cerebrovascular disorder, peripheral occlusive arterial disease, arteriovenous malformation, and an aneurysm.

17. A method for treating tissue edema associated with a vascular disorder, comprising administering a connexin mimetic peptide comprising the amino acid sequence of SEQ ID NO:35, or SEQ ID NO:36 to a subject in an amount capable of modulating a connexin hemichannel in a tissue associated with said vascular disorder, wherein tissue edema associated with said vascular disorder is ameliorated, wherein the connexin mimetic peptide is administered in connection with a vascular or coronary procedure performed on the subject, and further wherein the connexin mimetic peptide is administered during the vascular or coronary procedure.

18. The method of claim 17 wherein the connexin mimetic peptide is administered in connection with a heart surgery performed on a subject.

19. A method for treating tissue edema associated with a vascular disorder, comprising administering a connexin mimetic peptide comprising the amino acid sequence of SEQ ID NO:35, or SEQ ID NO:36 to a subject in an amount capable of modulating a connexin hemichannel in a tissue associated with said vascular disorder, wherein tissue edema associated with said vascular disorder is ameliorated, wherein the connexin mimetic peptide is administered in connection with a vascular or coronary procedure performed on the subject, and further wherein the connexin mimetic peptide is administered within about one hour after the vascular or coronary procedure is performed.

20. A method for treating tissue edema associated with a vascular disorder, comprising administering a connexin mimetic peptide comprising the amino acid sequence of SEQ ID NO:35, or SEQ ID NO:36 to a subject in an amount capable of modulating a connexin hemichannel in a tissue associated with said vascular disorder, wherein tissue edema associated with said vascular disorder is ameliorated, wherein the connexin mimetic peptide is administered in connection with a vascular or coronary procedure performed on the subject, and further wherein the connexin mimetic peptide is administered within about 2-24 hours after the vascular or coronary procedure is performed.

21. A method for treating tissue edema associated with a vascular disorder, comprising administering a connexin mimetic peptide comprising the amino acid sequence of SEQ ID NO:35, or SEQ ID NO:36 to a subject in an amount capable of modulating a connexin hemichannel in a tissue associated with said vascular disorder, wherein tissue edema associated with said vascular disorder is ameliorated, and further wherein the connexin mimetic peptide is administered in connection with a medical device for performing a vascular procedure.

22. A method for treating tissue edema associated with a vascular disorder, comprising administering a connexin mimetic peptide comprising the amino acid sequence of SEQ ID NO:35, or SEQ ID NO:36 to a subject in an amount capable of modulating a connexin hemichannel in a tissue associated with said vascular disorder, wherein tissue edema associated with said vascular disorder is ameliorated, wherein the connexin mimetic peptide is administered in combination with a second compound that reduces tissue damage or promotes healing and further wherein the second compound is a growth factor or cytokine.

23. The method of claim 22 wherein the growth factor or cytokine is selected from the group consisting of fibroblast growth factor (FGF), nerve growth factor (NGF), neutrophin 3 (NT3), platelet-derived growth factor (PDGF), tumor growth factor (TGF), vascular endothelial growth factor (VEGF), brain-derived growth factor (BDGF), epidermal growth factor (EGF), keratinocyte growth factor (KGF), plasmin, an integrin, an interleukin, and a semaphorin.

24. A method for treating tissue edema associated with a vascular disorder, comprising administering a connexin mimetic peptide comprising the amino acid sequence of SEQ ID NO:35 or SEQ ID NO:36 to a subject in an amount capable of modulating a connexin hemichannel in a tissue associated with said vascular disorder, wherein tissue edema associated with said vascular disorder is ameliorated, wherein the connexin mimetic peptide is administered systemically to the subject.

25. A method for treating tissue edema associated with any one of a vascular disorder, an inflammatory disorder, and a transplant or grafting procedure, comprising administering a connexin mimetic peptide comprising the amino acid sequence of SEQ ID NO:35 or SEQ ID NO:36 to a subject in an amount capable of modulating a connexin hemichannel in a tissue associated with any one of said vascular disorder, an inflammatory disorder, and a transplant or grafting procedure, wherein tissue edema associated with any one of said vascular disorder, an inflammatory disorder, and a transplant or grafting procedure, is ameliorated, wherein the connexin mimetic peptide is administered intravenously to the subject.

26. A method for treating tissue edema associated with a vascular disorder or an inflammatory disorder comprising administering a connexin mimetic peptide comprising the amino acid sequence of SEQ ID NO:35 or SEQ ID NO:36 to a subject in an amount capable of modulating a connexin hemichannel in a tissue associated with said vascular disorder or said inflammatory disorder, wherein tissue edema associated with said vascular disorder or said inflammatory disorder is ameliorated, wherein the connexin mimetic peptide is administered intraarticularly to said subject.

27. A method for treating tissue edema associated with a vascular disorder or an inflammatory disorder comprising administering a connexin mimetic peptide comprising the amino acid sequence of SEQ ID NO:35 or SEQ ID NO:36 to a subject in an amount capable of modulating a connexin hemichannel in a tissue associated with said vascular disorder or said inflammatory disorder, wherein tissue edema associated with said vascular disorder or said inflammatory disorder is ameliorated, wherein the connexin mimetic peptide is administered periarticularly to said subject.

28. A method for treating tissue edema associated with a vascular disorder or an inflammatory disorder comprising administering a connexin mimetic peptide comprising the amino acid sequence of SEQ ID NO:35 or SEQ ID NO:36 to a subject in an amount capable of modulating a connexin hemichannel in a tissue associated with said vascular disorder or said inflammatory disorder, wherein tissue edema associated with said vascular disorder or said inflammatory disorder is ameliorated, wherein the connexin mimetic peptide is administered intraportally to said subject.

29. A method for treating tissue edema associated with a vascular disorder or an inflammatory disorder comprising administering a connexin mimetic peptide comprising the amino acid sequence of SEQ ID NO:35 or SEQ ID NO:36 to a subject in an amount capable of modulating a connexin hemichannel in a tissue associated with said vascular disorder or said inflammatory disorder, wherein tissue edema associated with said vascular disorder or said inflammatory disorder is ameliorated, wherein the connexin mimetic peptide is administered directly into an organ of said subject.

30. A method for treating tissue edema associated with a vascular disorder or an inflammatory disorder comprising administering a connexin mimetic peptide comprising the amino acid sequence of SEQ ID NO:35 or SEQ ID NO:36 to a subject in an amount capable of modulating a connexin hemichannel in a tissue associated with said vascular disorder or said inflammatory disorder, wherein tissue edema associated with said vascular disorder or said inflammatory disorder is ameliorated, wherein the connexin mimetic peptide is administered into the cerebrospinal fluid (ICSF) of said subject.

31. A method for treating tissue edema associated with a vascular disorder or an inflammatory disorder comprising administering a connexin mimetic peptide comprising the amino acid sequence of SEQ ID NO:35 or SEQ ID NO:36 to a subject in an amount capable of modulating a connexin hemichannel in a tissue associated with said vascular disorder or said inflammatory disorder, wherein tissue edema associated with said vascular disorder or said inflammatory disorder is ameliorated, wherein the connexin mimetic peptide is administered intracranially to said subject.

32. A method for treating tissue edema associated with a vascular disorder or an inflammatory disorder comprising administering a connexin mimetic peptide comprising the amino acid sequence of SEQ ID NO:35 or SEQ ID NO:36 to a subject in an amount capable of modulating a connexin hemichannel in a tissue associated with said vascular disorder or said inflammatory disorder, wherein tissue edema associated with said vascular disorder or said inflammatory disorder is ameliorated, wherein the connexin mimetic peptide is administered into the spinal medulla of said subject.

33. A method for treating tissue edema associated with a vascular disorder or an inflammatory disorder comprising administering a connexin mimetic peptide comprising the amino acid sequence of SEQ ID NO:35 or SEQ ID NO:36 to a subject in an amount capable of modulating a connexin hemichannel in a tissue associated with said vascular disorder or said inflammatory disorder, wherein tissue edema associated with said vascular disorder or said inflammatory disorder is ameliorated, wherein the connexin mimetic peptide is administered directly into the heart of said subject.

34. A method for treating tissue edema associated with a vascular disorder, comprising administering a connexin mimetic peptide comprising the amino acid sequence of SEQ ID NO:35 or SEQ ID NO:36 to a subject in an amount capable of modulating a connexin hemichannel in a tissue associated with said vascular disorder, wherein tissue edema associated with said vascular disorder is ameliorated, wherein the connexin mimetic peptide is administered as a bolus dose.

35. A method for treating tissue edema associated with a vascular disorder, comprising administering a connexin mimetic peptide comprising the amino acid sequence of SEQ ID NO:35 or SEQ ID NO:36 to a subject in an amount capable of modulating a connexin hemichannel in a tissue associated with said vascular disorder, wherein tissue edema associated with said vascular disorder is ameliorated, wherein the connexin mimetic peptide is administered by sustained delivery.

36. A method for treating tissue edema associated with a vascular disorder, comprising administering a connexin mimetic peptide comprising the amino acid sequence of SEQ ID NO:35 or SEQ ID NO:36 to a subject in an amount capable of modulating a connexin hemichannel in a tissue associated with said vascular disorder, wherein tissue edema associated with said vascular disorder is ameliorated, and wherein the connexin mimetic peptide is administered for at least 72 hours.

37. A method of any one of claim 24, or 34-36 wherein the connexin mimetic peptide is administered in connection with a vascular or coronary procedure performed on the subject.

38. The method of any one of claim 24, or 34-36 wherein the connexin mimetic peptide is administered in combination with a second compound that reduces tissue damage or promotes healing.

39. The method of any one of claim 24, or 34-36 wherein the vascular disorder is associated with one or more of coronary heart disease, coronary vascular disorder, atherosclerotic vascular disease, athersclerotic plaque rupture, and/or thromboembolic, a vascular disorder associated with hypertension, myocardial infarction, angina, ischemic heart disease, aortic disorder, peripheral arterial diseases, fibromuscular dysplasia, moyamo disease, or thromboangiitis.

40. The method of any one of claims 24 and 34-36 wherein the subject has one or more of hemostatis, thrombosis, fibrinolysis, cardiovascular disease, diabetes mellitus, an endocrine disorder affecting the heart, cardiovascular disease associated with pregnancy, rheumatic fever, a cardiovascular disorder associated with HIV-infection, a hematological or oncological disorder associated with heart disease, a neurological disorder associated with heart disease, and a renal disorder associated with heart disease.

41. A method for treating a subject for tissue edema associated with an inflammatory disorder comprising administering to said subject a therapeutically effective amount of a connexin mimetic peptide comprising the amino acid sequence of SEQ ID NO:35 or SEQ ID NO:36 capable of inhibiting the expression, formation, or activity of a connexin hemichannel, wherein tissue edema associated with said inflammatory disorder is ameliorated, wherein the connexin mimetic peptide is administered systemically to the subject.

42. A method for treating a subject for tissue edema associated with a transplant or grafting procedure comprising administration to said subject an amount of a connexin mimetic peptide comprising the amino acid sequence of SEQ ID NO:35 or SEQ ID NO:36, capable of inhibiting the expression, formation or activity of a connexin hemichannel, wherein tissue edema associated with said transplant or grafting procedure is ameliorated, wherein the connexin mimetic peptide is administered systemically to the subject.

43. A method for treating a subject for tissue edema associated with an inflammatory disorder comprising administering to said subject a therapeutically effective amount of a connexin mimetic peptide comprising the amino acid sequence of SEQ ID NO:35 or SEQ ID NO:36 capable of inhibiting the expression, formation, or activity of a connexin hemichannel, wherein tissue edema associated with said inflammatory disorder is ameliorated, wherein the connexin mimetic peptide is administered as a bolus dose.

44. A method for treating a subject for tissue edema associated with a transplant or grafting procedure comprising administration to said subject an amount of a connexin mimetic peptide comprising the amino acid sequence of SEQ ID NO:35 or SEQ ID NO:36, capable of inhibiting the expression, formation or activity of a connexin hemichannel, wherein tissue edema associated with said transplant or grafting procedure is ameliorated, wherein the connexin mimetic peptide is administered as a bolus dose.

45. A method for treating a subject for tissue edema associated with an inflammatory disorder comprising administration to said subject an amount of a connexin mimetic peptide comprising the amino acid sequence of SEQ ID NO:35 or SEQ ID NO:36, capable of inhibiting the expression, formation or activity of a connexin hemichannel, wherein tissue edema associated with said inflammatory disorder transplant or grafting procedure is ameliorated, wherein the connexin mimetic peptide is administered by sustained delivery.

46. A method for treating a subject for tissue edema associated with a transplant or grafting procedure comprising administration to said subject an amount of a connexin mimetic peptide comprising the amino acid sequence of SEQ ID NO:35 or SEQ ID NO:36, capable of inhibiting the expression, formation or activity of a connexin hemichannel, wherein tissue edema associated with said transplant or grafting procedure is ameliorated, wherein the connexin mimetic peptide is administered by sustained delivery.

47. A method for treating a subject for tissue edema associated with an inflammatory disorder comprising administration to said subject an amount of a connexin mimetic peptide comprising the amino acid sequence of SEQ ID NO:35 or SEQ ID NO:36, capable of inhibiting the expression, formation or activity of a connexin hemichannel, wherein tissue edema associated with said inflammatory disorder is ameliorated, wherein the connexin mimetic peptide is administered for at least 72 hours.

48. A method for treating a subject for tissue edema associated with a transplant or grafting procedure comprising administration to said subject an amount of a connexin mimetic peptide comprising the amino acid sequence of SEQ ID NO:35 or SEQ ID NO:36, capable of inhibiting the expression, formation or activity of a connexin hemichannel, wherein tissue edema associated with said transplant or grafting procedure is ameliorated, wherein the connexin mimetic peptide is administered for at least 72 hours.

49. The method of any one of claim 24, 34-36, 41, 42, 45, or 47 wherein a hemichannel expression, formation, or activity is inhibited in endothelial cells.

50. The method of any one of claim 24, 34-36, 41, 43, 45, or 47 wherein transmission of molecules from the cytoplasm of a cell bearing the hemichannel into an extracellular space is inhibited.

51. The method of any one of claim 41, 43, 45, or 47 wherein the inflammatory disorder is selected from the group consisting of arthritis, rheumatoid arthritis (RA), inflammation, destruction or damage of joints, inflammatory disorder, grave's disease, hashimoto's disease, rheumatoid arthritis, systemic lupus erythematosus, sjogrens syndrome, immune thrombocytopenic purpura, multiple sclerosis, myasthenia gravis, scleroderma, psoriasis, inflammatory bowel disease, Crohn's disease, ulcerative colitis, sepsis and septic shock, and autoimmune diseases of the digestive system.

52. The method of any one of claim 42, 44, 46, or 48 wherein the subject is treated with a transplant or grafting procedure associated with heart failure, congenital heart disease, acquired heart disease in children, valvular heart disease, infective endocarditis, cardiomypopathy, tumors of the heart, pericardial heart disease, traumatic heart disease, pulmonary embolism, pulmonary hypertension, cor pulmonale, and athletic heart syndrome, peripheral arterial circulation disorder, vascular disorder affecting an organ system, vascular disorder affecting the central nervous system, vascular disorder affecting the brain, vascular disorder affecting the retina, vascular disorder affecting the kidney, vascular disorder affecting and nerves, microvascular disorder, and macrovascular disorder.

53. The method of any one of claim 42, 44, 46, or 48 wherein the transplant is a heart transplant, kidney transplant, liver transplant, lung transplant, pancreatic transplant, intestinal transplant, or a combined organ transplant.

54. The method of any one of claim 42, 44, 46, or 48 wherein the transplant or grafting procedure involves one or more of eye tissue, skin, heart valves, bones, tendons, veins, ligaments, bone marrow transplants, dental or gum tissue, grafting or implantation associated with cosmetic surgery, grafting or implantation associated with a hip or joint replacement procedure, and tissue grafting or implants involving stem cells.

* * * * *

SEQUENCE LISTING

<160> NUMBER OF SEQ ID NOS: 131

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: AS ODN

<400> SEQUENCE: 1
gtaattgcgg caagaagaat tgtttctgtc                                         30

<210> SEQ ID NO 2
<211> LENGTH: 30
<212> TYPE: DNA
<213> ORGANISM: Artificial Sequence
<220> FEATURE:
<223> OTHER INFORMATION: Description of Artificial Sequence: AS ODN

<400> SEQUENCE: 2
gtaattgcgg caggaggaat tgtttctgtc                                         30

<210> SEQ ID NO 3
<211> LENGTH: 30
<212> TYPE: DNA
<213> ORGANISM: Artificial Sequence
<220> FEATURE:
<223> OTHER INFORMATION: Description of Artificial Sequence: AS ODN

<400> SEQUENCE: 3
ggcaagagac accaaagaca ctaccagcat                                         30

<210> SEQ ID NO 4
<211> LENGTH: 27
<212> TYPE: DNA
<213> ORGANISM: Artificial Sequence
<220> FEATURE:
<223> OTHER INFORMATION: Description of Artificial Sequence: AS ODN

<400> SEQUENCE: 4
tcctgagcaa tacctaacga acaaata                                            27

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: AS ODN

<400> SEQUENCE: 5
catctccttg gtgctcaacc                                                    20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: AS ODN

<400> SEQUENCE: 6
ctgaagtcga cttggcttgg                                                    20

<210> SEQ ID NO 7
<211> LENGTH: 21
<212> TYPE: DNA
<213> ORGANISM: Artificial Sequence

```
<220> FEATURE:
<223> OTHER INFORMATION: Description of Artificial Sequence: AS ODN

<400> SEQUENCE: 7
ctcagatagt ggccagaatg c                                         21

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: AS ODN

<400> SEQUENCE: 8
ttgtccaggt gactccaagg                                           20

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence: AS ODN

<400> SEQUENCE: 9
cgtccgagcc cagaaagatg aggtc                                     25

<210> SEQ ID NO 10
<211> LENGTH: 19
<212> TYPE: DNA
<213> ORGANISM: Artificial Sequence
<220> FEATURE:
<223> OTHER INFORMATION: Description of Artificial Sequence: AS ODN

<400> SEQUENCE: 10
agaggcgcac gtgagacac                                            19

<210> SEQ ID NO 11
<211> LENGTH: 19
<212> TYPE: DNA
<213> ORGANISM: Artificial Sequence
<220> FEATURE:
<223> OTHER INFORMATION: Description of Artificial Sequence: AS ODN

<400> SEQUENCE: 11
tgaagacaat gaagatgtt                                            19

<210> SEQ ID NO 12
<211> LENGTH: 3088
<212> TYPE: DNA
<213> ORGANISM: Homo sapiens

<400> SEQUENCE: 12
acaaaaaagc ttttacgagg tatcagcact tttctttcat taggggggaag gcgtgaggaa    60 agtaccaaac agcagcggag ttttaaactt taaatagaca ggtctgagtg cctgaacttg   120 cctttttcatt ttacttcatc ctccaaggag ttcaatcact ggcgtgact tcactacttt    180 taagcaaaag agtggtgccc aggcaacatg ggtgactgga gcgccttagg caaactcctt   240
gacaaggttc aagcctactc aactgctgga gggaaggtgt ggctgtcagt acttttcatt   300
ttccgaatcc tgctgctggg gacagcggtt gagtcagcct ggggagatga gcagtctgcc   360
tttcgttgta acactcagca acctggttgt gaaaatgtct gctatgacaa gtcttttccca   420 atctctcatg tgcgcttctg ggtcctgcag atcatatttg tgtctgtacc cacactcttg   480
```

```
tacctggctc atgtgttcta tgtgatgcga aaggaagaga aactgaacaa gaaagaggaa      540
gaactcaagg ttgcccaaac tgatggtgtc aatgtggaca tgcacttgaa gcagattgag      600
ataaagaagt tcaagtacgg tattgaagag catggtaagg tgaaaatgcg agggggggttg     660
ctgcgaacct acatcatcag tatcctcttc aagtctatct ttgaggtggc cttcttgctg      720
atccagtggt acatctatgg attcagcttg agtgctgttt acacttgcaa aagagatccc      780
tgcccacatc aggtggactg tttcctctct cgccccacgg agaaaaccat cttcatcatc      840
ttcatgctgg tggtgtcctt ggtgtccctg gccttgaata tcattgaact cttctatgtt      900
ttcttcaagg gcgttaagga tcgggttaag ggaaagagcg acccttacca tgcgaccagt      960
ggtgcgctga gccctgccaa agactgtggg tctcaaaaat atgcttattt caatggctgc     1020
tcctcaccaa ccgctcccct ctcgcctatg tctcctcctg ggtacaagct ggttactggc     1080
gacagaaaca attcttcttg ccgcaattac aacaagcaag caagtgagca aaactgggct     1140
aattacagtg cagaacaaaa tcgaatgggg caggcgggaa gcaccatctc taactcccat     1200
gcacagcctt ttgatttccc cgatgataac cagaattcta aaaaactagc tgctggacat     1260
gaattacagc cactagccat tgtggaccag cgaccttcaa gcagagccag cagtcgtgcc     1320
agcagcagac ctcggcctga tgacctggag atctagatac aggcttgaaa gcatcaagat     1380
tccactcaat tgtggagaag aaaaaaggtg ctgtagaaag tgcaccaggt gttaattttg     1440
atccggtgga ggtggtactc aacagcctta ttcatgaggc ttagaaaaca caagacatt      1500
agaataccta ggttcactgg gggtgtatgg ggtagatggg tggagaggga ggggataaga     1560
gaggtgcatg ttggtattta aagtagtgga ttcaaagaac ttagattata aataagagtt     1620
ccattaggtg atacatagat aagggctttt tctccccgca acacccccta agaatggttc     1680
tgtgtatgtg aatgagcggg tggtaattgt ggctaaatat ttttgtttta ccaagaaact     1740
gaaataattc tggccaggaa taaatacttc ctgaacatct taggtctttt caacaagaaa     1800
aagacagagg attgtcctta agtccctgct aaaacattcc attgttaaaa tttgcacttt     1860
gaaggtaagc tttctaggcc tgaccctcca ggtgtcaatg gacttgtgct actatatttt     1920
tttattcttg gtatcagttt aaaattcaga caaggcccac agaataagat tttccatgca     1980
tttgcaaata cgtatattct ttttccatcc acttgcacaa tatcattacc atcactttt      2040
catcattcct cagctactac tcacattcat ttaatggttt ctgtaaacat ttttaagaca     2100
gttgggatgt cacttaacat ttttttttt tgagctaaag tcagggaatc aagccatgct     2160
taatatttaa caatcactta tatgtgtgtc gaagagtttg ttttgtttgt catgtattgg     2220
tacaagcaga tacagtataa actcacaaac acagatttga aaataatgca catatggtgt     2280
tcaaatttga acctttctca tggatttttg tggtgtgggc caatatggtg tttacattat     2340
ataattcctg ctgtggcaag taaagcacac ttttttttc tcctaaaatg ttttcccctg      2400
tgtatcctat tatggatact ggttttgtta attatgattc tttatttct ctcctttttt       2460
taggatatag cagtaatgct attactgaaa tgaatttcct ttttctgaaa tgtaatcatt     2520
gatgcttgaa tgatagaatt ttagtactgt aaacaggctt tagtcattaa tgtgagagac     2580
ttagaaaaaa tgcttagagt ggactattaa atgtgcctaa atgaatttg cagtaactgg       2640
tattcttggg ttttcctact aatacacag taattcagaa cttgtattct attatgagtt       2700
tagcagtctt ttggagtgac cagcaacttt gatgtttgca ctaagatttt atttggaatg     2760
caagagaggt tgaaagagga ttcagtagta cacatacaac taatttattt gaactatatg     2820
ttgaagacat ctaccagttt ctccaaatgc cttttttaaa actcatcaca gaagattggt     2880
```

| | |
|---|---|
| gaaaatgctg agtatgacac ttttcttctt gcatgcatgt cagctacata aacagttttg | 2940 |
| tacaatgaaa attactaatt tgtttgacat tccatgttaa actacggtca tgttcagctt | 3000 |
| cattgcatgt aatgtagacc tagtccatca gatcatgtgt tctggagagt gttctttatt | 3060 |
| caataaagtt ttaatttagt ataaacat | 3088 |

<210> SEQ ID NO 13
<211> LENGTH: 1308
<212> TYPE: DNA
<213> ORGANISM: Homo sapiens

<400> SEQUENCE: 13

| | |
|---|---|
| atgggcgact ggagctttct gggaagactc ttagaaaatg cacaggagca ctccacggtc | 60 |
| atcggcaagg tttggctgac cgtgctgttc atcttccgca tcttggtgct gggggccgcg | 120 |
| gcggaggacg tgtggggcga tgagcagtca gacttcacct gcaacaccca gcagccgggc | 180 |
| tgcgagaact ctgctacga cagggccttc cccatctccc acatccgctt ctgggcgctg | 240 |
| cagatcatct tcgtgtccac gcccacccte atctacctgg ccacgtgct gcacatcgtg | 300 |
| cgcatggaag agaagaagaa agagagggag gaggaggage agctgaagag agagagcccc | 360 |
| agccccaagg agccaccgca ggacaatccc tcgtcgcggg acgaccgcgg cagggtgcgc | 420 |
| atggccgggg cgctgctgcg gacctacgtc ttcaacatca tcttcaagac gctgttcgag | 480 |
| gtgggcttca tcgccggcca gtactttctg tacggcttcg agctgaagcc gctctaccgc | 540 |
| tgcgaccgct ggccctgccc caacacggtg gactgcttca ctccaggcc cacggagaag | 600 |
| accatcttca tcatcttcat gctggcggtg gcctgcgcgt ccctgctgct caacatgctg | 660 |
| gagatctacc acctgggctg gaagaagctc aagcagggcg tgaccagccg cctcggcccg | 720 |
| gacgcctccg aggccccgct ggggacagcc gatccccgc ccctgccccc cagctcccgg | 780 |
| ccgcccgccg ttgccatcgg gttcccaccc tactatgcgc acaccgctgc gcccctggga | 840 |
| caggcccgcg ccgtgggcta ccccggggcc ccgccaccag ccgcggactt caaactgcta | 900 |
| gccctgaccg aggcgcgcgg aaagggccag tccgccaagc tctacaacgg ccaccaccac | 960 |
| ctgctgatga ctgagcagaa ctgggccaac caggcggccg agcggcagcc cccggcgctc | 1020 |
| aaggcttacc cggcagcgtc cacgcctgca gccccagcc ccgtcggcag cagctccccg | 1080 |
| ccactcgcgc acgaggctga gcggggcgcg gcgcccctgc tgctggatgg gagcggcagc | 1140 |
| agtctggagg ggagcgccct ggcagggacc cccgaggagg aggagcaggc cgtgaccacc | 1200 |
| gcggcccaga tgcaccagcc gcccttgccc tcggagacc aggtcgggc cagcaaggcc | 1260 |
| agcagggcca gcagcgggcg ggccagaccg gaggacttgg ccatctag | 1308 |

<210> SEQ ID NO 14
<211> LENGTH: 1601
<212> TYPE: DNA
<213> ORGANISM: Homo sapiens

<400> SEQUENCE: 14

| | |
|---|---|
| ctccggccat cgtccccacc tccacctggg ccgcccgcga ggcagcggac ggaggccggg | 60 |
| agccatgggt gactggggct tcctggagaa gttgctggac caggtccgag agcactcgac | 120 |
| cgtggtgggt aagatctggc tgacggtgct cttcatcttc cgcatcctca tcctgggcct | 180 |
| ggccggcgag tcagtgtggg gtgacgagca gtcagatttc gagtgtaaca cggcccagcc | 240 |
| aggctgcacc aacgtctgct atgaccaggc cttccccatc tcccacatcc gctactgggt | 300 |

```
gctgcagttc tcttcgtca gcacacccac cctggtctac ctgggccatg tcatttacct    360
gtctcggcga aagagcggc tggcgcagaa ggaggggag ctgcgggcac tgccggccaa     420
ggacccacag gtggagcggg cgctggccgg catagagctt cagatggcca agatctcggt   480
ggcagaagat ggtcgcctgc gcattccgcg agcactgatg gcacctatg tcgccagtgt    540 gctctgcaag agtgtgctag aggcaggctt cctctatggc cagtggcgcc tgtacggctg   600
gaccatggag cccgtgtttg tgtgccagcg agcaccctgc ccctacctcg tggactgctt   660
tgtctctcgc cccacggaga agaccatctt catcatcttc atgttggtgg ttggactcat   720
ctccctggtg cttaacctgc tggagttggt gcacctgctg tgtcgctgcc tcagccgggg   780
gatgagggca cggcaaggcc aagacgcacc cccgacccag ggcacctcct cagacccta    840 cacggaccag ggtcttcttc tacctccccg tggccagggg ccctcatccc caccatgccc   900
cacctacaat gggctctcat ccagtgagca gaactgggcc aacctgacca cagaggagag   960
gctggcgtct tccaggcccc ctctcttcct ggacccaccc cctcagaatg ccaaaaaacc   1020
cccaagtcgt cccagcagct ctgcttctaa gaagcagtat gtatagaggc ctgtggctta   1080
tgtcacccaa cagaggggtc ctgagaagtc tggctgcctg ggatgcccc tgccccctcc    1140 tggaaggctc tgcagagatg actgggctgg ggaagcagat gcttgctggc catggagcct   1200
cattgcaagt tgttcttgaa cacctgaggc cttcctgtgg cccaccaggc actacggctt   1260 cctctcccaga tgtgctttgc ctgagcacag acagtcagca tggaatgctc ttggccaagg   1320 gtactgggc cctctggcct tttgcagctg atccagagga acccagagcc aacttacccc    1380
aacctcaccc tatggaacag tcacctgtgc gcaggttgtc ctcaaaccct ctcctcacag   1440
gaaaaggcgg attgaggctg ctgggtcagc cttgatcgca cagacagagc ttgtgccgga   1500
tttggccctg tcaaggggac tggtgccttg ttttcatcac tccttcctag ttctactgtt   1560
caagcttctg aaataaacag gacttgatca caaaaaaaaa a                       1601
```

<210> SEQ ID NO 15
<211> LENGTH: 2574
<212> TYPE: DNA
<213> ORGANISM: Homo sapiens

<400> SEQUENCE: 15

```
gcaaaaagcg tgggcagttg gagaagaagc agccagagtg tgaagaagcc cacggaagga    60
aagtccaggg aggaggaaaa gaagcagaag ttttggcatc tgttccctgg ctgtgccaag   120
atgggcgatt ggagcttcct gggaaatttc ctggaggaag tacacaagca ctcgaccgtg   180
gtaggcaagg tctggctcac tgtcctcttc atattccgta tgctcgtgct gggcacagct   240
gctgagtctt cctgggggga tgagcaggct gatttccggt gtgatacgat tcagcctggc   300
tgccagaatg tctgctacga ccaggctttc cccatctccc acattcgcta ctgggtgctg   360
cagatcatct tcgtctccac gccctctctg gtgtacatgg ccacgccat gcacactgtg   420 cgcatgcagg agaagcgcaa gctacgggag gccgagaggg ccaaagaggt ccggggctct   480
ggctcttacg agtacccggt ggcagagaag gcagaactgt cctgctggga ggaagggaat   540
ggaaggattg ccctccaggg cactctgctc aacacctatg tgtgcagcat cctgatccgc   600
accaccatgg aggtgggctt cattgtgggc cagtacttca tctacggaat cttcctgacc   660
accctgcatg tctgccgcag gagtcccgt ccccacccgg tcaactgtta cgtatcccgg   720
cccacagaga agaatgtctt cattgtcttt atgctggctc tggctgcact gtccctcctc   780
cttagcctgg ctgaactcta ccacctgggc tggaagaaga tcagacagcg atttgtcaaa   840
```

| | | | | |
|---|---|---|---|---|
| ccgcggcagc | acatggctaa | gtgccagctt | tctggcccct | ctgtgggcat agtccagagc | 900 |
| tgcacaccac | cccccgactt | taatcagtgc | ctggagaatg | ccctgggggg aaaattcttc | 960 |
| aatcccttca | gcaataatat | ggcctcccaa | caaaacacag | acaacctggt caccgagcaa | 1020 |
| gtacgaggtc | aggagcagac | tcctggggaa | ggtttcatcc | aggttcgtta tggccagaag | 1080 |
| cctgaggtgc | ccaatggagt | ctcaccaggt | caccgccttc | cccatggcta tcatagtgac | 1140 |
| aagcgacgtg | ttagtaaggc | cagcagcaag | gcaaggtcag | atgacctatc agtgtgaccc | 1200 |
| tcctttatgg | gaggatcagg | accaggtggg | aacaaaggag | gctcagagaa gaaagacgtg | 1260 |
| tcccttctga | actgatgctt | tctcactgtc | atcactgctt | ggctcctttg agccccgggt | 1320 |
| ctcaatgacg | ttgctcatta | attctagaaa | ctataaccag | ggctctggga tagtaagaga | 1380 |
| ggtgacaacc | cacccagact | gcagttccct | cccccaccctc | tacccagtat acgaagcctt | 1440 |
| tcagattact | catgaaacag | ggtagaggga | agaagggaa | gcatggcaaa agctggcctg | 1500 |
| gaagggatag | ccagagggat | agaatgactc | tctctctaca | taccagcagc ataccaaatg | 1560 |
| cgttctctaa | gttcctacct | ccttgacctg | atcaccctcc | ctcctccaag gaagagctca | 1620 |
| aagttcccag | ccaatagaca | gcatgaatca | aggaacttgc | attatatgtg ctcttgaatc | 1680 |
| tgttgtctcc | atggaccatt | cctcggagta | gtggtgagat | ggccttgggt tgcccttggc | 1740 |
| ttctcctccc | tctactcagc | cttaaaaagg | gcttcttgga | actttaccag cagcctcagc | 1800 |
| tttacaaatg | ccttggtatg | tacctctggc | aaatgcccca | ccttggtgat gttgcaacct | 1860 |
| ttccttctgc | tagggtgtac | acctagcctg | tgcaggtgtc | agccctgcta gggagtcact | 1920 |
| gtacacacaa | actctactgg | aattcctgcc | aacatctgtc | accctgcagc tcctttacag | 1980 |
| ttcaatccaa | tgatagaaac | catcccttcc | ctttctccct | tggctgttca cccagccatt | 2040 |
| ccctgaaggc | cttaccaaca | ggaatatcca | agaagctgtt | gtcccctctc gaaccctgac | 2100 |
| cagatcatca | gccactgagg | ccagtggaat | ttccccaggc | cttgttaaaa caaagaaagc | 2160 |
| attgtacctc | tcagattccc | cttgtggaaa | aaaaaattct | gctgtgaaga tgaaaataaa | 2220 |
| aatggagaga | aaacactgga | aaactatttt | cccctcctat | ttacttcctt tgctgactgc | 2280 |
| caacttagtg | ccaagaggag | gtgtgatgac | agctatggag | gccccagat ctctctctcc | 2340 |
| tggaggcttt | agcaggggca | aggaaatagt | aggggaatct | ccagctctct tggcagggcc | 2400 |
| tttatttaaa | gagcgcagag | attcctatgt | ctccctagtg | cccctaatga gactgccaag | 2460 |
| tgggggctgt | agaaaagcct | tgccttcccc | agggattggc | ctggtctctg tattcactgg | 2520 |
| atccataatg | ggttgctgtt | gttttggatg | aaggtaaacg | atgcttggaa ttgg | 2574 |

<210> SEQ ID NO 16
<211> LENGTH: 1191
<212> TYPE: DNA
<213> ORGANISM: Homo sapiens

<400> SEQUENCE: 16

| | | | | |
|---|---|---|---|---|
| atgagttgga | gctttctgac | tcgcctgcta | gaggagattc | acaaccattc cacatttgtg | 60 |
| gggaagatct | ggctcactgt | tctgattgtc | ttccggatcg | tccttacagc tgtaggagga | 120 |
| gaatccatct | attacgatga | gcaaagcaaa | tttgtgtgca | acacagaaca gccgggctgt | 180 |
| gagaatgtct | gttatgatgc | gtttgcacct | ctctcccatg | tacgcttctg ggtgttccag | 240 |
| atcatcctgg | tggcaactcc | ctctgtgatg | tacctgggct | atgctatcca caagattgcc | 300 |
| aaaatggagc | acggtgaagc | agacaagaag | gcagctcgga | gcaagccctg tgcaatgcgc | 360 |

| | |
|---|---|
| tggaaacaac accgggctct ggaagaaacg gaggaggaca acgaagagga tcctatgatg | 420 |
| tatccagaga tggagttaga aagtgataag gaaaataaag agcagagcca acccaaacct | 480 |
| aagcatgatg gccgacgacg gattcgggaa gatgggctca tgaaaatcta tgtgctgcag | 540 |
| ttgctggcaa ggaccgtgtt tgaggtgggt tttctgatag gcagtatttt ctgtatggc | 600 |
| ttccaagtcc acccgtttta tgtgtgcagc agacttcctt gtcctcataa gatagactgc | 660 |
| tttatttcta gacccactga aaagaccatc ttccttctga taatgtatgg tgttacaggc | 720 |
| cttttgcctct tgcttaacat ttgggagatg cttcatttag ggtttgggac cattcgagac | 780 |
| tcactaaaca gtaaaaggag ggaacttgag gatccgggtg cttataatta tcctttcact | 840 |
| tggaatacac catctgctcc ccctggctat aacattgctg tcaaaccaga tcaaatccag | 900 |
| tacaccgaac tgtccaatgc taagatcgcc tacaagcaaa acaaggccaa cacagcccag | 960 |
| gaacagcagt atggcagcca tgaggagaac ctcccagctg acctggaggc tctgcagcgg | 1020 |
| gagatcagga tggctcagga acgcttggat ctggcagttc aggcctacag tcaccaaaac | 1080 |
| aaccctcatg gtccccggga gaagaaggcc aaagtggggt ccaaagctgg gtccaacaaa | 1140 |
| agcactgcca gtagcaaatc aggggatggg aagaactctg tctggattta a | 1191 |

<210> SEQ ID NO 17
<211> LENGTH: 1362
<212> TYPE: DNA
<213> ORGANISM: Homo sapiens

<400> SEQUENCE: 17

| | |
|---|---|
| agcgccaaga gagaaagagc acatatttct ccgtgggaca ctccttgtat tggtgggtga | 60 |
| gaaatgggcg actggagttt cctggggaac atcttggagg aggtgaatga gcactccacc | 120 |
| gtcatcggca gagtctggct caccgtgctt ttcatcttcc ggatcctcat ccttggcacg | 180 |
| gccgcagagt tcgtgtgggg ggatgagcaa tccgacttcg tgtgcaacac ccagcagcct | 240 |
| ggctgcgaga acgtctgcta cgacgaggcc tttcccatct cccacattcg cctctgggtg | 300 |
| ctgcagatca tcttcgtctc caccccgtcc ctgatgtacg tggggcacgc ggtgcactac | 360 |
| gtccgcatgg aggagaagcg caaaagccgc gacgaggagc tgggccagca ggcggggact | 420 |
| aacggcggcc cggaccaggg cagcgtcaag aagagcagcg gcagcaaagg cactaagaag | 480 |
| ttccggctgg aggggaccct gctgaggacc tacatctgcc acatcatctt caagaccctc | 540 |
| tttgaagtgg gcttcatcgt gggccactac ttcctgtacg ggttccggat cctgcctctg | 600 |
| taccgctgca gccggtggcc ctgccccaat gtggtggact gcttcgtgtc ccggcccacg | 660 |
| gagaaaacca tcttcatcct gttcatgttg tctgtggcct ctgtgtccct attcctcaac | 720 |
| gtgatggagt tgagccacct gggcctgaag gggatccggt ctgccttgaa gaggcctgta | 780 |
| gagcagcccc tgggggagat tcctgagaaa tccctccact ccattgctgt ctcctccatc | 840 |
| cagaaagcca agggctatca gcttctagaa gaagagaaaa tcgtttccca ctatttcccc | 900 |
| ttgaccgagg ttgggatggt ggagaccagc ccactgcctg ccaagccttt caatcagttc | 960 |
| gaggagaaga tcagcacagg acccctgggg gacttgtccc ggggctacca agagacactg | 1020 |
| ccttcctacg ctcaggtggg ggcacaagaa gtggagggcg aggggccgcc tgcagaggag | 1080 |
| ggagccgaac ccgaggtggg agagaagaag gaggaagcag agaggctgac cacggaggag | 1140 |
| caggagaagg tggccgtgcc agagggggag aaagtagaga ccccggagt ggataaggag | 1200 |
| ggtgaaaaag aagagccgca gtcggagaag gtgtcaaagc aagggctgcc agctgagaag | 1260 |
| acaccttcac tctgtccaga gctgacaaca gatgatgcca gaccctgag caggctaagc | 1320 | aaagccagca gccgagccag gtcagacgat ctaaccgtat ga        1362

<210> SEQ ID NO 18
<211> LENGTH: 966
<212> TYPE: DNA
<213> ORGANISM: Homo sapiens

<400> SEQUENCE: 18
atgggggaat ggaccatctt ggagaggctg ctagaagccg cggtgcagca gcactccact    60
atgatcggaa ggatcctgtt gactgtggtg gtgatcttcc ggatcctcat tgtggccatt   120
gtggggagga cggtgtacga tgatgagcag accatgtttg tgtgcaacac cctgcagccc   180
ggctgtaacc aggcctgcta tgaccgggcc ttccccatct cccacatacg ttactgggtc   240
ttccagatca taatggtgtg taccccagt ctttgcttca tcacctactc tgtgcaccag   300
tccgccaagc agcgagaacg ccgctactct acagtcttcc tagccctgga cagagacccc   360
cctgagtcca taggaggtcc tggaggaact ggggtgggg cagtggtgg gggcaaacga   420 gaagataaga agttgcaaaa tgctattgtg aatggggtgc tgcagaacac agagaacacc   480
agtaaggaga cagagccaga ttgtttagag gttaaggagc tgactccaca cccatcaggt   540
ctacgcactg catcaaaatc caagctcaga aggcaggaag gcatctcccg cttctacatt   600
atccaagtgg tgttccgaaa tgccctggaa attgggttcc tggttggcca atattttctc   660
tatggcttta gtgtcccagg gttgtatgag tgtaaccgct accctgcat caaggaggtg   720 gaatgttatg tgtcccggcc aactgagaag actgtctttc tagtgttcat gtttgctgta   780
agtggcatct gtgttgtgct caacctggct gaactcaacc acctgggatg gcgcaagatc   840
aagctggctg tgcgaggggc tcaggccaag agaaagtcaa tctatgagat cgtaacaag   900 gacctgccaa gggtcagtgt tcccaatttt ggcaggactc agtccagtga ctctgcctat   960
gtgtga                                                              966

<210> SEQ ID NO 19
<211> LENGTH: 1901
<212> TYPE: DNA
<213> ORGANISM: Homo sapiens

<400> SEQUENCE: 19
cagggagttg tggttgcaac actgtactcc agcctgggca acagagggag actctgtctc    60
aacaaacaaa caaacaaaga aaaaccccca cagctatcta gggaaaaagt aaagcaacca   120
gcatatagaa gtgacatatt gttatatttt caccataggt ttgctttaag aaatagtgct   180
cccttcagaa tggaagaatt tatctgcctc ttatttgatg tggatcagag ctaagatggc   240
tgactaaata aacatggggg actggaatct ccttggagat actctggagg aagttcacat   300
ccactccacc atgattggaa agatctggct caccatcctg ttcatatttc gaatgcttgt   360
tctgggtgta gcagctgaag atgtctgaa tgatgagcag tctggcttca tctgcaatac   420
agaacaacca ggctgcagaa atgtatgcta cgaccaggcc tttcctatct ccctcattag   480
atactgggtt ctgcaggtga tatttgtgtc ttcaccatcc ctggtctaca tgggccatgc   540
attgtaccga ctgagagttc ttgaggaaga gaggcaaagg atgaaagctc agttaagagt   600
agaactggag gaggtagagt ttgaaatgcc tagggatcgg aggagattgg agcaagagct   660
ttgtcagctg gagaaaagga aactaaataa agctccactc agaggaacct tgctttgcac   720
ttatgtgata cacattttca ctcgctctgt ggttgaagtt ggattcatga ttggacagta   780

```
cctttttatat ggatttcact tagagccgct atttaagtgc catggccacc cgtgtccaaa    840
tataatcgac tgttttgtct caagaccaac agaaaagaca atattcctat tatttatgca    900
atctatagcc actatttcac ttttcttaaa cattcttgaa attttccacc taggttttaa    960
aaagattaaa agagggcttt ggggaaaata caagttgaag aaggaacata atgaattcca   1020
tgcaaacaag gcaaaacaaa atgtagccaa ataccagagc acatctgcaa attcactgaa   1080
gcgactccct tctgcccctg attataatct gttagtggaa aagcaaacac acactgcagt   1140
gtaccctagt ttaaattcat cttctgtatt ccagccaaat cctgacaatc atagtgtaaa   1200
tgatgagaaa tgcattttgg atgaacagga aactgtactt tctaatgaga tttccacact   1260
tagtactagt tgtagtcatt ttcaacacat cagttcaaac aataacaaag acactcataa   1320
aatatttgga aaagaactta atggtaacca gttaatggaa aaagagaaa ctgaaggcaa    1380 agacagcaaa aggaactact actctagagg tcaccgttct attccaggtg ttgctataga   1440
tggagagaac aacatgaggc agtcacccca aacagttttc tccttgccag ctaactgcga   1500
ttggaaaccg cggtggctta gagctacatg gggttcctct acagaacatg aaaaccgggg   1560
gtcacctcct aaaggtaacc tcaagggcca gttcagaaag ggcacagtca gaacccttcc   1620
tccttcacaa ggagattctc aatcacttga cattccaaac actgctgatt ctttgggagg   1680
gctgtccttt gagccagggt tggtcagaac ctgtaataat cctgtttgtc ctccaaatca   1740
cgtagtgtcc ctaacgaaca atctcattgg taggcgggtt cccacagatc ttcagatcta   1800
aacagcggtt ggcttttaga cattatatat attatcagag aagtagccta gtggtcgtgg   1860
ggcacagaaa aaatagatag gggcagctct aaagaccagc t                       1901

<210> SEQ ID NO 20
<211> LENGTH: 1311
<212> TYPE: DNA
<213> ORGANISM: Homo sapiens

<400> SEQUENCE: 20
atgagctgga gcttcctgac gcggctgctg gaggagatcc acaaccactc caccttcgtg     60
ggcaaggtgt ggctcacggt gctggtggtc ttccgcatcg tgctgacggc tgtgggcggc    120
gaggccatct actcggacga gcaggccaag ttcacttgca acacgcggca gccaggctgc    180
gacaacgtct gctatgacgc cttcgcgccc tgtcgcacg tgcgcttctg ggtcttccag    240
attgtggtca tctccacgcc ctcggtcatg tacctgggct acgccgtgca ccgcctggcc    300
cgtgcgtctg agcaggagcg gcgccgcgcc tcccgccgcc gcccgggcc acgccgcgcg    360 ccccgagcgc acctgccgcc cccgcacgcc ggctggcctg agcccgccga cctgggcgag    420
gaggagccca tgctgggcct gggcgaggag gaggaggagg aggagacggg ggcagccgag    480
ggcgccggcg aggaagcgga ggaggcaggc gcggaggagg cgtgcactaa ggcggtcggc    540
gctgacggca aggcggcagg gaccccgggc ccgaccgggc aacacgatgg gcggaggcgc    600
atccagcggg agggcctgat gcgcgtgtac gtggcccagc tggtgccagg gcagctttc    660 gaggtggcct tcctggtggg ccagtacctg ctgtacggct tcgaggtgcg accgttcttt    720
ccctgcagcc gccagcctg cccgcacgtg gtggactgct tcgtgtcgcg ccctactgaa    780
aagacggtct tcctgctggt tatgtacgtg gtcagctgcc tgtgcctgct gctcaacctc    840
tgtgagatgg cccacctggg cttgggcagc gcgcaggacg cggtgcgcgg ccgccgcggc    900
cccccggcct ccgcccccgc cccgcgccg cggcccccgc cctgcgcctt ccctgcggcg    960
gccgctggct tggcctgccc gcccgactac agcctggtgg tgcgggcggc cgagcgcgct   1020
```

```
cgggcgcatg accagaacct ggcaaacctg gccctgcagg cgctgcgcga cggggcagcg    1080 gctgggacc gcgaccggga cagttcgccg tgcgtcggcc tccctgcggc ctcccggggg    1140 cccccagag caggcgcccc cgcgtcccgg acgggcagtg ctacctctgc gggcactgtc    1200
ggggagcagg gccggcccgg cacccacgag cggccaggag ccaagcccag ggctggctcc    1260
gagaagggca gtgccagcag cagggacggg aagaccaccg tgtggatctg a             1311
```

<210> SEQ ID NO 21
<211> LENGTH: 1588
<212> TYPE: DNA
<213> ORGANISM: Homo sapiens

<400> SEQUENCE: 21

```
agacattctc tgggaaaggg cagcagcagc caggtgtggc agtgacaggg aggtgtgaat      60
gaggcaggat gaactggaca ggtttgtaca ccttgctcag tggcgtgaac cggcattcta     120
ctgccattgg ccgagtatgg ctctcggtca tcttcatctt cagaatcatg gtgctggtgg     180
tggctgcaga gagtgtgtgg ggtgatgaga aatcttcctt catctgcaac acactccagc    240
ctggctgcaa cagcgtttgc tatgaccaat tcttccccat ctcccatgtg cggctgtggt    300
ccctgcagct catcctagtt tccaccccag ctctcctcgt ggccatgcac gtggctcacc    360
agcaacacat agagaagaaa atgctacggc ttgagggcca tggggacccc ctacacctgg    420
aggaggtgaa gaggcacaag gtccacatct cagggacact gtggtggacc tatgtcatca    480
gcgtggtgtt ccggctgttg tttgaggccg tcttcatgta tgtcttttat ctgctctacc    540
ctggctatgc catggtgcgg ctggtcaagt gcgacgtcta cccctgcccc aacacagtgg    600
actgcttcgt gtcccgcccc accgagaaaa ccgtcttcac cgtcttcatg ctagctgcct    660
ctggcatctg catcatcctc aatgtggccg aggtggtgta cctcatcatc cgggcctgtg    720
cccgccgagc ccagcgccgc tccaatccac cttcccgcaa gggctcgggc ttcggccacc    780
gcctctcacc tgaatacaag cagaatgaga tcaacaagct gctgagtgag caggatggct    840
ccctgaaaga catactgcgc cgcagccctg gcaccggggc tgggctggct gaaaagagcg    900
accgctgctc ggcctgctga tgccacatac caggcaacct cccatcccac ccccgaccct    960
gccctgggcg agcccctcct tctcccctgc cggtgcacag gcctctgcct gctgggggatt   1020 actcgatcaa aaccttcctt ccctggctac ttcccttcct cccggggcct tccttttgag   1080
gagctggagg ggtggggagc tagaggccac ctatgccagt gctcaaggtt actgggagtg    1140
tgggctgccc ttgttgcctg cacccttccc tcttccctct ccctctctct gggaccactg    1200
ggtacaagag atgggatgct ccgacagcgt ctccaattat gaaactaatc ttaaccctgt    1260
gctgtcagat accctgtttc tggagtcaca tcagtgagga gggatgtggg taagaggagc    1320
agagggcagg ggtgctgtgg acatgtgggt ggagaaggga gggtggccag cactagtaaa    1380
ggaggaatag tgcttgctgg ccacaaggaa aaggaggagg tgtctgggggt gagggagtta   1440 gggagagaga agcaggcaga taagttggag caggggttgg tcaaggccac ctctgcctct    1500
agtccccaag gcctctctct gcctgaaatg ttacacatta aacaggattt tacagcaaaa    1560
aaaaaaaaaa aaaaaaaaa aaaaaaa                                         1588
```

<210> SEQ ID NO 22
<211> LENGTH: 2263
<212> TYPE: DNA
<213> ORGANISM: Homo sapiens

<400> SEQUENCE: 22

```
cggagcccct cggcggcgcc cggcccagga cccgcctagg agcgcaggag ccccagcgca      60
gagacgccaa cgccgagacc cccgccccgg ccccgccgcg cttcctcccg acgcagagca     120
aaccgcccag agtagaagat ggattggggc acgctgcaga cgatcctggg gggtgtgaac     180
aaacactcca ccagcattgg aaagatctgg ctcaccgtcc tcttcatttt tcgcattatg     240
atcctcgttg tggctgcaaa ggaggtgtgg ggagatgagc aggccgactt tgtctgcaac     300
accctgcagc caggctgcaa gaacgtgtgc tacgatcact acttccccat ctcccacatc     360
cggctatggg ccctgcagct gatcttcgtg tccacgccag cgctcctagt ggccatgcac     420
gtggcctacc ggagacatga agaagagg aagttcatca aggggagat aaagagtgaa        480
tttaaggaca tcgaggagat caaaacccag aaggtccgca tcgaaggctc cctgtggtgg     540
acctacacaa gcagcatctt cttccgggtc atcttcgaag ccgccttcat gtacgtcttc     600
tatgtcatgt acgacggctt ctccatgcag cggctggtga agtgcaacgc ctggccttgt     660
cccaacactg tggactgctt tgtgtcccgg cccacggaga agactgtctt cacagtgttc     720
atgattgcag tgtctggaat ttgcatcctg ctgaatgtca ctgaattgtg ttatttgcta     780
attagatatt gttctgggaa gtcaaaaaag ccagtttaac gcattgccca gttgttagat     840
taagaaatag acagcatgag agggatgagg caacccgtgc tcagctgtca aggctcagtc     900
gccagcattt cccaacacaa agattctgac cttaaatgca accatttgaa accctgtag    960
gcctcaggtg aaactccaga tgccacaatg gagctctgct ccctaaagc ctcaaaacaa    1020
aggcctaatt ctatgcctgt cttaattttc tttcacttaa gttagttcca ctgagacccc    1080
aggctgttag gggttattgg tgtaaggtac tttcatattt taaacagagg atatcggcat    1140
ttgtttcttt ctctgaggac aagagaaaaa agccaggttc cacagaggac acagagaagg    1200
tttgggtgtc ctcctggggt tcttttgcc aactttcccc acgttaaagg tgaacattgg    1260
ttctttcatt tgctttggaa gttttaatct ctaacagtgg acaaagttac cagtgcctta    1320
aactctgtta cactttttgg aagtgaaaac tttgtagtat gataggttat tttgatgtaa    1380
agatgttctg gataccatta tatgttcccc ctgtttcaga ggctcagatt gtaatatgta    1440
aatggtatgt cattcgctac tatgatttaa tttgaaatat ggtcttttgg ttatgaatac    1500
tttgcagcac agctgagagg ctgtctgttg tattcattgt ggtcatagca cctaacaaca    1560
ttgtagcctc aatcgagtga gacagactag aagttcctag tgatggctta tgatagcaaa    1620
tggcctcatg tcaaatattt agatgtaatt ttgtgtaaga atacagact ggatgtacca     1680
ccaactacta cctgtaatga caggcctgtc caacacatct ccctttcca tgactgtggt    1740
agccagcatc ggaaagaacg ctgatttaaa gaggtcgctt gggaatttta ttgacacagt    1800
accatttaat ggggaggaca aaatggggca ggggagggag aagtttctgt cgttaaaaac    1860
agatttggaa agactggact ctaaattctg ttgattaaag atgagctttg tctacttcaa    1920
aagtttgttt gcttaccct tcagcctcca attttttaag tgaaaatata actaataaca     1980
tgtgaaaaga atagaagcta aggtttagat aaatattgag cagatctata ggaagattga    2040
acctgaatat tgccattatg cttgacatgg tttccaaaaa atggtactcc acatacttca    2100
gtgagggtaa gtattttcct gttgtcaaga atagcattgt aaaagcattt tgtaataata    2160
aagaatagct ttaatgatat gcttgtaact aaaataattt tgtaatgtat caaatacatt    2220
taaaacatta aaatataatc tctataataa aaaaaaaaaa aaa                       2263
```

<210> SEQ ID NO 23
<211> LENGTH: 2220
<212> TYPE: DNA
<213> ORGANISM: Homo sapiens

<400> SEQUENCE: 23

| | | | | | |
|---|---|---|---|---|---|
| gaacttctttt | cctggcacag | gactcactgt | gcccctccc | gctgtgggta | caaggtctgc | 60 |
| cccccacccc | agctctccaa | agcccaccgg | cctccctgga | ggccgaggtc | gacggcccgt | 120 |
| cgcaccggga | gggggggctc | ccaggggtgc | cccacgcacg | gtcaaggtcc | cgcgccaagc | 180 |
| ggggaccggg | ctggccgga | agcgggcacg | gtactcgcgg | caaactagcg | tgggcgagtc | 240 |
| ctgattgcag | tcggacctgc | cgccgcggca | cttaacagtt | tgcagagtgc | ttcccgcccc | 300 |
| tgatctcatt | ggagccttcg | gacagcccag | cccatggcca | ccgatgcccc | catttcacgc | 360 |
| ctgaggaagc | ggaggctcag | acgggccacc | agccctccg | gaggctggcc | cgggagcgcc | 420 |
| tggcagcgtc | gggtctagga | gccggctccc | tcctgctccc | tcctccgcgc | cgcccggggt | 480 |
| gtgcccgccg | tctgtgtgca | ccactgctga | gccagctcc | ggcgcccctcg | cctctgctgt | 540 |
| gggccccggg | gacgcggggt | caggccaccg | cgttggccag | gccgctgcag | gtaggcacgg | 600 |
| cccccaccag | cgccatggaa | ctggaagaca | ctccaggccc | tactgagcgg | tgtgaacaag | 660 |
| tactccacag | cgttcgggcg | catctggctg | tccgtggtgt | tcgtcttccg | ggtgctggta | 720 |
| tacgtggtgg | ctgcagagcg | cgtgtggggg | gatgagcaga | aggactttga | ctgcaacacc | 780 |
| aagcagcccg | gctgcaccaa | cgtctgctac | gacaactact | tcccccatctc | caacatccgc | 840 |
| ctctgggccc | tgcagctcat | cttcgtcaca | tgcccctcgc | tgctggtcat | cctgcacgtg | 900 |
| gcctaccgtg | aggagcggga | gcgccggcac | cgccagaaac | acgggaccca | gtgcgccaag | 960 |
| ctgtacgaca | cgcaggcaa | gaagcacgga | ggcctgtggt | ggacctacct | gttcagcctc | 1020 |
| atcttcaagc | tcatcattga | gttcctcttc | ctctacctgc | tgcacactct | ctggcatggc | 1080 |
| ttcaatatgc | cgcgcctggt | gcagtgtgcc | aacgtggccc | cctgccccaa | catcgtggac | 1140 |
| tgctacattg | cccgacctac | cgagaagaaa | atcttcacct | acttcatggt | gggcgcctcc | 1200 |
| gccgtctgca | tcgtactcac | catctgtgag | ctctgctacc | tcatctgcca | cagggtcctg | 1260 |
| cgaggcctgc | acaaggacaa | gcctcgaggg | ggttgcagcc | cctcgtcctc | cgccagccga | 1320 |
| gcttccacct | gccgctgcca | ccacaagctg | gtggaggctg | ggaggtgga | tccagaccca | 1380 |
| ggcaataaca | agctgcaggc | ttcagcaccc | aacctgaccc | ccatctgacc | acagggcagg | 1440 |
| ggtggggcaa | catgcgggct | gccaatggga | catgcagggc | ggtgtggcag | gtggagaggt | 1500 |
| cctacagggg | ctgagtgacc | ccactctgag | ttcactaagt | tatgcaactt | tcgttttggc | 1560 |
| agatatttttt | tgacactggg | aactgggctg | tctagccggg | tataggtaac | ccacaggccc | 1620 |
| agtgccagcc | ctcaaaggac | atagactttg | aaacaagcga | attaactatc | tacgctgcct | 1680 |
| gcaaggggcc | acttagggca | ctgctagcag | ggcttcaacc | aggaagggat | caacccagga | 1740 |
| agggatgatc | aggagaggct | tccctgagga | cataatgtgt | aagagaggtg | agaagtgctc | 1800 |
| ccaagcagac | acaacagcag | cacagaggtc | tggaggccac | acaaaaagtg | atgctcgccc | 1860 |
| tgggctagcc | tcagcagacc | taaggcatct | ctactccctc | cagaggagcc | gcccagattc | 1920 |
| ctgcagtgga | gaggaggtct | tccagcagca | gcaggtctgg | agggctgaga | atgaacctga | 1980 |
| ctagaggttc | tggagatacc | cagaggtccc | ccaggtcatc | acttggctca | gtggaagccc | 2040 |
| tctttcccca | aatcctactc | cctcagcctc | aggcagtggt | gctcccatct | tcctcccac | 2100 |
| aactgtgctc | aggctggtgc | cagccttttca | gaccctgctc | ccagggactt | gggtggatgc | 2160 | gctgatagaa catcctcaag acagtttcct tgaaatcaat aaatactgtg ttttataaaa    2220

<210> SEQ ID NO 24
<211> LENGTH: 1243
<212> TYPE: DNA
<213> ORGANISM: Homo sapiens

<400> SEQUENCE: 24
caaggctccc aaggcctgag tgggcaggta gcacccaggt atagaccttc cacgtgcagc      60
acccaggaca cagccagcat gaactgggca tttctgcagg gcctgctgag tggcgtgaac     120
aagtactcca cagtgctgag ccgcatctgg ctgtctgtgg tgttcatctt tcgtgtgctg     180
gtgtacgtgg tggcagcgga ggaggtgtgg gacgatgagc agaaggactt tgtctgcaac     240
accaagcagc ccggctgccc caacgtctgc tatgacgagt tcttcccgcgt gtcccacgtg    300
cgcctctggg ccctacagct catcctggtc acgtgcccct cactgctcgt ggtcatgcac     360
gtggcctacc gcgaggaacg cgagcgcaag caccacctga acacgggcc caatgccccg      420
tccctgtacg acaacctgag caagaagcgg ggcggactgt ggtggacgta cttgctgagc     480
ctcatcttca aggccgccgt ggatgctggc ttcctctata tcttccaccg cctctacaag     540
gattatgaca tgccccgcgt ggtggcctgc tccgtggagc cttgccccca cactgtggac     600
tgttacatct cccggcccac ggagaagaag gtcttcacct acttcatggt gaccacagct     660
gccatctgca tcctgctcaa cctcagtgaa gtcttctacc tggtgggcaa gaggtgcatg     720
gagatcttcg gccccaggca ccggcggcct cggtgccggg aatgcctacc cgatacgtgc     780
ccaccatatg tcctctccca gggagggcac cctgaggatg ggaactctgt cctaatgaag     840
gctgggtcgg ccccagtgga tgcaggtggg tatccataac ctgcgagatc agcagataag     900
atcaacaggt cccccccaca tgaggccacc caggaaaaaa ggcaggggca gtggcatcct     960
tgccgtagca gggtggtgag gagggtggct gtggggctc aggaagctcg cccaggggcc    1020
aatgtgggag gttgggggta gtttggtccc tgggtcctga gcctcagggg agggaggttg    1080
atagctactg gggattttgt atatggcaac agtatatgtc aaacctctta ttaaatatga    1140
ttttcccagt aaaaaaaaaa aaaaaaaaaa aaaaaaaaaa aaaaaaaaaa aaaaaaaaaa    1200
aaaaaaaaaa aaaaaaaaaa aaaaaaaaaa aaaaaaaaa aaa                       1243

<210> SEQ ID NO 25
<211> LENGTH: 1299
<212> TYPE: DNA
<213> ORGANISM: Homo sapiens

<400> SEQUENCE: 25
atgaaattca agctgcttgc tgagtcctat tgccggctgc tgggagccag gagagccctg      60
aggagtagtc actcagtagc agctgacgcg tgggtccacc atgaactgga gtatctttga     120
gggactcctg agtggggtca acaagtactc cacagccttt gggcgcatct ggctgtctct     180
ggtcttcatc ttccgcgtgc tggtgtacct ggtgacggcc gagcgtgtgt ggagtgatga     240
ccacaaggac ttcgactgca atactcgcca gcccggctgc tccaacgtct gctttgatga     300
gttcttccct gtgtcccatg tgcgcctctg gccctgcag cttatcctgg tgacatgccc     360
ctcactgctc gtggtcatgc acgtggccta ccgggaggtt caggagaaga ggcaccgaga     420
agcccatggg gagaacagtg ggcctctca cctgaacccc ggcaagaagc ggggtgggct     480
ctggtggaca tatgtctgca gcctagtgtt caaggcgagc gtggacatcg cctttctcta     540
tgtgttccac tcattctacc ccaaatatat cctcccctcct gtggtcaagt gccacgcaga     600

```
tccatgtccc aatatagtgg actgcttcat ctccaagccc tcagagaaga acatttcac      660 cctcttcatg gtggccacag ctgccatctg catcctgctc aacctcgtgg agctcatcta    720
cctggtgagc aagagatgcc acgagtgcct ggcagcaagg aaagctcaag ccatgtgcac    780
aggtcatcac ccccacggta ccacctcttc ctgcaaacaa gacgacctcc tttcgggtga    840
cctcatcttt ctgggctcag acagtcatcc tcctctctta ccagaccgcc cccgagacca    900
tgtgaagaaa accatcttgt gaggggctgc tggactggt ctgcaggtt gggcctggat      960 ggggaggctc tagcatctct cataggtgca acctgagagt ggggagcta agccatgagg    1020 taggggcagg caagagagag gattcagacg ctctgggagc cagttcctag tcctcaactc   1080
cagccacctg ccccagctcg acggcactgg gccagttccc cctctgctct gcagctcggt   1140
ttccttttct agaatggaaa tagtgagggc caatgcccag ggttggaggg aggagggcgt   1200
tcatagaaga acacacatgc gggcaccttc atcgtgtgtg gcccactgtc agaacttaat   1260
aaaagtcaac tcatttgctg gaaaaaaaaa aaaaaaaaa                           1299

<210> SEQ ID NO 26
<211> LENGTH: 1805
<212> TYPE: DNA
<213> ORGANISM: Homo sapiens

<400> SEQUENCE: 26
ctgggaagac gctggtcagt tcacctgccc cactggttgt ttttaaaca aattctgata     60 caggcgacat cctcactgac cgagcaaaga ttgacattcg tatcatcact gtgcaccatt   120
ggcttctagg cactccagtg gggtaggaga aggaggtctg aaaccctcgc agagggatct   180
tgccctcatt ctttgggtct gaaacactgg cagtcgttgg aaacaggact cagggataaa   240
ccagcgcaat ggattggggg acgctgcaca cttttcatcgg gggtgtcaac aaacactcca   300
ccagcatcgg gaaggtgtgg atcacagtca tctttatttt ccgagtcatg atcctcgtgg   360
tggctgccca ggaagtgtgg ggtgacgagc aagaggactt cgtctgcaac acactgcaac   420
cgggatgcaa aaatgtgtgc tatgaccact tttcccggt gtcccacatc cggctgtggg    480
ccctccagct gatcttcgtc tccacccag cgctgctgg ggccatgcat gtggcctact    540
acaggcacga aaccactcgc aagttcaggc gaggagagaa gaggaatgat ttcaaagaca   600
tagaggacat taaaaagcag aaggttcgga tagaggggtc gctgtggtgg acgtacacca   660
gcagcatctt tttccgaatc atctttgaag cagcctttat gtatgtgttt tacttccttt   720
acaatgggta ccacctgccc tgggtgttga atgtgggat tgaccctgc cccaaccttg     780 ttgactgctt tatttctagg ccaacagaga agaccgtgtt taccatttt atgatttctg    840 cgtctgtgat ttgcatgctg cttaacgtgg cagagttgtg ctacctgctg ctgaaagtgt   900 gtttttaggag atcaaagaga gcacagacgc aaaaaaatca ccccaatcat gccctaaagg  960
agagtaagca gaatgaaatg aatgagctga tttcagatag tggtcaaaat gcaatcacag  1020
gtttcccaag ctaaacattt caaggtaaaa tgtagctgcg tcataaggag acttctgtct   1080
tctccagaag gcaataccaa cctgaaagtt ccttctgtag cctgaagagt ttgtaaatga   1140 cttcataat aaatagacac ttgagttaac tttttgtagg atacttgctc cattcataca    1200
caacgtaatc aaatatgtgg tccatctctg aaaacaagag actgcttgac aaaggagcat   1260
tgcagtcact ttgacaggtt ccttttaagt ggactctctg acaaagtggg tactttctga   1320
aaatttatat aactgttgtt gataaggaac atttatccag gaattgatac ttttattagg   1380
```

| | |
|---|---|
| aaaagatatt tttataggct tggatgtttt tagttctgac tttgaattta tataaagtat | 1440 |
| ttttataatg actggtcttc cttacctgga aaaacatgcg atgttagttt tagaattaca | 1500 |
| ccacaagtat ctaaatttgg aacttacaaa gggtctatct tgtaaatatt gttttgcatt | 1560 |
| gtctgttggc aaatttgtga actgtcatga tacgcttaag gtggaaagtg ttcattgcac | 1620 |
| aatatatttt tactgctttc tgaatgtaga cggaacagtg tggaagcaga aggctttttt | 1680 |
| aactcatccg tttgccaatc attgcaaaca actgaaatgt ggatgtgatt gcctcaataa | 1740 |
| agctcgtccc cattgcttaa gccttcaaaa aaaaaaaaa aaaaaaaaa aaaaaaaaa | 1800 |
| aaaaa | 1805 |

<210> SEQ ID NO 27
<211> LENGTH: 2094
<212> TYPE: DNA
<213> ORGANISM: Homo sapiens

<400> SEQUENCE: 27

| | |
|---|---|
| aaatgaaaga gggagcagga ggcgccggtc ccagccacct cccaaggtcc ctggctcagc | 60 |
| tctgacaccc cagtcccggc cccagggtga gtggggttgg gtggcggttt aggggcacca | 120 |
| ggggcgtgtg gggacctgtg taagtgtggg gtggggagga tctcaggaga tgtggaggct | 180 |
| ggaggcacag gaggccaggg aggagggaga agcctggtgc cgcactccca ccacgctggg | 240 |
| gtaggagggc agggacacct ccgacaaagg accctgtgag agttatgaaa gcggagttgc | 300 |
| ctctgtacca gccccccacc ctgagaggag ttcactgcag taaaaatggt gagagaaatg | 360 |
| gtgggccaag aaaggagtgg tctcgctgcc tctgccactc ccactcctcc catgggcacc | 420 |
| aaattgggtc tagcgtctcg ggttcgaggc tccactcttc ccacagcatc cttgacagct | 480 |
| aagggcaccg ctgggtttcc gcttccgaaa ccagcaagt caggggctgg tccagctgat | 540 |
| ctccaaggtc cttcctaaga atctgggatc tggaggatcc cagggtcgaa cggagacggc | 600 |
| tcagggggtg cggctaaaat gcaaatgggg gatcctcccc agcacccatc ggtcccaaag | 660 |
| agaaggtaac ccatagctga gcgtcgcctg ctcccctcgg gccctcccgt ggccctccgt | 720 |
| ttcatactgg tctcatcgct aaacccgggc ctctcctacc tcacgactca ccctgaagtc | 780 |
| agagaaggtc caacggaccc caccccgata ggcttggaag gggcaggggt ccctgacttg | 840 |
| ccccatcccc tgactccccg ccccgcgtcc ccagcgccat gggggagtgg gcgttcctgg | 900 |
| gctcgctgct ggacgccgtg cagctgcagt cgccgctcgt gggccgcctc tggctggtgg | 960 |
| tcatgctgat cttccgcatc ctggtgctgg ccacggtggg cggcgccgtg ttcgaggacg | 1020 |
| agcaagagga gttcgtgtgc aacacgctgc agccgggctg tcgccagacc tgctacgacc | 1080 |
| gcgccttccc ggtctcccac taccgcttct ggctcttcca catcctgctg ctctcggcgc | 1140 |
| ccccggtgct gttcgtcgtc tactccatgc accgggcagg caaggaggcg ggcggcgctg | 1200 |
| aggcggcggc gcagtgcgcc cccggactgc ccgaggccca gtgcgcgccg tgcgccctgc | 1260 |
| gcgcccgccg cgcgcgccgc tgctacctgc tgagcgtggc gctgcgcctg ctggccgagc | 1320 |
| tgaccttcct gggcggccag gcgctgctct acggcttccg cgtggccccg cacttcgcgt | 1380 |
| gcgccggtcc gccctgcccg cacacggtcg actgcttcgt gagccggccc accgagaaga | 1440 |
| ccgtcttcgt gctcttctat ttcgcggtgg ggctgctgtc ggcgctgctc agcgtagccg | 1500 |
| agctgggcca cctgctctgg aagggccgcc cgcgcgccgg ggagcgtgac aaccgctgca | 1560 |
| accgtgcaca cgaagaggcg cagaagctgc tcccgccgcc gccgccgcca cctattgttg | 1620 |
| tcacttggga agaaaacaga caccttcaag gagagggctc ccctggtagc cccacccca | 1680 |

```
agacagagct ggatgcccct cgcttccgta gggaaagcac ttctcctgca ggatggcatt   1740
gctctctccc cttccatggc acgtagtatg tgctcagtaa atatgtgttg gatgagaaac   1800
tgaaggtgtc cccaggccta caccactgcc atgcccgaac actatccatg ctatggtggg   1860
caccatctct ctgatgacag ttctgtgtcc acaacccaga cccctccaca caaacccaga   1920
tggggctgtg ccgctgtttt ccagatgtat tcattcaaca atatttgta gggtacctac    1980 tgtgtgtcag aagatgttca agatcagcat catccgatgg aaatagcata tgagccatgt   2040
atgtagtttc aagttttttca ttagccgcat taaaaaagta aaggaaaca aatg          2094
```

<210> SEQ ID NO 28
<211> LENGTH: 840
<212> TYPE: DNA
<213> ORGANISM: Homo sapiens

<400> SEQUENCE: 28

```
atgtgtggca ggttcctgcg gcggctgctg gcggaggaga gccggcgctc caccccgtg     60 gggcgcctct tgcttcccgt gctcctggga ttccgccttg tgctgctggc tgccagtggg   120
cctggagtct atggtgatga gcagagtgaa ttcgtgtgtc acacccagca gccgggctgc   180
aaggctgcct gcttcgatgc cttccacccc ctctccccgc tgcgtttctg ggtcttccag   240
gtcatcttgg tggctgtacc cagcgccctc tatatgggtt tcactctgta tcacgtgatc   300
tggcactggg aattatcagg aaaggggaag gaggaggaga ccctgatcca gggacgggag   360
ggcaacacag atgtcccagg ggctggaagc ctcaggctgc tctgggctta tgtggctcag   420
ctgggggctc ggcttgtcct ggagggggca gccctggggt tgcagtacca cctgtatggg   480
ttccagatgc ccagctcctt tgcatgtcgc cgagaacctt gccttggtag tataacctgc   540
aatctgtccc gccccctctga aagaccatt ttcctaaaga ccatgtttgg agtcagcggt   600
ttctgtctct tgtttacttt tttggagctt gtgcttctgg gtttggggag atggtggagg   660
acctggaagc acaaatcttc ctcttctaaa tacttcctaa cttcagagag caccagaaga   720
cacaagaaag caaccgatag cctcccagtg gtggaaacca agagcaatt tcaagaagca    780 gttccaggaa gaagcttagc ccaggaaaaa caaagaccag ttggacccag agatgcctga   840
```

<210> SEQ ID NO 29
<211> LENGTH: 672
<212> TYPE: DNA
<213> ORGANISM: Homo sapiens

<400> SEQUENCE: 29

```
atgagttgga tgttcctcag agatctcctg agtggagtaa ataaatactc cactgggact    60
ggatggattt ggctggctgt cgtgtttgtc ttccgtttgc tggtctacat ggtggcagca   120
gagcacatgt ggaaagatga gcagaaagag tttgagtgca acagtagaca gcccggttgc   180
aaaaatgtgt gttttgatga cttcttcccc atttccaaag tcagactttg gccttacaa    240 ctgataatgg tctccacacc ttcacttctg gtggttttac atgtagccta tcatgagggt   300
agagagaaaa ggcacagaaa gaaactctat gtcagcccag gtacaatgga tgggggccta   360
tggtacgctt atcttatcag cctcattgtt aaaactggtt ttgaaattgg cttccttgtt   420 ttatttata agctatatga tggctttagt gttccctacc ttataaagtg tgatttgaag   480
ccttgtccca acactgtgga ctgcttcatc tccaaaccca ctgagaagac gatcttcatc   540
ctcttcttgg tcatcaccctc atgcttgtgt attgtgttga atttcattga actgagtttt   600
```
ttggttctca agtgctttat taagtgctgt ctccaaaaat atttaaaaaa acctcaagtc    660
ctcagtgtgt ga                                                       672

```
<210> SEQ ID NO 30
<211> LENGTH: 1113
<212> TYPE: DNA
<213> ORGANISM: Homo sapiens

<400> SEQUENCE: 30
```
atggaaggcg tggacttgct agggtttctc atcatcacat taaactgcaa cgtgaccatg     60
gtaggaaagc tctggttcgt cctcacgatg ctgctgcgga tgctggtgat tgtcttggcg    120
gggcgacccg tctaccagga cgagcaggag aggtttgtct gcaacacgct gcagccggga    180
tgcgccaatg tttgctacga cgtcttctcc cccgtgtctc acctgcggtt ctggctgatc    240
cagggcgtgt gcgtcctcct ccctccgcc gtcttcagcg tctatgtcct gcaccgagga    300
gccacgctcg ccgcgctggg ccccgccgc tgccccgacc ccggagcc ggcctccggg       360 cagagacgct gcccgcggcc attcgggag cgcggcggcc tccaggtgcc cgactttcg     420 gccggctaca tcatccacct cctcctccgg accctgctgg aggcagcctt cggggccttg    480
cactactttc tctttggatt cctggccccg aagaagttcc cttgcacgcg ccctccgtgc    540
acgggcgtgg tggactgcta cgtgtcgcgg cccacagaga agtccctgct gatgctgttc    600
ctctgggcgg tcagcgcgct gtcttttctg ctgggcctcg ccgacctggt ctgcagcctg    660
cggcggcgga tgcgcaggag gccgggaccc ccacaagcc cctccatccg gaagcagagc    720
ggagcctcag gccacgcgga gggacgccgg actgacgagg agggtgggcg ggaggaagag    780
ggggcaccgg cgcccccggg tgcacgcgcc ggaggggagg gggctggcag ccccaggcgt    840
acatccaggg tgtcagggca cacgaagatt ccggatgagg atgagagtga ggtgacatcc    900
tccgccagcg aaaagctggg cagacagccc cggggcaggc cccaccgaga ggccgcccag    960
gaccccaggg gctcaggatc cgaggagcag ccctcagcag ccccccagccg cctggccgcg   1020 ccccccttcct gcagcagcct gcagccccct gacccgcctg ccagctccag tggtgctccc   1080
cacctgagag ccaggaagtc tgagtgggtg tga                                1113

```
<210> SEQ ID NO 31
<211> LENGTH: 1632
<212> TYPE: DNA
<213> ORGANISM: Homo sapiens

<400> SEQUENCE: 31
```
atgggggact ggaacttatt gggtggcatc ctagaggaag ttcactccca ctcaaccata     60
gtggggaaaa tctggctgac catcctcttc atcttccgaa tgctggtact tcgtgtggct    120
gctgaggatg tctgggatga tgaacagtca gcatttgcct gcaacacccg gcagccaggt    180
tgcaacaata tctgttatga tgatgcattc cctatctctt tgatcaggtt ctgggttttta    240 cagatcatct ttgtgtcttc tccttctttg gtctatatgg ccatgcact ttataggctc    300 agggccttg agaaagacag gcagaggaaa agtcacacc ttagagccca gatggagaat    360
ccagatcttg acttggagga gcagcaaaga atagataggg aactgaggag gttagaggag    420
cagaagagga tccataaagt ccctctgaaa ggatgtctgc tgcgtactta tgtcttacac    480
atcttgacca gatctgtgct ggaagtagga ttcatgatag ccaatatat tctctatggg    540 tttcaaatgc acccccttta caatgcact caacctcctt gccccaatgc ggtggattgc    600
tttgtatcca ggcccactga gaagacaatt ttcatgcttt ttatgcacag cattgcagcc    660

```
atttccttgt tactcaatat actggaaata tttcatctag gcatcagaaa aattatgagg    720
acactttata agaaatccag cagtgagggc attgaggatg aaacaggccc tccattccat    780
ttgaagaaat attctgtggc ccagcagtgt atgatttgct cttcattgcc tgaaagaatc    840
tctccacttc aagctaacaa tcaacagcaa gtcattcgag ttaatgtgcc aaagtctaaa    900
accatgtggc aaatcccaca gccaaggcaa cttgaagtag acccttccaa tgggaaaaag    960
gactggtctg agaaggatca gcatagcgga cagctccatg ttcacagccc gtgtccctgg   1020
gctggcagtg ctggaaatca gcacctggga cagcaatcag accattcctc atttggcctg   1080
cagaatacaa tgtctcagtc ctggctaggt acaactacgg ctcctagaaa ctgtccatcc   1140
tttgcagtag gaacctggga gcagtcccag gacccagaac cctcaggtga gcctctcaca   1200
gatcttcata gtcactgcag agacagtgaa ggcagcatga gagagagtgg ggtctggata   1260
gacagatctc gcccaggcag tcgcaaggcc agctttctgt ccagattgtt gtctgaaaag   1320
cgacatctgc acagtgactc aggaagctct ggttctcgga atagctcctg cttggatttt   1380
cctcactggg aaaacagccc ctcacctctg ccttcagtca ctgggcacag aacatcaatg   1440
gtaagacagg cagccctacc gatcatgaaa ctatcacaag agctgttcca ttctggatgc   1500 tttcttttc ctttctttct tcctggggtg tgtatgtatg tttgtgttga cagagaggca   1560
gatggagggg gagattattt atggagagat aaaattattc attcgataca ttcagttaaa   1620
ttcaattcat aa                                                       1632
```

<210> SEQ ID NO 32
<211> LENGTH: 11
<212> TYPE: PRT
<213> ORGANISM: Artificial Sequence
<220> FEATURE:
<223> OTHER INFORMATION: Description of Artificial Sequence: connexin/anti-connexin peptide sequence

<400> SEQUENCE: 32

Phe Glu Val Ala Phe Leu Leu Ile Gln Trp Ile
1               5                   10

<210> SEQ ID NO 33
<211> LENGTH: 11
<212> TYPE: PRT
<213> ORGANISM: Artificial Sequence
<220> FEATURE:
<223> OTHER INFORMATION: Description of Artificial Sequence: connexin/anti-connexin peptide sequence

<400> SEQUENCE: 33

Leu Leu Ile Gln Trp Tyr Ile Gly Phe Ser Leu
1               5                   10

<210> SEQ ID NO 34
<211> LENGTH: 16
<212> TYPE: PRT
<213> ORGANISM: Artificial Sequence
<220> FEATURE:
<223> OTHER INFORMATION: Description of Artificial Sequence: connexin/anti-connexin peptide sequence

<400> SEQUENCE: 34

Ser Leu Ser Ala Val Tyr Thr Cys Lys Arg Asp Pro Cys Pro His Gln
1               5                   10                  15

<210> SEQ ID NO 35

```
<211> LENGTH: 12
<212> TYPE: PRT
<213> ORGANISM: Artificial Sequence
<220> FEATURE:
<223> OTHER INFORMATION: Description of Artificial Sequence:
      connexin/anti-connexin peptide sequence

<400> SEQUENCE: 35

Val Asp Cys Phe Leu Ser Arg Pro Thr Glu Lys Thr
1               5                   10

<210> SEQ ID NO 36
<211> LENGTH: 11
<212> TYPE: PRT
<213> ORGANISM: Artificial Sequence
<220> FEATURE:
<223> OTHER INFORMATION: Description of Artificial Sequence:
      connexin/anti-connexin peptide sequence

<400> SEQUENCE: 36

Ser Arg Pro Thr Glu Lys Thr Ile Phe Ile Ile
1               5                   10

<210> SEQ ID NO 37
<211> LENGTH: 13
<212> TYPE: PRT
<213> ORGANISM: Artificial Sequence
<220> FEATURE:
<223> OTHER INFORMATION: Description of Artificial Sequence:
      connexin/anti-connexin peptide sequence

<400> SEQUENCE: 37

Leu Gly Thr Ala Val Glu Ser Ala Trp Gly Asp Glu Gln
1               5                   10

<210> SEQ ID NO 38
<211> LENGTH: 12
<212> TYPE: PRT
<213> ORGANISM: Artificial Sequence
<220> FEATURE:
<223> OTHER INFORMATION: Description of Artificial Sequence:
      connexin/anti-connexin peptide sequence

<400> SEQUENCE: 38

Gln Ser Ala Phe Arg Cys Asn Thr Gln Gln Pro Gly
1               5                   10

<210> SEQ ID NO 39
<211> LENGTH: 12
<212> TYPE: PRT
<213> ORGANISM: Artificial Sequence
<220> FEATURE:
<223> OTHER INFORMATION: Description of Artificial Sequence:
      connexin/anti-connexin peptide sequence

<400> SEQUENCE: 39

Gln Gln Pro Gly Cys Glu  Asn Val Cys Tyr Asp Lys
1               5                   10

<210> SEQ ID NO 40
<211> LENGTH: 13
<212> TYPE: PRT
<213> ORGANISM: Artificial Sequence
<220> FEATURE:
<223> OTHER INFORMATION: Description of Artificial Sequence:
      connexin/anti-connexin peptide sequence

<400> SEQUENCE: 40
```

Val Cys Tyr Asp Lys Ser Phe Pro Ile Ser His Val Arg
1               5                   10

<210> SEQ ID NO 41
<211> LENGTH: 38
<212> TYPE: PRT
<213> ORGANISM: Artificial Sequence
<220> FEATURE:
<223> OTHER INFORMATION: Description of Artificial Sequence:
      connexin/anti-connexin peptide sequence

<400> SEQUENCE: 41

Ala Ala Glu Ser Val Trp Gly Asp Glu Ile Lys Ser Ser Phe Ile Cys
1               5                   10                  15

Asn Thr Leu Gln Pro Gly Cys Asn Ser Val Cys Tyr Asp His Phe Phe
            20                  25                  30

Pro Ile Ser His Val Arg
            35

<210> SEQ ID NO 42
<211> LENGTH: 12
<212> TYPE: PRT
<213> ORGANISM: Artificial Sequence
<220> FEATURE:
<223> OTHER INFORMATION: Description of Artificial Sequence:
      connexin/anti-connexin peptide sequence

<400> SEQUENCE: 42

Glu Ser Val Trp Gly Asp Glu Lys Ser Ser Phe Ile
1               5                   10

<210> SEQ ID NO 43
<211> LENGTH: 12
<212> TYPE: PRT
<213> ORGANISM: Artificial Sequence
<220> FEATURE:
<223> OTHER INFORMATION: Description of Artificial Sequence:
      connexin/anti-connexin peptide sequence

<400> SEQUENCE: 43

Ile Cys Asn Thr Leu Gln Pro Gly Cys Asn Ser Val
1               5                   10

<210> SEQ ID NO 44
<211> LENGTH: 12
<212> TYPE: PRT
<213> ORGANISM: Artificial Sequence
<220> FEATURE:
<223> OTHER INFORMATION: Description of Artificial Sequence:
      connexin/anti-connexin peptide sequence

<400> SEQUENCE: 44

Ser Val Cys Tyr Asp His Phe Phe Pro Ile Ser His
1               5                   10

<210> SEQ ID NO 45
<211> LENGTH: 25
<212> TYPE: PRT
<213> ORGANISM: Artificial Sequence
<220> FEATURE:
<223> OTHER INFORMATION: Description of Artificial Sequence:
      connexin/anti-connexin peptide sequence

<400> SEQUENCE: 45

Arg Leu Val Lys Cys Glu Ala Phe Pro Cys Pro Asn Thr Val Asp Cys
1               5                   10                  15

```
Phe Val Ser Arg Pro Thr Glu Lys Thr
            20                  25

<210> SEQ ID NO 46
<211> LENGTH: 12
<212> TYPE: PRT
<213> ORGANISM: Artificial Sequence
<220> FEATURE:
<223> OTHER INFORMATION: Description of Artificial Sequence:
      connexin/anti-connexin peptide sequence

<400> SEQUENCE: 46

Val Lys Cys Glu Ala Phe Pro Cys Pro Asn Thr Val
1               5                   10

<210> SEQ ID NO 47
<211> LENGTH: 12
<212> TYPE: PRT
<213> ORGANISM: Artificial Sequence
<220> FEATURE:
<223> OTHER INFORMATION: Description of Artificial Sequence:
      connexin/anti-connexin peptide sequence

<400> SEQUENCE: 47

Val Asp Cys Phe Val Ser Arg Pro Thr Glu Lys Thr
1               5                   10

<210> SEQ ID NO 48
<211> LENGTH: 13
<212> TYPE: PRT
<213> ORGANISM: Artificial Sequence
<220> FEATURE:
<223> OTHER INFORMATION: Description of Artificial Sequence:
      connexin/anti-connexin peptide sequence

<400> SEQUENCE: 48

Val Cys Tyr Asp His Phe Phe Pro Ile Ser His Val Arg
1               5                   10

<210> SEQ ID NO 49
<211> LENGTH: 18
<212> TYPE: PRT
<213> ORGANISM: Artificial Sequence
<220> FEATURE:
<223> OTHER INFORMATION: Description of Artificial Sequence:
      connexin/anti-connexin peptide sequence

<400> SEQUENCE: 49

Val Trp Gly Asp Glu Lys Ser Ser Phe Ile Cys Asn Thr Leu Gln Pro Gly Tyr
1               5                   10                  15

<210> SEQ ID NO 50
<211> LENGTH: 15
<212> TYPE: PRT
<213> ORGANISM: Artificial Sequence
<220> FEATURE:
<223> OTHER INFORMATION: Description of Artificial Sequence:
      connexin/anti-connexin peptide sequence

<400> SEQUENCE: 50

Asp Glu Lys Ser Ser Phe Ile Cys Asn Thr Leu Gln Pro Gly Tyr
1               5                   10                  15

<210> SEQ ID NO 51
<211> LENGTH: 11
<212> TYPE: PRT
<213> ORGANISM: Artificial Sequence
<220> FEATURE:
```

<223> OTHER INFORMATION: Description of Artificial Sequence:
      connexin/anti-connexin peptide sequence

<400> SEQUENCE: 51

Ser Arg Pro Thr Glu Lys Thr Val Phe Thr Val
1               5                   10

<210> SEQ ID NO 52
<211> LENGTH: 7
<212> TYPE: PRT
<213> ORGANISM: Artificial Sequence
<220> FEATURE:
<223> OTHER INFORMATION: Description of Artificial Sequence:
      connexin/anti-connexin peptide sequence

<400> SEQUENCE: 52

Ser Arg Pro Thr Glu Lys Thr
1               5

<210> SEQ ID NO 53
<211> LENGTH: 13
<212> TYPE: PRT
<213> ORGANISM: Artificial Sequence
<220> FEATURE:
<223> OTHER INFORMATION: Description of Artificial Sequence:
      connexin/anti-connexin peptide sequence

<400> SEQUENCE: 53

Val Cys Tyr Asp Lys Ser Phe Pro Ile Ser His Val Arg
1               5                   10

<210> SEQ ID NO 54
<211> LENGTH: 11
<212> TYPE: PRT
<213> ORGANISM: Artificial Sequence
<220> FEATURE:
<223> OTHER INFORMATION: Description of Artificial Sequence:
      connexin/anti-connexin peptide sequence

<400> SEQUENCE: 54

Ser Arg Pro Thr Glu Lys Thr Ile Phe Ile Ile
1               5                   10

<210> SEQ ID NO 55
<211> LENGTH: 12
<212> TYPE: PRT
<213> ORGANISM: Artificial Sequence
<220> FEATURE:
<223> OTHER INFORMATION: Description of Artificial Sequence:
      connexin/anti-connexin peptide sequence

<400> SEQUENCE: 55

Ile Cys Asn Thr Leu Gln Pro Gly Cys Asn Ser Val
1               5                   10

<210> SEQ ID NO 56
<211> LENGTH: 16
<212> TYPE: PRT
<213> ORGANISM: Artificial Sequence
<220> FEATURE:
<223> OTHER INFORMATION: Description of Artificial Sequence:
      connexin/anti-connexin peptide sequence

<400> SEQUENCE: 56

Phe Leu Asp Thr Leu His Val Cys Arg Arg Ser Pro Cys Pro His Pro
1               5                   10                  15

```
<210> SEQ ID NO 57
<211> LENGTH: 16
<212> TYPE: PRT
<213> ORGANISM: Artificial Sequence
<220> FEATURE:
<223> OTHER INFORMATION: Description of Artificial Sequence:
      connexin/anti-connexin peptide sequence

<400> SEQUENCE: 57

Ser Leu Ser Ala Val Tyr Thr Cys Lys Arg Asp Pro Cys Pro His Gln
1               5                   10                  15

<210> SEQ ID NO 58
<211> LENGTH: 13
<212> TYPE: PRT
<213> ORGANISM: Artificial Sequence
<220> FEATURE:
<223> OTHER INFORMATION: Description of Artificial Sequence:
      connexin/anti-connexin peptide sequence

<400> SEQUENCE: 58

Val Cys Tyr Asp Lys Ser Phe Pro Ile Ser His Val Arg
1               5                   10

<210> SEQ ID NO 59
<211> LENGTH: 11
<212> TYPE: PRT
<213> ORGANISM: Artificial Sequence
<220> FEATURE:
<223> OTHER INFORMATION: Description of Artificial Sequence:
      connexin/anti-connexin peptide sequence

<400> SEQUENCE: 59

Ser Arg Pro Thr Glu Lys Thr Ile Phe Ile Ile
1               5                   10

<210> SEQ ID NO 60
<211> LENGTH: 18
<212> TYPE: PRT
<213> ORGANISM: Artificial Sequence
<220> FEATURE:
<223> OTHER INFORMATION: Description of Artificial Sequence:
      connexin/anti-connexin peptide sequence

<400> SEQUENCE: 60

Lys Arg Asp Pro Cys His Gln Val Asp Cys Phe Leu Ser Arg Pro Thr Glu Lys
1               5                   10                  15

<210> SEQ ID NO 61
<211> LENGTH: 11
<212> TYPE: PRT
<213> ORGANISM: Artificial Sequence
<220> FEATURE:
<223> OTHER INFORMATION: Description of Artificial Sequence:
      connexin/anti-connexin control peptide sequence

<400> SEQUENCE: 61

Ser Arg Gly Gly Glu Lys Asn Val Phe Ile Val
1               5                   10

<210> SEQ ID NO 62
<211> LENGTH: 396
<212> TYPE: PRT
<213> ORGANISM: Homo sapiens
<220> FEATURE:
<223> OTHER INFORMATION: Connexin 45

<400> SEQUENCE: 62
```

-continued

```
Met Ser Trp Ser Phe Leu Thr Arg Leu Leu Glu Glu Ile His Asn His
1               5                   10                  15

Ser Thr Phe Val Gly Lys Ile Trp Leu Thr Val Leu Ile Val Phe Arg
            20                  25                  30

Ile Val Leu Thr Ala Val Gly Gly Glu Ser Ile Tyr Tyr Asp Glu Gln
            35                  40                  45

Ser Lys Phe Val Cys Asn Thr Glu Gln Pro Gly Cys Glu Asn Val Cys
50                  55                  60

Tyr Asp Ala Phe Ala Pro Leu Ser His Val Arg Phe Trp Val Phe Gln
65                  70                  75                  80

Ile Ile Leu Val Ala Thr Pro Ser Val Met Tyr Leu Gly Tyr Ala Ile
            85                  90                  95

His Lys Ile Ala Lys Met Glu His Gly Glu Ala Asp Lys Lys Ala Ala
            100                 105                 110

Arg Ser Lys Pro Tyr Ala Met Arg Trp Lys Gln His Arg Ala Leu Glu
            115                 120                 125

Glu Thr Glu Glu Asp Asn Glu Glu Asp Pro Met Met Tyr Pro Glu Met
            130                 135                 140

Glu Leu Glu Ser Asp Lys Glu Asn Lys Glu Gln Ser Gln Pro Lys Pro
145                 150                 155                 160

Lys His Asp Gly Arg Arg Arg Ile Arg Glu Asp Gly Leu Met Lys Ile
            165                 170                 175

Tyr Val Leu Gln Leu Leu Ala Arg Thr Val Phe Glu Val Gly Phe Leu
            180                 185                 190

Ile Gly Gln Tyr Phe Leu Tyr Gly Phe Gln Val His Pro Phe Tyr Val
            195                 200                 205

Cys Ser Arg Leu Pro Cys Pro His Lys Ile Asp Cys Phe Ile Ser Arg
210                 215                 220

Pro Thr Glu Lys Thr Ile Phe Leu Leu Ile Met Tyr Gly Val Thr Gly
225                 230                 235                 240

Leu Cys Leu Leu Leu Asn Ile Trp Glu Met Leu His Leu Gly Phe Gly
            245                 250                 255

Thr Ile Arg Asp Ser Leu Asn Ser Lys Arg Arg Glu Leu Glu Asp Pro
            260                 265                 270

Gly Ala Tyr Asn Tyr Pro Phe Thr Trp Asn Thr Pro Ser Ala Pro Pro
            275                 280                 285

Gly Tyr Asn Ile Ala Val Lys Pro Asp Gln Ile Gln Tyr Thr Glu Leu
            290                 295                 300

Ser Asn Ala Lys Ile Ala Tyr Lys Gln Asn Lys Ala Asn Thr Ala Gln
305                 310                 315                 320

Glu Gln Gln Tyr Gly Ser His Glu Glu Asn Leu Pro Ala Asp Leu Glu
            325                 330                 335

Ala Leu Gln Arg Glu Ile Arg Met Ala Gln Glu Arg Leu Asp Leu Ala
            340                 345                 350

Val Gln Ala Tyr Ser His Gln Asn Asn Pro His Gly Pro Arg Glu Lys
            355                 360                 365

Lys Ala Lys Val Gly Ser Lys Ala Gly Ser Asn Lys Ser Thr Ala Ser
            370                 375                 380

Ser Lys Ser Gly Asp Gly Lys Asn Ser Val Trp Ile
385                 390                 395
```

<210> SEQ ID NO 63
<211> LENGTH: 382
<212> TYPE: PRT

```
<213> ORGANISM: Homo sapiens
<220> FEATURE:
<223> OTHER INFORMATION: Connexin 43

<400> SEQUENCE: 63

Met Gly Asp Trp Ser Ala Leu Gly Lys Leu Leu Asp Lys Val Gln Ala
1               5                   10                  15

Tyr Ser Thr Ala Gly Gly Lys Val Trp Leu Ser Val Leu Phe Ile Phe
            20                  25                  30

Arg Ile Leu Leu Leu Gly Thr Ala Val Glu Ser Ala Trp Gly Asp Glu
        35                  40                  45

Gln Ser Ala Phe Arg Cys Asn Thr Gln Gln Pro Gly Cys Glu Asn Val
    50                  55                  60

Cys Tyr Asp Lys Ser Phe Pro Ile Ser His Val Arg Phe Trp Val Leu
65                  70                  75                  80

Gln Ile Ile Phe Val Ser Val Pro Thr Leu Leu Tyr Leu Ala His Val
                85                  90                  95

Phe Tyr Val Met Arg Lys Glu Glu Lys Leu Asn Lys Lys Glu Glu Glu
            100                 105                 110

Leu Lys Val Ala Gln Thr Asp Gly Val Asn Val Asp Met His Leu Lys
        115                 120                 125

Gln Ile Glu Ile Lys Lys Phe Lys Tyr Gly Ile Glu Glu His Gly Lys
    130                 135                 140

Val Lys Met Arg Gly Gly Leu Leu Arg Thr Tyr Ile Ile Ser Ile Leu
145                 150                 155                 160

Phe Lys Ser Ile Phe Glu Val Ala Phe Leu Leu Ile Gln Trp Tyr Ile
                165                 170                 175

Tyr Gly Phe Ser Leu Ser Ala Val Tyr Thr Cys Lys Arg Asp Pro Cys
            180                 185                 190

Pro His Gln Val Asp Cys Phe Leu Ser Arg Pro Thr Glu Lys Thr Ile
        195                 200                 205

Phe Ile Ile Phe Met Leu Val Val Ser Leu Val Ser Leu Ala Leu Asn
    210                 215                 220

Ile Ile Glu Leu Phe Tyr Val Phe Phe Lys Gly Val Lys Asp Arg Val
225                 230                 235                 240

Lys Gly Lys Ser Asp Pro Tyr His Ala Thr Ser Gly Ala Leu Ser Pro
                245                 250                 255

Ala Lys Asp Cys Gly Ser Gln Lys Tyr Ala Tyr Phe Asn Gly Cys Ser
            260                 265                 270

Ser Pro Thr Ala Pro Leu Ser Pro Met Ser Pro Pro Gly Tyr Lys Leu
        275                 280                 285

Val Thr Gly Asp Arg Asn Asn Ser Ser Cys Arg Asn Tyr Asn Lys Gln
    290                 295                 300

Ala Ser Glu Gln Asn Trp Ala Asn Tyr Ser Ala Glu Gln Asn Arg Met
305                 310                 315                 320

Gly Gln Ala Gly Ser Thr Ile Ser Asn Ser His Ala Gln Pro Phe Asp
                325                 330                 335

Phe Pro Asp Asp Asn Gln Asn Ser Lys Lys Leu Ala Ala Gly His Glu
            340                 345                 350

Leu Gln Pro Leu Ala Ile Val Asp Gln Arg Pro Ser Ser Arg Ala Ser
        355                 360                 365

Ser Arg Ala Ser Ser Arg Pro Arg Pro Asp Asp Leu Glu Ile
    370                 375                 380
```

```
<210> SEQ ID NO 64
<211> LENGTH: 226
<212> TYPE: PRT
<213> ORGANISM: Homo sapiens
<220> FEATURE:
<223> OTHER INFORMATION: Connexin 26

<400> SEQUENCE: 64

Met Asp Trp Gly Thr Leu Gln Thr Ile Leu Gly Gly Val Asn Lys His
1               5                   10                  15

Ser Thr Ser Ile Gly Lys Ile Trp Leu Thr Val Leu Phe Ile Phe Arg
            20                  25                  30

Ile Met Ile Leu Val Val Ala Ala Lys Glu Val Trp Gly Asp Glu Gln
        35                  40                  45

Ala Asp Phe Val Cys Asn Thr Leu Gln Pro Gly Cys Lys Asn Val Cys
    50                  55                  60

Tyr Asp His Tyr Phe Pro Ile Ser His Ile Arg Leu Trp Ala Leu Gln
65                  70                  75                  80

Leu Ile Phe Val Ser Thr Pro Ala Leu Leu Val Ala Met His Val Ala
                85                  90                  95

Tyr Arg Arg His Glu Lys Lys Arg Lys Phe Ile Lys Gly Glu Ile Lys
            100                 105                 110

Ser Glu Phe Lys Asp Ile Glu Glu Ile Lys Thr Gln Lys Val Arg Ile
        115                 120                 125

Glu Gly Ser Leu Trp Trp Thr Tyr Thr Ser Ser Ile Phe Phe Arg Val
    130                 135                 140

Ile Phe Glu Ala Ala Phe Met Tyr Val Phe Tyr Val Met Tyr Asp Gly
145                 150                 155                 160

Phe Ser Met Gln Arg Leu Val Lys Cys Asn Ala Trp Pro Cys Pro Asn
                165                 170                 175

Thr Val Asp Cys Phe Val Ser Arg Pro Thr Glu Lys Thr Val Phe Thr
            180                 185                 190

Val Phe Met Ile Ala Val Ser Gly Ile Cys Ile Leu Leu Asn Val Thr
        195                 200                 205

Glu Leu Cys Tyr Leu Leu Ile Arg Tyr Cys Ser Gly Lys Ser Lys Lys
    210                 215                 220

Pro Val
225

<210> SEQ ID NO 65
<211> LENGTH: 266
<212> TYPE: PRT
<213> ORGANISM: Homo sapiens
<220> FEATURE:
<223> OTHER INFORMATION: Connexin 30

<400> SEQUENCE: 65

Met Asn Trp Ala Phe Leu Gln Gly Leu Leu Ser Gly Val Asn Lys Tyr
1               5                   10                  15

Ser Thr Val Leu Ser Arg Ile Trp Leu Ser Val Val Phe Ile Phe Arg
            20                  25                  30

Val Leu Val Tyr Val Val Ala Ala Glu Glu Val Trp Asp Asp Glu Gln
        35                  40                  45

Lys Asp Phe Val Cys Asn Thr Lys Gln Pro Gly Cys Pro Asn Val Cys
    50                  55                  60

Tyr Asp Glu Phe Phe Pro Val Ser His Val Arg Leu Trp Ala Leu Gln
65                  70                  75                  80
```

```
Leu Ile Leu Val Thr Cys Pro Ser Leu Leu Val Met His Val Ala
                85                  90                  95

Tyr Arg Glu Glu Arg Glu Arg Lys His His Leu Lys His Gly Pro Asn
            100                 105                 110

Ala Pro Ser Leu Tyr Asp Asn Leu Ser Lys Lys Arg Gly Gly Leu Trp
            115                 120                 125

Trp Thr Tyr Leu Leu Ser Leu Ile Phe Lys Ala Ala Val Asp Ala Gly
130                 135                 140

Phe Leu Tyr Ile Phe His Arg Leu Tyr Lys Asp Tyr Asp Met Pro Arg
145                 150                 155                 160

Val Val Ala Cys Ser Val Glu Pro Cys Pro His Thr Val Asp Cys Tyr
                165                 170                 175

Ile Ser Arg Pro Thr Glu Lys Lys Val Phe Thr Tyr Phe Met Val Thr
            180                 185                 190

Thr Ala Ala Ile Cys Ile Leu Leu Asn Leu Ser Glu Val Phe Tyr Leu
            195                 200                 205

Val Gly Lys Arg Cys Met Glu Ile Phe Gly Pro Arg His Arg Arg Pro
            210                 215                 220

Arg Cys Arg Glu Cys Leu Pro Asp Thr Cys Pro Pro Tyr Val Leu Ser
225                 230                 235                 240

Gln Gly Gly His Pro Glu Asp Gly Asn Ser Val Leu Met Lys Ala Gly
                245                 250                 255

Ser Ala Pro Val Asp Ala Gly Tyr Pro
            260                 265

<210> SEQ ID NO 66
<211> LENGTH: 273
<212> TYPE: PRT
<213> ORGANISM: Homo sapiens
<220> FEATURE:
<223> OTHER INFORMATION: Connexin 31.1

<400> SEQUENCE: 66

Met Asn Trp Ser Ile Phe Glu Gly Leu Leu Ser Gly Val Asn Lys Tyr
1               5                   10                  15

Ser Thr Ala Phe Gly Arg Ile Trp Leu Ser Leu Val Phe Ile Phe Arg
            20                  25                  30

Val Leu Val Tyr Leu Val Thr Ala Glu Arg Val Trp Ser Asp Asp His
        35                  40                  45

Lys Asp Phe Asp Cys Asn Thr Arg Gln Pro Gly Cys Ser Asn Val Cys
50                  55                  60

Phe Asp Glu Phe Phe Pro Val Ser His Val Arg Leu Trp Ala Leu Gln
65                  70                  75                  80

Leu Ile Leu Val Thr Cys Pro Ser Leu Leu Val Met His Val Ala
                85                  90                  95

Tyr Arg Glu Val Gln Glu Lys Arg His Arg Glu Ala His Gly Glu Asn
            100                 105                 110

Ser Gly Arg Leu Tyr Leu Asn Pro Gly Lys Lys Arg Gly Gly Leu Trp
            115                 120                 125

Trp Thr Tyr Val Cys Ser Leu Val Phe Lys Ala Ser Val Asp Ile Ala
130                 135                 140

Phe Leu Tyr Val Phe His Ser Phe Tyr Pro Lys Tyr Ile Leu Pro Pro
145                 150                 155                 160

Val Val Lys Cys His Ala Asp Pro Cys Pro Asn Ile Val Asp Cys Phe
                165                 170                 175
```

```
Ile Ser Lys Pro Ser Glu Lys Asn Ile Phe Thr Leu Phe Met Val Ala
            180                 185                 190

Thr Ala Ala Ile Cys Ile Leu Leu Asn Leu Val Glu Leu Ile Tyr Leu
        195                 200                 205

Val Ser Lys Arg Cys His Glu Cys Leu Ala Ala Arg Lys Ala Gln Ala
    210                 215                 220

Met Cys Thr Gly His His Pro His Gly Thr Thr Ser Ser Cys Lys Gln
225                 230                 235                 240

Asp Asp Leu Leu Ser Gly Asp Leu Ile Phe Leu Gly Ser Asp Ser His
                245                 250                 255

Pro Pro Leu Leu Pro Asp Arg Pro Arg Asp His Val Lys Lys Thr Ile
            260                 265                 270

Leu
```

<210> SEQ ID NO 67
<211> LENGTH: 333
<212> TYPE: PRT
<213> ORGANISM: Homo sapiens
<220> FEATURE:
<223> OTHER INFORMATION: Connexin 37

<400> SEQUENCE: 67

```
Met Gly Asp Trp Gly Phe Leu Glu Lys Leu Leu Asp Gln Val Gln Glu
1               5                   10                  15

His Ser Thr Val Val Gly Lys Ile Trp Leu Thr Val Leu Phe Ile Phe
            20                  25                  30

Arg Ile Leu Ile Leu Gly Leu Ala Gly Glu Ser Val Trp Gly Asp Glu
        35                  40                  45

Gln Ser Asp Phe Glu Cys Asn Thr Ala Gln Pro Gly Cys Thr Asn Val
    50                  55                  60

Cys Tyr Asp Gln Ala Phe Pro Ile Ser His Ile Arg Tyr Trp Val Leu
65                  70                  75                  80

Gln Phe Leu Phe Val Ser Thr Pro Thr Leu Val Tyr Leu Gly His Val
                85                  90                  95

Ile Tyr Leu Ser Arg Arg Glu Glu Arg Leu Arg Gln Lys Glu Gly Glu
            100                 105                 110

Leu Arg Ala Leu Pro Ala Lys Asp Pro Gln Val Glu Arg Ala Leu Ala
        115                 120                 125

Ala Val Glu Arg Gln Met Ala Lys Ile Ser Val Ala Glu Asp Gly Arg
    130                 135                 140

Leu Arg Ile Arg Gly Ala Leu Met Gly Thr Tyr Val Ala Ser Val Leu
145                 150                 155                 160

Cys Lys Ser Val Leu Glu Ala Gly Phe Leu Tyr Gly Gln Trp Arg Leu
                165                 170                 175

Tyr Gly Trp Thr Met Glu Pro Val Phe Val Cys Gln Arg Ala Pro Cys
            180                 185                 190

Pro Tyr Leu Val Asp Cys Phe Val Ser Arg Pro Thr Glu Lys Thr Ile
        195                 200                 205

Phe Ile Ile Phe Met Leu Val Val Gly Leu Ile Ser Leu Val Leu Asn
    210                 215                 220

Leu Leu Glu Leu Val His Leu Leu Cys Arg Cys Leu Ser Arg Gly Met
225                 230                 235                 240

Arg Ala Arg Gln Gly Gln Asp Ala Pro Pro Thr Gln Gly Thr Ser Ser
                245                 250                 255

Asp Pro Tyr Thr Asp Gln Val Phe Phe Tyr Leu Pro Val Gly Gln Gly
```

```
                    260                 265                 270
Pro Ser Ser Pro Pro Cys Pro Thr Tyr Asn Gly Leu Ser Ser Ser Glu
            275                 280                 285

Gln Asn Trp Ala Asn Leu Thr Thr Glu Glu Arg Leu Ala Ser Ser Arg
        290                 295                 300

Pro Pro Leu Phe Leu Asp Pro Pro Gln Asn Gly Gln Lys Pro Pro
305                 310                 315                 320

Ser Arg Pro Ser Ser Ser Ala Ser Lys Lys Gln Tyr Val
                325                 330

<210> SEQ ID NO 68
<211> LENGTH: 35
<212> TYPE: PRT
<213> ORGANISM: Artificial Sequence
<220> FEATURE:
<223> OTHER INFORMATION: Description of Artificial Sequence: connexin
      extracellular domain

<400> SEQUENCE: 68

Lys Glu Val Trp Gly Asp Glu Gln Ala Asp Phe Val Cys Asn Thr Leu
1               5                   10                  15

Gln Pro Gly Cys Lys Asn Val Cys Tyr Asp His Tyr Phe Pro Ile Ser
            20                  25                  30

His Ile Arg
        35

<210> SEQ ID NO 69
<211> LENGTH: 35
<212> TYPE: PRT
<213> ORGANISM: Artificial Sequence
<220> FEATURE:
<223> OTHER INFORMATION: Description of Artificial Sequence: connexin
      extracellular domain

<400> SEQUENCE: 69

Gln Glu Val Trp Gly Asp Glu Gln Glu Asp Phe Val Cys Asn Thr Leu
1               5                   10                  15

Gln Pro Gly Cys Lys Asn Val Cys Tyr Asp His Phe Phe Pro Val Ser
            20                  25                  30

His Ile Arg
        35

<210> SEQ ID NO 70
<211> LENGTH: 35
<212> TYPE: PRT
<213> ORGANISM: Artificial Sequence
<220> FEATURE:
<223> OTHER INFORMATION: Description of Artificial Sequence: connexin
      extracellular domain

<400> SEQUENCE: 70

Glu Glu Val Trp Asp Asp Glu Gln Lys Asp Phe Val Cys Asn Thr Lys
1               5                   10                  15

Gln Pro Gly Cys Pro Asn Val Cys Tyr Asp Glu Phe Phe Pro Val Ser
            20                  25                  30

His Val Arg
        35

<210> SEQ ID NO 71
<211> LENGTH: 35
<212> TYPE: PRT
<213> ORGANISM: Artificial Sequence
```

```
<220> FEATURE:
<223> OTHER INFORMATION: Description of Artificial Sequence: connexin
      extracellular domain

<400> SEQUENCE: 71

Glu Arg Val Trp Gly Asp Glu Gln Lys Asp Phe Asp Cys Asn Thr Lys
1               5                   10                  15

Gln Pro Gly Cys Thr Asn Val Cys Tyr Asp Asn Tyr Phe Pro Ile Ser
            20                  25                  30

Asn Ile Arg
        35

<210> SEQ ID NO 72
<211> LENGTH: 35
<212> TYPE: PRT
<213> ORGANISM: Artificial Sequence
<220> FEATURE:
<223> OTHER INFORMATION: Description of Artificial Sequence: connexin
      extracellular domain

<400> SEQUENCE: 72

Glu Arg Val Trp Ser Asp Asp His Lys Asp Phe Asp Cys Asn Thr Arg
1               5                   10                  15

Gln Pro Gly Cys Ser Asn Val Cys Phe Asp Glu Phe Phe Pro Val Ser
            20                  25                  30

His Val Arg
        35

<210> SEQ ID NO 73
<211> LENGTH: 35
<212> TYPE: PRT
<213> ORGANISM: Artificial Sequence
<220> FEATURE:
<223> OTHER INFORMATION: Description of Artificial Sequence: connexin
      extracellular domain

<400> SEQUENCE: 73

Glu Ser Val Trp Gly Asp Glu Lys Ser Ser Phe Ile Cys Asn Thr Leu
1               5                   10                  15

Gln Pro Gly Cys Asn Ser Val Cys Tyr Asp Gln Phe Phe Pro Ile Ser
            20                  25                  30

His Val Arg
        35

<210> SEQ ID NO 74
<211> LENGTH: 35
<212> TYPE: PRT
<213> ORGANISM: Artificial Sequence
<220> FEATURE:
<223> OTHER INFORMATION: Description of Artificial Sequence: connexin
      extracellular domain

<400> SEQUENCE: 74

Glu Ser Val Trp Gly Asp Glu Gln Ser Asp Phe Glu Cys Asn Thr Ala
1               5                   10                  15

Gln Pro Gly Cys Thr Asn Val Cys Tyr Asp Gln Ala Phe Pro Ile Ser
            20                  25                  30

His Ile Arg
        35

<210> SEQ ID NO 75
<211> LENGTH: 35
<212> TYPE: PRT
```

```
<213> ORGANISM: Artificial Sequence
<220> FEATURE:
<223> OTHER INFORMATION: Description of Artificial Sequence: connexin
      extracellular domain

<400> SEQUENCE: 75

Glu Ser Val Trp Gly Asp Glu Gln Ser Asp Phe Glu Cys Asn Thr Ala
1               5                   10                  15

Gln Pro Gly Cys Thr Asn Val Cys Tyr Asp Gln Ala Phe Pro Ile Ser
            20                  25                  30

His Ile Arg
        35

<210> SEQ ID NO 76
<211> LENGTH: 35
<212> TYPE: PRT
<213> ORGANISM: Artificial Sequence
<220> FEATURE:
<223> OTHER INFORMATION: Description of Artificial Sequence: connexin
      extracellular domain

<400> SEQUENCE: 76

Arg Pro Val Tyr Gln Asp Glu Gln Arg Phe Val Cys Asn Thr Leu
1               5                   10                  15

Gln Pro Gly Cys Ala Asn Val Cys Tyr Asp Val Phe Ser Pro Val Ser
            20                  25                  30

His Leu Arg
        35

<210> SEQ ID NO 77
<211> LENGTH: 35
<212> TYPE: PRT
<213> ORGANISM: Artificial Sequence
<220> FEATURE:
<223> OTHER INFORMATION: Description of Artificial Sequence: connexin
      extracellular domain

<400> SEQUENCE: 77

Glu Ser Ala Trp Gly Asp Glu Gln Ser Ala Phe Arg Cys Asn Thr Gln
1               5                   10                  15

Gln Pro Gly Cys Glu Asn Val Cys Tyr Asp Lys Ser Phe Pro Ile Ser
            20                  25                  30

His Val Arg
        35

<210> SEQ ID NO 78
<211> LENGTH: 35
<212> TYPE: PRT
<213> ORGANISM: Artificial Sequence
<220> FEATURE:
<223> OTHER INFORMATION: Description of Artificial Sequence: connexin
      extracellular domain

<400> SEQUENCE: 78

Glu Asp Val Trp Gly Asp Glu Gln Ser Asp Phe Thr Cys Asn Thr Gln
1               5                   10                  15

Gln Pro Gly Cys Glu Asn Val Cys Tyr Asp Arg Ala Phe Pro Ile Ser
            20                  25                  30

His Ile Arg
        35

<210> SEQ ID NO 79
<211> LENGTH: 35
```

```
<212> TYPE: PRT
<213> ORGANISM: Artificial Sequence
<220> FEATURE:
<223> OTHER INFORMATION: Description of Artificial Sequence: connexin
      extracellular domain

<400> SEQUENCE: 79

Glu Ala Ile Tyr Ser Asp Glu Gln Ala Lys Phe Thr Cys Asn Thr Arg
1               5                   10                  15

Gln Pro Gly Cys Asp Asn Val Cys Tyr Asp Ala Phe Ala Pro Leu Ser
            20                  25                  30

His Val Arg
        35

<210> SEQ ID NO 80
<211> LENGTH: 35
<212> TYPE: PRT
<213> ORGANISM: Artificial Sequence
<220> FEATURE:
<223> OTHER INFORMATION: Description of Artificial Sequence: connexin
      extracellular domain

<400> SEQUENCE: 80

Glu Ser Ser Trp Gly Asp Glu Gln Ala Asp Phe Arg Cys Asp Thr Ile
1               5                   10                  15

Gln Pro Gly Cys Gln Asn Val Cys Thr Asp Gln Ala Phe Pro Ile Ser
            20                  25                  30

His Ile Arg
        35

<210> SEQ ID NO 81
<211> LENGTH: 36
<212> TYPE: PRT
<213> ORGANISM: Artificial Sequence
<220> FEATURE:
<223> OTHER INFORMATION: Description of Artificial Sequence: connexin
      extracellular domain

<400> SEQUENCE: 81

Gly Glu Ser Ile Tyr Tyr Asp Glu Gln Ser Lys Phe Val Cys Asn Thr
1               5                   10                  15

Glu Gln Pro Gly Cys Glu Asn Val Cys Tyr Asp Ala Phe Ala Pro Leu
            20                  25                  30

Ser His Val Arg
        35

<210> SEQ ID NO 82
<211> LENGTH: 39
<212> TYPE: PRT
<213> ORGANISM: Artificial Sequence
<220> FEATURE:
<223> OTHER INFORMATION: Description of Artificial Sequence: connexin
      extracellular domain

<400> SEQUENCE: 82

Met Tyr Val Phe Tyr Val Met Tyr Asp Gly Phe Ser Met Gln Arg Leu
1               5                   10                  15

Val Lys Cys Asn Ala Trp Pro Cys Pro Asn Thr Val Asp Cys Phe Val
            20                  25                  30

Ser Arg Pro Thr Glu Lys Thr
        35

<210> SEQ ID NO 83
```

```
<211> LENGTH: 39
<212> TYPE: PRT
<213> ORGANISM: Artificial Sequence
<220> FEATURE:
<223> OTHER INFORMATION: Description of Artificial Sequence: connexin
      extracellular domain

<400> SEQUENCE: 83

Met Tyr Val Phe Tyr Phe Leu Tyr Asn Gly Tyr His Leu Pro Trp Val
1               5                   10                  15

Leu Lys Cys Gly Ile Asp Pro Cys Pro Asn Leu Val Asp Cys Phe Ile
            20                  25                  30

Ser Arg Pro Thr Glu Lys Thr
        35

<210> SEQ ID NO 84
<211> LENGTH: 39
<212> TYPE: PRT
<213> ORGANISM: Artificial Sequence
<220> FEATURE:
<223> OTHER INFORMATION: Description of Artificial Sequence: connexin
      extracellular domain

<400> SEQUENCE: 84

Leu Tyr Ile Phe His Arg Leu Tyr Lys Asp Tyr Asp Met Pro Arg Val
1               5                   10                  15

Val Ala Cys Ser Val Glu Pro Cys Pro His Thr Val Asp Cys Tyr Ile
            20                  25                  30

Ser Arg Pro Thr Glu Lys Lys
        35

<210> SEQ ID NO 85
<211> LENGTH: 40
<212> TYPE: PRT
<213> ORGANISM: Artificial Sequence
<220> FEATURE:
<223> OTHER INFORMATION: Description of Artificial Sequence: connexin
      extracellular domain

<400> SEQUENCE: 85

Leu Tyr Leu Leu His Thr Leu Trp His Gly Phe Asn Met Pro Arg Leu
1               5                   10                  15

Val Gln Cys Ala Asn Val Ala Pro Cys Pro Asn Ile Val Asp Cys Tyr
            20                  25                  30

Ile Ala Arg Pro Thr Glu Lys Lys
        35                  40

<210> SEQ ID NO 86
<211> LENGTH: 39
<212> TYPE: PRT
<213> ORGANISM: Artificial Sequence
<220> FEATURE:
<223> OTHER INFORMATION: Description of Artificial Sequence: connexin
      extracellular domain

<400> SEQUENCE: 86

Leu Tyr Val Phe His Ser Phe Tyr Pro Lys Tyr Ile Leu Pro Pro Val
1               5                   10                  15

Val Lys Cys His Ala Asp Pro Cys Pro Asn Ile Val Asp Cys Phe Ile
            20                  25                  30

Ser Lys Pro Ser Glu Lys Asn
        35
```

```
<210> SEQ ID NO 87
<211> LENGTH: 39
<212> TYPE: PRT
<213> ORGANISM: Artificial Sequence
<220> FEATURE:
<223> OTHER INFORMATION: Description of Artificial Sequence: connexin
      extracellular domain

<400> SEQUENCE: 87

Met Tyr Val Phe Tyr Leu Leu Tyr Pro Gly Tyr Ala Met Val Arg Leu
1               5                   10                  15

Val Lys Cys Asp Val Tyr Pro Cys Pro Asn Thr Val Asp Cys Phe Val
                20                  25                  30

Ser Arg Pro Thr Glu Lys Thr
            35

<210> SEQ ID NO 88
<211> LENGTH: 32
<212> TYPE: PRT
<213> ORGANISM: Artificial Sequence
<220> FEATURE:
<223> OTHER INFORMATION: Description of Artificial Sequence: connexin
      extracellular domain

<400> SEQUENCE: 88

Leu Tyr Gly Trp Thr Met Glu Pro Val Phe Val Cys Gln Arg Ala Pro
1               5                   10                  15

Cys Pro Tyr Leu Val Asp Cys Phe Val Ser Arg Pro Thr Glu Lys Thr
                20                  25                  30

<210> SEQ ID NO 89
<211> LENGTH: 32
<212> TYPE: PRT
<213> ORGANISM: Artificial Sequence
<220> FEATURE:
<223> OTHER INFORMATION: Description of Artificial Sequence: connexin
      extracellular domain

<400> SEQUENCE: 89

Leu Tyr Gly Trp Thr Met Glu Pro Val Phe Val Cys Gln Arg Ala Pro
1               5                   10                  15

Cys Pro Tyr Leu Val Asp Cys Phe Val Ser Arg Pro Thr Glu Lys Thr
                20                  25                  30

<210> SEQ ID NO 90
<211> LENGTH: 38
<212> TYPE: PRT
<213> ORGANISM: Artificial Sequence
<220> FEATURE:
<223> OTHER INFORMATION: Description of Artificial Sequence: connexin
      extracellular domain

<400> SEQUENCE: 90

Gly Ala Leu His Tyr Phe Leu Phe Gly Phe Leu Ala Pro Lys Lys Phe
1               5                   10                  15

Pro Cys Thr Arg Pro Pro Cys Thr Gly Val Val Asp Cys Tyr Val Ser
                20                  25                  30

Arg Pro Thr Glu Lys Ser
            35

<210> SEQ ID NO 91
<211> LENGTH: 38
<212> TYPE: PRT
<213> ORGANISM: Artificial Sequence
<220> FEATURE:
```

```
<223> OTHER INFORMATION: Description of Artificial Sequence: connexin
      extracellular domain

<400> SEQUENCE: 91

Leu Leu Ile Gln Trp Tyr Ile Tyr Gly Phe Ser Leu Ser Ala Val Tyr
1               5                   10                  15

Thr Cys Lys Arg Asp Pro Cys Pro His Gln Val Asp Cys Phe Leu Ser
            20                  25                  30

Arg Pro Thr Glu Lys Thr
        35

<210> SEQ ID NO 92
<211> LENGTH: 38
<212> TYPE: PRT
<213> ORGANISM: Artificial Sequence
<220> FEATURE:
<223> OTHER INFORMATION: Description of Artificial Sequence: connexin
      extracellular domain

<400> SEQUENCE: 92

Ile Ala Gly Gln Tyr Phe Leu Tyr Gly Phe Glu Leu Lys Pro Leu Tyr
1               5                   10                  15

Arg Cys Asp Arg Trp Pro Cys Pro Asn Thr Val Asp Cys Phe Ile Ser
            20                  25                  30

Arg Pro Thr Glu Lys Thr
        35

<210> SEQ ID NO 93
<211> LENGTH: 38
<212> TYPE: PRT
<213> ORGANISM: Artificial Sequence
<220> FEATURE:
<223> OTHER INFORMATION: Description of Artificial Sequence: connexin
      extracellular domain

<400> SEQUENCE: 93

Leu Val Gly Gln Tyr Leu Leu Tyr Gly Phe Glu Val Arg Pro Phe Phe
1               5                   10                  15

Pro Cys Ser Arg Gln Pro Cys Pro His Val Val Asp Cys Phe Val Ser
            20                  25                  30

Arg Pro Thr Glu Lys Thr
        35

<210> SEQ ID NO 94
<211> LENGTH: 38
<212> TYPE: PRT
<213> ORGANISM: Artificial Sequence
<220> FEATURE:
<223> OTHER INFORMATION: Connexin extracellular domain

<400> SEQUENCE: 94

Ile Val Gly Gln Tyr Phe Ile Tyr Gly Ile Phe Leu Thr Thr Leu His
1               5                   10                  15

Val Cys Arg Arg Ser Pro Cys Pro His Pro Val Asn Cys Tyr Val Ser
            20                  25                  30

Arg Pro Thr Glu Lys Asn
        35

<210> SEQ ID NO 95
<211> LENGTH: 38
<212> TYPE: PRT
<213> ORGANISM: Artificial Sequence
<220> FEATURE:
```

<223> OTHER INFORMATION: Artificial Sequence: Connexin extracellular
      domain

<400> SEQUENCE: 95

Leu Ile Gly Gln Tyr Phe Leu Tyr Gly Phe Gln Val His Pro Phe Tyr
1               5                   10                  15

Val Cys Ser Arg Leu Pro Cys His Pro Lys Ile Asp Cys Phe Ile Ser
            20                  25                  30

Arg Pro Thr Glu Lys Thr
            35

<210> SEQ ID NO 96
<211> LENGTH: 42
<212> TYPE: PRT
<213> ORGANISM: Artificial Sequence
<220> FEATURE:
<223> OTHER INFORMATION: Artificial Sequence: Connexin extracellular
      domain

<400> SEQUENCE: 96

Leu Leu Ile Gln Trp Tyr Ile Tyr Gly Phe Ser Leu Ser Ala Val Tyr
1               5                   10                  15

Thr Cys Lys Arg Asp Pro Cys Pro His Gln Val Asp Cys Phe Leu Ser
            20                  25                  30

Arg Pro Thr Glu Lys Thr Ile Phe Ile Ile
            35                  40

<210> SEQ ID NO 97
<211> LENGTH: 43
<212> TYPE: PRT
<213> ORGANISM: Artificial Sequence
<220> FEATURE:
<223> OTHER INFORMATION: Artificial Sequence: Connexin extracellular
      domain

<400> SEQUENCE: 97

Met Tyr Val Phe Tyr Val Met Tyr Asp Gly Phe Ser Met Gln Arg Leu
1               5                   10                  15

Val Lys Cys Asn Ala Trp Pro Cys Pro Asn Thr Val Asp Cys Phe Val
            20                  25                  30

Ser Arg Pro Thr Glu Lys Thr Val Phe Thr Val
            35                  40

<210> SEQ ID NO 98
<211> LENGTH: 43
<212> TYPE: PRT
<213> ORGANISM: Artificial Sequence
<220> FEATURE:
<223> OTHER INFORMATION: Artificial Sequence: Connexin extracellular
      domain

<400> SEQUENCE: 98

Met Tyr Val Phe Tyr Phe Leu Tyr Asn Gly Tyr His Leu Pro Trp Val
1               5                   10                  15

Leu Lys Cys Gly Ile Asp Pro Cys Pro Asn Leu Val Asp Cys Phe Ile
            20                  25                  30

Ser Arg Pro Thr Glu Lys Thr Val Phe Thr Ile
            35                  40

<210> SEQ ID NO 99
<211> LENGTH: 43
<212> TYPE: PRT
<213> ORGANISM: Artificial Sequence

```
<220> FEATURE:
<223> OTHER INFORMATION: Artificial Sequence: Connexin extracellular
      domain

<400> SEQUENCE: 99

Leu Tyr Ile Phe His Arg Leu Tyr Lys Asp Tyr Asp Met Pro Arg Val
1               5                   10                  15

Val Ala Cys Ser Val Glu Pro Cys Pro His Thr Val Asp Cys Tyr Ile
            20                  25                  30

Ser Arg Pro Thr Glu Lys Lys Val Phe Thr Tyr
        35                  40

<210> SEQ ID NO 100
<211> LENGTH: 44
<212> TYPE: PRT
<213> ORGANISM: Artificial Sequence
<220> FEATURE:
<223> OTHER INFORMATION: Artificial Sequence: Connexin extracellular
      domain

<400> SEQUENCE: 100

Leu Tyr Leu Leu His Thr Leu Trp His Gly Phe Asn Met Pro Arg Leu
1               5                   10                  15

Val Gln Cys Ala Asn Val Ala Pro Cys Pro Asn Ile Val Asp Cys Tyr
            20                  25                  30

Ile Ala Arg Pro Thr Glu Lys Lys Ile Phe Thr Tyr
        35                  40

<210> SEQ ID NO 101
<211> LENGTH: 43
<212> TYPE: PRT
<213> ORGANISM: Artificial Sequence
<220> FEATURE:
<223> OTHER INFORMATION: Artificial Sequence: Connexin extracellular
      domain

<400> SEQUENCE: 101

Leu Tyr Val Phe His Ser Phe Tyr Pro Lys Tyr Ile Leu Pro Pro Val
1               5                   10                  15

Val Lys Cys His Ala Asp Pro Cys Pro Asn Ile Val Asp Cys Phe Ile
            20                  25                  30

Ser Lys Pro Ser Glu Lys Asn Ile Phe Thr Leu
        35                  40

<210> SEQ ID NO 102
<211> LENGTH: 43
<212> TYPE: PRT
<213> ORGANISM: Artificial Sequence
<220> FEATURE:
<223> OTHER INFORMATION: Artificial Sequence: Connexin extracellular
      domain

<400> SEQUENCE: 102

Met Tyr Val Phe Tyr Leu Leu Tyr Pro Gly Tyr Ala Met Val Arg Leu
1               5                   10                  15

Val Lys Cys Asp Val Tyr Pro Cys Pro Asn Thr Val Asp Cys Phe Val
            20                  25                  30

Ser Arg Pro Thr Glu Lys Thr Val Phe Thr Val
        35                  40

<210> SEQ ID NO 103
<211> LENGTH: 36
<212> TYPE: PRT
```

<213> ORGANISM: Artificial Sequence
<220> FEATURE:
<223> OTHER INFORMATION: Artificial Sequence: Connexin extracellular
      domain

<400> SEQUENCE: 103

Leu Tyr Gly Trp Thr Met Glu Pro Val Phe Val Cys Gln Arg Ala Pro
1               5                   10                  15

Cys Pro Tyr Leu Val Asp Cys Phe Val Ser Arg Pro Thr Glu Lys Thr
            20                  25                  30

Ile Phe Ile Ile
        35

<210> SEQ ID NO 104
<211> LENGTH: 36
<212> TYPE: PRT
<213> ORGANISM: Artificial Sequence
<220> FEATURE:
<223> OTHER INFORMATION: Artificial Sequence: Connexin extracellular
      domain

<400> SEQUENCE: 104

Leu Tyr Gly Trp Thr Met Glu Pro Val Phe Val Cys Gln Arg Ala Pro
1               5                   10                  15

Cys Pro Tyr Leu Val Asp Cys Phe Val Ser Arg Pro Thr Glu Lys Thr
            20                  25                  30

Ile Phe Ile Ile
        35

<210> SEQ ID NO 105
<211> LENGTH: 42
<212> TYPE: PRT
<213> ORGANISM: Artificial Sequence
<220> FEATURE:
<223> OTHER INFORMATION: Artificial Sequence: Connexin extracellular
      domain

<400> SEQUENCE: 105

Gly Ala Leu His Tyr Phe Leu Phe Gly Phe Leu Ala Pro Lys Lys Phe
1               5                   10                  15

Pro Cys Thr Arg Pro Pro Cys Thr Gly Val Val Asp Cys Tyr Val Ser
            20                  25                  30

Arg Pro Thr Glu Lys Ser Leu Leu Met Leu
            35                  40

<210> SEQ ID NO 106
<211> LENGTH: 42
<212> TYPE: PRT
<213> ORGANISM: Artificial Sequence
<220> FEATURE:
<223> OTHER INFORMATION: Artificial Sequence: Connexin extracellular
      domain

<400> SEQUENCE: 106

Ile Ala Gly Gln Tyr Phe Leu Tyr Gly Phe Glu Leu Lys Pro Leu Tyr
1               5                   10                  15

Arg Cys Asp Arg Trp Pro Cys Pro Asn Thr Val Asp Cys Phe Ile Ser
            20                  25                  30

Arg Pro Thr Glu Lys Thr Ile Phe Ile Ile
            35                  40

<210> SEQ ID NO 107
<211> LENGTH: 42

```
<212> TYPE: PRT
<213> ORGANISM: Artificial Sequence
<220> FEATURE:
<223> OTHER INFORMATION: Artificial Sequence: Connexin extracellular
      domain

<400> SEQUENCE: 107

Leu Val Gly Gln Tyr Leu Leu Tyr Gly Phe Glu Val Arg Pro Phe Phe
1               5                   10                  15

Pro Cys Ser Arg Gln Pro Cys Pro His Val Val Asp Cys Phe Val Ser
            20                  25                  30

Arg Pro Thr Glu Lys Thr Val Phe Leu Leu
        35                  40

<210> SEQ ID NO 108
<211> LENGTH: 42
<212> TYPE: PRT
<213> ORGANISM: Artificial Sequence
<220> FEATURE:
<223> OTHER INFORMATION: Artificial Sequence: Connexin extracellular
      domain

<400> SEQUENCE: 108

Ile Val Gly Gln Tyr Phe Ile Tyr Gly Ile Phe Leu Thr Thr Leu His
1               5                   10                  15

Val Cys Arg Arg Ser Pro Cys Pro His Pro Val Asn Cys Tyr Val Ser
            20                  25                  30

Arg Pro Thr Glu Lys Asn Val Phe Ile Val
        35                  40

<210> SEQ ID NO 109
<211> LENGTH: 42
<212> TYPE: PRT
<213> ORGANISM: Artificial Sequence
<220> FEATURE:
<223> OTHER INFORMATION: Artificial Sequence: Connexin extracellular
      domain

<400> SEQUENCE: 109

Leu Ile Gly Gln Tyr Phe Leu Tyr Gly Phe Gln Val His Pro Phe Tyr
1               5                   10                  15

Val Cys Ser Arg Leu Pro Cys His Pro Lys Ile Asp Cys Phe Ile Ser
            20                  25                  30

Arg Pro Thr Glu Lys Thr Ile Phe Leu Leu
        35                  40

<210> SEQ ID NO 110
<211> LENGTH: 45
<212> TYPE: PRT
<213> ORGANISM: Artificial Sequence
<220> FEATURE:
<223> OTHER INFORMATION: Artificial Sequence: Connexin domain

<400> SEQUENCE: 110

Leu Gly Thr Ala Ala Glu Ser Ser Trp Gly Asp Glu Gln Ala Asp Phe
1               5                   10                  15

Arg Cys Asp Thr Ile Gln Pro Gly Cys Gln Asn Val Cys Thr Asp Gln
            20                  25                  30

Ala Phe Pro Ile Ser His Ile Arg Phe Trp Val Leu Gln
        35                  40                  45

<210> SEQ ID NO 111
<211> LENGTH: 14
```

<212> TYPE: PRT
<213> ORGANISM: Artificial Sequence
<220> FEATURE:
<223> OTHER INFORMATION: Artificial Sequence: Connexin domain

<400> SEQUENCE: 111

Leu Gly Thr Ala Ala Glu Ser Ser Trp Gly Asp Glu Gln Ala
1               5                   10

<210> SEQ ID NO 112
<211> LENGTH: 13
<212> TYPE: PRT
<213> ORGANISM: Artificial Sequence
<220> FEATURE:
<223> OTHER INFORMATION: Artificial Sequence: Connexin domain

<400> SEQUENCE: 112

Asp Glu Gln Ala Asp Phe Arg Cys Asp Thr Ile Gln Pro
1               5                   10

<210> SEQ ID NO 113
<211> LENGTH: 13
<212> TYPE: PRT
<213> ORGANISM: Artificial Sequence
<220> FEATURE:
<223> OTHER INFORMATION: Artificial Sequence: Connexin domain

<400> SEQUENCE: 113

Thr Ile Gln Pro Gly Cys Gln Asn Val Cys Thr Asp Gln
1               5                   10

<210> SEQ ID NO 114
<211> LENGTH: 13
<212> TYPE: PRT
<213> ORGANISM: Artificial Sequence
<220> FEATURE:
<223> OTHER INFORMATION: Artificial Sequence: Connexin domain

<400> SEQUENCE: 114

Val Cys Thr Asp Gln Ala Phe Pro Ile Ser His Ile Arg
1               5                   10

<210> SEQ ID NO 115
<211> LENGTH: 13
<212> TYPE: PRT
<213> ORGANISM: Artificial Sequence
<220> FEATURE:
<223> OTHER INFORMATION: Artificial Sequence: Connexin domain

<400> SEQUENCE: 115

Ala Phe Pro Ile Ser His Ile Arg Phe Trp Val Leu Gln
1               5                   10

<210> SEQ ID NO 116
<211> LENGTH: 47
<212> TYPE: PRT
<213> ORGANISM: Artificial Sequence
<220> FEATURE:
<223> OTHER INFORMATION: Artificial Sequence: Connexin domain

<400> SEQUENCE: 116

Met Glu Val Gly Phe Ile Val Gly Gln Tyr Phe Ile Tyr Gly Ile Phe
1               5                   10                  15

Leu Thr Thr Leu His Val Cys Arg Arg Ser Pro Cys Pro His Pro Val
            20                  25                  30

Asn Cys Tyr Val Ser Arg Pro Thr Glu Lys Asn Val Phe Ile Val

<210> SEQ ID NO 117
<211> LENGTH: 11
<212> TYPE: PRT
<213> ORGANISM: Artificial Sequence
<220> FEATURE:
<223> OTHER INFORMATION: Artificial Sequence: Connexin domain

<400> SEQUENCE: 117

Met Glu Val Gly Phe Ile Val Gly Gln Tyr Phe
1               5                   10

<210> SEQ ID NO 118
<211> LENGTH: 12
<212> TYPE: PRT
<213> ORGANISM: Artificial Sequence
<220> FEATURE:
<223> OTHER INFORMATION: Artificial Sequence: Connexin domain

<400> SEQUENCE: 118

Ile Val Gly Gln Tyr Phe Ile Tyr Gly Ile Phe Leu
1               5                   10

<210> SEQ ID NO 119
<211> LENGTH: 14
<212> TYPE: PRT
<213> ORGANISM: Artificial Sequence
<220> FEATURE:
<223> OTHER INFORMATION: Artificial Sequence: Connexin domain

<400> SEQUENCE: 119

Gly Ile Phe Leu Thr Thr Leu His Val Cys Arg Arg Ser Pro
1               5                   10

<210> SEQ ID NO 120
<211> LENGTH: 12
<212> TYPE: PRT
<213> ORGANISM: Artificial Sequence
<220> FEATURE:
<223> OTHER INFORMATION: Artificial Sequence: Connexin domain

<400> SEQUENCE: 120

Arg Arg Ser Pro Cys Pro His Pro Val Asn Cys Tyr
1               5                   10

<210> SEQ ID NO 121
<211> LENGTH: 46
<212> TYPE: PRT
<213> ORGANISM: Artificial Sequence
<220> FEATURE:
<223> OTHER INFORMATION: Artificial Sequence: Connexin domain

<400> SEQUENCE: 121

Leu Thr Ala Val Gly Gly Glu Ser Ile Tyr Tyr Asp Glu Gln Ser Lys
1               5                   10                  15

Phe Val Cys Asn Thr Glu Gln Pro Gly Cys Glu Asn Val Cys Tyr Asp
            20                  25                  30

Ala Phe Ala Pro Leu Ser His Val Arg Phe Trp Val Phe Gln
        35                  40                  45

<210> SEQ ID NO 122
<211> LENGTH: 15
<212> TYPE: PRT
<213> ORGANISM: Artificial Sequence
<220> FEATURE:

```
<223> OTHER INFORMATION: Artificial Sequence: Connexin domain

<400> SEQUENCE: 122

Leu Thr Ala Val Gly Gly Glu Ser Ile Tyr Tyr Asp Glu Gln Ser
1               5                   10                  15

<210> SEQ ID NO 123
<211> LENGTH: 13
<212> TYPE: PRT
<213> ORGANISM: Artificial Sequence
<220> FEATURE:
<223> OTHER INFORMATION: Artificial Sequence: Connexin domain

<400> SEQUENCE: 123

Asp Glu Gln Ser Lys Phe Val Cys Asn Thr Glu Gln Pro
1               5                   10

<210> SEQ ID NO 124
<211> LENGTH: 13
<212> TYPE: PRT
<213> ORGANISM: Artificial Sequence
<220> FEATURE:
<223> OTHER INFORMATION: Artificial Sequence: Connexin domain

<400> SEQUENCE: 124

Thr Glu Gln Pro Gly Cys Glu Asn Val Cys Tyr Asp Ala
1               5                   10

<210> SEQ ID NO 125
<211> LENGTH: 13
<212> TYPE: PRT
<213> ORGANISM: Artificial Sequence
<220> FEATURE:
<223> OTHER INFORMATION: Artificial Sequence: Connexin domain

<400> SEQUENCE: 125

Val Cys Tyr Asp Ala Phe Ala Pro Leu Ser His Val Arg
1               5                   10

<210> SEQ ID NO 126
<211> LENGTH: 12
<212> TYPE: PRT
<213> ORGANISM: Artificial Sequence
<220> FEATURE:
<223> OTHER INFORMATION: Artificial Sequence: Connexin domain

<400> SEQUENCE: 126

Ala Pro Leu Ser His Val Arg Phe Trp Val Phe Gln
1               5                   10

<210> SEQ ID NO 127
<211> LENGTH: 47
<212> TYPE: PRT
<213> ORGANISM: Artificial Sequence
<220> FEATURE:
<223> OTHER INFORMATION: Artificial Sequence: Connexin domain

<400> SEQUENCE: 127

Phe Glu Val Gly Phe Leu Ile Gly Gln Tyr Phe Leu Tyr Gly Phe Gln
1               5                   10                  15

Val His Pro Phe Tyr Val Cys Ser Arg Leu Pro Cys His Pro Lys Ile
                20                  25                  30

Asp Cys Phe Ile Ser Arg Pro Thr Glu Lys Thr Ile Phe Leu Leu
            35                  40                  45
```

```
<210> SEQ ID NO 128
<211> LENGTH: 11
<212> TYPE: PRT
<213> ORGANISM: Artificial Sequence
<220> FEATURE:
<223> OTHER INFORMATION: Artificial Sequence: Connexin domain

<400> SEQUENCE: 128

Phe Glu Val Gly Phe Leu Ile Gly Gln Tyr Phe
1               5                   10

<210> SEQ ID NO 129
<211> LENGTH: 12
<212> TYPE: PRT
<213> ORGANISM: Artificial Sequence
<220> FEATURE:
<223> OTHER INFORMATION: Artificial Sequence: Connexin domain

<400> SEQUENCE: 129

Leu Ile Gly Gln Tyr Phe Leu Tyr Gly Phe Gln Val
1               5                   10

<210> SEQ ID NO 130
<211> LENGTH: 14
<212> TYPE: PRT
<213> ORGANISM: Artificial Sequence
<220> FEATURE:
<223> OTHER INFORMATION: Artificial Sequence: Connexin domain

<400> SEQUENCE: 130

Gly Phe Gln Val His Pro Phe Tyr Val Cys Ser Arg Leu Pro
1               5                   10

<210> SEQ ID NO 131
<211> LENGTH: 12
<212> TYPE: PRT
<213> ORGANISM: Artificial Sequence
<220> FEATURE:
<223> OTHER INFORMATION: Artificial Sequence: Connexin domain

<400> SEQUENCE: 131

Ser Arg Leu Pro Cys His Pro Lys Ile Asp Cys Phe
1               5                   10
```